US012781197B2

(12) United States Patent
Mercaldi et al.

(10) Patent No.: US 12,781,197 B2
(45) Date of Patent: Nov. 3, 2026

(54) METHODS AND COMPOSITIONS FOR THE PURIFICATION OF ADENO-ASSOCIATED VIRUS

(71) Applicant: Oxford Biomedica (US) LLC, Bedford, MA (US)

(72) Inventors: Michael Mercaldi, Bedford, MA (US); Ashish Sharma, Bedford, MA (US); Thomas Thiers, Bedford, MA (US); Luke Mustich, Bedford, MA (US); Shanshan Zhou, Bedford, MA (US); Zaid Junaid, Bedford, MA (US); Iraj Ghazi, Bedford, MA (US); Achyuta Teella, Bedford, MA (US); Alex Meola, Bedford, MA (US)

(73) Assignee: Oxford Biomedica (US) LLC, Bedford, MA (US)

( * ) Notice: Subject to any disclaimer, the term of this patent is extended or adjusted under 35 U.S.C. 154(b) by 1042 days.

(21) Appl. No.: 18/050,834

(22) Filed: Oct. 28, 2022

(65) Prior Publication Data

US 2023/0183658 A1 Jun. 15, 2023

Related U.S. Application Data

(60) Provisional application No. 63/263,305, filed on Oct. 29, 2021.

(51) Int. Cl.

| | |
|---|---|
| ***C12N 7/02*** | (2006.01) |
| ***B01D 15/20*** | (2006.01) |
| ***B01D 15/36*** | (2006.01) |
| ***C07K 14/005*** | (2006.01) |
| ***C12N 7/00*** | (2006.01) |
| ***C12N 15/864*** | (2006.01) |

(52) U.S. Cl.

CPC ............. *C12N 7/02* (2013.01); *B01D 15/203* (2013.01); *B01D 15/363* (2013.01); *C07K 14/005* (2013.01); *C12N 7/00* (2013.01); *C12N 15/8645* (2013.01); *C12N 2750/14121* (2013.01); *C12N 2750/14122* (2013.01); *C12N 2750/14123* (2013.01); *C12N 2750/14143* (2013.01); *C12N 2750/14151* (2013.01)

(58) Field of Classification Search

None

See application file for complete search history.

(56) References Cited

U.S. PATENT DOCUMENTS

| | | | |
|---|---|---|---|
| 6,143,548 | A | 11/2000 | Oriordan et al. |
| 6,146,874 | A | 11/2000 | Zolotukhin et al. |
| 6,194,191 | B1 | 2/2001 | Zhang et al. |
| 6,221,646 | B1 | 4/2001 | Dwarki et al. |
| 6,383,794 | B1 | 5/2002 | Mountz et al. |
| 6,410,300 | B1 | 6/2002 | Samulski et al. |
| 6,479,273 | B1 | 11/2002 | Bogedain et al. |
| 6,593,123 | B1 | 7/2003 | Wright et al. |
| 6,596,172 | B1 | 7/2003 | Kopf |
| 6,989,264 | B2 | 1/2006 | Atkinson et al. |
| 7,261,544 | B2 | 8/2007 | Qu et al. |
| 7,319,002 | B2 | 1/2008 | Wilson et al. |
| 7,419,817 | B2 | 9/2008 | Chiorini et al. |
| 7,625,570 | B1 | 12/2009 | Schaffer et al. |
| 7,704,721 | B2 | 4/2010 | Wright et al. |
| 7,833,796 | B2 | 11/2010 | Pellaux et al. |
| 7,851,196 | B2 | 12/2010 | Schaffer et al. |
| 8,163,543 | B2 | 4/2012 | Urabe et al. |
| 9,198,984 | B2 | 12/2015 | Lock et al. |
| 9,408,904 | B2 | 8/2016 | Wright et al. |
| 9,428,768 | B2 | 8/2016 | Pham et al. |
| 9,644,187 | B2 | 5/2017 | Asher et al. |
| 9,840,694 | B2 | 12/2017 | Hermens et al. |
| 9,862,936 | B2 | 1/2018 | Merino et al. |
| 9,884,071 | B2 | 2/2018 | Wilson et al. |
| 10,017,746 | B2 | 7/2018 | Sheldon et al. |
| 10,023,846 | B2 | 7/2018 | Nishie et al. |
| 10,072,250 | B2 | 9/2018 | Sakamoto et al. |
| 10,253,301 | B2 | 4/2019 | Hermens et al. |
| 10,266,810 | B2 | 4/2019 | Leuchs et al. |
| 10,294,452 | B2 | 5/2019 | He |
| 10,336,988 | B2 | 7/2019 | Buno et al. |
| 10,358,626 | B2 | 7/2019 | Cattaneo et al. |
| 10,526,583 | B2 | 1/2020 | Potter et al. |
| 10,626,376 | B2 | 4/2020 | Mcnally et al. |
| 10,662,237 | B2 | 5/2020 | Mehta |
| 10,889,797 | B2 | 1/2021 | Chen |
| 10,894,079 | B2 | 1/2021 | Müllner et al. |

(Continued)

FOREIGN PATENT DOCUMENTS

| | | |
|---|---|---|
| WO | 2011/097447 A2 | 8/2011 |
| WO | 2016/100575 A1 | 6/2016 |

(Continued)

OTHER PUBLICATIONS

Adli , "The CRISPR Tool Kit for Genome Editing and Beyond ," Nature Communications, vol. 9, May 15, 2018, pp. 1-13.

(Continued)

*Primary Examiner* — Michael D Burkhart

(74) *Attorney, Agent, or Firm* — Grimes & Yvon LLP

(57) ABSTRACT

Provided herein are methods and compositions for the separation of an adeno-associated virus (AAV) particle from a mixture of the AAV and at least one contaminant using anion exchange chromatography. These methods and compositions allow for improved purification of complete AAV particles from contaminants such as AAV particles that lack a complete genome (e.g., empty capsids) and AAV degradation products.

19 Claims, 27 Drawing Sheets

Specification includes a Sequence Listing.

(56) References Cited

U.S. PATENT DOCUMENTS

| | | | |
|---|---|---|---|
| 10,961,512 | B2 | 3/2021 | He |
| 11,015,173 | B2 | 5/2021 | Lock et al. |
| 11,015,174 | B2 | 5/2021 | Lock et al. |
| 11,021,689 | B2 | 6/2021 | Brument |
| 11,028,372 | B2 | 6/2021 | Lock et al. |
| 11,098,286 | B2 | 8/2021 | Lock et al. |
| 2001/0031463 | A1 | 10/2001 | Kleinschmidt et al. |
| 2004/0101964 | A1 | 5/2004 | Takashima et al. |
| 2005/0009168 | A1 | 1/2005 | Robbins et al. |
| 2007/0243615 | A1 | 10/2007 | Qu et al. |
| 2014/0121115 | A1 | 5/2014 | Arnould et al. |
| 2014/0359799 | A1 | 12/2014 | Wang et al. |
| 2015/0159173 | A1 | 6/2015 | Vandenberghe et al. |
| 2015/0376607 | A1 | 12/2015 | Lisowski et al. |
| 2017/0081680 | A1 | 3/2017 | Chatterjee et al. |
| 2017/0360962 | A1 | 12/2017 | Kay et al. |
| 2018/0051275 | A1 | 2/2018 | Carter et al. |
| 2018/0163183 | A1 | 6/2018 | Brument |
| 2018/0216133 | A1 | 8/2018 | Wilson et al. |
| 2018/0371426 | A1 | 12/2018 | Müllner et al. |
| 2019/0002842 | A1 | 1/2019 | Lock et al. |
| 2019/0161725 | A1 | 5/2019 | Chen |
| 2019/0255513 | A1 | 8/2019 | Scanlon |
| 2019/0284576 | A1 | 9/2019 | Qu et al. |
| 2019/0292561 | A1 | 9/2019 | Qu et al. |
| 2019/0365835 | A1 | 12/2019 | Fiedler et al. |
| 2019/0382733 | A1 | 12/2019 | Brument |
| 2020/0032223 | A1 | 1/2020 | Reid et al. |
| 2020/0048641 | A1 | 2/2020 | Jing et al. |
| 2020/0165632 | A1 | 5/2020 | Qu et al. |
| 2020/0224219 | A1 | 7/2020 | Büning et al. |
| 2020/0231986 | A1 | 7/2020 | Ayuso et al. |
| 2020/0289674 | A1 | 9/2020 | Seymour et al. |
| 2020/0299650 | A1 | 9/2020 | Qu et al. |
| 2020/0332266 | A1 | 10/2020 | Fiedler et al. |
| 2021/0009964 | A1 | 1/2021 | Khatwani et al. |
| 2021/0079422 | A1 | 3/2021 | Oh et al. |
| 2021/0145929 | A1 | 5/2021 | Girard et al. |
| 2021/0317474 | A1 | 10/2021 | Kaspar et al. |
| 2021/0355454 | A1 | 11/2021 | Cardinal et al. |
| 2021/0370199 | A1 | 12/2021 | Zhang et al. |
| 2022/0033782 | A1 | 2/2022 | Hejmowski |
| 2022/0064671 | A1 | 3/2022 | Maranga et al. |
| 2022/0119526 | A1 | 4/2022 | Guhan et al. |
| 2022/0119843 | A1 | 4/2022 | Dai et al. |
| 2022/0169991 | A1 | 6/2022 | Pizzi et al. |
| 2022/0213447 | A1 | 7/2022 | Dodson et al. |
| 2022/0267796 | A1 | 8/2022 | Fiedler et al. |
| 2022/0315622 | A1 | 10/2022 | Gagnon et al. |
| 2022/0325250 | A1 | 10/2022 | Reinauer et al. |
| 2022/0364064 | A1 | 11/2022 | Nishihachijyo et al. |

FOREIGN PATENT DOCUMENTS

| | | | |
|---|---|---|---|
| WO | 2020/227515 | A1 | 11/2020 |
| WO | 2021/138381 | A1 | 7/2021 |
| WO | 2021/154923 | A2 | 8/2021 |
| WO | 2021/158915 | A1 | 8/2021 |
| WO | 2021/165537 | A1 | 8/2021 |
| WO | 2021/168276 | A1 | 8/2021 |
| WO | 2021/188449 | A1 | 9/2021 |
| WO | 2021/188740 | A1 | 9/2021 |
| WO | 2021/245248 | A1 | 12/2021 |
| WO | 2021/247476 | A1 | 12/2021 |
| WO | 2021/252782 | A1 | 12/2021 |
| WO | 2022/038164 | A1 | 2/2022 |
| WO | 2022/038190 | A1 | 2/2022 |
| WO | 2022/043926 | A1 | 3/2022 |
| WO | 2022/094461 | A1 | 5/2022 |
| WO | 2022/097008 | A1 | 5/2022 |
| WO | 2022/112333 | A1 | 6/2022 |
| WO | 2022/137076 | A1 | 6/2022 |
| WO | 2022/159679 | A2 | 7/2022 |
| WO | 2022/191168 | A1 | 9/2022 |

OTHER PUBLICATIONS

Anderson et al., "A Method for the Preparation of Highly Purified Adeno-associated Virus Using Affinity Column Chromatography, Protease Digestion and Solvent Extraction ," Journal of Virological Methods, vol. 85, Mar. 2000, pp. 23-34.

Boch et al., "Breaking the Code of DNA Binding Specificity of TAL-type III Effector ," Science, vol. 326, No. 5959, Dec. 11, 2009, pp. 1509-1512.

Chen , "Adeno-Associated Virus Vectors for Human Gene Therapy ," World Journal of Medical Genetics, vol. 5, No. 3, Aug. 27, 2015, pp. 28-45.

Christian et al., "Targeting DNA Double-Strand Breaks with TAL Effector Nucleases ," Genetics, vol. 186, No. 2, Oct. 1, 2010, 13 pages.

Clark et al., "Highly Purified Recombinant Adeno-Associated Virus Vectors Are Biologically Active and Free of Detectable Helper and Wild-type Viruses ," Human Gene Therapy, vol. 10, No. 6, Apr. 1999, pp. 1031-1039.

Dickerson et al., "Separating Empty and Full Recombinant Adeno-Associated Virus Particles Using Isocratic Anion Exchange Chromatography ," Biotechnology Journal, vol. 16, No. 1, Oct. 2020, 9 pages.

Gagnon et al., "The Emerging Generation of Chromatography Tools for Virus Purification ," BioProcess International, Oct. 2008, pp. 24-30.

Hauswirth et al., "Production and Purification of Recombinant Adeno-Associated Virus ," Methods in Enzymology, vol. 316, 2000, pp. 743-761.

Jacobson et al., "Safety of Recombinant Adeno-associated Virus Type 2-RPE65 Vector Delivered by Ocular Subretinal Injection ," Molecular Therapy, vol. 13, No. 6, Jun. 2006, pp. 1074-1084.

Kelley et al., "Weak Partitioning Chromatography for Anion Exchange Purification of Monoclonal Antibodies ," Biotechnology and Bioengineering, vol. 13, 2008, pp. 553-566.

Kim et al., "Use of the Human Elongation Factor 1 Alpha Promoter as a Versatile and Efficient Expression System ," Gene, vol. 91, No. 2, Jul. 16, 1990, pp. 217-223.

Leskovec et al., "An Industrial Purification Platform for AAV ," BIA Separations, 2018, 1 page.

Lodeiro et al., "Transcription from the Second Heavy-Strand Promoter of Human mtDNA is Repressed by Transcription Factor A in Vitro ," Proceedings of the National Academy of Sciences, vol. 107, No. 17, Apr. 24, 2012, pp. 6513-6518.

Makarova et al., "Classification and Nomenclature of CRISPR-Cas Systems: Where from Here? ," The CRISPR Journal, vol. 1, No. 5, Oct. 1, 2018, pp. 325-336.

Miller et al., "A TALE Nuclease Architecture for Efficient Genome Editing ," Nature Biotechnology, vol. 29, No. 2, Feb. 2011, pp. 143-148.

Miller et al., "An Improved Zinc-Finger Nuclease Architecture for Highly Specific Genome Editing ," Nature Biotechnology, vol. 25, No. 7, Jul. 2007, pp. 778-785.

Miyazaki et al., "Expression Vector System Based on the Chicken Beta-actin Promoter Directs Efficient Production of Interleukin-5 ," Gene, vol. 79, No. 2, Jul. 15, 1989, pp. 269-277.

Moscou et al., "A Simple Cipher Governs DNA Recognition by TAL Effectors ," Science, vol. 326, Dec. 11, 2009, 1 page.

PCT Patent Application No. PCT/US2022/078902, International Search Report and Written Opinion, Apr. 24, 2023, 18 pages.

PCT Patent Application No. PCT/US2022/078902, Invitation to Pay Additional Fees and, Where Applicable, Protest Fee, Mar. 1, 2023, 5 pages.

Porteus et al., "Chimeric Nucleases Stimulate Gene Targeting in Human Cells ," Science, vol. 300, No. 5620, May 2, 2003, 12 pages.

Potter et al., "A Simplified Purification Protocol for Recombinant Adeno-Associated Virus Vectors ," Molecular Therapy—Methods & Clinical Development, 2014, pp. 1-8.

Qu et al., "Separation of Adeno-Associated Virus Type 2 Empty Particles From Genome Containing Vectors by Anion-Exchange Column Chromatography ," Journal of Virological Methods, vol. 140, Nos. 1-2, Mar. 2007, pp. 183-192.

(56) References Cited

OTHER PUBLICATIONS

Reyon et al., "FLASH Assembly of TALENs Enables High-Throughput Genome Editing ," Nature Biotechnology, vol. 30, No. 5, May 2012, pp. 460-465.
Sander et al., "Selection-Free Zinc-Finger-Nuclease Engineering by Context-Dependent Assembly (CoDA) ," Nature Methods, vol. 8, No. 1, Jan. 2011, pp. 67-69.
Singer-Sam et al., "Sequence of the Promoter Region of the Gene for Human X-linked 3-Phosphoglycerate Kinase ," Gene, vol. 32, No. 3, Dec. 1984, pp. 409-417.
Tomono et al., "Highly Efficient Ultracentrifugation-Free Chromatographic Purification of Recombinant AAV Serotype 9 ," Molecular Therapy-Methods & Clinical Development, Nov. 2018, pp. 180-190.
Urabe et al., "Removal of Empty Capsids From Type 1 Adeno-associated Virus Vector Stocks by Anion-exchange Chromatography Potentiates Transgene Expression ," Molecular Therapy, vol. 13, No. 4, Apr. 2006, pp. 823-828.
Wang et al., "Developing an Anion Exchange Chromatography Assay for Determining Empty and Full Capsid Contents in AAV6.2 ," Molecular Therapy-Methods & Clinical Development, vol. 15, Sep. 26, 2019, pp. 257-263.
Wood et al., "Targeted Genome Editing Across Species Using ZFNs and TALENs ," Science, vol. 333, No. 6040, Jul. 15, 2011, pp. 1-4.
Wright et al., "Identification of Factors That Contribute to Recombinant AAV2 Particle Aggregation and Methods to Prevent Its Occurrence During Vector Purification and Formulation ," Molecular Therapy, vol. 12, No. 1, Jul. 2005, pp. 171-178.
Wulff et al., "Partial Processing of the Neuropeptide Y Precursor in Transfected CHO Cells ," FEBS Letters, vol. 261, No. 1, Feb. 12, 1990, pp. 101-105.
Yang et al., "Anion-Exchange Chromatography for Determining Empty and Full Capsid Contents in Adeno-Associated Virus ," Application Note, Feb. 1, 2021, 7 pages.
Zhang et al., "Programmable Sequence-Specific Transcriptional Regulation of Mammalian Genome Using Designer TAL Effectors ," Nature Biotechnology, vol. 29, No. 2, Feb. 2011, pp. 149-153.

| Condition | % Empty Capsids in Product Peak |
|---|---|
| Magnesium Chloride | 25 |
| No Magnesium Chloride | 35 |

| Condition | % Empty Capsids in Product Peak |
|---|---|
| 3 mS/cm Wash Prior to Elution | 31 |
| 1 mS/cm Wash Prior to Elution | 14 |

METHODS AND COMPOSITIONS FOR THE PURIFICATION OF ADENO-ASSOCIATED VIRUS

RELATED APPLICATIONS

This application claims priority to U.S. Provisional Patent Application Ser. Nos. 63/263,305, filed Oct. 29, 2021, the entire disclosure of which is hereby incorporated herein by reference.

SEQUENCE LISTING

The content of the electronically submitted sequence listing in ASCII format (Name: "HMW-148_SL_ST26"; Size: 125,540 bytes; and Date of Creation: Oct. 27, 2022) is incorporated herein by reference in its entirety.

BACKGROUND

Gene therapy using adeno-associated virus (AAV) vectors has the potential to treat a wide variety of human disorders. Commercial therapeutic use of AAV vectors requires the large-scale manufacture of highly purified preparations of these vectors. A major challenge in the large-scale manufacture of AAV vectors is the separation of intact AAV particles from process-related contaminants, such as incomplete AAV particles, e.g., AAV particles that lack a complete genome (e.g., empty capsids).

Accordingly, there is a need in the art for novel AAV manufacturing methods that can provide for the consistent large-scale purification of intact AAV particles.

SUMMARY

The present disclosure provides methods for the separation of an adeno-associated virus (AAV) particle from a mixture of the AAV and at least one contaminant. The methods generally comprise contacting a mixture of an AAV particle and at least one contaminant with an anion exchange chromatography (AEX) medium such that the AAV particle binds to the AEX medium, and washing the AEX medium with a first wash solution under conditions such that the AAV particle remains bound to the AEX medium and the at least one contaminant does not bind the AEX medium. The present disclosure provides in certain embodiments, that the mixture and the first wash solution comprise an acetate. In certain embodiments, the mixture further comprises magnesium chloride ($MgCl_2$). In certain embodiments, the first wash solution further comprises urea. The present disclosure also provides methods further comprising washing the AEX medium with a second wash solution under conditions such that the AAV particle remains bound to the AEX medium and the at least one contaminant does not bind to the AEX medium, wherein the second wash solution is a low conductivity wash solution that has a conductivity of less than about 3 mS/cm. The low conductivity wash is performed prior to elution. Also provided herein are compositions comprising an AEX medium and a mixture comprising $MgCl_2$ and an acetate, and compositions comprising an AEX medium and a wash solution comprising urea and an acetate. The methods and compositions provided by the present disclosure allow for the improved purification of intact AAV particles from contaminants such as AAV particles that lack a complete genome (e.g., empty capsids) and AAV degradation products. Consequently, the methods disclosed herein, and the compositions disclosed herein for use in such methods, result in compositions having a high purity of intact AAV particles. Without wishing to be bound by any particular theory, the improved purification of intact AAV particles is at least partly achieved through "weak partitioning", a process by which a stronger binding species displaces or "weakly partitions" a weaker binding species from the chromatography column by inhibiting the binding of the weaker binding species to the column.

Accordingly, in one aspect, the present disclosure provides a method for the separation of an adeno-associated virus (AAV) particle from a mixture of the AAV particle and at least one contaminant, the method comprising: contacting the mixture with an anion exchange chromatography (AEX) medium under conditions such that a subset of empty AAV particles does not bind to the AEX medium and the full AAV particle binds to the AEX medium, wherein the mixture comprises magnesium chloride and an acetate; and washing the AEX medium with a first wash solution under conditions such that the AAV particle remains bound to the AEX medium and the at least one contaminant does not bind the AEX medium, thereby separating the AAV particle from the at least one contaminant.

In certain embodiments, the first wash solution comprises an acetate. In certain embodiments, the first wash solution comprises urea.

In another aspect, the present disclosure provides a method for the separation of an adeno-associated virus (AAV) particle from a mixture of the AAV particle and at least one contaminant, the method comprising: contacting the mixture with an anion exchange chromatography (AEX) medium under conditions such that the AAV particle binds to the AEX medium; and washing the AEX medium with a first wash solution comprising urea and an acetate under conditions such that the AAV particle remains bound to the AEX medium and the at least one contaminant does not bind to the AEX medium, thereby separating the AAV particle from the at least one contaminant. In another aspect, the method comprises contacting the mixture of the AAV particle and at least one contaminant with an AEX medium under conditions such that a subset of empty AAV particles does not bind to the AEX medium and the full AAV particle binds to the AEX medium, and washing the AEX medium with a first wash solution comprising urea and an acetate under conditions such that the AAV particle remains bound to the AEX medium and the at least one contaminant does not bind the AEX medium, thereby separating the AAV particle from the at least one contaminant.

In certain embodiments, the method further comprises washing the anion exchange chromatography medium with a second wash solution.

In another aspect, the present disclosure provides a method for the separation of an adeno-associated virus (AAV) particle from a mixture of the AAV particle and at least one contaminant, the method comprising: providing an AEX medium that has been contacted with the mixture, wherein the mixture comprises magnesium chloride and an acetate, and wherein the AEX medium comprises the AAV particle bound thereto and has been washed with a first wash solution such that the AAV particle remained bound to the AEX medium and the at least one contaminant did not bind to the AEX medium; and washing the AEX medium with a second wash solution under conditions such that the AAV particle remains bound to the AEX medium and the at least one contaminant does not bind to the AEX medium, thereby separating the AAV particle from the at least one contaminant.

In certain embodiments, the first wash solution comprises an acetate. In certain embodiments, the first wash solution comprises urea.

In another aspect, the present disclosure provides a method for the separation of an adeno-associated virus (AAV) particle from a mixture of the AAV particle and at least one contaminant, the method comprising: providing an AEX medium that has been contacted with the mixture, wherein the AEX medium comprises the AAV particle bound thereto and has been washed with a first wash solution comprising urea and an acetate such that the AAV particle remained bound to the AEX medium and the at least one contaminant did not bind to the AEX medium; and washing the AEX medium with a second wash solution under conditions such that the AAV particle remains bound to the AEX medium and the at least one contaminant does not bind to the AEX medium, thereby separating the AAV particle from the at least one contaminant.

In certain embodiments, the at least one contaminant is selected from the group consisting of an AAV particle lacking a complete genome, an AAV degradation product, a host cell protein, a host cell fragment, and any combination thereof. In certain embodiments, the at least one contaminant is an AAV particle that lacks a complete genome.

In certain embodiments, the AEX medium has an average pore size of at least about 100 nm. In certain embodiments, the AEX medium has an average pore size of at least about 500 nm. In certain embodiments, the AEX medium comprises a quaternary amine. In certain embodiments, the AEX medium comprises a quaternary polyethyleneimine group.

In certain embodiments, the mixture comprises a partially purified AAV composition. In certain embodiments, the mixture comprises an eluate of an affinity chromatography column.

In certain embodiments, the mixture comprises about 10 mM to about 40 mM of an acetate. In certain embodiments, the mixture comprises about 10 mM to about 40 mM ammonium acetate. In certain embodiments, the mixture comprises about 28 mM ammonium acetate.

In certain embodiments, the mixture comprises about 2 mM to about 6 mM magnesium chloride. In certain embodiments, the mixture comprises about 2 mM magnesium chloride.

In certain embodiments, the mixture comprises about 0.001% (w/v) to about 0.05% (w/v) Poloxamer 188. In certain embodiments, the mixture comprises about 0.01% (w/v) Poloxamer 188.

In certain embodiments, the pH of the mixture is about 9 to about 10.5. In certain embodiments, the pH of the mixture is about 9.3.

In certain embodiments, the first wash solution comprises about 0.1 M to about 4 M urea. In certain embodiments, the first wash solution comprises about 2 M urea.

In certain embodiments, the first wash solution comprises an acetate selected from the group consisting of ammonium acetate, potassium acetate, sodium acetate, and cesium acetate. In certain embodiments, the first wash solution comprises ammonium acetate. In certain embodiments, the first wash solution comprises about 10 mM to about 40 mM of the acetate. In certain embodiments, the first wash solution comprises about 10 mM to about 40 mM ammonium acetate. In certain embodiments, the first wash solution comprises about 28 mM ammonium acetate.

In certain embodiments, the first wash solution comprises about 2 mM to about 6 mM magnesium chloride. In certain embodiments, the first wash solution comprises about 2 mM magnesium chloride.

In certain embodiments, the first wash solution comprises about 0.001% (w/v) to about 0.05% (w/v) Poloxamer 188. In certain embodiments, the first wash solution comprises about 0.01% (w/v) Poloxamer 188.

In certain embodiments, the pH of the first wash solution is about 9 to about 10.5. In certain embodiments, the pH of the first wash solution is about 9.3.

In certain embodiments, the first wash solution has a conductivity of about 1 mS/cm to about 3 mS/cm.

In certain embodiments, the second wash solution comprises about 0.1 mM to about 15 mM ammonium acetate. In certain embodiments, the second wash solution comprises about 10 mM ammonium acetate.

In certain embodiments, the second wash solution comprises about 0.001% (w/v) to about 0.05% (w/v) Poloxamer 188. In certain embodiments, the second wash solution comprises about 0.01% (w/v) Poloxamer 188.

In certain embodiments, the pH of the second wash solution is about 9 to about 10.5. In certain embodiments, the pH of the second wash solution is about 9.3.

In certain embodiments, the second wash solution has a conductivity of less than about 3 mS/cm. In certain embodiments, the second wash solution has a conductivity of about 1 mS/cm to about 3 mS/cm. In certain embodiments, the second wash solution has a conductivity of about 1 mS/cm.

In certain embodiments, the method further comprises eluting the AAV particle from the AEX medium. In certain embodiments, the AAV particle is eluted from the AEX medium with an eluant using a step gradient. In certain embodiments, the AAV particle is eluted from the AEX medium with an eluant using a linear gradient.

In certain embodiments, the eluant comprises a salt at a concentration of about 10 mM to about 1 M. In certain embodiments, the salt is an acetate salt. In certain embodiments, the acetate salt is selected from the group consisting of ammonium acetate, potassium acetate, sodium acetate, and cesium acetate. In certain embodiments, the acetate salt is ammonium acetate. In certain embodiments, the acetate salt is sodium acetate.

In certain embodiments, the eluant comprises about 10 mM to about 1 M ammonium acetate. In certain embodiments, the eluant comprises about 10 mM to about 150 mM ammonium acetate. In certain embodiments, the eluant comprises about 100 mM to about 300 mM ammonium acetate.

In certain embodiments, the eluant comprises about 0.001% (w/v) to about 0.05% (w/v) Poloxamer 188. In certain embodiments, the eluant comprises about 0.01% (w/v) Poloxamer 188.

In certain embodiments, the pH of the eluant is about 9 to about 10.5. In certain embodiments, the pH of the eluant is about 9.3.

In certain embodiments, the eluant further comprises about 50 mM ethanolamine.

In certain embodiments, the eluant has a conductivity of about 8.5 mS/cm to about 30 mS/cm. In certain embodiments, the eluant has a conductivity of about 8.5 mS/cm to about 10.5 mS/cm. In certain embodiments, the eluant has a conductivity of about 10 mS/cm to about 11.5 mS/cm. In certain embodiments, the eluant has a conductivity of about 14 mS/cm to about 17.5 mS/cm. In certain embodiments, the eluant has a conductivity of about 18.5 mS/cm. In certain embodiments, the eluant has a conductivity of about 19 mS/cm. In certain embodiments, the eluant has a conductivity of about 26 mS/cm.

In certain embodiments, the method results in an eluate comprising less than about 15% AAV particles that lack a complete genome. In certain embodiments, the method results in an eluate comprising less than about 10% AAV particles that lack a complete genome.

In certain embodiments, the method further comprises formulating the eluted AAV particle in a formulation buffer suitable for administration to a human subject.

In certain embodiments, the AAV is a recombinant AAV (rAAV) comprising an rAAV genome comprising a transgene. In certain embodiments, the transgene encodes a polypeptide. In certain embodiments, the transgene encodes an miRNA, shRNA, siRNA, antisense RNA, gRNA, antagomir, miRNA sponge, RNA aptazyme, RNA aptamer, lncRNA, ribozyme, or mRNA. In certain embodiments, the transgene encodes a protein selected from the group consisting of iduronate-2-sulfatase (I2S), frataxin (FXN), glucose-6-phosphatase (G6Pase), phosphoenolpyruvate carboxykinase (PEPCK), cyclin-dependent kinase-like 5 (CDKL5/STK9), galactose-1 phosphate uridyltransferase, phenylalanine hydroxylase (PAH), branched-chain alpha-keto acid dehydrogenase, fumarylacetoacetate hydrolase, methylmalonyl-CoA mutase, medium-chain acyl-CoA dehydrogenase, ornithine transcarbamylase (OTC), argininosuccinic acid synthetase (ASS1), low density lipoprotein receptor (LDLR) protein, UDP-glucuronosyltransferase, adenosine deaminase, hypoxanthine guanine phosphoribosyltransferase, biotinidase, alpha-galactosidase A, copper-transporting ATPase 2 (ATP7B), beta-glucocerebrosidase, 70 kDa peroxisomal membrane protein (PMP70), and arylsulfatase A (ARSA). In certain embodiments, the transgene encodes an antibody or a fragment thereof selected from the group consisting of: muromonab-cd3, efalizumab, tositumomab, daclizumab, nebacumab, catumaxomab, edrecolomab, abciximab, rituximab, basiliximab, palivizumab, infliximab, trastuzumab, adalimumab, ibritumomab tiuxetan, omalizumab, cetuximab, bevacizumab, natalizumab, panitumumab, ranibizumab, eculizumab, certolizumab, ustekinumab, canakinumab, golimumab, ofatumumab, tocilizumab, denosumab, belimumab, ipilimumab, brentuximab vedotin, pertuzumab, raxibacumab, obinutuzumab, alemtuzumab, siltuximab, ramucirumab, vedolizumab, blinatumomab, nivolumab, pembrolizumab, idarucizumab, necitumumab, dinutuximab, secukinumab, mepolizumab, alirocumab, evolocumab, daratumumab, elotuzumab, ixekizumab, reslizumab, olaratumab, bezlotoxumab, atezolizumab, obiltoxaximab, inotuzumab ozogamicin, brodalumab, guselkumab, dupilumab, sarilumab, avelumab, ocrelizumab, emicizumab, benralizumab, gemtuzumab ozogamicin, durvalumab, burosumab, erenumab, galcanezumab, lanadelumab, mogamulizumab, tildrakizumab, cemiplimab, fremanezumab, ravulizumab, emapalumab, ibalizumab, moxetumomab, caplacizumab, romosozumab, risankizumab, polatuzumab, eptinezumab, leronlimab, sacituzumab, brolucizumab, isatuximab, and teprotumumab. In certain embodiments, the transgene encodes a protein which is not selected from the group consisting of phenylalanine hydroxylase (PAH), iduronate-2-sulfatase (I2S), arylsulfatase A (ARSA), and an anti-complement component 5 antibody.

In certain embodiments, the transgene encodes a protein selected from the group consisting of frataxin (FXN), glucose-6-phosphatase (G6Pase), phosphoenolpyruvate carboxykinase (PEPCK), cyclin-dependent kinase-like 5 (CDKL5/STK9), galactose-1 phosphate uridyltransferase, branched-chain alpha-keto acid dehydrogenase, fumarylacetoacetate hydrolase, methylmalonyl-CoA mutase, medium-chain acyl-CoA dehydrogenase, ornithine transcarbamylase (OTC), argininosuccinic acid synthetase (ASS1), low density lipoprotein receptor (LDLR) protein, UDP-glucuronosyltransferase, adenosine deaminase, hypoxanthine guanine phosphoribosyltransferase, biotinidase, alpha-galactosidase A, copper-transporting ATPase 2 (ATP7B), beta-glucocerebrosidase, and 70 kDa peroxisomal membrane protein (PMP70).

In certain embodiments, the rAAV genome further comprises a transcriptional regulatory element operably linked to the transgene. In certain embodiments, the transcriptional regulatory element comprises a promoter element and/or an intron element.

In certain embodiments, the rAAV genome further comprises a polyadenylation sequence. In certain embodiments, the polyadenylation sequence is 3' to the transgene.

In certain embodiments, the rAAV genome comprises a nucleotide sequence that is at least 85%, 86%, 87%, 88%, 89%, 90%, 91%, 92%, 93%, 94%, 95%, 96%, 97%, 98%, 99%, or 100% identical to the nucleotide sequence set forth in SEQ ID NO: 50, 51, 52, 53, or 54

In certain embodiments, the rAAV genome further comprises a 5' inverted terminal repeat (5' ITR) nucleotide sequence 5' of the transgene, and a 3' inverted terminal repeat (3' ITR) nucleotide sequence 3' of the transgene. In certain embodiments, the 5' ITR nucleotide sequence is at least 85%, 86%, 87%, 88%, 89%, 90%, 91%, 92%, 93%, 94%, 95%, 96%, 97%, 98%, 99% or 100% identical to the nucleotide sequence set forth in SEQ ID NO: 39, 41, or 42, and/or the 3' ITR nucleotide sequence is at least 85%, 86%, 87%, 88%, 89%, 90%, 91%, 92%, 93%, 94%, 95%, 96%, 97%, 98%, 99% or 100% identical to the nucleotide sequence set forth in SEQ ID NO: 40, 43, or 44.

In certain embodiments, the rAAV genome comprises a nucleotide sequence that is at least 85%, 86%, 87%, 88%, 89%, 90%, 91%, 92%, 93%, 94%, 95%, 96%, 97%, 98%, 99%, or 100% identical to the nucleotide sequence set forth in SEQ ID NO: 55, 56, 57, 58, or 59.

In certain embodiments, the rAAV comprises an AAV capsid comprising an AAV capsid protein. In certain embodiments, the AAV capsid protein is selected from the group consisting of AAV1, AAV2, AAV3, AAV4, AAV5, AAV6, AAV7, AAV8, AAV9, AAV-DJ, AAV-LK03, NP59, VOY101, VOY201, VOY701, VOY801, VOY1101, AAVPHP.N, AAVPHP.A, AAVPHP.B, PHP.B2, PHP.B3, G2A3, G2B4, G2B5, and PHP.S.

In certain embodiments, the AAV capsid protein does not comprise an amino acid sequence that is at least 85% identical to the amino acid sequence of amino acids 203-736 of SEQ ID NO: 1, 2, 3, 4, 5, 6, 7, 8, 9, 10, 11, 12, 13, 15, 16, or 17, wherein: the amino acid in the capsid protein corresponding to amino acid 206 of SEQ ID NO: 16 is C; the amino acid in the capsid protein corresponding to amino acid 296 of SEQ ID NO: 16 is H; the amino acid in the capsid protein corresponding to amino acid 312 of SEQ ID NO: 16 is Q; the amino acid in the capsid protein corresponding to amino acid 346 of SEQ ID NO: 16 is A; the amino acid in the capsid protein corresponding to amino acid 464 of SEQ ID NO: 16 is N; the amino acid in the capsid protein corresponding to amino acid 468 of SEQ ID NO: 16 is S; the amino acid in the capsid protein corresponding to amino acid 501 of SEQ ID NO: 16 is I; the amino acid in the capsid protein corresponding to amino acid 505 of SEQ ID NO: 16 is R; the amino acid in the capsid protein corresponding to amino acid 590 of SEQ ID NO: 16 is R; the amino acid in the capsid protein corresponding to amino acid 626 of SEQ ID NO: 16 is G or Y; the amino acid in the capsid protein corresponding to amino acid 681 of SEQ ID NO: 16 is M; the amino acid in the capsid protein corresponding to amino acid 687 of SEQ ID NO: 16 is R; the amino acid in the capsid protein corresponding to amino acid 690 of SEQ ID NO: 16 is K; the amino acid in the capsid protein corresponding to amino acid 706 of SEQ ID NO: 16 is C; or, the amino acid in the capsid protein corresponding to amino acid 718 of SEQ ID NO: 16 is G. In certain embodiments, the AAV capsid protein does not comprise an amino acid sequence that is at least 85% identical to the amino acid sequence of amino acids 203-736 of SEQ ID NO: 1, 2, 3, 4, 5, 6, 7, 8, 9, 10, 11, 12, 13, 15, 16, or 17, wherein: (a) the amino acid in the capsid protein corresponding to amino acid 626 of SEQ ID NO: 16 is G, and the amino acid in the capsid protein corresponding to amino acid 718 of SEQ ID NO: 16 is G; (b) the amino acid in the capsid protein corresponding to amino acid 296 of SEQ ID NO: 16 is H, the amino acid in the capsid protein corresponding to amino acid 464 of SEQ ID NO: 16 is N, the amino acid in the capsid protein corresponding to amino acid 505 of SEQ ID NO: 16 is R, and the amino acid in the capsid protein corresponding to amino acid 681 of SEQ ID NO: 16 is M; (c) the amino acid in the capsid protein corresponding to amino acid 505 of SEQ ID NO: 16 is R, and the amino acid in the capsid protein corresponding to amino acid 687 of SEQ ID NO: 16 is R; (d) the amino acid in the capsid protein corresponding to amino acid 346 of SEQ ID NO: 16 is A, and the amino acid in the capsid protein corresponding to amino acid 505 of SEQ ID NO: 16 is R; or (e) the amino acid in the capsid protein corresponding to amino acid 501 of SEQ ID NO: 16 is I, the amino acid in the capsid protein corresponding to amino acid 505 of SEQ ID NO: 16 is R, and the amino acid in the capsid protein corresponding to amino acid 706 of SEQ ID NO: 16 is C. In certain embodiments, the AAV capsid protein does not comprise the amino acid sequence of amino acids 203-736 of SEQ ID NO: 1, 2, 3, 4, 5, 6, 7, 8, 9, 10, 11, 12, 13, 15, 16, or 17.

In certain embodiments, the AAV capsid protein does not comprise an amino acid sequence that is at least 85% identical to the amino acid sequence of amino acids 138-736 of SEQ ID NO: 1, 2, 3, 4, 5, 6, 7, 8, 9, 10, 11, 12, 13, 15, 16, or 17, wherein: the amino acid in the capsid protein corresponding to amino acid 151 of SEQ ID NO: 16 is R; the amino acid in the capsid protein corresponding to amino acid 160 of SEQ ID NO: 16 is D; the amino acid in the capsid protein corresponding to amino acid 206 of SEQ ID NO: 16 is C; the amino acid in the capsid protein corresponding to amino acid 296 of SEQ ID NO: 16 is H; the amino acid in the capsid protein corresponding to amino acid 312 of SEQ ID NO: 16 is Q; the amino acid in the capsid protein corresponding to amino acid 346 of SEQ ID NO: 16 is A; the amino acid in the capsid protein corresponding to amino acid 464 of SEQ ID NO: 16 is N; the amino acid in the capsid protein corresponding to amino acid 468 of SEQ ID NO: 16 is S; the amino acid in the capsid protein corresponding to amino acid 501 of SEQ ID NO: 16 is I; the amino acid in the capsid protein corresponding to amino acid 505 of SEQ ID NO: 16 is R; the amino acid in the capsid protein corresponding to amino acid 590 of SEQ ID NO: 16 is R; the amino acid in the capsid protein corresponding to amino acid 626 of SEQ ID NO: 16 is G or Y; the amino acid in the capsid protein corresponding to amino acid 681 of SEQ ID NO: 16 is M; the amino acid in the capsid protein corresponding to amino acid 687 of SEQ ID NO: 16 is R; the amino acid in the capsid protein corresponding to amino acid 690 of SEQ ID NO: 16 is K; the amino acid in the capsid protein corresponding to amino acid 706 of SEQ ID NO: 16 is C; or, the amino acid in the capsid protein corresponding to amino acid 718 of SEQ ID NO: 16 is G. In certain embodiments, the AAV capsid protein does not comprise an amino acid sequence that is at least 85% identical to the amino acid sequence of amino acids 138-736 of SEQ ID NO: 1, 2, 3, 4, 5, 6, 7, 8, 9, 10, 11, 12, 13, 15, 16, or 17, wherein: (a) the amino acid in the capsid protein corresponding to amino acid 626 of SEQ ID NO: 16 is G, and the amino acid in the capsid protein corresponding to amino acid 718 of SEQ ID NO: 16 is G; (b) the amino acid in the capsid protein corresponding to amino acid 296 of SEQ ID NO: 16 is H, the amino acid in the capsid protein corresponding to amino acid 464 of SEQ ID NO: 16 is N, the amino acid in the capsid protein corresponding to amino acid 505 of SEQ ID NO: 16 is R, and the amino acid in the capsid protein corresponding to amino acid 681 of SEQ ID NO: 16 is M; (c) the amino acid in the capsid protein corresponding to amino acid 505 of SEQ ID NO: 16 is R, and the amino acid in the capsid protein corresponding to amino acid 687 of SEQ ID NO: 16 is R; (d) the amino acid in the capsid protein corresponding to amino acid 346 of SEQ ID NO: 16 is A, and the amino acid in the capsid protein corresponding to amino acid 505 of SEQ ID NO: 16 is R; or (e) the amino acid in the capsid protein corresponding to amino acid 501 of SEQ ID NO: 16 is I, the amino acid in the capsid protein corresponding to amino acid 505 of SEQ ID NO: 16 is R, and the amino acid in the capsid protein corresponding to amino acid 706 of SEQ ID NO: 16 is C. In certain embodiments, the AAV capsid protein does not comprise the amino acid sequence of amino acids 138-736 of SEQ ID NO: 1, 2, 3, 4, 5, 6, 7, 9, 10, 11, 12, 13, 15, 16, or 17.

In certain embodiments, the AAV capsid protein does not comprise an amino acid sequence that is at least 85% identical to the amino acid sequence of amino acids 1-736 of SEQ ID NO: 1, 2, 3, 4, 5, 6, 7, 8, 9, 10, 11, 12, 13, 15, 16, or 17, wherein: the amino acid in the capsid protein corresponding to amino acid 2 of SEQ ID NO: 16 is T; the amino acid in the capsid protein corresponding to amino acid 65 of SEQ ID NO: 16 is I; the amino acid in the capsid protein corresponding to amino acid 68 of SEQ ID NO: 16 is V; the amino acid in the capsid protein corresponding to amino acid 77 of SEQ ID NO: 16 is R; the amino acid in the capsid protein corresponding to amino acid 119 of SEQ ID NO: 16 is L; the amino acid in the capsid protein corresponding to amino acid 151 of SEQ ID NO: 16 is R; the amino acid in the capsid protein corresponding to amino acid 160 of SEQ ID NO: 16 is D; the amino acid in the capsid protein corresponding to amino acid 206 of SEQ ID NO: 16 is C; the amino acid in the capsid protein corresponding to amino acid 296 of SEQ ID NO: 16 is H; the amino acid in the capsid protein corresponding to amino acid 312 of SEQ ID NO: 16 is Q; the amino acid in the capsid protein corresponding to amino acid 346 of SEQ ID NO: 16 is A; the amino acid in the capsid protein corresponding to amino acid 464 of SEQ ID NO: 16 is N; the amino acid in the capsid protein corresponding to amino acid 468 of SEQ ID NO: 16 is S; the amino acid in the capsid protein corresponding to amino acid 501 of SEQ ID NO: 16 is I; the amino acid in the capsid protein corresponding to amino acid 505 of SEQ ID NO: 16 is R; the amino acid in the capsid protein corresponding to amino acid 590 of SEQ ID NO: 16 is R; the amino acid in the capsid protein corresponding to amino acid 626 of SEQ ID NO: 16 is G or Y; the amino acid in the capsid protein corresponding to amino acid 681 of SEQ ID NO: 16 is M; the amino acid in the capsid protein corresponding to amino acid 687 of SEQ ID NO: 16 is R; the amino acid in the capsid protein corresponding to amino acid 690 of SEQ ID NO: 16 is K; the amino acid in the capsid protein corresponding to amino acid 706 of SEQ ID NO: 16 is C; or, the amino acid in the capsid protein corresponding to amino acid 718 of SEQ ID NO: 16 is G. In certain embodiments, the AAV capsid protein does not comprise an amino acid sequence that is at least 85% identical to the amino acid sequence of amino acids 1-736 of SEQ ID NO: 1, 2, 3, 4, 5, 6, 7, 8, 9, 10, 11, 12, 13, 15, 16, or 17, wherein: (a) the amino acid in the capsid protein corresponding to amino acid 2 of SEQ ID NO: 16 is T, and the amino acid in the capsid protein corresponding to amino acid 312 of SEQ ID NO: 16 is Q; (b) the amino acid in the capsid protein corresponding to amino acid 65 of SEQ ID NO: 16 is I, and the amino acid in the capsid protein corresponding to amino acid 626 of SEQ ID NO: 16 is Y; (c) the amino acid in the capsid protein corresponding to amino acid 77 of SEQ ID NO: 16 is R, and the amino acid in the capsid protein corresponding to amino acid 690 of SEQ ID NO: 16 is K; (d) the amino acid in the capsid protein corresponding to amino acid 119 of SEQ ID NO: 16 is L, and the amino acid in the capsid protein corresponding to amino acid 468 of SEQ ID NO: 16 is S; (e) the amino acid in the capsid protein corresponding to amino acid 626 of SEQ ID NO: 16 is G, and the amino acid in the capsid protein corresponding to amino acid 718 of SEQ ID NO: 16 is G; (f) the amino acid in the capsid protein corresponding to amino acid 296 of SEQ ID NO: 16 is H, the amino acid in the capsid protein corresponding to amino acid 464 of SEQ ID NO: 16 is N, the amino acid in the capsid protein corresponding to amino acid 505 of SEQ ID NO: 16 is R, and the amino acid in the capsid protein corresponding to amino acid 681 of SEQ ID NO: 16 is M; (g) the amino acid in the capsid protein corresponding to amino acid 505 of SEQ ID NO: 16 is R, and the amino acid in the capsid protein corresponding to amino acid 687 of SEQ ID NO: 16 is R; (h) the amino acid in the capsid protein corresponding to amino acid 346 of SEQ ID NO: 16 is A, and the amino acid in the capsid protein corresponding to amino acid 505 of SEQ ID NO: 16 is R; or (i) the amino acid in the capsid protein corresponding to amino acid 501 of SEQ ID NO: 16 is I, the amino acid in the capsid protein corresponding to amino acid 505 of SEQ ID NO: 16 is R, and the amino acid in the capsid protein corresponding to amino acid 706 of SEQ ID NO: 16 is C. In certain embodiments, the AAV capsid protein does not comprise the amino acid sequence of amino acids 1-736 of SEQ ID NO: 1, 2, 3, 4, 5, 6, 7, 8, 9, 10, 11, 12, 13, 15, 16, or 17.

In certain embodiments, the AAV capsid protein comprises an amino acid sequence that is at least 85% identical to the amino acid sequence of amino acids 203-736 of SEQ ID NO: 1, 2, 3, 4, 5, 6, 7, 8, 9, 10, 11, 12, 13, 15, 16, or 17. In certain embodiments, the amino acid in the capsid protein corresponding to amino acid 206 of SEQ ID NO: 16 is C; the amino acid in the capsid protein corresponding to amino acid 296 of SEQ ID NO: 16 is H; the amino acid in the capsid protein corresponding to amino acid 312 of SEQ ID NO: 16 is Q; the amino acid in the capsid protein corresponding to amino acid 346 of SEQ ID NO: 16 is A; the amino acid in the capsid protein corresponding to amino acid 464 of SEQ ID NO: 16 is N; the amino acid in the capsid protein corresponding to amino acid 468 of SEQ ID NO: 16 is S; the amino acid in the capsid protein corresponding to amino acid 501 of SEQ ID NO: 16 is I; the amino acid in the capsid protein corresponding to amino acid 505 of SEQ ID NO: 16 is R; the amino acid in the capsid protein corresponding to amino acid 590 of SEQ ID NO: 16 is R; the amino acid in the capsid protein corresponding to amino acid 626 of SEQ ID NO: 16 is G or Y; the amino acid in the capsid protein corresponding to amino acid 681 of SEQ ID NO: 16 is M; the amino acid in the capsid protein corresponding to amino acid 687 of SEQ ID NO: 16 is R; the amino acid in the capsid protein corresponding to amino acid 690 of SEQ ID NO: 16 is K; the amino acid in the capsid protein corresponding to amino acid 706 of SEQ ID NO: 16 is C; or, the amino acid in the capsid protein corresponding to amino acid 718 of SEQ ID NO: 16 is G. In certain embodiments: (a) the amino acid in the capsid protein corresponding to amino acid 626 of SEQ ID NO: 16 is G, and the amino acid in the capsid protein corresponding to amino acid 718 of SEQ ID NO: 16 is G; (b) the amino acid in the capsid protein corresponding to amino acid 296 of SEQ ID NO: 16 is H, the amino acid in the capsid protein corresponding to amino acid 464 of SEQ ID NO: 16 is N, the amino acid in the capsid protein corresponding to amino acid 505 of SEQ ID NO: 16 is R, and the amino acid in the capsid protein corresponding to amino acid 681 of SEQ ID NO: 16 is M; (c) the amino acid in the capsid protein corresponding to amino acid 505 of SEQ ID NO: 16 is R, and the amino acid in the capsid protein corresponding to amino acid 687 of SEQ ID NO: 16 is R; (d) the amino acid in the capsid protein corresponding to amino acid 346 of SEQ ID NO: 16 is A, and the amino acid in the capsid protein corresponding to amino acid 505 of SEQ ID NO: 16 is R; or (e) the amino acid in the capsid protein corresponding to amino acid 501 of SEQ ID NO: 16 is I, the amino acid in the capsid protein corresponding to amino acid 505 of SEQ ID NO: 16 is R, and the amino acid in the capsid protein corresponding to amino acid 706 of SEQ ID NO: 16 is C. In certain embodiments, the AAV capsid protein comprises the amino acid sequence of amino acids 203-736 of SEQ ID NO: 1, 2, 3, 4, 5, 6, 7, 8, 9, 10, 11, 12, 13, 15, 16, or 17.

In certain embodiments, the AAV capsid protein comprises an amino acid sequence that is at least 85% identical to the amino acid sequence of amino acids 138-736 of SEQ ID NO: 1, 2, 3, 4, 5, 6, 7, 8, 9, 10, 11, 12, 13, 15, 16, or 17. In certain embodiments, the amino acid in the capsid protein corresponding to amino acid 151 of SEQ ID NO: 16 is R; the amino acid in the capsid protein corresponding to amino acid 160 of SEQ ID NO: 16 is D; the amino acid in the capsid protein corresponding to amino acid 206 of SEQ ID NO: 16 is C; the amino acid in the capsid protein corresponding to amino acid 296 of SEQ ID NO: 16 is H; the amino acid in the capsid protein corresponding to amino acid 312 of SEQ ID NO: 16 is Q; the amino acid in the capsid protein corresponding to amino acid 346 of SEQ ID NO: 16 is A; the amino acid in the capsid protein corresponding to amino acid 464 of SEQ ID NO: 16 is N; the amino acid in the capsid protein corresponding to amino acid 468 of SEQ ID NO: 16 is S; the amino acid in the capsid protein corresponding to amino acid 501 of SEQ ID NO: 16 is I; the amino acid in the capsid protein corresponding to amino acid 505 of SEQ ID NO: 16 is R; the amino acid in the capsid protein corresponding to amino acid 590 of SEQ ID NO: 16 is R; the amino acid in the capsid protein corresponding to amino acid 626 of SEQ ID NO: 16 is G or Y; the amino acid in the capsid protein corresponding to amino acid 681 of SEQ ID NO: 16 is M; the amino acid in the capsid protein corresponding to amino acid 687 of SEQ ID NO: 16 is R; the amino acid in the capsid protein corresponding to amino acid 690 of SEQ ID NO: 16 is K; the amino acid in the capsid protein corresponding to amino acid 706 of SEQ ID NO: 16 is C; or, the amino acid in the capsid protein corresponding to amino acid 718 of SEQ ID NO: 16 is G. In certain embodiments: (a) the amino acid in the capsid protein corresponding to amino acid 626 of SEQ ID NO: 16 is G, and the amino acid in the capsid protein corresponding to amino acid 718 of SEQ ID NO: 16 is G; (b) the amino acid in the capsid protein corresponding to amino acid 296 of SEQ ID NO: 16 is H, the amino acid in the capsid protein corresponding to amino acid 464 of SEQ ID NO: 16 is N, the amino acid in the capsid protein corresponding to amino acid 505 of SEQ ID NO: 16 is R, and the amino acid in the capsid protein corresponding to amino acid 681 of SEQ ID NO: 16 is M; (c) the amino acid in the capsid protein corresponding to amino acid 505 of SEQ ID NO: 16 is R, and the amino acid in the capsid protein corresponding to amino acid 687 of SEQ ID NO: 16 is R; (d) the amino acid in the capsid protein corresponding to amino acid 346 of SEQ ID NO: 16 is A, and the amino acid in the capsid protein corresponding to amino acid 505 of SEQ ID NO: 16 is R; or (e) the amino acid in the capsid protein corresponding to amino acid 501 of SEQ ID NO: 16 is I, the amino acid in the capsid protein corresponding to amino acid 505 of SEQ ID NO: 16 is R, and the amino acid in the capsid protein corresponding to amino acid 706 of SEQ ID NO: 16 is C. In certain embodiments, the AAV capsid protein comprises the amino acid sequence of amino acids 138-736 of SEQ ID NO: 1, 2, 3, 4, 5, 6, 7, 9, 10, 11, 12, 13, 15, 16, or 17.

In certain embodiments, the AAV capsid protein comprises an amino acid sequence that is at least 85% identical to the amino acid sequence of amino acids 1-736 of SEQ ID NO: 1, 2, 3, 4, 5, 6, 7, 8, 9, 10, 11, 12, 13, 15, 16, or 17. In certain embodiments, the amino acid in the capsid protein corresponding to amino acid 2 of SEQ ID NO: 16 is T; the amino acid in the capsid protein corresponding to amino acid 65 of SEQ ID NO: 16 is I; the amino acid in the capsid protein corresponding to amino acid 68 of SEQ ID NO: 16 is V; the amino acid in the capsid protein corresponding to amino acid 77 of SEQ ID NO: 16 is R; the amino acid in the capsid protein corresponding to amino acid 119 of SEQ ID NO: 16 is L; the amino acid in the capsid protein corresponding to amino acid 151 of SEQ ID NO: 16 is R; the amino acid in the capsid protein corresponding to amino acid 160 of SEQ ID NO: 16 is D; the amino acid in the capsid protein corresponding to amino acid 206 of SEQ ID NO: 16 is C; the amino acid in the capsid protein corresponding to amino acid 296 of SEQ ID NO: 16 is H; the amino acid in the capsid protein corresponding to amino acid 312 of SEQ ID NO: 16 is Q; the amino acid in the capsid protein corresponding to amino acid 346 of SEQ ID NO: 16 is A; the amino acid in the capsid protein corresponding to amino acid 464 of SEQ ID NO: 16 is N; the amino acid in the capsid protein corresponding to amino acid 468 of SEQ ID NO: 16 is S; the amino acid in the capsid protein corresponding to amino acid 501 of SEQ ID NO: 16 is I; the amino acid in the capsid protein corresponding to amino acid 505 of SEQ ID NO: 16 is R; the amino acid in the capsid protein corresponding to amino acid 590 of SEQ ID NO: 16 is R; the amino acid in the capsid protein corresponding to amino acid 626 of SEQ ID NO: 16 is G or Y; the amino acid in the capsid protein corresponding to amino acid 681 of SEQ ID NO: 16 is M; the amino acid in the capsid protein corresponding to amino acid 687 of SEQ ID NO: 16 is R; the amino acid in the capsid protein corresponding to amino acid 690 of SEQ ID NO: 16 is K; the amino acid in the capsid protein corresponding to amino acid 706 of SEQ ID NO: 16 is C; or, the amino acid in the capsid protein corresponding to amino acid 718 of SEQ ID NO: 16 is G. In certain embodiments: (a) the amino acid in the capsid protein corresponding to amino acid 2 of SEQ ID NO: 16 is T, and the amino acid in the capsid protein corresponding to amino acid 312 of SEQ ID NO: 16 is Q; (b) the amino acid in the capsid protein corresponding to amino acid 65 of SEQ ID NO: 16 is I, and the amino acid in the capsid protein corresponding to amino acid 626 of SEQ ID NO: 16 is Y; (c) the amino acid in the capsid protein corresponding to amino acid 77 of SEQ ID NO: 16 is R, and the amino acid in the capsid protein corresponding to amino acid 690 of SEQ ID NO: 16 is K; (d) the amino acid in the capsid protein corresponding to amino acid 119 of SEQ ID NO: 16 is L, and the amino acid in the capsid protein corresponding to amino acid 468 of SEQ ID NO: 16 is S; (e) the amino acid in the capsid protein corresponding to amino acid 626 of SEQ ID NO: 16 is G, and the amino acid in the capsid protein corresponding to amino acid 718 of SEQ ID NO: 16 is G; (f) the amino acid in the capsid protein corresponding to amino acid 296 of SEQ ID NO: 16 is H, the amino acid in the capsid protein corresponding to amino acid 464 of SEQ ID NO: 16 is N, the amino acid in the capsid protein corresponding to amino acid 505 of SEQ ID NO: 16 is R, and the amino acid in the capsid protein corresponding to amino acid 681 of SEQ ID NO: 16 is M; (g) the amino acid in the capsid protein corresponding to amino acid 505 of SEQ ID NO: 16 is R, and the amino acid in the capsid protein corresponding to amino acid 687 of SEQ ID NO: 16 is R; (h) the amino acid in the capsid protein corresponding to amino acid 346 of SEQ ID NO: 16 is A, and the amino acid in the capsid protein corresponding to amino acid 505 of SEQ ID NO: 16 is R; or (i) the amino acid in the capsid protein corresponding to amino acid 501 of SEQ ID NO: 16 is I, the amino acid in the capsid protein corresponding to amino acid 505 of SEQ ID NO: 16 is R, and the amino acid in the capsid protein corresponding to amino acid 706 of SEQ ID NO: 16 is C. In certain embodiments, the AAV capsid protein comprises the amino acid sequence of amino acids 1-736 of SEQ ID NO: 1, 2, 3, 4, 5, 6, 7, 8, 9, 10, 11, 12, 13, 15, 16, or 17.

In another aspect, the present disclosure provides a composition comprising an AEX medium and a mixture comprising magnesium chloride ($MgCl_2$) and an acetate.

In certain embodiments, the mixture comprises an eluate of an affinity chromatography column.

In certain embodiments, the mixture comprises about 10 mM to about 200 mM of an acetate. In certain embodiments, the mixture comprises about 10 mM to about 155 mM of an acetate. In certain embodiments, the mixture comprises about 10 mM to about 200 mM of ammonium acetate. In certain embodiments, the mixture comprises about 10 mM to about 155 mM of ammonium acetate. In certain embodiments the mixture comprises about 153 mM ammonium acetate. In certain embodiments, the mixture comprises about 10 mM to about 40 mM of an acetate. In certain embodiments, the mixture comprises about 10 mM to about 40 mM ammonium acetate. In certain embodiments, the mixture comprises about 28 mM ammonium acetate.

In certain embodiments, the mixture comprises about 2 mM to about 6 mM magnesium chloride. In certain embodiments, the mixture comprises about 2 mM magnesium chloride.

In certain embodiments, the mixture comprises about 0.001% (w/v) to about 0.05% (w/v) Poloxamer 188. In certain embodiments, the mixture comprises about 0.01% (w/v) Poloxamer 188.

In certain embodiments, the pH of the mixture is about 9 to about 10.5. In certain embodiments, the pH of the mixture is about 9.3.

In another aspect, the present disclosure provides a composition comprising an AEX medium and a first wash solution, wherein the first wash solution comprises urea and an acetate.

In certain embodiments, the AEX medium has an average pore size of at least about 100 nm. In certain embodiments, the AEX medium has an average pore size of at least about 500 nm.

In certain embodiments, the AEX medium comprises a quaternary amine. In certain embodiments, the AEX medium comprises a quaternary polyethyleneimine group.

In certain embodiments, the first wash solution comprises about 0.1 M to about 4 M urea. In certain embodiments, the first wash solution comprises about 2 M urea.

In certain embodiments, the first wash solution comprises about 10 mM to about 200 mM of an acetate. In certain embodiments, the first wash solution comprises about 10 mM to about 155 mM of an acetate. In certain embodiments, the first wash solution comprises about 10 mM to about 200 mM of ammonium acetate. In certain embodiments, the first wash solution comprises about 10 mM to about 155 mM of ammonium acetate. In certain embodiments the first wash solution comprises about 153 mM ammonium acetate. In certain embodiments, the first wash solution comprises about 10 mM to about 32 mM of the acetate. In certain embodiments, the first wash solution comprises about 10 mM to about 32 mM ammonium acetate. In certain embodiments, the first wash solution comprises about 28 mM ammonium acetate.

In certain embodiments, the first wash solution comprises about 2 mM to about 5.7 mM magnesium chloride. In certain embodiments, the first wash solution comprises about 2 mM magnesium chloride.

In certain embodiments, the first wash solution comprises about 0.001% (w/v) to about 0.05% (w/v) Poloxamer 188. In certain embodiments, the first wash solution comprises about 0.01% (w/v) Poloxamer 188.

In certain embodiments, the pH of the first wash solution is about 9 to about 10.5. In certain embodiments, the pH of the first wash solution is about 9.3.

In certain embodiments, the first wash solution has a conductivity of about 3 mS/cm.

BRIEF DESCRIPTION OF DRAWINGS

In FIGS. 1A-1D, the A260 (dashed lines) and A280 (solid lines) profiles are shown; the y-axis absorbance units are in mAU, and the x-axis represents run volume in ml. In general, an A260 value higher than A280 value indicates an enrichment of intact AAV, and an A280 value higher than A260 value indicates an enrichment of empty AAV.

In FIGS. 9A-9B, the A260 (black lines) and A280 (grey lines) profiles are shown; the y-axis absorbance units are in mAU, and the x-axis represents run volume in ml.

In FIGS. 10A-10B, the A260 (black lines) and A280 (grey lines) profiles are shown; the y-axis absorbance units are in mAU, and the x-axis represents run volume in ml. In FIG. 10C the A280 profiles are shown; the y-axis absorbance units are in mAU, and the x-axis represents run volume in ml.

In FIGS. 11A-11B, the A260 (dashed lines) and A280 (solid lines) profiles are shown; the y-axis absorbance units are in mAU, and the x-axis represents run volume in ml.

In FIGS. 12A-12B, the A260 (dashed lines) and A280 (solid lines) profiles are shown; the y-axis absorbance units are in mAU, and the x-axis represents run volume in ml.

In FIGS. 13A-13B, the A260 (black lines) and A280 (grey lines) profiles are shown; the y-axis absorbance units are in mAU, and the x-axis represents run volume in ml.

In FIGS. 14A-14C, the A260 (black lines) and A280 (grey lines) profiles are shown; the y-axis absorbance units are in mAU, and the x-axis represents run volume in ml.

DETAILED DESCRIPTION

Figure 1A:
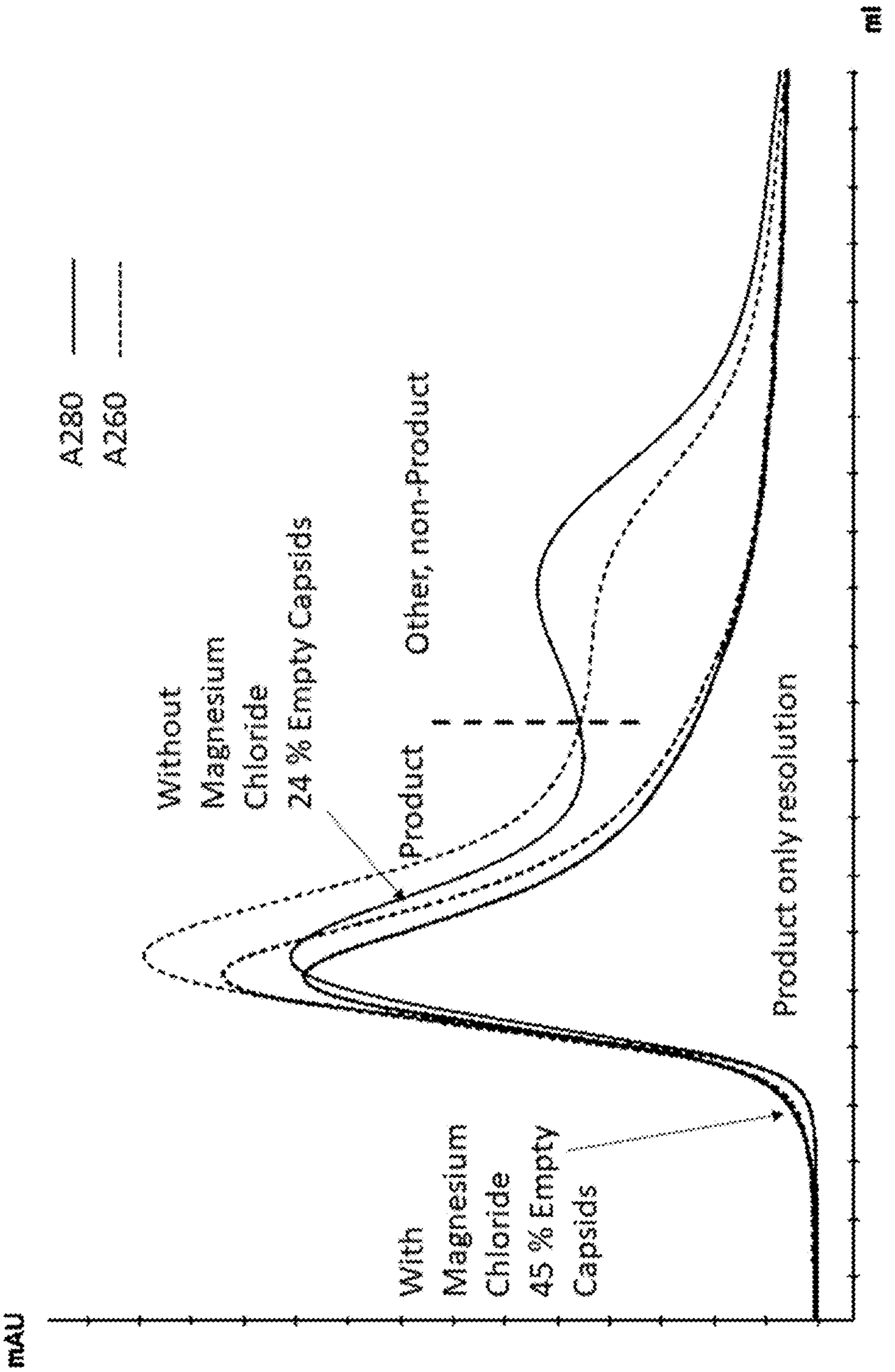
FIG. 1A is a plot showing the chromatographic overlay of the elution profiles obtained from an AEX process that included Bis-Tris Propane and sodium chloride (BTP/NaCl) in the load composition and wash steps, with or without 5.7 mM $MgCl_2$ in the load composition.

The present disclosure provides methods for the separation of an adeno-associated virus (AAV) particle from a mixture of the AAV and at least one contaminant. The methods and compositions provided by the present disclosure allow for the improved purification of intact AAV particles from contaminants such as AAV particles that lack a complete genome (e.g., empty capsids) and AAV degradation products. Consequently, the methods disclosed herein, and the compositions disclosed herein for use in such methods, result in compositions having a high purity of intact AAV particles.

I. Definitions

As used herein, the term "recombinant adeno-associated virus" or "rAAV" refers to an adeno-associated virus (AAV) comprising a genome lacking functional rep and cap genes.

As used herein, the term "cap gene" refers to a nucleic acid sequence that encodes an AAV capsid protein.

As used herein, the term "rAAV genome" refers to a nucleic acid molecule comprising the genome sequence of an rAAV. The skilled artisan will appreciate that where an rAAV genome comprises a transgene, the rAAV genome can be in the sense or antisense orientation relative to the direction of transcription of the transgene.

As used herein, the term "editing genome" refers to a recombinant AAV genome that is capable of integrating an editing element (e.g., one or more nucleotides or an internucleotide bond) via homologous recombination into a target locus to correct a genetic defect in a target gene. The skilled artisan will appreciate that the portion of an editing genome comprising the 5' homology arm, editing element, and 3' homology arm can be in the sense or antisense orientation relative to the target locus.

As used herein, the term "editing element" refers to the portion of an editing genome that when integrated at a target locus modifies the target locus. An editing element can mediate insertion, deletion, or substitution of one or more nucleotides at the target locus. As used herein, the term "target locus" refers to a region of a chromosome or an internucleotide bond (e.g., a region or an internucleotide bond of a target gene) that is modified by an editing element.

As used herein, the term "homology arm" refers to a portion of an editing genome positioned 5' or 3' of an editing element that is substantially identical to the genome flanking a target locus.

As used herein, the "percentage identity" between two nucleotide sequences or between two amino acid sequences is calculated by multiplying the number of matches between the pair of aligned sequences by 100, and dividing by the length of the aligned region, including internal gaps. Identity scoring only counts perfect matches and does not consider the degree of similarity of amino acids to one another. Note that only internal gaps are included in the length, not gaps at the sequence ends.

As used herein, the term "coding sequence" refers to the portion of a complementary DNA (cDNA) that encodes a polypeptide, starting at the start codon and ending at the stop codon. A gene may have one or more coding sequences due to alternative splicing, alternative translation initiation, and variation within the population. A coding sequence may be wild-type or a non-naturally occurring variant (e.g., a codon optimized variant).

As used herein, the term "transcriptional regulatory element" or "TRE" refers to a cis-acting nucleotide sequence, for example, a DNA sequence, that regulates (e.g., controls, increases, or reduces) transcription of an operably linked nucleotide sequence by an RNA polymerase to form an RNA molecule. A TRE relies on one or more trans-acting molecules, such as transcription factors, to regulate transcription. Thus, one TRE may regulate transcription in different ways when it is in contact with different trans-acting molecules, for example, when it is in different types of cells. A TRE may comprise one or more promoter elements and/or enhancer elements. A skilled artisan would appreciate that the promoter and enhancer elements in a gene may be close in location, and the term "promoter" may refer to a sequence comprising a promoter element and an enhancer element. Thus, the term "promoter" does not exclude an enhancer element in the sequence. The promoter and enhancer elements do not need to be derived from the same gene or species, and the sequence of each promoter or enhancer element may be either identical or substantially identical to the corresponding endogenous sequence in the genome.

As used herein, the term "operably linked" is used to describe the connection between a TRE and a coding sequence to be transcribed. Typically, gene expression is placed under the control of a TRE comprising one or more promoter and/or enhancer elements. The coding sequence is "operably linked" to the TRE if the transcription of the coding sequence is controlled or influenced by the TRE. The promoter and enhancer elements of the TRE may be in any orientation and/or distance from the coding sequence, as long as the desired transcriptional activity is obtained. In certain embodiments, the TRE is upstream from the coding sequence.

As used herein, the term "polyadenylation sequence" refers to a DNA sequence that when transcribed into RNA constitutes a polyadenylation signal sequence. The polyadenylation sequence can be native or exogenous. The exogenous polyadenylation sequence can be a mammalian or a viral polyadenylation sequence (e.g., an SV40 polyadenylation sequence).

As used herein, "exogenous polyadenylation sequence" refers to a polyadenylation sequence not identical or substantially identical to the endogenous polyadenylation sequence of a transgene. In certain embodiments, an exogenous polyadenylation sequence is a polyadenylation sequence of a gene different from the transgene, but within the same species (e.g., human). In certain embodiments, an exogenous polyadenylation sequence is a polyadenylation sequence of a different organism (e.g., a virus).

As used herein, the term "contaminant" refers to any material present at any stage of a method disclosed herein that is not the desired intact AAV particle. Contaminants include, without limitation, viral and cellular proteins or nucleic acids, or byproducts thereof, that arise in the production process of the desired intact AAV particle, or any undesired AAV particle or byproduct thereof, including, for example, an AAV particle that lacks a complete vector genome (also referred to herein as an "empty capsid"). A contaminant also includes any host cell protein, host cell nucleic acids, or host cell fragment that results from any stage of an AAV production process. The terms "host cell protein," "host cell nucleic acid," and "host cell fragment" are used herein to refer to any unwanted protein, nucleic acid, or cell fragment that originates from the cell used to produce an AAV particle.

As used herein, the term "AAV degradation product" refers to a product or intermediate thereof that arises from the degradation (e.g., physical, chemical, or enzymatic degradation) of an AAV particle.

As used herein, the term "about," when in reference to a value or parameter herein, includes a variability of ±5% of the value or parameter. For example, when referring to a pH value, "about" refers to a range that includes the value 5% below the referenced value, and the value 5% above the referenced value. Thus, a pH of about 10 refers to a pH that encompasses a pH of 9.5 to a pH of 10.5, inclusive.

II. Anion Exchange Chromatography Methods and Compositions

One challenge in the downstream processing of AAV is the efficient separation of intact AAV from contaminants, including process-related impurities such as AAV particles that lack a complete genome (e.g., empty capsids) and AAV degradation products. In one aspect, the present disclosure provides methods for the separation of an adeno-associated virus (AAV) particle from a mixture of the AAV particle and at least one contaminant, using an anion exchange chromatography (AEX) process. In general, an AEX process comprises the following steps in sequential order: preparation of the load composition comprising a mixture of the AAV and at least one contaminant, application of the load composition to the AEX medium, washing of the AEX medium, and elution of the AAV. The skilled artisan will appreciate that depending on the desired purpose and outcome, the AEX process can comprise additional intermediate steps, and the skilled artisan will be able to determine the optimal AEX process for the desired purpose and outcome.

The present disclosure relates to improved methods for the separation of intact AAV from contaminants, such as AAV particles that lack a complete genome (e.g., empty capsids). In one aspect, such methods comprise the application of a mixture comprising the AAV and contaminants to an AEX medium, wherein the mixture further comprises MgCl2 and an acetate, followed by subsequent washing of the AEX medium having AAV bound thereto. In another aspect, such methods comprise the application of a mixture comprising the AAV and contaminants to an AEX medium, followed by subsequent washing of the AEX medium having AAV bound thereto with a wash solution that comprises urea and an acetate.

In certain embodiments, methods of the present disclosure include a low conductivity wash step prior to elution, and the low conductivity wash is believed to be important for allowing for the efficient step gradient (isocratic) elution of AAV particles. Further, it has been found that the presence of MgCl2 and/or urea in an AEX process to purify AAV particles, contributes to achieving compositions having a high purity of intact AAV particles. Without being bound by any theory, it is believed that the presence of MgCl2 diminishes the binding of empty capsids to the AEX media, and that the chaotropic nature of urea disrupts the structure of empty capsids and aids in dissociating the empty capsids from the column. Together, this facilitates the desorption of empty capsids from the AEX media, leading to compositions having high purity of intact AAV particles. In particular, this facilitates the inhibition of binding of empty capsids and the desorption of empty capsids, leading to compositions having high purity of intact AAV particles. Methods of the present disclosure achieve unexpected separation efficiencies, resulting in final eluates that comprise less than about 15% AAV particles that lack a complete genome (e.g., empty capsids), and in some cases, less than about 10% AAV particles that lack a complete genome.

In one aspect, the present disclosure provides a method for the separation of an adeno-associated virus (AAV) particle from a mixture of the AAV particle and at least one contaminant, comprising: contacting the mixture with an anion exchange chromatography (AEX) medium under conditions such that the AAV particle binds to the AEX medium, wherein the mixture comprises magnesium chloride ($MgCl_2$) and an acetate; and washing the AEX medium with a first wash solution under conditions such that the AAV particle remains bound to the AEX medium and the at least one contaminant does not bind to the AEX medium, thereby separating the AAV particle from the at least one contaminant. In another aspect, the method comprises contacting the mixture of the AAV particle and at least one contaminant with an AEX medium under conditions such that a subset of empty AAV particles does not bind to the AEX medium and the full AAV particle binds to the AEX medium, wherein the mixture comprises magnesium chloride ($MgCl_2$) and an acetate; and washing the AEX medium with a first wash solution comprising urea and an acetate under conditions such that the AAV particle remains bound to the AEX medium and the at least one contaminant does not bind the AEX medium, thereby separating the AAV particle from the at least one contaminant.

In another aspect, the present disclosure provides a method for the separation of an adeno-associated virus (AAV) particle from a mixture of the AAV particle and at least one contaminant, comprising: contacting the mixture with an anion exchange chromatography (AEX) medium under conditions such that the AAV particle binds to the AEX medium; and washing the AEX medium with a first wash solution comprising urea and an acetate under conditions such that the AAV particle remains bound to the AEX medium and the at least one contaminant does not bind to the AEX medium, thereby separating the AAV particle from the at least one contaminant. In another aspect, the method comprises contacting the mixture of the AAV particle and at least one contaminant with an AEX medium under conditions such that a subset of empty AAV particles does not bind to the AEX medium and the full AAV particle binds to the AEX medium; and washing the AEX medium with a first wash solution comprising urea and an acetate under conditions such that the AAV particle remains bound to the AEX medium and the at least one contaminant does not bind the AEX medium, thereby separating the AAV particle from the at least one contaminant. In certain embodiments, the method further comprises washing the AEX medium with a second wash solution.

In certain embodiments, the methods further comprise washing the AEX medium with a second wash solution.

In another aspect, the present disclosure provides a method for the separation of an adeno-associated virus (AAV) particle from a mixture of the AAV particle and at least one contaminant, comprising: providing an AEX medium that has been contacted with the mixture, wherein the mixture comprises magnesium chloride (MgCl2) and an acetate, and wherein the AEX medium comprises the AAV particle bound thereto and has been washed with a first wash solution such that the AAV particle remained bound to the AEX medium and the at least one contaminant did not bind to the AEX medium; and washing the AEX medium with a second wash solution under conditions such that the AAV particle remains bound to the AEX medium and the at least one contaminant does not bind to the AEX medium, thereby separating the AAV particle from the at least one contaminant.

In another aspect, the present disclosure provides a method for the separation of an adeno-associated virus (AAV) particle from a mixture of the AAV particle and at least one contaminant, comprising: providing an AEX medium that has been contacted with the mixture, wherein the AEX medium comprises the AAV particle bound thereto and has been washed with a first wash solution comprising urea and an acetate such that the AAV particle remained bound to the AEX medium and the at least one contaminant did not bind to the AEX medium; and washing the AEX medium with a second wash solution under conditions such that the AAV particle remains bound to the AEX medium and the at least one contaminant does not bind to the AEX medium, thereby separating the AAV particle from the at least one contaminant.

In certain embodiments, the methods of the present disclosure further comprise eluting the desired AAV from the AEX medium. In certain embodiments, the methods of the present disclosure further comprise eluting the desired AAV from the AEX medium, wherein the elution step is performed sequentially after the AEX medium has been washed with a low conductivity wash solution (e.g., a second wash solution described herein). In certain embodiments, the AEX medium is washed with a low conductivity wash solution (e.g., a second wash solution described herein) prior to eluting the AAV particle from the AEX medium. In certain embodiments, the methods of the present disclosure further comprise formulating the eluted AAV particle in a formulation buffer. In certain embodiments, the formulation buffer is suitable for administration to a human subject.

In another aspect, the present disclosure provides a composition comprising an AEX medium and a mixture comprising magnesium chloride and an acetate.

In another aspect, the present disclosure provides a composition comprising an AEX medium and a first wash solution, wherein the first wash solution comprises urea and an acetate.

Anion Exchange Chromatography Medium

The methods generally comprise contacting the mixture with an anion exchange chromatography (AEX) medium under conditions such that the AAV particle binds to the AEX medium, and washing the AEX medium comprising the AAV particle bound thereto with a first wash solution. In another aspect, the methods comprise contacting the mixture with an AEX medium under conditions such that a subset of empty AAV particles does not bind to the AEX medium and the full AAV particle binds to the AEX medium, and washing the AEX medium comprising the AAV particle bound thereto with a first wash solution. The methods disclosed herein separate the AAV particle from the at least one contaminant.

The contaminant can be any material present at any stage of a method disclosed herein that is not the desired AAV particle. Contaminants include, without limitation, viral and cellular proteins or nucleic acids, or byproducts thereof, that arise in the production process of the AAV particle. Contaminants also include any undesired AAV particles or byproducts thereof. Undesired AAV particles include, without limitation, AAV particles that lack a complete vector genome, for example, AAV particles that lack a complete vector genome (e.g., empty capsids). In certain embodiments, a method of the present disclosure is useful in separating desired AAV particles from undesired material such as, without limitation, viral and cellular proteins or nucleic acids, or byproducts thereof, e.g., host cell proteins and host cell fragments, AAV degradation products, AAV particles that lack a complete vector genome, and any combination thereof.

In particular, a method of the present disclosure provides improved separation of desired AAV particles from AAV particles that lack a complete genome (e.g. empty capsids), resulting in an eluate that comprises a higher percentage of desired AAV particles. In certain embodiments, the eluate comprising the desired AAV particles, comprises less than about 40%, e.g., less than about 35%, less than about 30%, less than about 25%, less than about 20%, less than about 15%, less than about 10%, less than about 5% AAV particles that lack a complete genome. In certain embodiments, a method of the present disclosure results in an eluate comprising the desired AAV particles, wherein the eluate comprises less than about 15% AAV particles that lack a complete genome (e.g., empty capsids). In certain embodiments, a method of the present disclosure results in an eluate comprising the desired AAV particles, wherein the eluate comprises less than about 10% AAV particles that lack a complete genome.

Methods of the present disclosure employ an AEX medium. In certain embodiments, the AEX medium includes an insoluble matrix or solid support (e.g., beads) capable of having a surface ionization. In certain embodiments, the AEX medium comprises acrylamides, agarose-based materials, cellulose, methacrylates, polystyrene divinyl benzene, or silica-based materials.

In certain embodiments, the AEX medium comprises a weak anion exchange resin comprising a solid support having a surface coated with a weak anion exchanger. In certain embodiments, the AEX medium comprises a strong anion exchange resin comprising a solid support having a surface coated with a weak anion exchanger. Examples of AEX media suitable for use in the methods described herein include, without limitation, those that comprise a quaternary amine, a quaternary polyethyleneimine, a quaternary ammonium, or a diethylaminoethanol (DEAE) ligand. In certain embodiments, a method of the present disclosure employs the use of an AEX medium comprising a quaternary amine. In certain embodiments, a method of the present disclosure employs the use of an AEX medium comprising a quaternary polyethyleneimine. In certain embodiments, the anion exchange chromatography medium is from the CIMMULTUS™ series of anion exchange media, e.g., CIMMULTUS™ QA (BIAseparations), or the POROS™ series of anion exchange media, e.g., POROS™ HQ, POROS™ XQ, POROS™ PI (ThermoFisher Scientific). Other examples of anion exchange chromatography media include, without limitation, Nuvia HP-Q, SOURCE™ 15Q (Cytiva), Q-Sepharose™ (Cytiva), NATRIX® Q, HITRAP® Q (Cytiva), and Capto™ Q (Cytiva).

Suitable AEX media for use in the methods of the present disclosure have an average pore size of at least about 100 nm. In certain embodiments, the AEX medium has an average pore size of about 100 nm or greater, e.g., at least about 150 nm, at least about 200 nm, at least about 250 nm, at least about 300 nm, at least about 350 nm, at least about 400 nm, at least about 450 nm, at least about 500 nm. In certain embodiments, the AEX medium has an average pore size of about 500 nm or greater.

In certain embodiments, the present disclosure provides a composition comprising an AEX medium and a mixture comprising magnesium chloride and an acetate. Various components of the mixture are further described herein. In certain embodiments, the present disclosure provides a composition comprising an AEX medium and a first wash solution, wherein the first wash solution comprises urea and an acetate. Various components of the first wash solution are further described herein.

Mixtures

Methods of the present disclosure comprise contacting a mixture of the AAV particle and at least one contaminant with an AEX medium under conditions such that the AAV particle binds to the AEX medium. In another aspect, the methods comprise contacting the mixture of the AAV particle and at least one contaminant with an AEX medium under conditions such that a subset of empty AAV particles does not bind to the AEX medium and the full AAV particle binds to the AEX medium.

In certain embodiments, the mixture comprises a partially purified AAV composition. For example, the mixture can comprise a partially purified AAV composition that has undergone an affinity chromatography step. In certain embodiments, the mixture comprises an eluate from an affinity chromatography step. Such an affinity chromatography step generally comprises separating AAV from a mixture that contains other non-AAV contaminants such as viral and cellular proteins or nucleic acids, or byproducts thereof. Briefly, affinity chromatography can utilize a solid support having an AAV-specific binding protein bound thereto that can capture AAV particles from the mixture. Affinity chromatography comprises the use of affinity chromatography media which may be in the form of a resin packed into a column. In certain embodiments, the mixture comprises an eluate of an affinity chromatography column. In certain embodiments, the mixture comprises a diluted eluate of an affinity chromatography column.

In certain embodiments, the mixture comprises one or more salts. The salt can encompass a monovalent cation or a bivalent cation. In certain embodiments, the mixture comprises a salt that encompasses a monovalent cation. It is understood by those of skill in the art, that salts that encompass a monovalent cation dissociate into the monovalent cation and a monovalent anion. For example, ammonium acetate dissociates into an ammonium cation and an acetate ion. Examples of salts that encompass a monovalent cation include, without limitation, ammonium acetate, potassium acetate, sodium acetate, cesium chloride, lithium chloride, potassium chloride, sodium chloride, and the like. In certain embodiments, the mixture comprises about 10 mM to about 200 mM of a salt that encompasses a monovalent cation. For example, the mixture comprises about 10 mM, about 15 mM, about 20 mM, about 25 mM, about 30 mM, about 35 mM, about 40 mM, about 45 mM, about 50 mM, about 55 mM, about 60 mM, about 65 mM, about 70 mM, about 75 mM, about 80 mM, about 85 mM, about 90 mM, about 95 mM, about 100 mM, about 105 mM, about 110 mM, about 115 mM, about 120 mM, about 125 mM, about 130 mM, about 135 mM, about 140 mM, about 145 mM, about 150 mM, about 155 mM, about 160 mM, about 165 mM, about 170 mM, about 175 mM, about 180 mM, about 185 mM, about 190 mM, about 195 mM, or about 200 mM of a salt that encompasses a monovalent cation. In certain embodiments, the mixture comprises about 10 mM to about 155 mM of a salt that encompasses a monovalent cation. In certain embodiments, the mixture comprises about 1 mM to about 50 mM of a salt that encompasses a monovalent cation. For example, the mixture comprises about 1 mM, about 5 mM, about 10 mM, about 15 mM, about 20 mM, about 25 mM, about 30 mM, about 35 mM, about 40 mM, about 45 mM, or about 50 mM of a salt that encompasses a monovalent cation. In certain embodiments, the mixture comprises about 10 mM to about 32 mM of a salt that encompasses a monovalent cation.

In certain embodiments, the mixture comprises an acetate. In certain embodiments, the mixture comprises about 10 mM to about 200 mM of an acetate or a salt equivalent thereof. For example, the mixture comprises about 10 mM, about 15 mM, about 20 mM, about 25 mM, about 30 mM, about 35 mM, about 40 mM, about 45 mM, about 50 mM, about 55 mM, about 60 mM, about 65 mM, about 70 mM, about 75 mM, about 80 mM, about 85 mM, about 90 mM, about 95 mM, about 100 mM, about 105 mM, about 110 mM, about 115 mM, about 120 mM, about 125 mM, about 130 mM, about 135 mM, about 140 mM, about 145 mM, about 150 mM, about 155 mM, about 160 mM, about 165 mM, about 170 mM, about 175 mM, about 180 mM, about 185 mM, about 190 mM, about 195 mM, or about 200 mM of an acetate or a salt equivalent thereof. In certain embodiments, the mixture comprises about 10 mM to about 155 mM of an acetate or a salt equivalent thereof. In certain embodiments, the mixture comprises about 153 mM of an acetate or a salt equivalent thereof. In certain embodiments, the mixture comprises about 1 mM to about 50 mM of an acetate or a salt equivalent thereof. In certain embodiments, the mixture comprises about 1 mM, about 5 mM, about 10 mM, about 15 mM, about 20 mM, about 25 mM, about 30 mM, about 35 mM, about 40 mM, about 45 mM, or about 50 mM of an acetate or a salt equivalent thereof. In certain embodiments, the mixture comprises about 10 mM to about 32 mM of an acetate or a salt equivalent thereof. In certain embodiments, the mixture comprises about 28 mM of an acetate or a salt equivalent thereof. In certain embodiments, the mixture comprises about 29 mM of an acetate or a salt equivalent thereof.

Examples of suitable acetates are known to those of skill in the art, and include, without limitation, ammonium acetate, sodium acetate, and potassium acetate. In certain embodiments, the mixture comprises ammonium acetate. In certain embodiments, the mixture comprises about 10 mM to about 200 mM ammonium acetate. For example, the mixture comprises about 10 mM, about 15 mM, about 20 mM, about 25 mM, about 30 mM, about 35 mM, about 40 mM, about 45 mM, about 50 mM, about 55 mM, about 60 mM, about 65 mM, about 70 mM, about 75 mM, about 80 mM, about 85 mM, about 90 mM, about 95 mM, about 100 mM, about 105 mM, about 110 mM, about 115 mM, about 120 mM, about 125 mM, about 130 mM, about 135 mM, about 140 mM, about 145 mM, about 150 mM, about 155 mM, about 160 mM, about 165 mM, about 170 mM, about 175 mM, about 180 mM, about 185 mM, about 190 mM, about 195 mM, or about 200 mM ammonium acetate. In certain embodiments, the mixture comprises about 10 mM to about 155 mM ammonium acetate. In certain embodiments, the mixture comprises about 153 ammonium acetate. In certain embodiments, the mixture comprises about 1 mM to about 50 mM ammonium acetate. In certain embodiments, the mixture comprises about 1 mM, about 5 mM, about 10 mM, about 15 mM, about 20 mM, about 25 mM, about 30 mM, about 35 mM, about 40 mM, about 45 mM, or about 50 mM ammonium acetate. In certain embodiments, the mixture comprises about 10 mM to about 32 mM ammonium acetate. In certain embodiments, the mixture comprises about 28 mM ammonium acetate. In certain embodiments, the mixture comprises about 29 mM ammonium acetate.

In certain embodiments, the mixture comprises a salt that encompasses a divalent cation. Examples of salts that encompass a divalent cation include, without limitation, magnesium chloride, manganese chloride, copper chloride, zinc chloride, and the like. In certain embodiments, the mixture comprises magnesium chloride. In certain embodiments, the mixture comprises about 1 mM to about 10 mM magnesium chloride. In certain embodiments, the mixture comprises about 1 mM, about 2 mM, about 3 mM, about 4 mM, about 5 mM, about 6 mM, about 7 mM, about 8 mM, about 9 mM, or about 10 mM magnesium chloride. In certain embodiments, the mixture comprises about 2 mM to about 6 mM magnesium chloride. In certain embodiments, the mixture comprises about 2 mM magnesium chloride. In certain embodiments, the mixture comprises about 5.7 mM magnesium chloride.

In certain embodiments, the mixture comprises a salt that encompasses a monovalent cation and magnesium chloride. In certain embodiments, the mixture comprises about 10 mM to about 200 mM salt that encompasses a monovalent cation, and about 1 mM to about 10 mM magnesium chloride. In certain embodiments, the mixture comprises about 10 mM to about 200 mM salt that encompasses a monovalent cation, and about 2 mM to 6 mM magnesium chloride. In certain embodiments, the mixture comprises about 10 mM to about 200 mM salt that encompasses a monovalent cation, and about 2 mM magnesium chloride. In certain embodiments, the mixture comprises about 1 mM to about 50 mM salt that encompasses a monovalent cation, and about 1 mM to about 10 mM magnesium chloride. In certain embodiments, the mixture comprises about 1 mM to about 50 mM salt that encompasses a monovalent cation, and about 2 mM to 6 mM magnesium chloride. In certain embodiments, the mixture comprises about 1 mM to about 50 mM salt that encompasses a monovalent cation, and about 2 mM magnesium chloride. In certain embodiments, the mixture comprises about 1 mM to about 50 mM salt that encompasses a monovalent cation, and about 5.7 mM magnesium chloride.

In certain embodiments, the mixture comprises an acetate or a salt equivalent thereof (e.g., ammonium acetate) and magnesium chloride. In certain embodiments, the mixture comprises about 10 mM to about 200 mM of an acetate or a salt equivalent thereof (e.g., ammonium acetate), and about 1 mM to about 10 mM magnesium chloride. In certain embodiments, the mixture comprises about 10 mM to about 200 mM of an acetate or a salt equivalent thereof (e.g., ammonium acetate), and about 2 mM to 6 mM magnesium chloride. In certain embodiments, the mixture comprises about 10 mM to about 200 mM of an acetate or a salt equivalent thereof (e.g., ammonium acetate), and about 2 mM magnesium chloride. In certain embodiments, the mixture comprises about 10 mM to about 155 mM of an acetate or a salt equivalent thereof (e.g., ammonium acetate), and about 2 mM magnesium chloride. In certain embodiments, the mixture comprises about 153 mM ammonium acetate and about 2 mM magnesium chloride. In certain embodiments, the mixture comprises about 1 mM to about 50 mM of an acetate or a salt equivalent thereof (e.g., ammonium acetate), and about 1 mM to about 10 mM magnesium chloride. In certain embodiments, the mixture comprises about 1 mM to about 50 mM of an acetate or a salt equivalent thereof (e.g., ammonium acetate), and about 2 mM to 6 mM magnesium chloride. In certain embodiments, the mixture comprises about 1 mM to about 50 mM of an acetate or a salt equivalent thereof (e.g., ammonium acetate), and about 2 mM magnesium chloride. In certain embodiments, the mixture comprises about 1 mM to about 50 mM of an acetate or a salt equivalent thereof (e.g., ammonium acetate), and about 5.7 mM magnesium chloride. In certain embodiments, the mixture comprises about 10 mM to about 32 mM of an acetate or a salt equivalent thereof (e.g., ammonium acetate), and about 1 mM to about 10 mM magnesium chloride. In certain embodiments, the mixture comprises about 10 mM to about 32 mM of an acetate or a salt equivalent thereof (e.g., ammonium acetate), and about 2 mM to 6 mM magnesium chloride. In certain embodiments, the mixture comprises about 10 mM to about 32 mM of an acetate or a salt equivalent thereof (e.g., ammonium acetate), and about 2 mM magnesium chloride. In certain embodiments, the mixture comprises about 10 mM to about 32 mM of an acetate or a salt equivalent thereof (e.g., ammonium acetate), and about 5.7 mM magnesium chloride. In certain embodiments, the mixture comprises about 28 mM of an acetate or a salt equivalent thereof (e.g., ammonium acetate) and about 2 mM magnesium chloride. In certain embodiments, the mixture comprises about 29 mM of an acetate or a salt equivalent thereof (e.g., ammonium acetate) and about 2 mM magnesium chloride. In certain embodiments, the mixture comprises about 28 mM of an acetate or a salt equivalent thereof (e.g., ammonium acetate) and about 5.7 mM magnesium chloride. In certain embodiments, the mixture comprises about 29 mM of an acetate or a salt equivalent thereof (e.g., ammonium acetate) and about 5.7 mM magnesium chloride. In certain embodiments, the mixture comprises about 28 mM ammonium acetate and about 2 mM magnesium chloride. In certain embodiments, the mixture comprises about 29 mM ammonium acetate and about 2 mM magnesium chloride. In certain embodiments, the mixture comprises about 28 mM ammonium acetate and about 5.7 mM magnesium chloride. In certain embodiments, the mixture comprises about 29 mM ammonium acetate and about 5.7 mM magnesium chloride.

In certain embodiments, the mixture comprises a surfactant. In certain embodiments, the surfactant is a non-ionic surfactant. Examples of non-ionic surfactants include, without limitation, Brij™-35, Brij™-58, NP-40, octyl-beta-glucoside, octylthioglucoside (OTG), poloxamer 188 (P-188), poloxamer 407, polysorbate 20, polysorbate 80, Triton X-100, or Triton X-114. In certain embodiments, the mixture comprises about 0.001% (w/v) to about 0.05% (w/v) of a non-ionic surfactant. In certain embodiments, the mixture comprises about 0.001% (w/v), about 0.005% (w/v), about 0.01% (w/v), about 0.015% (w/v), about 0.02% (w/v), about 0.03% (w/v), about 0.035% (w/v), about 0.04% (w/v), about 0.045% (w/v), or about 0.05% (w/v) of a non-ionic surfactant. In certain embodiments, the mixture comprises about 0.01% (w/v) of a non-ionic surfactant. In certain embodiments, the mixture comprises poloxamer 188. In certain embodiments, the mixture comprises about 0.001% (w/v) to about 0.05% (w/v) poloxamer 188. In certain embodiments, the mixture comprises about 0.001% (w/v), about 0.005% (w/v), about 0.01% (w/v), about 0.015% (w/v), about 0.02% (w/v), about 0.03% (w/v), about 0.035% (w/v), about 0.04%

(w/v), about 0.045% (w/v), or about 0.05% (w/v) poloxamer 188. In certain embodiments, the mixture comprises about 0.01% (w/v) poloxamer 188.

In certain embodiments, the pH of the mixture is about 9 to about 10.5. In certain embodiments, the pH of the mixture is about 9, about 9.1, about 9.2, about 9.3, about 9.4, about 9.5, about 9.6, about 9.7, about 9.8, about 9.9, about 10, about 10.1, about 10.2, about 10.3, about 10.4, or about 10.5. In certain embodiments, the pH of the mixture is about 9.3.

In certain embodiments, the mixture has a pH of about 9.2, a conductivity of about 3 mS/cm, and comprises about 28 mM ammonium acetate, about 2 mM magnesium chloride, and about 0.01% (w/v) poloxamer 188. In certain embodiments, the mixture has a pH of about 9.3, a conductivity of about 3 mS/cm, and comprises about 28 mM ammonium acetate, about 2 mM magnesium chloride, and about 0.01% (w/v) poloxamer 188. In certain embodiments, the mixture has a pH of about 9.3, a conductivity of about 3 mS/cm, and comprises about 29 mM ammonium acetate, about 2 mM magnesium chloride, and about 0.01% (w/v) poloxamer 188.

Wash Solutions and Methods

After contacting a mixture with the AEX medium, the AEX medium is washed with one or more wash solutions to remove contaminants. In certain embodiments, the AEX medium is washed with a first wash solution (e.g., in a first wash step). In certain embodiments, the AEX medium is washed with a first wash solution and/or a second wash solution (e.g., in a second wash step). In certain embodiments, the AEX medium is washed with a first wash solution and a second wash solution.

In certain embodiments, a method of the present disclosure comprises, after application of the mixture to an AEX medium, washing the AEX medium with a first wash solution. The first wash solution comprises urea. It has been found that a first wash using a first wash solution comprising urea provides enhanced separation of the desired AAV from unwanted contaminants (e.g., empty capsids). Without being bound by theory, it is believed that the chaotropic nature of urea disrupts the structure of the contaminants including empty capsids, dissociating them from the AEX medium, resulting in their removal prior to elution. In certain embodiments, the first wash solution comprises about 0.1 M to about 4 M urea. In certain embodiments, the first wash solution comprises about 0.1 M, about 0.2 M, about 0.3 M, about 0.4 M, about 0.5 M, about 0.6 M, about 0.7 M, about 0.8 M, about 0.9 M, about 1.0 M, about 1.1 M, about 1.2 M, about 1.3 M, about 1.4 M, about 1.5 M, about 1.6 M, about 1.7 M, about 1.8 M, about 1.9 M, about 2.0 M, about 2.1 M, about 2.2 M, about 2.3 M, about 2.4 M, about 2.5 M, about 2.6 M, about 2.7 M, about 2.8 M, about 2.9 M, about 3.0 M, about 3.1 M, about 3.2 M, about 3.3 M, about 3.4 M, about 3.5 M, about 3.6 M, about 3.7 M, about 3.8 M, about 3.9 M, about 4.0 M urea. In certain embodiments, the first wash solution comprises about 2 M urea.

In certain embodiments, the first wash solution comprises urea and an acetate. In certain embodiments, the first wash solution comprises about 10 mM to about 200 mM of an acetate or a salt equivalent thereof. For example, the first wash solution comprises about 10 mM, about 15 mM, about 20 mM, about 25 mM, about 30 mM, about 35 mM, about 40 mM, about 45 mM, about 50 mM, about 55 mM, about 60 mM, about 65 mM, about 70 mM, about 75 mM, about 80 mM, about 85 mM, about 90 mM, about 95 mM, about 100 mM, about 105 mM, about 110 mM, about 115 mM, about 120 mM, about 125 mM, about 130 mM, about 135 mM, about 140 mM, about 145 mM, about 150 mM, about 155 mM, about 160 mM, about 165 mM, about 170 mM, about 175 mM, about 180 mM, about 185 mM, about 190 mM, about 195 mM, or about 200 mM of an acetate or a salt equivalent thereof. In certain embodiments, the first wash solution comprises about 10 mM to about 155 mM of an acetate or a salt equivalent thereof. In certain embodiments, the first wash solution comprises about 153 mM of an acetate or a salt equivalent thereof. In certain embodiments, the first wash solution comprises about 1 mM to about 50 mM of an acetate or a salt equivalent thereof. In certain embodiments, the first wash solution comprises about 1 mM, about 5 mM, about 10 mM, about 15 mM, about 20 mM, about 25 mM, about 30 mM, about 35 mM, about 40 mM, about 45 mM, or about 50 mM of an acetate or a salt equivalent thereof. In certain embodiments, the first wash solution comprises about 10 mM to about 40 mM of an acetate or a salt equivalent thereof. In certain embodiments, the first wash solution comprises about 10 mM to about 32 mM of an acetate or a salt equivalent thereof. In certain embodiments, the first wash solution comprises about 28 mM of an acetate or a salt equivalent thereof. In certain embodiments, the first wash solution comprises about 29 mM of an acetate or a salt equivalent thereof.

Examples of suitable acetates are known to those of skill in the art, and include, without limitation, ammonium acetate, sodium acetate, and potassium acetate. In certain embodiments, the first wash solution comprises ammonium acetate. In certain embodiments, the first wash solution comprises about 1 mM to about 50 mM ammonium acetate. In certain embodiments, the first wash solution comprises about 1 mM, about 5 mM, about 10 mM, about 15 mM, about 20 mM, about 25 mM, about 30 mM, about 35 mM, about 40 mM, about 45 mM, or about 50 mM ammonium acetate. In certain embodiments, the first wash solution comprises about 10 mM to about 40 mM ammonium acetate. In certain embodiments, the first wash solution comprises about 10 mM to about 32 mM ammonium acetate. In certain embodiments, the first wash solution comprises about 28 mM ammonium acetate. In certain embodiments, the first wash solution comprises about 29 mM ammonium acetate.

In certain embodiments, the first wash solution comprises a salt that encompasses a divalent cation. Examples of salts that encompass a divalent cation include, without limitation, magnesium chloride, manganese chloride, copper chloride, zinc chloride, and the like. In certain embodiments, the first wash solution comprises magnesium chloride. In certain embodiments, the first wash solution comprises about 10 mM to about 200 mM of ammonium acetate. For example, the first wash solution comprises about 10 mM, about 15 mM, about 20 mM, about 25 mM, about 30 mM, about 35 mM, about 40 mM, about 45 mM, about 50 mM, about 55 mM, about 60 mM, about 65 mM, about 70 mM, about 75 mM, about 80 mM, about 85 mM, about 90 mM, about 95 mM, about 100 mM, about 105 mM, about 110 mM, about 115 mM, about 120 mM, about 125 mM, about 130 mM, about 135 mM, about 140 mM, about 145 mM, about 150 mM, about 155 mM, about 160 mM, about 165 mM, about 170 mM, about 175 mM, about 180 mM, about 185 mM, about 190 mM, about 195 mM, or about 200 mM ammonium acetate. In certain embodiments, the first wash solution comprises about 10 mM to about 155 mM ammonium acetate. In certain embodiments, the first wash solution comprises about 153 mM ammonium acetate. In certain embodiments, the first wash solution comprises about 1 mM to about 10 mM magnesium chloride. In certain embodiments, the first wash solution comprises about 1 mM, about 2 mM, about 3 mM, about 4 mM, about 5 mM, about 6 mM, about 7 mM, about 8 mM, about 9 mM, or about 10 mM magnesium chloride. In certain embodiments, the first wash solution comprises about 2 mM to about 6 mM magnesium chloride. In certain embodiments, the first wash solution comprises about 2 mM magnesium chloride. In certain embodiments, the first wash solution comprises about 5.7 mM magnesium chloride.

In certain embodiments, the first wash solution comprises a surfactant. In certain embodiments, the surfactant is a non-ionic surfactant. Examples of non-ionic surfactants include, without limitation, Brij™-35, Brij™-58, NP-40, octyl-beta-glucoside, octylthioglucoside (OTG), poloxamer 188 (P-188), poloxamer 407, polysorbate 20, polysorbate 80, Triton X-100, or Triton X-114. In certain embodiments, the first wash solution comprises about 0.001% (w/v) to about 0.05% (w/v) of a non-ionic surfactant. In certain embodiments, the first wash solution comprises about 0.001% (w/v), about 0.005% (w/v), about 0.01% (w/v), about 0.015% (w/v), about 0.02% (w/v), about 0.03% (w/v), about 0.035% (w/v), about 0.04% (w/v), about 0.045% (w/v), or about 0.05% (w/v) of a non-ionic surfactant. In certain embodiments, the first wash solution comprises about 0.01% (w/v) of a non-ionic surfactant. In certain embodiments, the first wash solution comprises poloxamer 188. In certain embodiments, the first wash solution comprises about 0.001% (w/v) to about 0.05% (w/v) poloxamer 188. In certain embodiments, the first wash solution comprises about 0.001% (w/v), about 0.005% (w/v), about 0.01% (w/v), about 0.015% (w/v), about 0.02% (w/v), about 0.03% (w/v), about 0.035% (w/v), about 0.04% (w/v), about 0.045% (w/v), or about 0.05% (w/v) poloxamer 188. In certain embodiments, the first wash solution comprises about 0.01% (w/v) poloxamer 188.

In certain embodiments, the pH of the first wash solution is about 9 to about 10.5. In certain embodiments, the pH of the first wash solution is about 9, about 9.1, about 9.2, about 9.3, about 9.4, about 9.5, about 9.6, about 9.7, about 9.8, about 9.9, about 10, about 10.1, about 10.2, about 10.3, about 10.4, or about 10.5. In certain embodiments, the pH of the first wash solution is about 9.3.

In certain embodiments, the first wash solution has a conductivity of about 1 mS/cm to about 20 mS/cm. In certain embodiments, the first wash solution has a conductivity of about 1 mS/cm, about 2 mS/cm, about 3 mS/cm, about 4 mS/cm, about 5 mS/cm, about 6 mS/cm, about 7 mS/cm, about 8 mS/cm, about 9 mS/cm, about 10 mS/cm, about 11 mS/cm, about 12 mS/cm, about 13 mS/cm, about 14 mS/cm, about 15 mS/cm, about 16 mS/cm, about 17 mS/cm, about 18 mS/cm, about 19 mS/cm, or about 20 mS/cm. In certain embodiments, the first wash solution has a conductivity of about 13 mS/cm. In certain embodiments, the first wash solution has a conductivity of about 1 mS/cm to about 3 mS/cm. In certain embodiments, the first wash solution has a conductivity of about 1 mS/cm, about 1.1 mS/cm, about 1.2 mS/cm, about 1.3 mS/cm, about 1.4 mS/cm, about 1.5 mS/cm, about 1.6 mS/cm, about 1.7 mS/cm, about 1.8 mS/cm, about 1.9 mS/cm, about 2 mS/cm, about 2.1 mS/cm, about 2.2 mS/cm, about 2.3 mS/cm, about 2.4 mS/cm, about 2.5 mS/cm, about 2.6 mS/cm, about 2.7 mS/cm, about 2.8 mS/cm, about 2.9 mS/cm, or about 3 mS/cm. In certain embodiments, the first wash solution has a conductivity of about 3 mS/cm.

In certain embodiments, the first wash solution has a pH of about 9.2, a conductivity of about 3 mS/cm, and comprises about 28 mM ammonium acetate, about 2 mM magnesium chloride, and 0.01% (w/v) poloxamer 188. In certain embodiments, the first wash solution has a pH of about 9.3, a conductivity of about 3 mS/cm, and comprises about 28 mM ammonium acetate, about 2 mM magnesium chloride, and 0.01% (w/v) poloxamer 188. In certain embodiments, the first wash solution has a pH of about 9.3, a conductivity of about 3 mS/cm, and comprises about 29 mM ammonium acetate, about 2 mM magnesium chloride, and 0.01% (w/v) poloxamer 188. In certain embodiments, the first wash solution has a pH of about 9.3, a conductivity of about 13 mS/cm, and comprises about 153 mM ammonium acetate, about 2 mM magnesium chloride, and 0.01% (w/v) poloxamer 188.

In certain embodiments, the first wash solution has a pH of about 9.2, a conductivity of about 3 mS/cm, and comprises about 28 mM ammonium acetate, up to about 2 M urea, about 2 mM magnesium chloride, and 0.01% (w/v) poloxamer 188. In certain embodiments, the first wash solution has a pH of about 9.3, a conductivity of about 3 mS/cm, and comprises about 28 mM ammonium acetate, up to about 2 M urea, about 2 mM magnesium chloride, and 0.01% (w/v) poloxamer 188. In certain embodiments, the first wash solution has a pH of about 9.3, a conductivity of about 3 mS/cm, and comprises about 29 mM ammonium acetate, up to about 2 M urea, about 2 mM magnesium chloride, and 0.01% (w/v) poloxamer 188.

In certain embodiments, the first wash solution has a pH of about 9.2, a conductivity of about 3 mS/cm, and comprises about 28 mM ammonium acetate, about 2 M urea, about 2 mM magnesium chloride, and 0.01% (w/v) poloxamer 188. In certain embodiments, the first wash solution has a pH of about 9.3, a conductivity of about 3 mS/cm, and comprises about 28 mM ammonium acetate, about 2 M urea, about 2 mM magnesium chloride, and 0.01% (w/v) poloxamer 188. In certain embodiments, the first wash solution has a pH of about 9.3, a conductivity of about 3 mS/cm, and comprises about 29 mM ammonium acetate, about 2 M urea, about 2 mM magnesium chloride, and 0.01% (w/v) poloxamer 188. In certain embodiments, the first wash solution has a pH of about 9.3, a conductivity of about 13 mS/cm, and comprises about 153 mM ammonium acetate, about 2 M urea, about 2 mM magnesium chloride, and 0.01% (w/v) poloxamer 188.

In certain embodiments, a method of the present disclosure comprises, after washing the AEX medium after application of the mixture with a first wash solution, washing the AEX medium with a second wash solution. In certain embodiments, the second wash solution comprises an acetate. In certain embodiments, the second wash solution comprises about 0.1 mM to about 20 mM of an acetate or a salt equivalent thereof. In certain embodiments, the second wash solution comprises about 0.1 mM, about 1 mM, about 2 mM, about 3 mM, about 4 mM, about 5 mM, about 6 mM, about 7 mM, about 8 mM, about 9 mM, about 10 mM, about 11 mM, about 12 mM, about 13 mM, about 14 mM, about 15 mM, about 16 mM, about 17 mM, about 18 mM, about 19 mM, or about 20 mM of an acetate or a salt equivalent thereof. In certain embodiments, the second wash solution comprises about 10 mM of an acetate or a salt equivalent thereof.

Examples of suitable acetates are known to those of skill in the art, and include, without limitation, ammonium acetate, sodium acetate, and potassium acetate. In certain embodiments, the second wash solution comprises ammonium acetate. In certain embodiments, the second wash solution comprises about 0.1 mM to about 20 mM ammonium acetate. In certain embodiments, the second wash solution comprises about 0.1 mM, about 1 mM, about 2 mM, about 3 mM, about 4 mM, about 5 mM, about 6 mM, about 7 mM, about 8 mM, about 9 mM, about 10 mM, about 11 mM, about 12 mM, about 13 mM, about 14 mM, about 15 mM, about 16 mM, about 17 mM, about 18 mM, about 19 mM, or about 20 mM ammonium acetate. In certain embodiments, the second wash solution comprises about 10 mM ammonium acetate.

In certain embodiments, the second wash solution comprises a surfactant. In certain embodiments, the surfactant is a non-ionic surfactant. Examples of non-ionic surfactants include, without limitation, Brij™-35, Brij™-58, NP-40, octyl-beta-glucoside, octylthioglucoside (OTG), poloxamer 188 (P-188), poloxamer 407, polysorbate 20, polysorbate 80, Triton X-100, or Triton X-114. In certain embodiments, the second wash solution comprises about 0.001% (w/v) to about 0.05% (w/v) of a non-ionic surfactant. In certain embodiments, the second wash solution comprises about 0.001% (w/v), about 0.005% (w/v), about 0.01% (w/v), about 0.015% (w/v), about 0.02% (w/v), about 0.03% (w/v), about 0.035% (w/v), about 0.04% (w/v), about 0.045% (w/v), or about 0.05% (w/v) of a non-ionic surfactant. In certain embodiments, the second wash solution comprises about 0.01% (w/v) of a non-ionic surfactant. In certain embodiments, the second wash solution comprises poloxamer 188. In certain embodiments, the second wash solution comprises about 0.001% (w/v) to about 0.05% (w/v) poloxamer 188. In certain embodiments, the second wash solution comprises about 0.001% (w/v), about 0.005% (w/v), about 0.01% (w/v), about 0.015% (w/v), about 0.02% (w/v), about 0.03% (w/v), about 0.035% (w/v), about 0.04% (w/v), about 0.045% (w/v), or about 0.05% (w/v) poloxamer 188. In certain embodiments, the second wash solution comprises about 0.01% (w/v) poloxamer 188.

In certain embodiments, the pH of the second wash solution is about 9 to about 10.5. In certain embodiments, the pH of the second wash solution is about 9, about 9.1, about 9.2, about 9.3, about 9.4, about 9.5, about 9.6, about 9.7, about 9.8, about 9.9, about 10, about 10.1, about 10.2, about 10.3, about 10.4, or about 10.5. In certain embodiments, the pH of the second wash solution is about 9.3.

In certain embodiments, the second wash solution has a conductivity of less than about 3 mS/cm. In certain embodiments, the second wash solution has a conductivity of about 1 mS/cm to about 3 mS/cm. In certain embodiments, the second wash solution has a conductivity of about 1 mS/cm, about 1.1 mS/cm, about 1.2 mS/cm, about 1.3 mS/cm, about 1.4 mS/cm, about 1.5 mS/cm, about 1.6 mS/cm, about 1.7 mS/cm, about 1.8 mS/cm, about 1.9 mS/cm, about 2 mS/cm, about 2.1 mS/cm, about 2.2 mS/cm, about 2.3 mS/cm, about 2.4 mS/cm, about 2.5 mS/cm, about 2.6 mS/cm, about 2.7 mS/cm, about 2.8 mS/cm, about 2.9 mS/cm, or about 3 mS/cm. In certain embodiments, the second wash solution has a conductivity of about 1 mS/cm.

In certain embodiments, the second wash solution has a pH of about 9.2, a conductivity of about 1 mS/cm, and comprises about 10 mM ammonium acetate, and 0.01% (w/v) poloxamer 188. In certain embodiments, the second wash solution has a pH of about 9.3, a conductivity of about 1 mS/cm, and comprises about 10 mM ammonium acetate, and 0.01% (w/v) poloxamer 188. In certain embodiments, the second wash solution has a pH of about 9.3, a conductivity of about 3 mS/cm, and comprises about 34 mM ammonium acetate, and 0.01% (w/v) poloxamer 188.

Elution from AEX Medium

Methods of the present disclosure further comprise eluting the AAV from the AEX medium. AAV bound to the AEX medium can be eluted using a gradient elution or a step isocratic elution (also referred to herein as a step elution). The gradient elution may be a linear gradient elution. In certain embodiments, methods of the present disclosure comprise eluting the AAV from the AEX medium under a linear gradient elution. In certain embodiments, methods of the present disclosure comprise eluting the AAV from the AEX medium under a step isocratic elution.

Elution of the AAV bound to the AEX medium is achieved by applying an eluant to the AEX medium. In certain embodiments, for linear gradient elution, elution is performed using a linear gradient volume of an eluant with an increasing conductivity. In certain embodiments, for step elution, elution is performed by sequential addition of an eluant at increasing conductivities.

In certain embodiments, the AEX medium is washed with a second wash solution prior to eluting the AAV from the AEX medium.

In certain embodiments, the eluant comprises a salt. In certain embodiments, the eluant comprises an acetate. In certain embodiments, the eluant comprises about 10 mM to about 1 M of an acetate or a salt equivalent thereof. In certain embodiments, the eluant comprises about 10 mM to about 150 mM of an acetate or a salt equivalent thereof. In certain embodiments, the eluant comprises about 100 mM to about 300 mM of an acetate or a salt equivalent thereof. In certain embodiments, the eluant comprises about 10 mM, about 15 mM, about 20 mM, about 25 mM, about 30 mM, about 35 mM, about 50 mM, about 100 mM, about 150 mM, about 200 mM, about 250 mM, about 300 mM, about 350 mM, about 400 mM, about 450 mM, about 500 mM, about 550 mM, about 600 mM, about 650 mM, about 700 mM, about 750 mM, about 800 mM, about 850 mM, about 900 mM, about 950 mM, or about 1 M of an acetate or a salt equivalent thereof.

Examples of suitable acetates are known to those of skill in the art, and include, without limitation, ammonium acetate, sodium acetate, and potassium acetate. In certain embodiments, the eluant comprises ammonium acetate. In certain embodiments, the eluant comprises about 10 mM to about 1 M ammonium acetate. In certain embodiments, the eluant comprises about 10 mM to about 150 mM ammonium acetate. In certain embodiments, the eluant comprises about 100 mM to about 300 mM ammonium acetate. In certain embodiments, the eluant comprises about 10 mM, about 15 mM, about 20 mM, about 25 mM, about 30 mM, about 35 mM, about 50 mM, about 100 mM, about 150 mM, about 200 mM, about 250 mM, about 300 mM, about 350 mM, about 400 mM, about 450 mM, about 500 mM, about 550 mM, about 600 mM, about 650 mM, about 700 mM, about 750 mM, about 800 mM, about 850 mM, about 900 mM, about 950 mM, or about 1 M ammonium acetate.

In certain embodiments, the eluant comprises a surfactant. In certain embodiments, the surfactant is a non-ionic surfactant. Examples of non-ionic surfactants include, without limitation, Brij™-35, Brij™-58, NP-40, octyl-beta-glucoside, octylthioglucoside (OTG), poloxamer 188 (P-188), poloxamer 407, polysorbate 20, polysorbate 80, Triton X-100, or Triton X-114. In certain embodiments, the eluant comprises about 0.001% (w/v) to about 0.05% (w/v) of a non-ionic surfactant. In certain embodiments, the eluant comprises about 0.001% (w/v), about 0.005% (w/v), about 0.01% (w/v), about 0.015% (w/v), about 0.02% (w/v), about 0.03% (w/v), about 0.035% (w/v), about 0.04% (w/v), about 0.045% (w/v), or about 0.05% (w/v) of a non-ionic surfactant. In certain embodiments, the eluant comprises about 0.01% (w/v) of a non-ionic surfactant. In certain embodiments, the eluant comprises poloxamer 188. In certain embodiments, the eluant comprises about 0.001% (w/v) to about 0.05% (w/v) poloxamer 188. In certain embodiments, the eluant comprises about 0.001% (w/v), about 0.005% (w/v), about 0.01% (w/v), about 0.015% (w/v), about 0.02% (w/v), about 0.03% (w/v), about 0.035% (w/v), about 0.04% (w/v), about 0.045% (w/v), or about 0.05% (w/v) poloxamer 188. In certain embodiments, the eluant comprises about 0.01% (w/v) poloxamer 188.

In certain embodiments, the pH of the eluant is about 9 to about 10.5. In certain embodiments, the pH of the eluant is about 9, about 9.1, about 9.2, about 9.3, about 9.4, about 9.5, about 9.6, about 9.7, about 9.8, about 9.9, about 10, about 10.1, about 10.2, about 10.3, about 10.4, or about 10.5. In certain embodiments, the pH of the eluant is about 9.3.

In certain embodiments, the eluant is applied to the AEX medium at a conductivity of about 1 mS/cm to about 40 mS/cm. In certain embodiments, the eluant is applied to the AEX medium at a conductivity of about 8.5 mS/cm to about 30 mS/cm. In certain embodiments, the eluant is applied to the AEX medium at a conductivity of about 8.5 mS/cm to about 10.5 mS/cm. In certain embodiments, the eluant is applied to the AEX medium at a conductivity of about 10 mS/cm to about 11.5 mS/cm. In certain embodiments, the eluant is applied to the AEX medium at a conductivity of about 14 mS/cm to about 17.5 mS/cm. In certain embodiments, the eluant is applied to the AEX medium at a conductivity of about 1 mS/cm, about 2 mS/cm, about 3 mS/cm, about 4 mS/cm, about 5 mS/cm, about 6 mS/cm, about 7 mS/cm, about 8 mS/cm, about 9 mS/cm, about 10 mS/cm, about 11 mS/cm, about 12 mS/cm, about 13 mS/cm, about 14 mS/cm, about 15 mS/cm, about 16 mS/cm, about 17 mS/cm, about 18 mS/cm, about 19 mS/cm, about 20 mS/cm, about 21 mS/cm, about 22 mS/cm, about 23 mS/cm, about 24 mS/cm, about 25 mS/cm, about 26 mS/cm, about 27 mS/cm, about 28 mS/cm, about 29 mS/cm, about 30 mS/cm, about 31 mS/cm, about 32 mS/cm, about 33 mS/cm, about 34 mS/cm, about 35 mS/cm, about 36 mS/cm, about 37 mS/cm, about 38 mS/cm, about 39 mS/cm, or about 40 mS/cm. In certain embodiments, the eluant is applied to the AEX medium at a conductivity of about 6.5 mS/cm. In certain embodiments, the eluant is applied to the AEX medium at a conductivity of about 7 mS/cm. In certain embodiments, the eluant is applied to the AEX medium at a conductivity of about 7.5 mS/cm. In certain embodiments, the eluant is applied to the AEX medium at a conductivity of about 8 mS/cm. In certain embodiments, the eluant is applied to the AEX medium at a conductivity of about 8.5 mS/cm. In certain embodiments, the eluant is applied to the AEX medium at a conductivity of about 9 mS/cm. In certain embodiments, the eluant is applied to the AEX medium at a conductivity of about 9.5 mS/cm. In certain embodiments, the eluant is applied to the AEX medium at a conductivity of about 10 mS/cm. In certain embodiments, the eluant is applied to the AEX medium at a conductivity of about 11 mS/cm. In certain embodiments, the eluant is applied to the AEX medium at a conductivity of about 18.5 mS/cm. In certain embodiments, the eluant is applied to the AEX medium at a conductivity of about 19 mS/cm. In certain embodiments, the eluant is applied to the AEX medium at a conductivity of about 26 mS/cm. In certain embodiments, the eluant is applied to the AEX medium at a conductivity of about 30 mS/cm.

In certain embodiments, the eluant has a pH of about 9.2, and comprises 110 mM ammonium acetate, and 0.01% (w/v) poloxamer 188, and is applied to the AEX medium at a conductivity of about 9.5 mS/cm. In certain embodiments, the eluant has a pH of about 9.3, and comprises 400 mM ammonium acetate, and 0.01% (w/v) poloxamer 188, and is applied to the AEX medium at a conductivity of about 30 mS/cm. In certain embodiments, the eluant has a pH of about 9.3 and comprises 500 mM ammonium acetate, and 0.01% (w/v) poloxamer 188, and is applied to the AEX medium at a conductivity of about 10 mS/cm. In certain embodiments, the eluant has a pH of about 9.3, and comprises about 293 mM ammonium acetate, and 0.01% (w/v) poloxamer 188, and is applied to the AEX medium at a conductivity of about 18.5 mS/cm. In certain embodiments, the eluant has a pH of about 9.3, and comprises about 305 mM ammonium acetate, and 0.01% (w/v) poloxamer 188, and is applied to the AEX medium at a conductivity of about 19 mS/cm. In certain embodiments, the eluant has a pH of about 9.3, and comprises about 89 mM ammonium acetate, and 0.01% (w/v) poloxamer 188, and is applied to the AEX medium at a conductivity of about 6.5 mS/cm. In certain embodiments, the eluant has a pH of about 9.3, and comprises about 89 mM ammonium acetate, and 0.01% (w/v) poloxamer 188, and is applied to the AEX medium at a conductivity of about 7 mS/cm. In certain embodiments, the eluant has a pH of about 9.3, and comprises about 89 mM ammonium acetate, and 0.01% (w/v) poloxamer 188, and is applied to the AEX medium at a conductivity of about 7.5 mS/cm. In certain embodiments, the eluant has a pH of about 9.3, and comprises about 89 mM ammonium acetate, and 0.01% (w/v) poloxamer 188, and is applied to the AEX medium at a conductivity of about 8 mS/cm. In certain embodiments, the eluant has a pH of about 9.3, and comprises about 89 mM ammonium acetate, and 0.01% (w/v) poloxamer 188, and is applied to the AEX medium at a conductivity of about 8.5 mS/cm. In certain embodiments, the eluant has a pH of about 9.3, and comprises about 89 mM ammonium acetate, and 0.01% (w/v) poloxamer 188, and is applied to the AEX medium at a conductivity of about 9 mS/cm. In certain embodiments, the eluant has a pH of about 9.3, and comprises about 89 mM ammonium acetate, and 0.01% (w/v) poloxamer 188, and is applied to the AEX medium at a conductivity of about 9.5 mS/cm. In certain embodiments, the eluant has a pH of about 9.3, and comprises about 89 mM ammonium acetate, and 0.01% (w/v) poloxamer 188, and is applied to the AEX medium at a conductivity of about 10 mS/cm. In certain embodiments, the eluant has a pH of about 9.3, and comprises about 89 mM ammonium acetate, and 0.01% (w/v) poloxamer 188, and is applied to the AEX medium at a conductivity of about 11 mS/cm.

Those of ordinary skill in the art will appreciate that the eluant may comprise additional components that aid in the elution of AAV from the AEX medium. Such components may include additional buffering agents and additives that aid in, for example, dissociation, solubilization, and metal chelation. In certain embodiments, the eluant further comprises ethanolamine. In certain embodiments, the eluant comprises about 1 mM to about 100 mM ethanolamine, e.g., about 1 mM, about 10 mM, about 20 mM, about 30 mM, about 40 mM, about 50 mM, about 60 mM, about 70 mM, about 80 mM, about 90 mM, about 100 mM ethanolamine. In certain embodiments, the eluant comprises about 50 mM ethanolamine. In certain embodiments, the eluant further comprises Bis-Tris Propane (BTP). In certain embodiments, the eluant comprises about 1 mM to about 100 mM BTP, e.g., about 1 mM, about 10 mM, about 20 mM, about 30 mM, about 40 mM, about 50 mM, about 60 mM, about 70 mM, about 80 mM, about 90 mM, about 100 mM BTP. In certain embodiments, the eluant further comprises glycine. In certain embodiments, the eluant comprises about 1 mM to about 2000 mM glycine, e.g., about 1 mM, about 10 mM, about 20 mM, about 30 mM, about 40 mM, about 50 mM, about 60 mM, about 70 mM, about 80 mM, about 90 mM, about 100 mM, about 110 mM, about 120 mM, about 130 mM, about 140 mM, about 150 mM, about 160 mM, about 170 mM, about 180 mM, about 190 mM, about 200 mM, about 300 mM, about 400 mM, about 500 mM, about 600 mM, about 700 mM, about 800 mM, about 900 mM, about 1000 mM, about 1100 mM, about 1200 mM, about 1300 mM, about 1400 mM, about 1500 mM, about 1600 mM, about 1700 mM, about 1800 mM, about 1900 mM, about 2000 mM glycine.

III. Recombinant Adeno-Associated Virus

The methods provided by the present disclosure are for the separation of an AAV particle from a mixture of the AAV particle and at least one contaminant. In certain embodiments, the AAV is a recombinant adeno-associated virus (rAAV).

rAAV Genome

In certain embodiments, the methods provided by the present disclosure are for the separation of an rAAV particle from a mixture of the rAAV and at least one contaminant. The rAAV comprises an rAAV genome. In certain embodiments, the rAAV genome comprises a transgene.

In certain embodiments, the transgene comprises one or more sequences encoding an RNA molecule. Suitable RNA molecules include, without limitation, miRNA, shRNA, siRNA, antisense RNA, gRNA, antagomirs, miRNA sponges, RNA aptazymes, RNA aptamers, mRNA, lncRNAs, ribozymes, and synthetic RNAs known in the art.

In certain embodiments, the transgene encodes one or more polypeptides, or a fragment thereof. Such transgenes can comprise the complete coding sequence of a polypeptide, or only a fragment of a coding sequence of a polypeptide. In certain embodiments, the transgene encodes a polypeptide that is useful to treat a disease or disorder in a subject. Suitable polypeptides include, without limitation, β-globin, hemoglobin, tissue plasminogen activator, and coagulation factors; colony stimulating factors (CSF); interleukins, such as IL-1, IL-2, IL-3, IL-4, IL-5, IL-6, IL-7, IL-8, IL-9, etc.; growth factors, such as keratinocyte growth factor (KGF), stem cell factor (SCF), fibroblast growth factor (FGF, such as basic FGF and acidic FGF), hepatocyte growth factor (HGF), insulin-like growth factors (IGFs), bone morphogenetic protein (BMP), epidermal growth factor (EGF), growth differentiation factor-9 (GDF-9), hepatoma derived growth factor (HDGF), myostatin (GDF-8), nerve growth factor (NGF), neurotrophins, platelet-derived growth factor (PDGF), thrombopoietin (TPO), transforming growth factor alpha (TGF-a), transforming growth factor beta (TGF-β), and the like; soluble receptors, such as soluble TNF-a receptors, soluble interleukin receptors (e.g., soluble IL-1 receptors and soluble type II IL-1 receptors), soluble γ/Δ T cell receptors, ligand-binding fragments of a soluble receptor, and the like; enzymes, such as a-glucosidase, imiglucerase, β-glucocerebrosidase, and alglucerase; enzyme activators, such as tissue plasminogen activator; chemokines, such as IP-10, monokine induced by interferon-gamma (Mig), Groα/IL-8, RANTES, MIP-1a, MCP-1β, MCP-1, PF-4, and the like; angiogenic agents, such as vascular endothelial growth factors (VEGFs, e.g., VEGF121, VEGF165, VEGF-C, VEGF-2), glioma-derived growth factor, angiogenin, angiogenin-2; and the like; anti-angiogenic agents, such as a soluble VEGF receptor; protein vaccine; neuroactive peptides, such as nerve growth factor (NGF), bradykinin, cholecystokinin, gastrin, secretin, oxytocin, gonadotropin-releasing hormone, beta-endorphin, enkephalin, substance P, somatostatin, prolactin, galanin, growth hormone-releasing hormone, bombesin, dynorphin, warfarin, neurotensin, motilin, thyrotropin, neuropeptide Y, luteinizing hormone, calcitonin, insulin, glucagons, vasopressin, angiotensin II, thyrotropin-releasing hormone, vasoactive intestinal peptide, a sleep peptide, and the like; thrombolytic agents; atrial natriuretic peptide; relaxin; glial fibrillary acidic protein; follicle stimulating hormone (FSH); human alpha-1 antitrypsin; leukemia inhibitory factor (LIF); tissue factors; macrophage activating factors; tumor necrosis factor (TNF); neutrophil chemotactic factor (NCF); tissue inhibitors of metalloproteinases; vasoactive intestinal peptide; angiogenin; angiotropin; fibrin; hirudin; IL-1 receptor antagonists; ciliary neurotrophic factor (CNTF); brain-derived neurotrophic factor (BDNF); neurotrophins 3 and 4/5 (NT-3 and -4/5); glial cell derived neurotrophic factor (GDNF); aromatic amino acid decarboxylase (AADC); Factor VIII, Factor IX, Factor X; dystrophin or mini-dystrophin; lysosomal acid lipase; phenylalanine hydroxylase (PAH); glycogen storage disease-related enzymes, such as glucose phosphatase, acid maltase, glycogen debranching enzyme, muscle glycogen phosphorylase, liver glycogen phosphorylase, muscle phosphofructokinase, phosphorylase kinase, glucose transporter, aldolase A, β-enolase, glycogen synthase; lysosomal enzymes, such as iduronate-2-sulfatase (I2S), and arylsulfatase A; and mitochondrial proteins, such as frataxin.

In certain embodiments, the transgene encodes a protein that may be defective in one or more lysosomal storage diseases. Suitable proteins include, without limitation, α-sialidase, cathepsin A, α-mannosidase, β-mannosidase, glycosylasparaginase, α-fucosidase, α-N-acetylglucosaminidase, β-galactosidase, β-hexosaminidase α-subunit, β-hexosaminidase β-subunit, GM2 activator protein, glucocerebrosidase, Saposin C, Arylsulfatase A, Saposin B, formyl-glycine generating enzyme, β-galactosylceramidase, α-galactosidase A, iduronate sulfatase, α-iduronidase, heparan N-sulfatase, acetyl-CoA transferase, N-acetyl glucosaminidase, β-glucuronidase, N-acetyl glucosamine 6-sulfatase, N-acetylgalactosamine 4-sulfatase, galactose 6-sulfatase, hyaluronidase, α-glucosidase, acid sphingomyelinase, acid ceramidase, acid lipase, cathepsin K, tripeptidyl peptidase, palmitoyl-protein thioesterase, cystinosin, sialin, UDP-N-acetylglucosamine, phosphotransferase γ-subunit, mucolipin-1, LAMP-2, NPC1, CLN3, CLN 6, CLN 8, LYST, MYOV, RAB27A, melanophilin, and AP3 β-subunit. In certain embodiments, suitable proteins include α-sialidase, cathepsin A, α-mannosidase, β-mannosidase, glycosylasparaginase, α-fucosidase, α-N-acetylglucosaminidase, β-galactosidase, β-hexosaminidase α-subunit, β-hexosaminidase β-subunit, GM2 activator protein, glucocerebrosidase, Saposin C, Saposin B, formyl-glycine generating enzyme, β-galactosylceramidase, α-galactosidase A, α-iduronidase, heparan N-sulfatase, acetyl-CoA transferase, N-acetyl glucosaminidase, β-glucuronidase, N-acetyl glucosamine 6-sulfatase, N-acetylgalactosamine 4-sulfatase, galactose 6-sulfatase, hyaluronidase, α-glucosidase, acid sphingomyelinase, acid ceramidase, acid lipase, cathepsin K, tripeptidyl peptidase, palmitoyl-protein thioesterase, cystinosin, sialin, UDP-N-acetylglucosamine, phosphotransferase γ-subunit, mucolipin-1, LAMP-2, NPC1, CLN3, CLN 6, CLN 8, LYST, MYOV, RAB27A, melanophilin, and AP3 β-subunit.

In certain embodiments, the transgene encodes a protein selected from the group consisting of iduronate-2-sulfatase (I2S), frataxin (FXN), glucose-6-phosphatase (G6Pase), phosphoenolpyruvate carboxykinase (PEPCK), cyclin-dependent kinase-like 5 (CDKL5/STK9), galactose-1 phosphate uridyltransferase, phenylalanine hydroxylase (PAH), branched-chain alpha-keto acid dehydrogenase, fumarylacetoacetate hydrolase, methylmalonyl-CoA mutase, medium-chain acyl-CoA dehydrogenase, ornithine transcarbamylase (OTC), argininosuccinic acid synthetase (ASS1), low density lipoprotein receptor (LDLR) protein, UDP-glucuronosyltransferase, adenosine deaminase, hypoxanthine guanine phosphoribosyltransferase, biotinidase, alpha-galactosidase A, copper-transporting ATPase 2 (ATP7B), beta-glucocerebrosidase, 70 kDa peroxisomal membrane protein (PMP70), and arylsulfatase A (ARSA). In certain embodiments, the transgene encodes a protein which is not selected from the group consisting of phenylalanine hydroxylase (PAH), iduronate-2-sulfatase (I2S), arylsulfatase A (ARSA), and an anti-complement component 5 antibody.

In certain embodiments, the transgene encodes an antibody or a fragment thereof (e.g., a Fab, scFv, or full-length antibody). Suitable antibodies include, without limitation, muromonab-cd3, efalizumab, tositumomab, daclizumab, nebacumab, catumaxomab, edrecolomab, abciximab, rituximab, basiliximab, palivizumab, infliximab, trastuzumab, adalimumab, ibritumomab tiuxetan, omalizumab, cetuximab, bevacizumab, natalizumab, panitumumab, ranibizumab, eculizumab, certolizumab, ustekinumab, canakinumab, golimumab, ofatumumab, tocilizumab, denosumab, belimumab, ipilimumab, brentuximab vedotin, pertuzumab, raxibacumab, obinutuzumab, alemtuzumab, siltuximab, ramucirumab, vedolizumab, blinatumomab, nivolumab, pembrolizumab, idarucizumab, necitumumab, dinutuximab, secukinumab, mepolizumab, alirocumab, evolocumab, daratumumab, elotuzumab, ixekizumab, reslizumab, olaratumab, bezlotoxumab, atezolizumab, obiltoxaximab, inotuzumab ozogamicin, brodalumab, guselkumab, dupilumab, sarilumab, avelumab, ocrelizumab, emicizumab, benralizumab, gemtuzumab ozogamicin, durvalumab, burosumab, erenumab, galcanezumab, lanadelumab, mogamulizumab, tildrakizumab, cemiplimab, fremanezumab, ravulizumab, emapalumab, ibalizumab, moxetumomab, caplacizumab, romosozumab, risankizumab, polatuzumab, eptinezumab, leronlimab, sacituzumab, brolucizumab, isatuximab, and teprotumumab.

In certain embodiments, the transgene encodes a nuclease. Suitable nucleases include, without limitation, zinc fingers nucleases (ZFN) (see, e.g., Porteus, and Baltimore (2003) Science 300: 763; Miller et al. (2007) Nat. Biotechnol. 25:778-785; Sander et al. (2011) Nature Methods 8:67-69; and Wood et al. (2011) Science 333:307, each of which is hereby incorporated by reference in its entirety), transcription activator-like effectors nucleases (TALEN) (see, e.g., Wood et al. (2011) Science 333:307; Boch et al. (2009) Science 326:1509-1512; Moscou and Bogdanove (2009) Science 326:1501; Christian et al. (2010) Genetics 186:757-761; Miller et al. (2011) Nat. Biotechnol. 29:143-148; Zhang et al. (2011) Nat. Biotechnol. 29:149-153; and Reyon et al. (2012) Nat. Biotechnol. 30(5): 460-465, each of which is hereby incorporated by reference in its entirety), homing endonucleases, meganucleases (see, e.g., U.S. Patent Publication No. US 2014/0121115, which is hereby incorporated by reference in its entirety), and RNA-guided nucleases (see, e.g., Makarova et al. (2018) The CRISPR Journal 1(5): 325-336; and Adli (2018) Nat. Communications 9:1911, each of which is hereby incorporated by reference in its entirety).

In certain embodiments, the transgene encodes an RNA-guided nuclease. Suitable RNA-guided nucleases include, without limitation, Class I and Class II clustered regularly interspaced short palindromic repeats (CRISPR)-associated nucleases. Class I is divided into types I, III, and IV, and includes, without limitation, type I (Cas3), type I-A (Cas8a, Cas5), type I-B (Cas8b), type I-C (Cas8c), type 1-D (Cas10d), type I-E (Cse1, Cse2), type I-F (Csy1, Csy2, Csy3), type I-U (GSU0054), type III (Cas10), type III-A (Csm2), type III-B (Cmr5), type III-C (Csx10 or Csx11), type III-D (Csx10), and type IV (Csf1). Class II is divided into types II, V, and VI, and includes, without limitation, type II (Cas9), type II-A (Csn2), type II-B (Cas4), type V (Cpf1, C2c1, C2c3), and type VI (Cas13a, Cas13b, Cas13c). RNA-guided nucleases also include naturally-occurring Class II CRISPR nucleases such as Cas9 (Type II) or Cas12a/Cpf1 (Type V), as well as other nucleases derived or obtained therefrom. Exemplary Cas9 nucleases that may be used in the present invention include, but are not limited to, *S. pyogenes* Cas9 (SpCas9), *S. aureus* Cas9 (SaCas9), *N. meningitidis* Cas9 (NmCas9), *C. jejuni* Cas9 (CjCas9), and *Geobacillus* Cas9 (GeoCas9).

In certain embodiments, the transgene encodes one or more reporter sequences, which upon expression produce a detectable signal. Such reporter sequences include, without limitation, DNA sequences encoding β-lactamase, -galactosidase (LacZ), alkaline phosphatase, thymidine kinase, green fluorescent protein (GFP), red fluorescent protein (RFP), chloramphenicol acetyltransferase (CAT), luciferase, membrane bound proteins, including, for example, CD2, CD4, CD8, the influenza hemagglutinin protein, and others well known in the art, to which high affinity antibodies directed thereto exist or can be produced by conventional means, and fusion proteins comprising a membrane bound protein appropriately fused to an antigen tag domain from, among others, hemagglutinin or Myc.

In certain embodiments, the rAAV genome comprises a transcriptional regulatory element (TRE) operably linked to the transgene, to control expression of an RNA or polypeptide encoded by the transgene. In certain embodiments, the TRE comprises a constitutive promoter. In certain embodiments, the TRE can be active in any mammalian cell (e.g., any human cell). In certain embodiments, the TRE is active in a broad range of human cells. Such TREs may comprise constitutive promoter and/or enhancer elements, including any of those described herein, and any of those known to one of skill in the art. In certain embodiments, the TRE comprises an inducible promoter. In certain embodiments, the TRE may be a tissue-specific TRE, i.e., it is active in specific tissue(s) and/or organ(s). A tissue-specific TRE comprises one or more tissue-specific promoter and/or enhancer elements, and optionally one or more constitutive promoter and/or enhancer elements. A skilled artisan would appreciate that tissue-specific promoter and/or enhancer elements can be isolated from genes specifically expressed in the tissue by methods well known in the art.

Suitable promoters include, e.g., cytomegalovirus promoter (CMV) (Stinski et al. (1985) Journal of Virology 55(2): 431-441), CMV early enhancer/chicken β-actin (CBA) promoter/rabbit β-globin intron (CAG) (Miyazaki et al. (1989) Gene 79(2): 269-277), $CB^{SB}$ (Jacobson et al. (2006) Molecular Therapy 13(6): 1074-1084), human elongation factor 1α promoter (EF1α) (Kim et al. (1990) Gene 91 (2): 217-223), human phosphoglycerate kinase promoter (PGK) (Singer-Sam et al. (1984) Gene 32(3): 409-417), mitochondrial heavy-strand promoter (Loderio et al. (2012) PNAS 109(17): 6513-6518), ubiquitin promoter (Wulff et al. (1990) FEBS Letters 261: 101-105). In certain embodiments, the TRE comprises a cytomegalovirus (CMV) promoter/enhancer (e.g., comprising a nucleotide sequence at least 90%, 91%, 92%, 93%, 94%, 95%, 96%, 97%, 98%, 99%, or 100% identical to SEQ ID NO: 18 or 19), an SV40 promoter, a chicken beta actin (CBA) promoter (e.g., comprising a nucleotide sequence at least 90%, 91%, 92%, 93%, 94%, 95%, 96%, 97%, 98%, 99%, or 100% identical to SEQ ID NO: 20 or 21), a smCBA promoter (e.g., comprising a nucleotide sequence at least 90%, 91%, 92%, 93%, 94%, 95%, 96%, 97%, 98%, 99%, or 100% identical to SEQ ID NO: 22), a human elongation factor 1 alpha (EF1α) promoter (e.g., comprising a nucleotide sequence at least 90%, 91%, 92%, 93%, 94%, 95%, 96%, 97%, 98%, 99%, or 100% identical to SEQ ID NO: 23), a minute virus of mouse (MVM) intron which comprises transcription factor binding sites (e.g., comprising a nucleotide sequence at least 90%, 91%, 92%, 93%, 94%, 95%, 96%, 97%, 98%, 99%, or 100% identical to SEQ ID NO: 24 or 25), a human phosphoglycerate kinase (PGK1) promoter, a human ubiquitin C (Ubc) promoter, a human beta actin promoter, a human neuron-specific enolase (ENO2) promoter, a human beta-glucuronidase (GUSB) promoter, a rabbit beta-globin element (e.g., comprising a nucleotide sequence at least 90%, 91%, 92%, 93%, 94%, 95%, 96%, 97%, 98%, 99%, or 100% identical to SEQ ID NO: 26 or 27), a human calmodulin 1 (CALM1) promoter (e.g., comprising a nucleotide sequence at least 90%, 91%, 92%, 93%, 94%, 95%, 96%, 97%, 98%, 99%, or 100% identical to SEQ ID NO: 28), a human ApoE/C-I hepatic control region (HCR1) (e.g., comprising a nucleotide sequence at least 90%, 91%, 92%, 93%, 94%, 95%, 96%, 97%, 98%, 99%, or 100% identical to SEQ ID NO: 29), a human α1-antitrypsin (hAAT) promoter (e.g., comprising a nucleotide sequence at least 90%, 91%, 92%, 93%, 94%, 95%, 96%, 97%, 98%, 99%, or 100% identical to SEQ ID NO: 30, 31, or 32), an extended HCR1 (e.g., comprising a nucleotide sequence at least 90%, 91%, 92%, 93%, 94%, 95%, 96%, 97%, 98%, 99%, or 100% identical to SEQ ID NO: 33), a HS-CRM8 element of an hAAT promoter (e.g., comprising a nucleotide sequence at least 90%, 91%, 92%, 93%, 94%, 95%, 96%, 97%, 98%, 99%, or 100% identical to SEQ ID NO: 34), a human transthyretin (TTR) promoter (e.g., comprising a nucleotide sequence at least 90%, 91%, 92%, 93%, 94%, 95%, 96%, 97%, 98%, 99%, or 100% identical to SEQ ID NO: 35), and/or a human Methyl-CpG Binding Protein 2 (MeCP2) promoter. Any of the TREs described herein can be combined in any order to drive efficient transcription. For example, an rAAV genome may comprise a TRE comprising a CMV enhancer, a CBA promoter, and the splice acceptor from exon 3 of the rabbit beta-globin gene, collectively called a CAG promoter (e.g., comprising a nucleotide sequence at least 90%, 91%, 92%, 93%, 94%, 95%, 96%, 97%, 98%, 99%, or 100% identical to SEQ ID NO: 36). For example, an rAAV genome may comprise a TRE comprising a hybrid of CMV enhancer and CBA promoter followed by a splice donor and splice acceptor, collectively called a CASI promoter region (e.g., comprising a nucleotide sequence at least 90%, 91%, 92%, 93%, 94%, 95%, 96%, 97%, 98%, 99%, or 100% identical to SEQ ID NO: 37). For example, an rAAV genome may comprise a TRE comprising an HCR1 and hAAT promoter (also referred to as an LP1 promoter, e.g., comprising a nucleotide sequence at least 90%, 91%, 92%, 93%, 94%, 95%, 96%, 97%, 98%, 99%, or 100% identical to SEQ ID NO: 38).

In certain embodiments, the TRE is brain-specific (e.g., neuron-specific, glial cell-specific, astrocyte-specific, oligodendrocyte-specific, microglia-specific and/or central nervous system-specific). Exemplary brain-specific TREs may comprise one or more elements from, without limitation, human glial fibrillary acidic protein (GFAP) promoter, human synapsin 1 (SYN1) promoter, human synapsin 2 (SYN2) promoter, human metallothionein 3 (MT3) promoter, and/or human proteolipid protein 1 (PLP1) promoter. More brain-specific promoter elements are disclosed in WO 2016/100575A1, which is incorporated by reference herein in its entirety.

In certain embodiments, the native promoter for the transgene may be used. The native promoter may be preferred when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

In certain embodiments, the rAAV genome comprises an editing genome. Editing genomes can be used to edit the genome of a cell by homologous recombination of the editing genome with a genomic region surrounding a target locus in the cell. In certain embodiments, the editing genome is designed to correct a genetic defect in a gene by homologous recombination. Editing genomes generally comprise: (i) an editing element for editing a target locus in a target gene, (ii) a 5' homology arm nucleotide sequence 5' of the editing element having homology to a first genomic region 5' to the target locus, and (iii) a 3' homology arm nucleotide sequence 3' of the editing element having homology to a second genomic region 3' to the target locus, wherein the portion of the editing genome comprising the 5' homology arm, editing element, and 3' homology arm can be in the sense or antisense orientation relative to the target locus. Suitable target genes for editing using an editing genome include, without limitation, phenylalanine hydroxylase (PAH), cystic fibrosis conductance transmembrane regulator (CFTR), beta hemoglobin (HBB), oculocutaneous albinism II (OCA2), Huntingtin (HTT), dystrophia myotonica-protein kinase (DMPK), low-density lipoprotein receptor (LDLR), apolipoprotein B (APOB), neurofibromin 1 (NF1), polycystic kidney disease 1 (PKD1), polycystic kidney disease 2 (PKD2), coagulation factor VIII (F8), dystrophin (DMD), phosphate-regulating endopeptidase homologue, X-linked (PHEX), methyl-CpG-binding protein 2 (MECP2), and ubiquitin-specific peptidase 9Y, Y-linked (USP9Y).

In certain embodiments, the rAAV genomes disclosed herein further comprise a transcription terminator (e.g., a polyadenylation sequence). In certain embodiments, the transcription terminator is 3' to the transgene. The transcription terminator may be any sequence that effectively terminates transcription, and a skilled artisan would appreciate that such sequences can be isolated from any genes that are expressed in the cell in which transcription of the at least a portion of an antibody coding sequence is desired. In certain embodiments, the transcription terminator comprises a polyadenylation sequence. In certain embodiments, the polyadenylation sequence is identical or substantially identical to the endogenous polyadenylation sequence of an immunoglobulin gene. In certain embodiments, the polyadenylation sequence is an exogenous polyadenylation sequence. In certain embodiments, the polyadenylation sequence is an SV40 polyadenylation sequence (e.g., comprising a nucleotide sequence at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 14, 47, or 48, or a nucleotide sequence complementary thereto). In certain embodiments, the polyadenylation sequence comprises the nucleotide sequence set forth in SEQ ID NO: 14. In certain embodiments, the polyadenylation sequence consists of the nucleotide sequence set forth in SEQ ID NO: 14. In certain embodiments, the polyadenylation sequence is a bovine growth hormone (BGH) polyadenylation sequence (e.g., comprising a nucleotide sequence at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 49, or a nucleotide sequence complementary thereto). In certain embodiments, the polyadenylation sequence comprises the nucleotide sequence set forth in SEQ ID NO: 49. In certain embodiments, the polyadenylation sequence consists of the nucleotide sequence set forth in SEQ ID NO: 49.

In certain embodiments, the rAAV genome comprises a nucleotide sequence at least 80%, 81%, 82%, 83%, 84%, 85%, 86%, 87%, 88%, 89%, 90%, 91%, 92%, 93%, 94%, 95%, 96%, 97%, 98%, 99%, or 100% identical to the sequence set forth in SEQ ID NO: 50, 51, 52, 53, 54, or 64. In certain embodiments, the editing element comprises the nucleotide sequence set forth in SEQ ID NO: 50, 51, 52, 53, 54, or 64. In certain embodiments, the editing element consists of the nucleotide sequence set forth in SEQ ID NO: 50, 51, 52, 53, 54, or 64.

In certain embodiments, the rAAV genomes disclosed herein further comprise a 5' inverted terminal repeat (5' ITR) nucleotide sequence 5' of the TRE, and a 3' inverted terminal repeat (3' ITR) nucleotide sequence 3' of the polyadenylation sequence associated with an antibody light chain coding sequence. ITR sequences from any AAV serotype or variant thereof can be used in the rAAV genomes disclosed herein. The 5' and 3' ITR can be from an AAV of the same serotype or from AAVs of different serotypes. Exemplary ITRs for use in the rAAV genomes disclosed herein are set forth in SEQ ID NOs: 39, 40, 41, 42, 43, and 44, herein.

In certain embodiments, the 5' ITR or 3' ITR is from AAV2. In certain embodiments, both the 5' ITR and the 3' ITR are from AAV2. In certain embodiments, the 5' ITR nucleotide sequence has at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 39, or the 3' ITR nucleotide sequence has at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 40. In certain embodiments, the 5' ITR nucleotide sequence has at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 39, and the 3' ITR nucleotide sequence has at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 40. In certain embodiments, the rAAV genome comprises a 5' ITR nucleotide sequence having the sequence of SEQ ID NO: 39, and a 3' ITR nucleotide sequence having the sequence of SEQ ID NO: 40.

In certain embodiments, the 5' ITR or 3' ITR are from AAVS. In certain embodiments, both the 5' ITR and 3' ITR are from AAVS. In certain embodiments, the 5' ITR nucleotide sequence has at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 42, or the 3' ITR nucleotide sequence has at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 43. In certain embodiments, the 5' ITR nucleotide sequence has at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 42, and the 3' ITR nucleotide sequence has at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 43. In certain embodiments, the rAAV genome comprises a 5' ITR nucleotide sequence having the sequence of SEQ ID NO: 42, and a 3' ITR nucleotide sequence having the sequence of SEQ ID NO: 43.

In certain embodiments, the 5' ITR nucleotide sequence and the 3' ITR nucleotide sequence are substantially complementary to each other (e.g., are complementary to each other except for mismatch at 1, 2, 3, 4, or 5 nucleotide positions in the 5' or 3' ITR).

In certain embodiments, the 5' ITR or the 3' ITR is modified to reduce or abolish resolution by Rep protein ("non-resolvable ITR"). In certain embodiments, the non-resolvable ITR comprises an insertion, deletion, or substitution in the nucleotide sequence of the terminal resolution site. Such modification allows formation of a self-complementary, double-stranded DNA genome of the AAV after the rAAV genome is replicated in an infected cell. Exemplary non-resolvable ITR sequences are known in the art (see, e.g., those provided in U.S. Pat. Nos. 7,790,154 and 9,783,824, which are incorporated by reference herein in their entirety). In certain embodiments, the 5' ITR comprises a nucleotide sequence at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 41. In certain embodiments, the 5' ITR consists of a nucleotide sequence at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 41. In certain embodiments, the 5' ITR consists of the nucleotide sequence set forth in SEQ ID NO: 41. In certain embodiments, the 3' ITR comprises a nucleotide sequence at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 44. In certain embodiments, the 5' ITR consists of a nucleotide sequence at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 44. In certain embodiments, the 3' ITR consists of the nucleotide sequence set forth in SEQ ID NO: 44. In certain embodiments, the 5' ITR consists of the nucleotide sequence set forth in SEQ ID NO: 41, and the 3' ITR consists of the nucleotide sequence set forth in SEQ ID NO: 44. In certain embodiments, the 5' ITR consists of the nucleotide sequence set forth in SEQ ID NO: 41, and the 3' ITR consists of the nucleotide sequence set forth in SEQ ID NO: 44.

In certain embodiments, the 5' ITR is flanked by an additional nucleotide sequence derived from a wild-type AAV2 genomic sequence. In certain embodiments, the 5' ITR is flanked by an additional 46 bp sequence derived from a wild-type AAV2 sequence that is adjacent to a wild-type AAV2 ITR in an AAV2 genome. In certain embodiments, the additional 46 bp sequence is 3' to the 5' ITR in the rAAV genome. In certain embodiments, the 46 bp sequence consists of the nucleotide sequence set forth in SEQ ID NO: 45.

In certain embodiments, the 3' ITR is flanked by an additional nucleotide sequence derived from a wild-type AAV2 genomic sequence. In certain embodiments, the 3' ITR is flanked by an additional 37 bp sequence derived from a wild-type AAV2 sequence that is adjacent to a wild-type AAV2 ITR in an AAV2 genome. See, e.g., Savy et al., Human Gene Therapy Methods (2017) 28(5): 277-289 (which is hereby incorporated by reference herein in its entirety). In certain embodiments, the additional 37 bp sequence is 5' to the 3' ITR in the rAAV genome. In certain embodiments, the 37 bp sequence consists of the nucleotide sequence set forth in SEQ ID NO: 46.

In certain embodiments, the rAAV genome comprises a nucleotide sequence at least 80%, 81%, 82%, 83%, 84%, 85%, 86%, 87%, 88%, 89%, 90%, 91%, 92%, 93%, 94%, 95%, 96%, 97%, 98%, 99%, or 100% identical to the sequence set forth in SEQ ID NO: 55, 56, 57, 58, 59, or 63. In certain embodiments, the editing element comprises the nucleotide sequence set forth in SEQ ID NO: 55, 56, 57, 58, 59, or 63. In certain embodiments, the editing element consists of the nucleotide sequence set forth in SEQ ID NO: 55, 56, 57, 58, 59, or 63.

AAV Capsid Protein

In certain embodiments, the rAAV comprises an AAV capsid. In certain embodiments, the AAV capsid comprises an AAV capsid protein. The rAAV can comprise an AAV capsid comprising an AAV capsid protein from any AAV capsid known in the art, including natural AAV isolates and variants thereof.

AAV capsid proteins include VP1, VP2, and VP3 capsid proteins. VP1, VP2, and/or VP3 capsid proteins assemble into a capsid that surrounds the rAAV genome. In certain embodiments, assembly of the capsid proteins is facilitated by the assembly-activating protein (AAP). Capsids of certain AAV serotypes require the role of AAP in transporting the capsid proteins to the nucleolus for assembly. For example, AAV1, AAV2, AAV3, AAV6, AAV7, AAV8, AAV9, AAV10, and AAV12 require AAP to form capsids, while capsids of AAV4, AAVS, and AAV11 can assemble without AAP. See, e.g., Earley et al. (2017) J. Virol. 91(3): e01980-16.

Different AAV serotypes or variants thereof comprise AAV capsid proteins having different amino acid sequences. Suitable AAV capsid proteins include, without limitation, a capsid protein from AAV1, AAV2 (e.g., comprising the amino acid sequence encoded by the sequence set forth in SEQ ID NO: 60), AAV3, AAV4, AAV5, AAV6, AAV7, AAV8 (e.g., comprising the amino acid sequence encoded by the sequence set forth in SEQ ID NO: 61), AAV9 (e.g., comprising the amino acid sequence encoded by the sequence set forth in SEQ ID NO: 62), AAV10, AAV11, AAV12, AAV13, AAV-DJ, AAV-LK03, NP59, VOY101, VOY201, VOY701, VOY801, VOY1101, AAVPHP.N, AAVPHP.A, AAVPHP.B, PHP.B2, PHP.B3, G2A3, G2B4, G2B5, PHP.S, AAVRh32.33, AAVrh74, AAVrh10, AAVHSC1, AAVHSC2, AAVHSC3, AAVHSC4, AAVHSC5, AAVHSC6, AAVHSC7, AAVHSC8, AAVHSC9, AAVHSC10, AAVHSC11, AAVHSC12, AAVHSC13, AAVHSC14, AAVHSC15, AAVHSC16, AAVHSC17, and any variants thereof. In certain embodiments, the AAV capsid protein is not from an AAVHSC. The sequences of the various AAV capsid proteins are disclosed in, e.g., U.S. Patent Publication Nos.: US20140359799, US20150376607, US20150159173, US20170081680, and US20170360962A1, and PCT Publication No. WO2020227515, the disclosures of which are incorporated by reference herein in their entireties.

For example, in certain embodiments, the capsid protein comprises an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the amino acid sequence of amino acids 203-736 of SEQ ID NO: 1, 2, 3, 4, 5, 6, 7, 8, 9, 10, 11, 12, 13, 15, 16, or 17. In certain embodiments, the capsid protein comprises an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the amino acid sequence of amino acids 203-736 of SEQ ID NO: 1, 2, 3, 4, 5, 6, 7, 8, 9, 10, 11, 12, 13, 15, 16, or 17, wherein: the amino acid in the capsid protein corresponding to amino acid 206 of SEQ ID NO: 16 is C; the amino acid in the capsid protein corresponding to amino acid 296 of SEQ ID NO: 16 is H; the amino acid in the capsid protein corresponding to amino acid 312 of SEQ ID NO: 16 is Q; the amino acid in the capsid protein corresponding to amino acid 346 of SEQ ID NO: 16 is A; the amino acid in the capsid protein corresponding to amino acid 464 of SEQ ID NO: 16 is N; the amino acid in the capsid protein corresponding to amino acid 468 of SEQ ID NO: 16 is S; the amino acid in the capsid protein corresponding to amino acid 501 of SEQ ID NO: 16 is I; the amino acid in the capsid protein corresponding to amino acid 505 of SEQ ID NO: 16 is R; the amino acid in the capsid protein corresponding to amino acid 590 of SEQ ID NO: 16 is R; the amino acid in the capsid protein corresponding to amino acid 626 of SEQ ID NO: 16 is G or Y; the amino acid in the capsid protein corresponding to amino acid 681 of SEQ ID NO: 16 is M; the amino acid in the capsid protein corresponding to amino acid 687 of SEQ ID NO: 16 is R; the amino acid in the capsid protein corresponding to amino acid 690 of SEQ ID NO: 16 is K; the amino acid in the capsid protein corresponding to amino acid 706 of SEQ ID NO: 16 is C; or, the amino acid in the capsid protein corresponding to amino acid 718 of SEQ ID NO: 16 is G. In certain embodiments, the amino acid in the capsid protein corresponding to amino acid 626 of SEQ ID NO: 16 is G, and the amino acid in the capsid protein corresponding to amino acid 718 of SEQ ID NO: 16 is G. In certain embodiments, the amino acid in the capsid protein corresponding to amino acid 296 of SEQ ID NO: 16 is H, the amino acid in the capsid protein corresponding to amino acid 464 of SEQ ID NO: 16 is N, the amino acid in the capsid protein corresponding to amino acid 505 of SEQ ID NO: 16 is R, and the amino acid in the capsid protein corresponding to amino acid 681 of SEQ ID NO: 16 is M. In certain embodiments, the amino acid in the capsid protein corresponding to amino acid 505 of SEQ ID NO: 16 is R, and the amino acid in the capsid protein corresponding to amino acid 687 of SEQ ID NO: 16 is R. In certain embodiments, the amino acid in the capsid protein corresponding to amino acid 346 of SEQ ID NO: 16 is A, and the amino acid in the capsid protein corresponding to amino acid 505 of SEQ ID NO: 16 is R. In certain embodiments, the amino acid in the capsid protein corresponding to amino acid 501 of SEQ ID NO: 16 is I, the amino acid in the capsid protein corresponding to amino acid 505 of SEQ ID NO: 16 is R, and the amino acid in the capsid protein corresponding to amino acid 706 of SEQ ID NO: 16 is C. In certain embodiments, the capsid protein comprises the amino acid sequence of amino acids 203-736 of SEQ ID NO: 1, 2, 3, 4, 5, 6, 7, 8, 9, 10, 11, 12, 13, 15, 16, or 17.

For example, in certain embodiments, the capsid protein comprises an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the amino acid sequence of amino acids 138-736 of SEQ ID NO: 1, 2, 3, 4, 5, 6, 7, 8, 9, 10, 11, 12, 13, 15, 16, or 17. In certain embodiments, the capsid protein comprises an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the amino acid sequence of amino acids 138-736 of SEQ ID NO: 1, 2, 3, 4, 5, 6, 7, 8, 9, 10, 11, 12, 13, 15, 16, or 17, wherein: the amino acid in the capsid protein corresponding to amino acid 151 of SEQ ID NO: 16 is R; the amino acid in the capsid protein corresponding to amino acid 160 of SEQ ID NO: 16 is D; the amino acid in the capsid protein corresponding to amino acid 206 of SEQ ID NO: 16 is C; the amino acid in the capsid protein corresponding to amino acid 296 of SEQ ID NO: 16 is H; the amino acid in the capsid protein corresponding to amino acid 312 of SEQ ID NO: 16 is Q; the amino acid in the capsid protein corresponding to amino acid 346 of SEQ ID NO: 16 is A; the amino acid in the capsid protein corresponding to amino acid 464 of SEQ ID NO: 16 is N; the amino acid in the capsid protein corresponding to amino acid 468 of SEQ ID NO: 16 is S; the amino acid in the capsid protein corresponding to amino acid 501 of SEQ ID NO: 16 is I; the amino acid in the capsid protein corresponding to amino acid 505 of SEQ ID NO: 16 is R; the amino acid in the capsid protein corresponding to amino acid 590 of SEQ ID NO: 16 is R; the amino acid in the capsid protein corresponding to amino acid 626 of SEQ ID NO: 16 is G or Y; the amino acid in the capsid protein corresponding to amino acid 681 of SEQ ID NO: 16 is M; the amino acid in the capsid protein corresponding to amino acid 687 of SEQ ID NO: 16 is R; the amino acid in the capsid protein corresponding to amino acid 690 of SEQ ID NO: 16 is K; the amino acid in the capsid protein corresponding to amino acid 706 of SEQ ID NO: 16 is C; or, the amino acid in the capsid protein corresponding to amino acid 718 of SEQ ID NO: 16 is G. In certain embodiments, the amino acid in the capsid protein corresponding to amino acid 626 of SEQ ID NO: 16 is G, and the amino acid in the capsid protein corresponding to amino acid 718 of SEQ ID NO: 16 is G. In certain embodiments, the amino acid in the capsid protein corresponding to amino acid 296 of SEQ ID NO: 16 is H, the amino acid in the capsid protein corresponding to amino acid 464 of SEQ ID NO: 16 is N, the amino acid in the capsid protein corresponding to amino acid 505 of SEQ ID NO: 16 is R, and the amino acid in the capsid protein corresponding to amino acid 681 of SEQ ID NO: 16 is M. In certain embodiments, the amino acid in the capsid protein corresponding to amino acid 505 of SEQ ID NO: 16 is R, and the amino acid in the capsid protein corresponding to amino acid 687 of SEQ ID NO: 16 is R. In certain embodiments, the amino acid in the capsid protein corresponding to amino acid 346 of SEQ ID NO: 16 is A, and the amino acid in the capsid protein corresponding to amino acid 505 of SEQ ID NO: 16 is R. In certain embodiments, the amino acid in the capsid protein corresponding to amino acid 501 of SEQ ID NO: 16 is I, the amino acid in the capsid protein corresponding to amino acid 505 of SEQ ID NO: 16 is R, and the amino acid in the capsid protein corresponding to amino acid 706 of SEQ ID NO: 16 is C. In certain embodiments, the capsid protein comprises the amino acid sequence of amino acids 138-736 of SEQ ID NO: 1, 2, 3, 4, 5, 6, 7, 8, 9, 10, 11, 12, 13, 15, 16, or 17.

For example, in certain embodiments, the capsid protein comprises an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the amino acid sequence of amino acids 1-736 of SEQ ID NO: 1, 2, 3, 4, 5, 6, 7, 8, 9, 10, 11, 12, 13, 15, 16, or 17. In certain embodiments, the capsid protein comprises an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the amino acid sequence of amino acids 1-736 of SEQ ID NO: 1, 2, 3, 4, 5, 6, 7, 8, 9, 10, 11, 12, 13, 15, 16, or 17, wherein: the amino acid in the capsid protein corresponding to amino acid 2 of SEQ ID NO: 16 is T; the amino acid in the capsid protein corresponding to amino acid 65 of SEQ ID NO: 16 is I; the amino acid in the capsid protein corresponding to amino acid 68 of SEQ ID NO: 16 is V; the amino acid in the capsid protein corresponding to amino acid 77 of SEQ ID NO: 16 is R; the amino acid in the capsid protein corresponding to amino acid 119 of SEQ ID NO: 16 is L; the amino acid in the capsid protein corresponding to amino acid 151 of SEQ ID NO: 16 is R; the amino acid in the capsid protein corresponding to amino acid 160 of SEQ ID NO: 16 is D; the amino acid in the capsid protein corresponding to amino acid 206 of SEQ ID NO: 16 is C; the amino acid in the capsid protein corresponding to amino acid 296 of SEQ ID NO: 16 is H; the amino acid in the capsid protein corresponding to amino acid 312 of SEQ ID NO: 16 is Q; the amino acid in the capsid protein corresponding to amino acid 346 of SEQ ID NO: 16 is A; the amino acid in the capsid protein corresponding to amino acid 464 of SEQ ID NO: 16 is N; the amino acid in the capsid protein corresponding to amino acid 468 of SEQ ID NO: 16 is S; the amino acid in the capsid protein corresponding to amino acid 501 of SEQ ID NO: 16 is I; the amino acid in the capsid protein corresponding to amino acid 505 of SEQ ID NO: 16 is R; the amino acid in the capsid protein corresponding to amino acid 590 of SEQ ID NO: 16 is R; the amino acid in the capsid protein corresponding to amino acid 626 of SEQ ID NO: 16 is G or Y; the amino acid in the capsid protein corresponding to amino acid 681 of SEQ ID NO: 16 is M; the amino acid in the capsid protein corresponding to amino acid 687 of SEQ ID NO: 16 is R; the amino acid in the capsid protein corresponding to amino acid 690 of SEQ ID NO: 16 is K; the amino acid in the capsid protein corresponding to amino acid 706 of SEQ ID NO: 16 is C; or, the amino acid in the capsid protein corresponding to amino acid 718 of SEQ ID NO: 16 is G. In certain embodiments, the amino acid in the capsid protein corresponding to amino acid 2 of SEQ ID NO: 16 is T, and the amino acid in the capsid protein corresponding to amino acid 312 of SEQ ID NO: 16 is Q. In certain embodiments, the amino acid in the capsid protein corresponding to amino acid 65 of SEQ ID NO: 16 is I, and the amino acid in the capsid protein corresponding to amino acid 626 of SEQ ID NO: 16 is Y. In certain embodiments, the amino acid in the capsid protein corresponding to amino acid 77 of SEQ ID NO: 16 is R, and the amino acid in the capsid protein corresponding to amino acid 690 of SEQ ID NO: 16 is K. In certain embodiments, the amino acid in the capsid protein corresponding to amino acid 119 of SEQ ID NO: 16 is L, and the amino acid in the capsid protein corresponding to amino acid 468 of SEQ ID NO: 16 is S. In certain embodiments, the amino acid in the capsid protein corresponding to amino acid 626 of SEQ ID NO: 16 is G, and the amino acid in the capsid protein corresponding to amino acid 718 of SEQ ID NO: 16 is G. In certain embodiments, the amino acid in the capsid protein corresponding to amino acid 296 of SEQ ID NO: 16 is H, the amino acid in the capsid protein corresponding to amino acid 464 of SEQ ID NO: 16 is N, the amino acid in the capsid protein corresponding to amino acid 505 of SEQ ID NO: 16 is R, and the amino acid in the capsid protein corresponding to amino acid 681 of SEQ ID NO: 16 is M. In certain embodiments, the amino acid in the capsid protein corresponding to amino acid 505 of SEQ ID NO: 16 is R, and the amino acid in the capsid protein corresponding to amino acid 687 of SEQ ID NO: 16 is R. In certain embodiments, the amino acid in the capsid protein corresponding to amino acid 346 of SEQ ID NO: 16 is A, and the amino acid in the capsid protein corresponding to amino acid 505 of SEQ ID NO: 16 is R. In certain embodiments, the amino acid in the capsid protein corresponding to amino acid 501 of SEQ ID NO: 16 is I, the amino acid in the capsid protein corresponding to amino acid 505 of SEQ ID NO: 16 is R, and the amino acid in the capsid protein corresponding to amino acid 706 of SEQ ID NO: 16 is C. In certain embodiments, the capsid protein comprises the amino acid sequence of amino acids 1-736 of SEQ ID NO: 1, 2, 3, 4, 5, 6, 7, 8, 9, 10, 11, 12, 13, 15, 16, or 17.

In certain embodiments, the AAV capsid comprises two or more of: (a) a capsid protein comprising the amino acid sequence of amino acids 203-736 of SEQ ID NO: 1, 2, 3, 4, 6, 7, 10, 11, 12, 13, 15, 16, or 17; (b) a capsid protein comprising the amino acid sequence of amino acids 138-736 of SEQ ID NO: 1, 2, 3, 4, 5, 6, 7, 9, 10, 11, 12, 13, 15, 16, or 17; and (c) a capsid protein comprising the amino acid sequence of amino acids 1-736 of SEQ ID NO: 1, 2, 3, 4, 5, 6, 7, 8, 9, 10, 11, 12, 13, 15, 16, or 17. In certain embodiments, the AAV capsid comprises: (a) a capsid protein having an amino acid sequence consisting of amino acids 203-736 of SEQ ID NO: 1, 2, 3, 4, 6, 7, 10, 11, 12, 13, 15, 16, or 17; (b) a capsid protein having an amino acid sequence consisting of amino acids 138-736 of SEQ ID NO: 1, 2, 3, 4, 5, 6, 7, 9, 10, 11, 12, 13, 15, 16, or 17; and (c) a capsid protein having an amino acid sequence consisting of amino acids 1-736 of SEQ ID NO: 1, 2, 3, 4, 5, 6, 7, 8, 9, 10, 11, 12, 13, 15, 16, or 17.

In certain embodiments, the AAV capsid comprises one or more of: (a) a capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with the sequence of amino acids 203-736 of SEQ ID NO: 8; (b) a capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with the sequence of amino acids 138-736 of SEQ ID NO: 8; and (c) a capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with the sequence of amino acids 1-736 of SEQ ID NO: 8. In certain embodiments, the AAV capsid comprises one or more of: (a) a capsid protein comprising the amino acid sequence of amino acids 203-736 of SEQ ID NO: 8; (b) a capsid protein comprising the amino acid sequence of amino acids 138-736 of SEQ ID NO: 8; and (c) a capsid protein comprising the amino acid sequence of amino acids 1-736 of SEQ ID NO: 8. In certain embodiments, the AAV capsid comprises two or more of: (a) a capsid protein comprising the amino acid sequence of amino acids 203-736 of SEQ ID NO: 8; (b) a capsid protein comprising the amino acid sequence of amino acids 138-736 of SEQ ID NO: 8; and (c) a capsid protein comprising the amino acid sequence of amino acids 1-736 of SEQ ID NO: 8. In certain embodiments, the AAV capsid comprises: (a) a capsid protein having an amino acid sequence consisting of amino acids 203-736 of SEQ ID NO: 8; (b) a capsid protein having an amino acid sequence consisting of amino acids 138-736 of SEQ ID NO: 8; and (c) a capsid protein having an amino acid sequence consisting of amino acids 1-736 of SEQ ID NO: 8.

In certain embodiments, the AAV capsid comprises one or more of: (a) a capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with the sequence of amino acids 203-736 of SEQ ID NO: 11; (b) a capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with the sequence of amino acids 138-736 of SEQ ID NO: 11; and (c) a capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with the sequence of amino acids 1-736 of SEQ ID NO: 11. In certain embodiments, the AAV capsid comprises one or more of: (a) a capsid protein comprising the amino acid sequence of amino acids 203-736 of SEQ ID NO: 11; (b) a capsid protein comprising the amino acid sequence of amino acids 138-736 of SEQ ID NO: 11; and (c) a capsid protein comprising the amino acid sequence of amino acids 1-736 of SEQ ID NO: 11. In certain embodiments, the AAV capsid comprises two or more of: (a) a capsid protein comprising the amino acid sequence of amino acids 203-736 of SEQ ID NO: 11; (b) a capsid protein comprising the amino acid sequence of amino acids 138-736 of SEQ ID NO: 11; and (c) a capsid protein comprising the amino acid sequence of amino acids 1-736 of SEQ ID NO: 11. In certain embodiments, the AAV capsid comprises: (a) a capsid protein having an amino acid sequence consisting of amino acids 203-736 of SEQ ID NO: 11; (b) a capsid protein having an amino acid sequence consisting of amino acids 138-736 of SEQ ID NO: 11; and (c) a capsid protein having an amino acid sequence consisting of amino acids 1-736 of SEQ ID NO: 11.

In certain embodiments, the AAV capsid comprises one or more of: (a) a capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with the sequence of amino acids 203-736 of SEQ ID NO: 13; (b) a capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with the sequence of amino acids 138-736 of SEQ ID NO: 13; and (c) a capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with the sequence of amino acids 1-736 of SEQ ID NO: 13. In certain embodiments, the AAV capsid comprises one or more of: (a) a capsid protein comprising the amino acid sequence of amino acids 203-736 of SEQ ID NO: 13; (b) a capsid protein comprising the amino acid sequence of amino acids 138-736 of SEQ ID NO: 13; and (c) a capsid protein comprising the amino acid sequence of amino acids 1-736 of SEQ ID NO: 13. In certain embodiments, the AAV capsid comprises two or more of: (a) a capsid protein comprising the amino acid sequence of amino acids 203-736 of SEQ ID NO: 13; (b) a capsid protein comprising the amino acid sequence of amino acids 138-736 of SEQ ID NO: 13; and (c) a capsid protein comprising the amino acid sequence of amino acids 1-736 of SEQ ID NO: 13. In certain embodiments, the AAV capsid comprises: (a) a capsid protein having an amino acid sequence consisting of amino acids 203-736 of SEQ ID NO: 13; (b) a capsid protein having an amino acid sequence consisting of amino acids acids 138-736 of SEQ ID NO: 13; and (c) a capsid protein having an amino acid sequence consisting of amino acids 1-736 of SEQ ID NO: 13.

In certain embodiments, the AAV capsid comprises one or more of: (a) a capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the sequence of amino acids 203-736 of SEQ ID NO: 16; (b) a capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the sequence of amino acids 138-736 of SEQ ID NO: 16; and (c) a capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the sequence of amino acids 1-736 of SEQ ID NO: 16. In certain embodiments, the AAV capsid comprises one or more of: (a) a capsid protein comprising the amino acid sequence of amino acids 203-736 of SEQ ID NO: 16; (b) a capsid protein comprising the amino acid sequence of amino acids 138-736 of SEQ ID NO: 16; and (c) a capsid protein comprising the amino acid sequence of amino acids 1-736 of SEQ ID NO: 16. In certain embodiments, the AAV capsid comprises two or more of: (a) a capsid protein comprising the amino acid sequence of amino acids 203-736 of SEQ ID NO: 16; (b) a capsid protein comprising the amino acid sequence of amino acids 138-736 of SEQ ID NO: 16; and (c) a capsid protein comprising the amino acid sequence of amino acids 1-736 of SEQ ID NO: 16. In certain embodiments, the AAV capsid comprises: (a) a capsid protein having an amino acid sequence consisting of amino acids 203-736 of SEQ ID NO: 16; (b) a capsid protein having an amino acid sequence consisting of amino acids 138-736 of SEQ ID NO: 16; and (c) a capsid protein having an amino acid sequence consisting of amino acids 1-736 of SEQ ID NO: 16.

EXAMPLES

The following examples are offered by way of illustration, and not by way of limitation.

Example 1: Optimization of AEX Process: $MgCl_2$ and Ammonium Acetate

In order to investigate the impact of magnesium chloride ($MgCl_2$) on the AEX process, the presence of $MgCl_2$ in the mixture (e.g., load composition) that was applied to the AEX medium was tested for its ability to improve the separation of intact AAV particles from AAV particles that lack a complete genome (e.g., empty capsids).

Representative AAV affinity chromatography product was used as starting material and the AEX media used were 0.2 mL Natrix® Q anion exchange chromatography membranes (Millipore Sigma). A load challenge of 1.5E15 capsids/mL membrane volume was used.

A comparison was made between a process that included Bis-Tris Propane and sodium chloride (BTP/NaCl) in the load composition and wash steps, with 5.7 mM $MgCl_2$ or without $MgCl_2$ in the load composition. The product was eluted in a Sodium Chloride gradient (BTP/NaCl) of increasing conductivity. FIG. 1A shows a chromatographic overlay of the gradient elution profiles obtained from a +BTP/NaCl process run with 5.7 mM $MgCl_2$ in the load composition and a +BTP/NaCl process run without $MgCl_2$ in the load composition. The elution profile of the +BTP/NaCl process run with 5.7 mM $MgCl_2$ in the load composition showed one single first peak with significant tailing and no discernable second peak. The +BTP/NaCl process run without $MgCl_2$ in the load composition resulted in about 24% empty capsids in the product peak, compared to about 45% empty capsids in the product peak that resulted from the +BTP/NaCl process run with 5.7 mM $MgCl_2$ in the load composition. This data is summarized in Table 1.

TABLE 1

Summary of analytical data

| Condition | % Empty capsids |
|---|---|
| +BTP/NaCl without $MgCl_2$ in the load composition | 23.6% |
| +BTP/NaCl with 5.7 mM $MgCl_2$ in the load composition | 44.7% |
| +AmAc without $MgCl_2$ in the load composition | 16.5% |
| +AmAc with 5.7 mM $MgCl_2$ in the load composition | 7.9% |

A comparison was made between a process that included ammonium acetate (AmAc) in the load composition and wash steps, with or without $MgCl_2$ in the load composition, and a control process that included Bis-Tris Propane and sodium chloride (BTP/NaCl) in the load composition and wash steps, with or without $MgCl_2$ in the load composition.

Figure 1B:
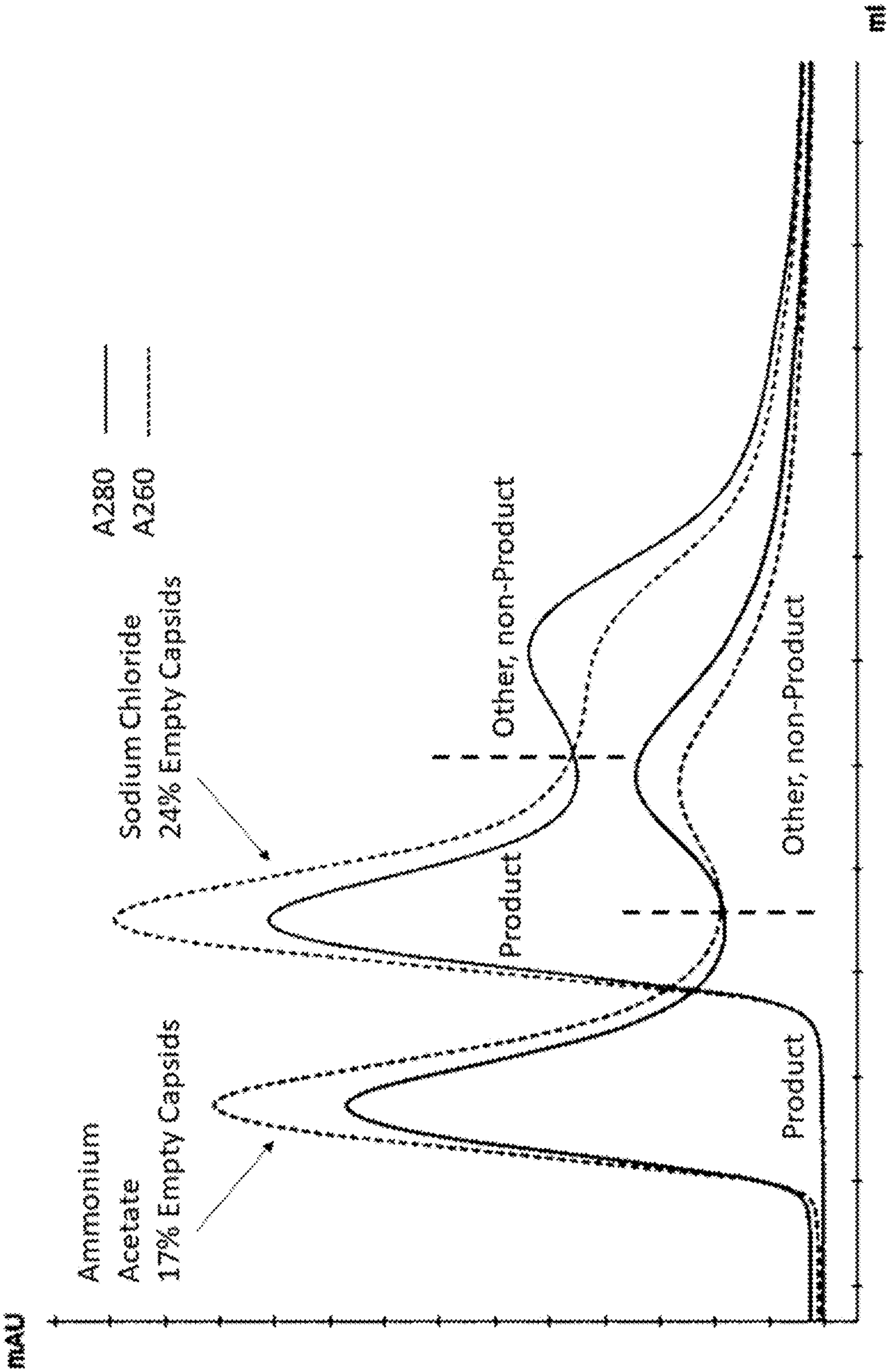
FIG. 1B is a plot showing the chromatographic overlay of the elution profiles obtained from an AEX process to separate intact AAV particles from empty capsids that included ammonium acetate (AmAc) in the load composition and wash steps, and an AEX process that included Bis-Tris Propane and sodium chloride (BTP/NaCl) in the load composition and wash steps.

FIG. 1B shows a chromatographic overlay of the gradient elution profiles obtained from AEX processes run using load compositions, wash and elution steps that contained AmAc (+AmAc) or BTP/NaCl (+BTP/NaCl). The product was eluted in an Ammonium Acetate gradient (+AmAc) or a Sodium Chloride gradient (+BTP/NaCl) of increasing conductivity. It was found that the +AmAc process run resulted in significantly improved resolution between the first (product) peak and the second peak. As shown in FIG. 1B and Table 1, the full peak area of the +BTP/NaCl process run was about 10% larger than the peak area of the +AmAc run, however, the increased recovery appeared to be at the expense of enrichment. The +AmAc run resulted in about 17% empty capsids in the product peak compared to about 24% empty capsids in the product peak that resulted from the +BTP/NaCl run. Taken together, this shows that the presence of ammonium acetate in the load and elution results in increased peak resolution and increased purity.

Figure 1C:
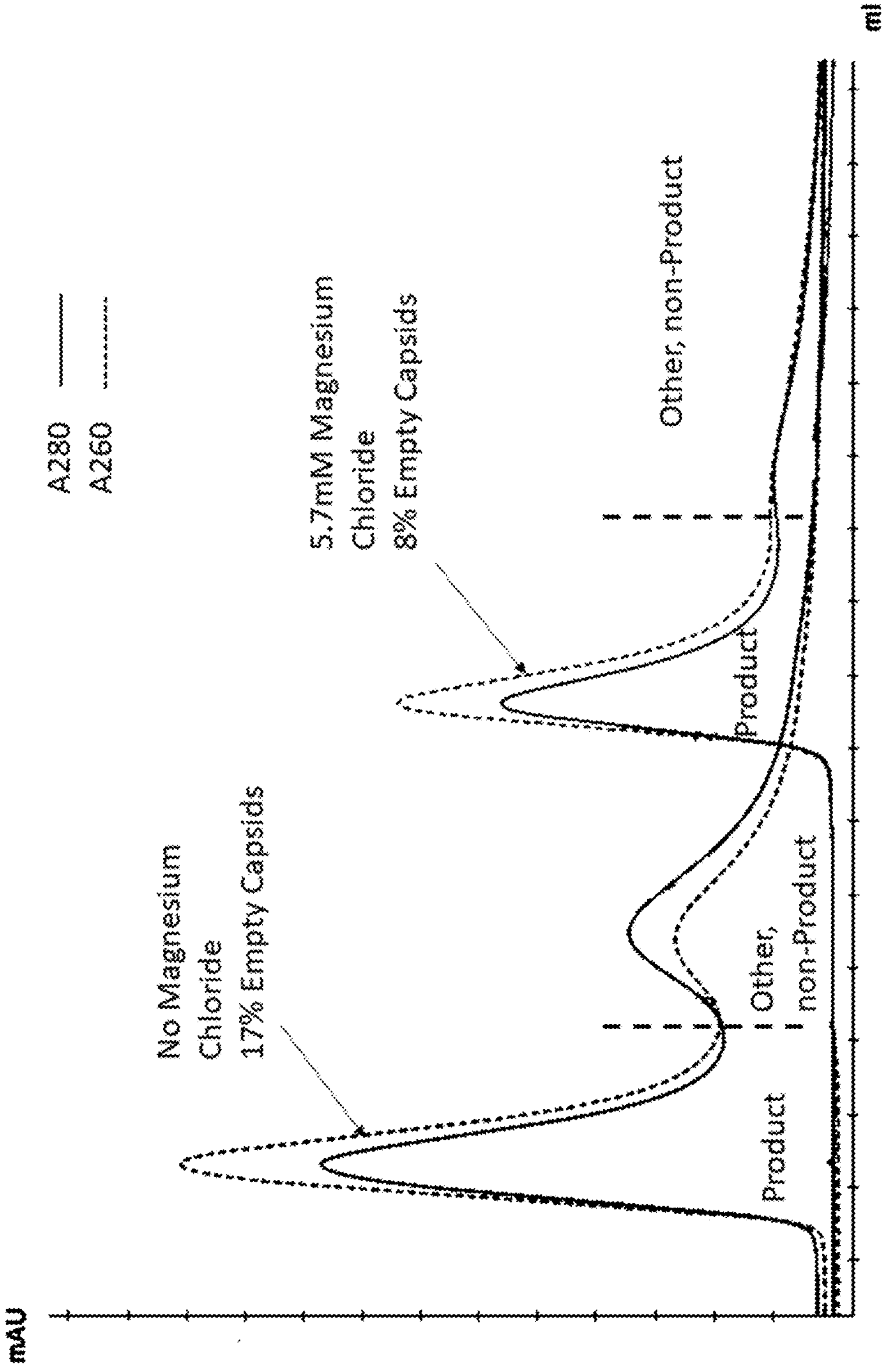
FIG. 1C is a plot showing the chromatographic overlay of the elution profiles obtained from an AEX process that included AmAc in the load composition and wash steps, with 5.7 mM $MgCl_2$, or without $MgCl_2$ in the load composition.
Figure 1D:
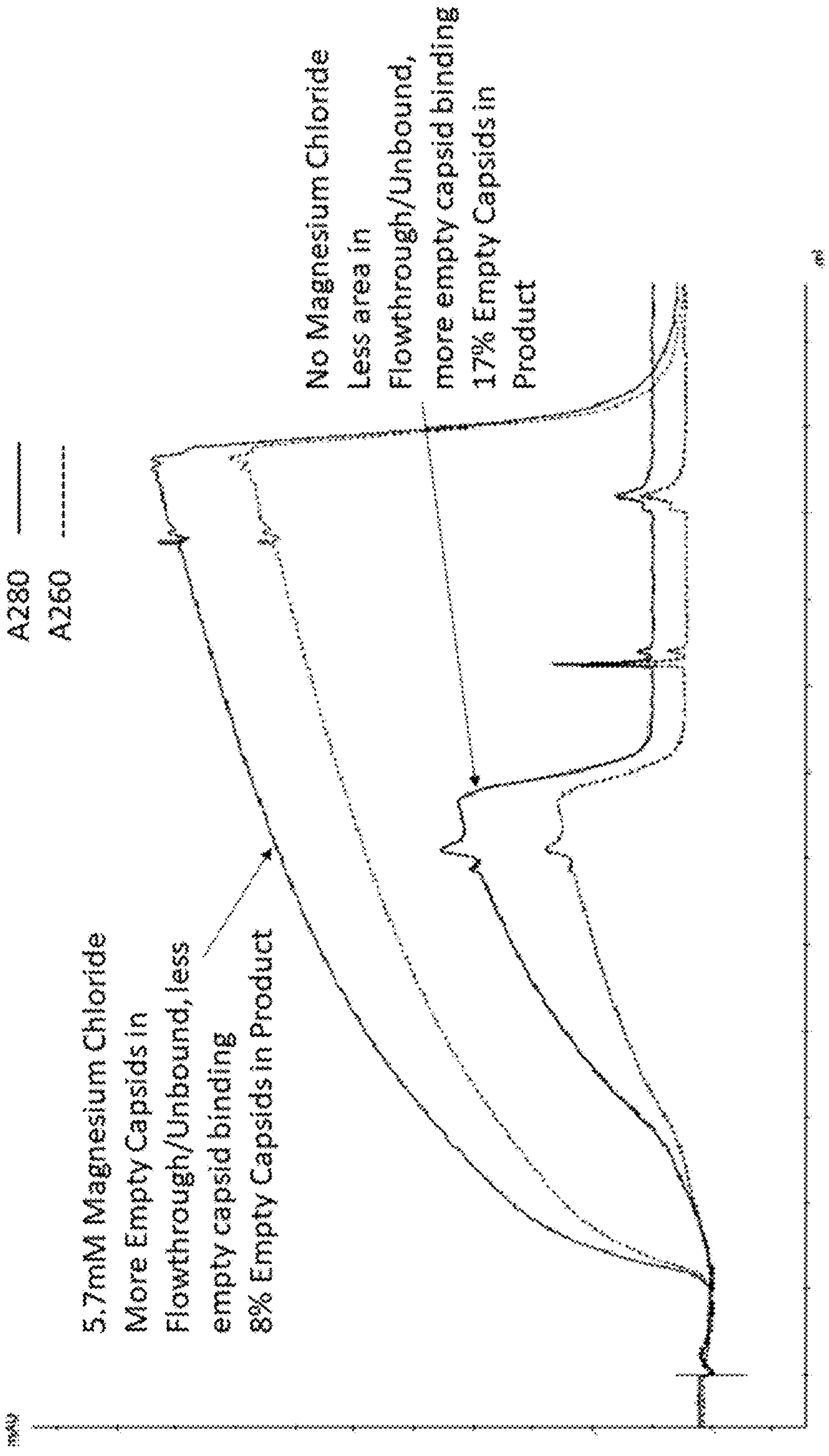
FIG. 1D is a plot showing the chromatographic profiles of samples collected from the flowthrough and wash (FT/Wash) steps of AEX processes that included ammonium acetate in the load composition and wash steps, with or without 5.7 mM $MgCl_2$ in the load composition.

Next, a comparison was made between +AmAc process runs with or without $MgCl_2$ in the load composition. FIG. 1C shows a chromatographic overlay of the gradient elution profiles obtained from a +AmAc process run with 5.7 mM $MgCl_2$ in the load composition, and a +AmAc process run without $MgCl_2$ in the load composition. The product was eluted in an Ammonium Acetate gradient (+AmAc) of increasing conductivity As shown in FIG. 1C and Table 1, the +AmAc process run without MgCl2 in the load composition resulted in about 17% empty capsids in the product peak, compared to about 8% empty capsids in the product peak that resulted from the +AmAc process run with MgCl2 in the load composition. Further, the presence of $MgCl_2$ in the load composition resulted in a reduction in the overall area of both first and second peaks. Without being bound by any theory, the decrease in peak area observed may be due to the presence of $MgCl_2$ causing significantly more capsids to flow through the AEX medium (FIG. 1D). The A260/A280 ratios of the flow through and wash step (FT/Wash) for the +AmAc process run with 5.7 mM $MgCl_2$ in the load composition and the +AmAc process run without $MgCl_2$ in the load composition are almost identical at 0.82, suggesting that the presence of $MgCl_2$ in the load composition did not change the population of capsids flowing through the AEX membrane, and that most of the unbound capsids (i.e., capsids in the flow through) were empty capsids.

Based on the foregoing, the addition of $MgCl_2$ to the load composition impacts the AEX process in different ways depending on whether BTP/NaCl or AmAc is used. Adding $MgCl_2$ to the load composition of a +BTP/NaCl process resulted in a negative impact on product enrichment. Adding $MgCl_2$ to the load composition of a +AmAc process resulted in improved purity (Table 1).

Figure 2:
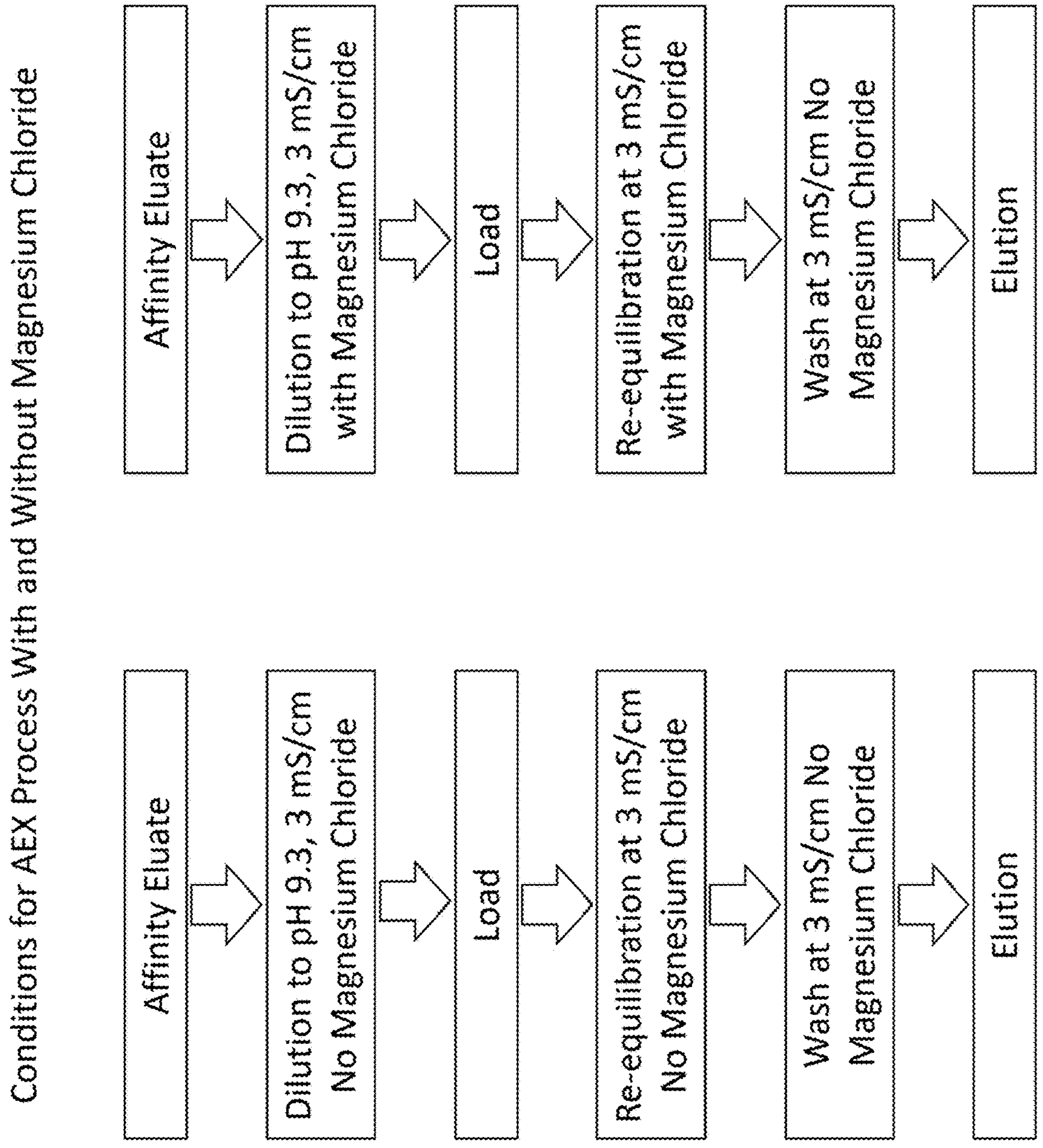
FIG. 2 shows a flow diagram of an AEX process with and without magnesium chloride.

To confirm the benefit of the addition of $MgCl_2$ to an AEX process, the presence of 2 mM $MgCl_2$ was tested in a process using a CIMmultus QA ("CIM-QA"; BIA Separations) monolith at a load challenge of 3.92E14 capsids/ml. The presence of 2 mM $MgCl_2$ in the CIM-QA load preparation as well as in the re-equilibration buffer (+$MgCl_2$) was compared to an analogous CIM-QA process in which no $MgCl_2$ was used (−$MgCl_2$). In each case, the load composition had a target pH of 9.3 and a conductivity of 3 mS/cm. FIG. 2 shows a flow diagram of the two processes.

In both conditions, the capsids were eluted with an Ammonium Acetate gradient of increasing conductivity. The conditions used are described in Table 2.

TABLE 2

Summary of conditions for CIMQ processes with and without magnesium chloride

| Process | CIM-QA Load Dilution Buffer | CIM-QA Re-Equilibration Buffer |
|---|---|---|
| 2 mM Magnesium Chloride | 29 mM Ammonium Acetate<br>0.01% Poloxamer-188<br>2 mM $MgCl_2$<br>pH 9.3 | 29 mM Ammonium Acetate<br>0.01% Poloxamer-188<br>2 mM $MgCl_2$<br>pH 9.3 |
| No Magnesium Chloride | 34 mM Ammonium Acetate<br>0.01% Poloxamer-188<br>pH 9.3 | 34 mM Ammonium Acetate<br>0.01% Poloxamer-188<br>pH 9.3 |

Figure 3:
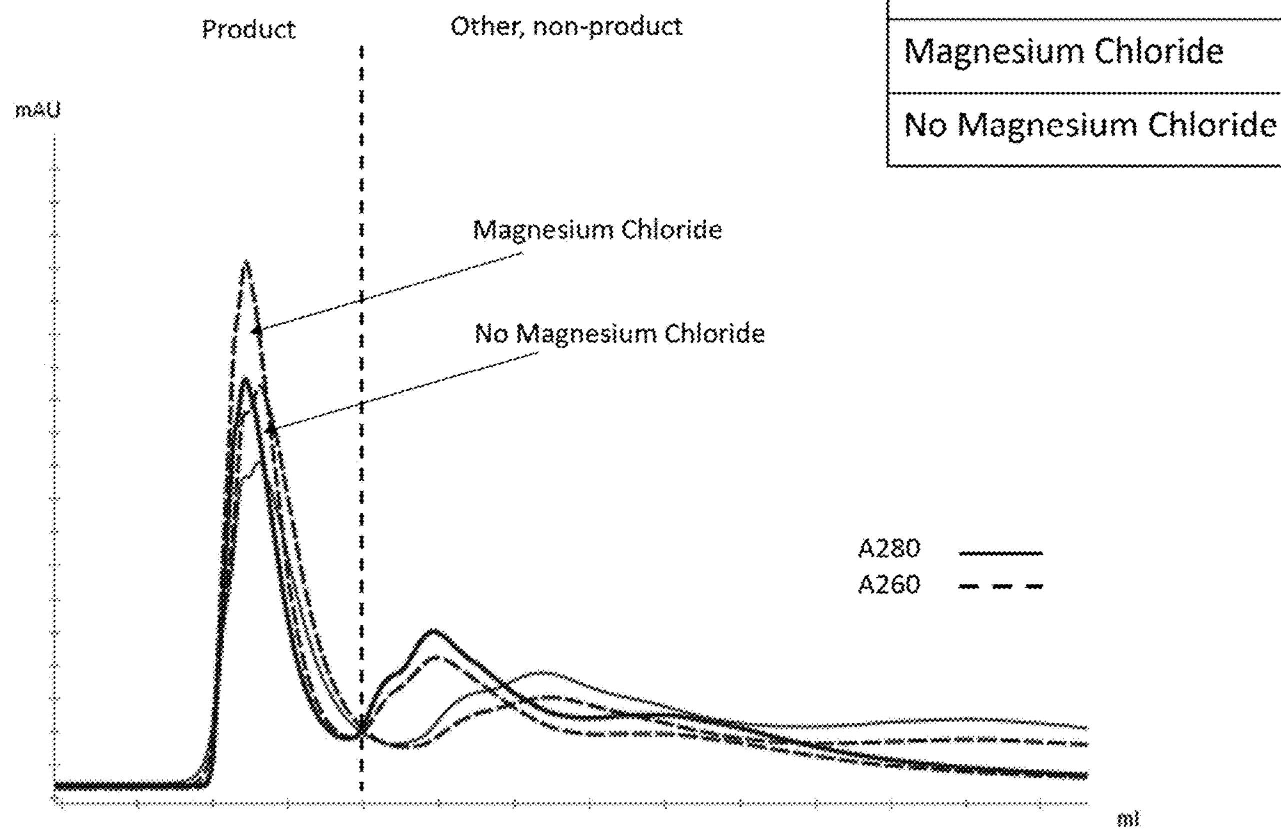
FIG. 3 is a plot showing the chromatographic overlay of elution profiles obtained from an AEX process that included magnesium chloride in both the load composition and the first wash solution, and an AEX process run that did not include magnesium chloride in the load composition and first wash solution. Profiles and axis units are identical to those described for FIGS. 1A-1D.

Chromatograms for the CIM-QA process runs with and without $MgCl_2$ in the load composition are shown in FIG. 3. FIG. 3 shows a chromatographic overlay of +$MgCl_2$ and −$MgCl_2$ CIM-QA process runs, with the elution peak magnified. As shown in FIG. 3, the CIM-QA process run without $MgCl_2$ in the load composition resulted in about 35% empty capsids in the product peak, compared to about 25% empty capsids in the product peak that resulted from the CIM-QA process run with $MgCl_2$ in the load composition. Without being bound by any theory, it is believed that magnesium chloride may diminish binding of empty capsids to the AEX media.

Example 2: Optimization of AEX Process: Wash Step Prior to Elution

Figure 4:
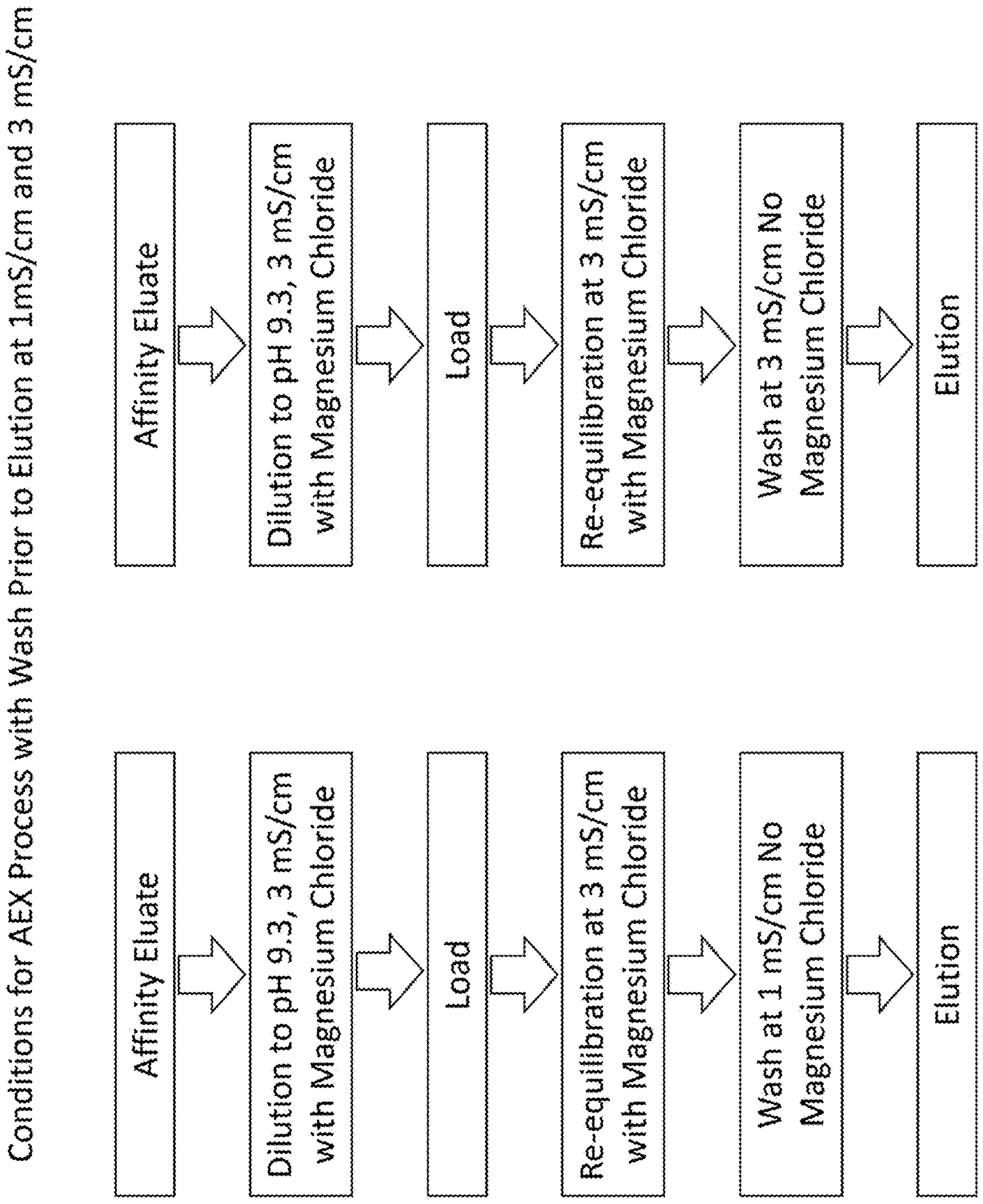
FIG. 4 is a flow diagram of an AEX process with wash prior to elution at 1 mS/cm conductivity and an AEX process with wash prior to elution at 3 mS/cm conductivity.

Based on the above findings, the presence of 2 mM $MgCl_2$ was maintained in the load composition and re-equilibration buffer. To investigate the impact of wash buffer conductivity prior to elution in an AEX process on the purity of resultant AAV drug substance, an AEX process carried out with a 3 mS/cm conductivity wash prior to elution was compared to an AEX process carried out with a 1 mS/cm conductivity wash prior to elution. FIG. 4 shows a flow diagram of the two processes. A CIM-QA monolith was challenged at 3.92E14 capsids/ml for each run and various step elution conductivities using AmAc were tested to investigate their impact on the separation of intact and empty capsids.

3 mS/cm Wash Step Prior to Elution

Elution steps at five different conductivities were tested at pH 9.3: 6.5 mS/cm, 7.0 mS/cm, 7.5 mS/cm, 8.5 mS/cm, and 9.5 mS/cm. Elution steps were performed with a 3 mS/cm wash step (second wash step) just prior to elution.

Table 3 summarizes the purification results from the elution peaks from different elution conductivities.

TABLE 3

Summary of purification results

| Step elution conductivity (mS/cm) | % Empty capsids |
|---|---|
| 6.5<br>7.0 | Did not assay due to low A260:280 ratio observed (in the range of process runs without $MgCl_2$) indicating > 30% empty capsids |
| 7.5 | 31 |
| 8.5 | 34 |
| 9.5 | 36 |

The eluates from the step elutions conducted at 6.5 and 7.0 mS/cm were not assayed as their A260:A280 ratio was under 1.21. Such ratios were similar to the −$MgCl_2$ CIM-QA process runs which resulted in >30% empty capsids as determined by analytical ultracentrifugation (AUC) analysis, a method used to quantify macromolecules based on sedimentation coefficients (see, Table 5). The percent empty capsids obtained in the elution peaks at step elutions ranging from 7.5-9.5 mS/cm (pH 9.3) was above 30% (Table 5).

1 mS/cm Wash Step Prior to Elution

Elution steps at six different conductivities with AmAc were tested at pH 9.3: 7.0 mS/cm, 8.0 mS/cm, 9.0 mS/cm, 9.5 mS/cm, 10.0 mS/cm and 11 mS/cm. To investigate if an AEX process comprising a lower conductivity wash step prior to elution would lower the percent empty capsids in the product peak, elution steps were performed with a 1 mS/cm wash step (second wash step) just prior to elution on a CIM-QA monolith challenged at 3.92E14 capsids/ml.

Table 4 summarizes the purification results from the elution peaks from different elution conductivities.

TABLE 4

Summary of purification results

| Step elution conductivity (mS/cm) | % Empty capsids |
|---|---|
| 7.5 | 14 |
| 8.0 | 12 |
| 9.0 | 14 |
| 9.5 | 16 |
| 10.0 | 28 |
| 11.0 | 32 |

As shown in Table 4, with a 1 mS/cm wash step prior to elution and 2 mM $MgCl_2$ in the load composition, most elution conductivities tested resulted in <30% empty capsids obtained from the elution peaks.

Figure 5:
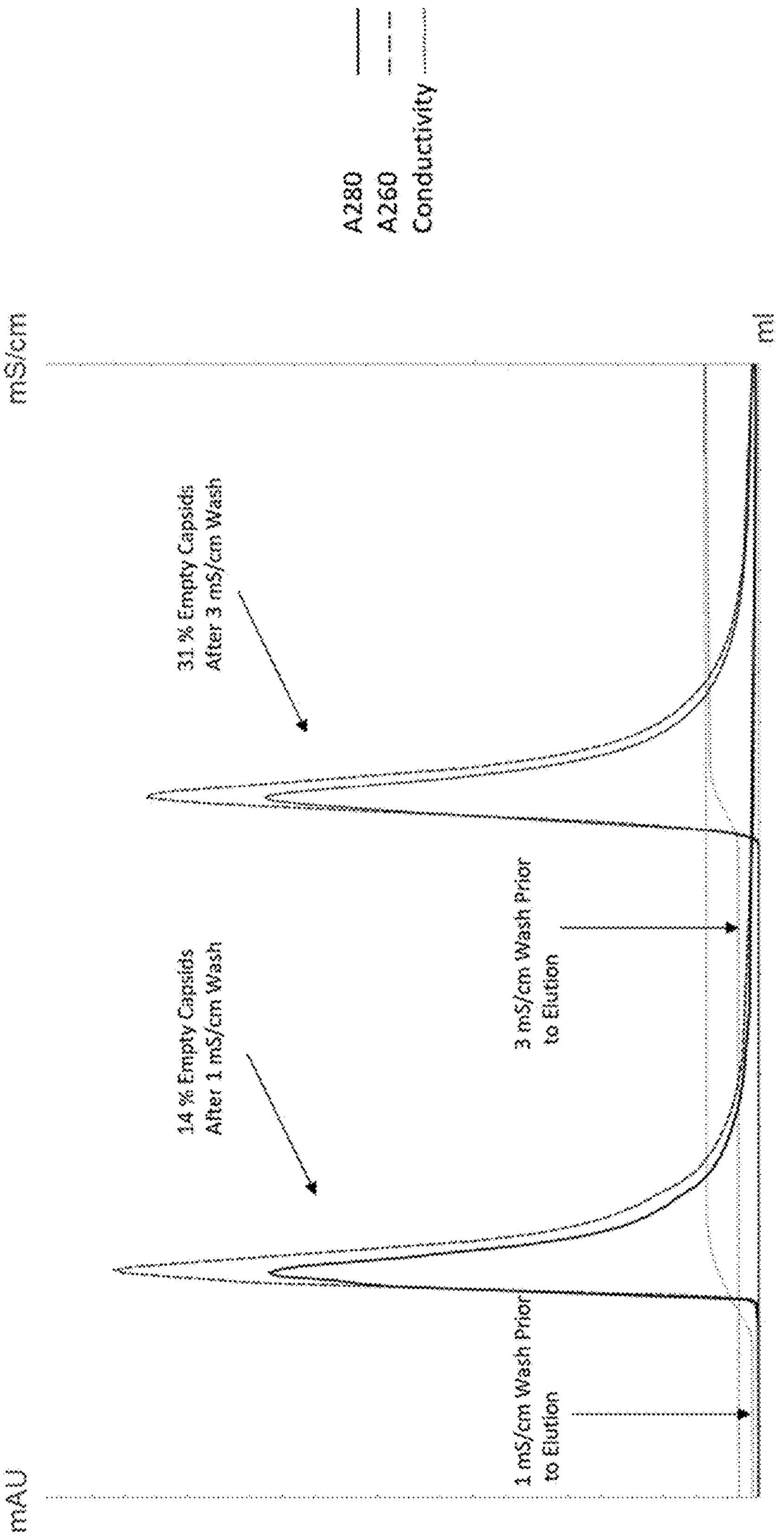
FIG. 5 is a plot showing the chromatographic overlay of the step gradient elution profiles obtained from an AEX process that included a 1 mS/cm conductivity wash prior to elution, and an AEX process that included a 3 mS/cm conductivity wash prior to elution. Profiles and axis units are identical to those described for FIGS. 1A-1D.

FIG. 5 shows a chromatographic overlay of the step gradient elution profiles obtained from an AEX process performed with a 1 mS/cm wash step prior to elution as described above, and an AEX process performed with a 3 mS/cm wash step prior to elution as described above. As shown, 14% empty capsids were recovered from an AEX process that included a 1 mS/cm wash prior to elution, compared to 31% empty capsids recovered from an AEX process that included a 3 mS/cm wash prior to elution.

The foregoing data supports an AEX process to separate empty capsids and full capsids, comprising $MgCl_2$ in the load composition, followed by a low conductivity second wash solution (1 mS/cm) prior to a linear gradient elution or step elution.

Example 3: Optimization of AEX Process: Urea Wash Step

Figure 6:
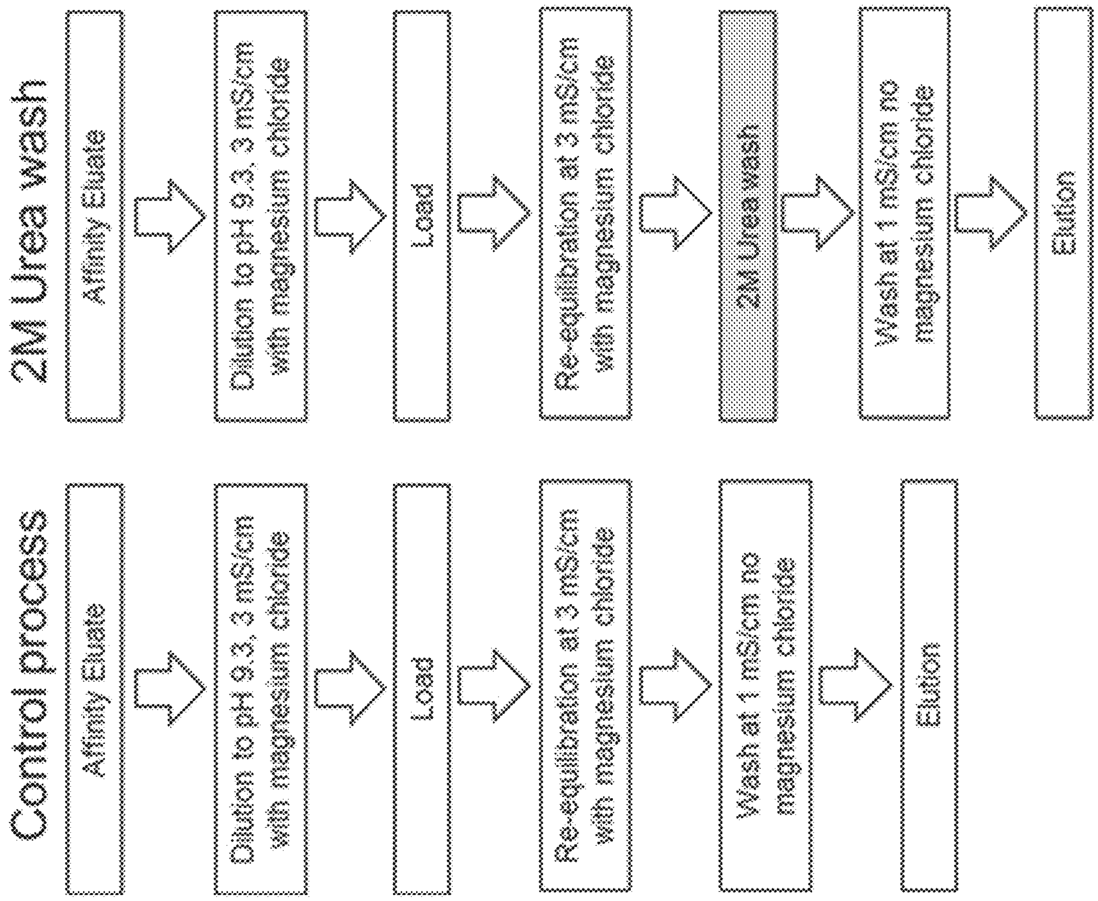
FIG. 6 is a flow diagram of an AEX process run with and without the use of a wash step with a wash solution comprising urea.

In order to investigate the impact of a urea wash step on the AEX process, an addition of a 2M urea wash step was evaluated to determine its impact on the % empty capsids obtained in the product. A comparison was made between a process that includes the 2M urea wash step and a previously established control process that did not include the 2M urea wash step (Table 5). The product in each case was eluted at pH 9.3 with a conductivity of 9.5 mS/cm using AmAc. FIG. 6 and Table 5 shows a flow diagram of the two processes.

TABLE 5

| Summary of conditions | |
|---|---|
| Control Run | 2M urea wash Run |
| No wash buffer used | 2M Urea<br>28 mM Ammonium Acetate<br>2 mM Magnesium Chloride<br>0.01% Poloxamer-188<br>pH 9.3<br>Conductivity: 3 mS/cm |

Affinity chromatography product was used as starting material and a POROS HQ column was used at a load ratio of 7E+14 capsids/ml.

Table 6 summarizes the purification results from the elution peaks comparing the control process and the process that includes a 2M urea wash step.

TABLE 6

Summary of purification results

| Condition | % Empty capsids |
|---|---|
| Control (No Urea Wash) | 26 |
| 2M Urea Wash | 12 |

Figure 7A:
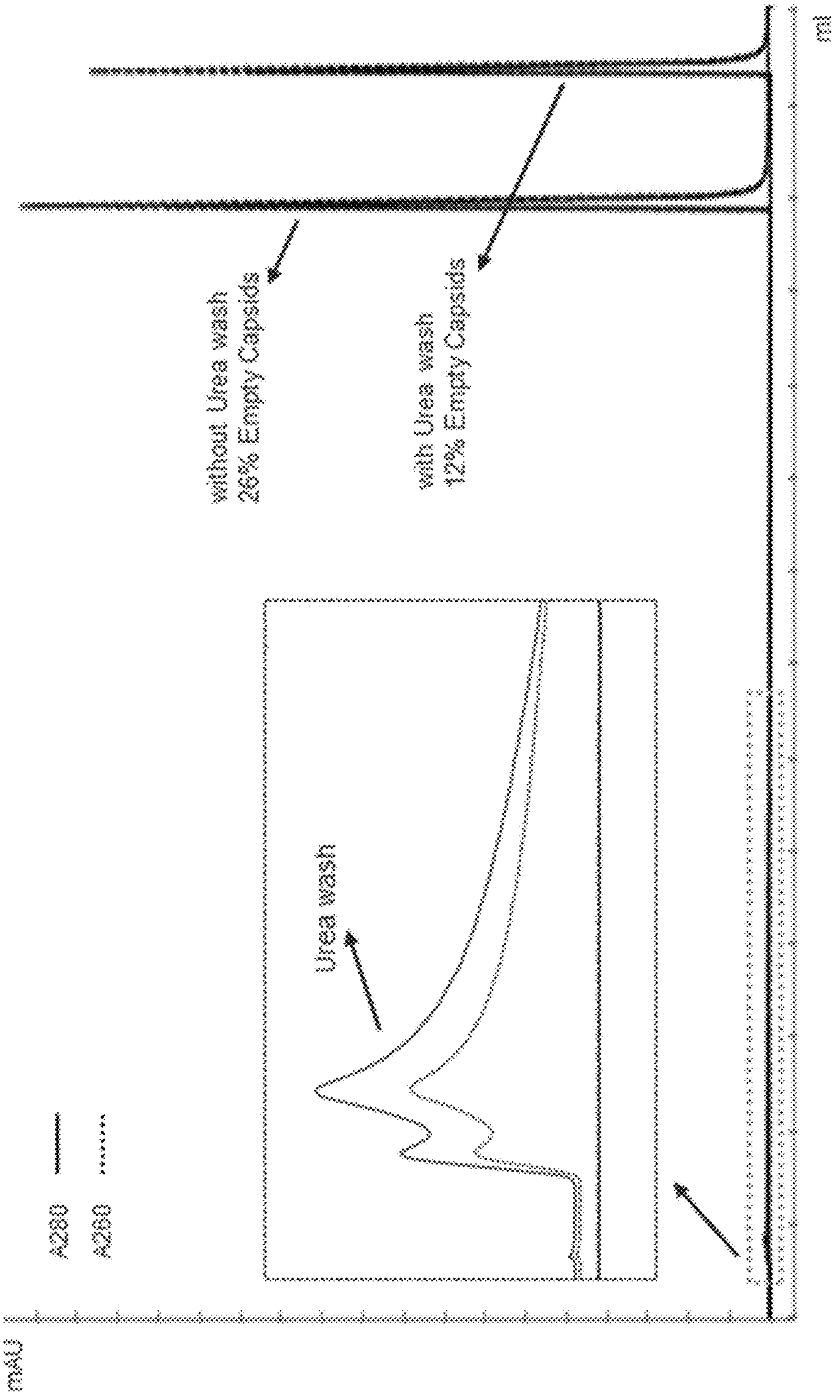
FIGS. 7A-7B are plots showing the chromatographic overlay of wash (FIG. 7A) and elution (FIG. 7B) profiles obtained from an AEX process that did not employ the use of a wash solution comprising urea and an AEX process that employed the use of a wash solution comprising urea. Profiles and axis units are identical to those described for FIGS. 1A-1D.
Figure 7B:
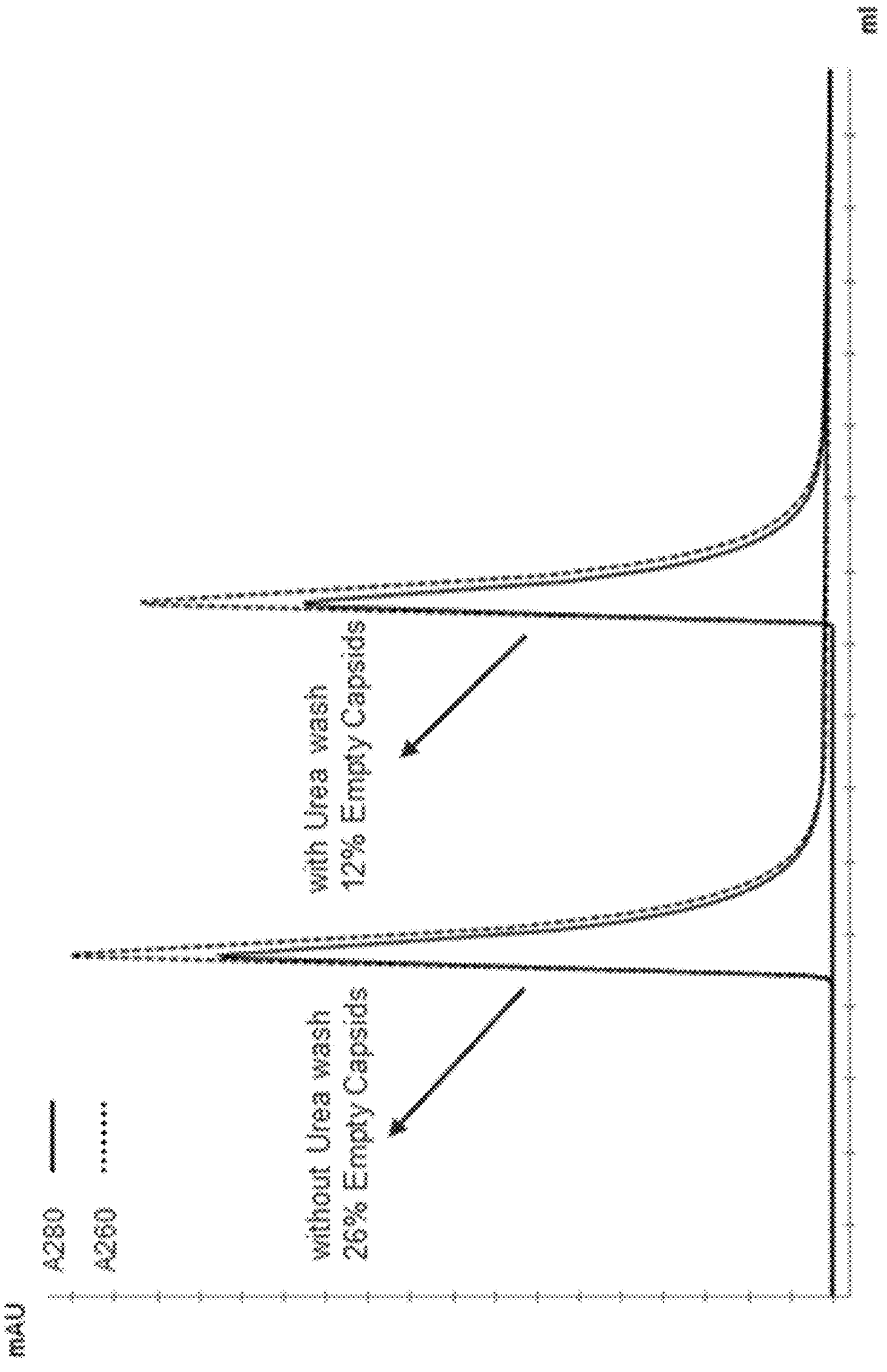

As shown in Table 6 and FIGS. 7A and 7B, the addition of a 2M urea wash step significantly improved chromatographic separation and reduced the percent of empty capsids in the product from about 26% to less than 15%. The AEX process that included a 2M urea wash step resulted in recovery of 12% empty capsids under a step elution, compared to 26% empty capsids recovered under a step elution from an AEX process that did not include a 2M urea wash step.

Taken together, it is hypothesized that the addition of the urea wash step enhanced separation by removing additional empty capsids that co-elute with the product in the first peak. Without being bound by theory, it is believed that the chaotropic nature of urea disrupts the structure of empty capsids and aids in dissociating the empty capsids from the column. This may occur by breaking down non-specific hydrogen bond interactions between the empty capsids and the AEX medium, thus facilitating desorption of empty capsids.

Example 4: Optimization of AEX Process: Choice of AEX Media

In order to investigate the effect of AEX chromatography media pore size on peak resolution, single strand (SS) and self complementary (SC) AAV vectors were processed on various AEX media as shown in Table 7.

TABLE 7

AEX Media Used

| AAV Vector Type Used | AEX Media Type | Approximate Average Pore Size (nm) |
|---|---|---|
| SC | Fractogel TMAE Hicap (M) | 80 |
| | Praesto Q | 100 |
| | Poros HQ50 | 200 |
| SS | Eshmuno Q | 80 |
| | Poros HQ50 | 200 |
| | Nuvia HP-Q | 500 |

Figure 8A:
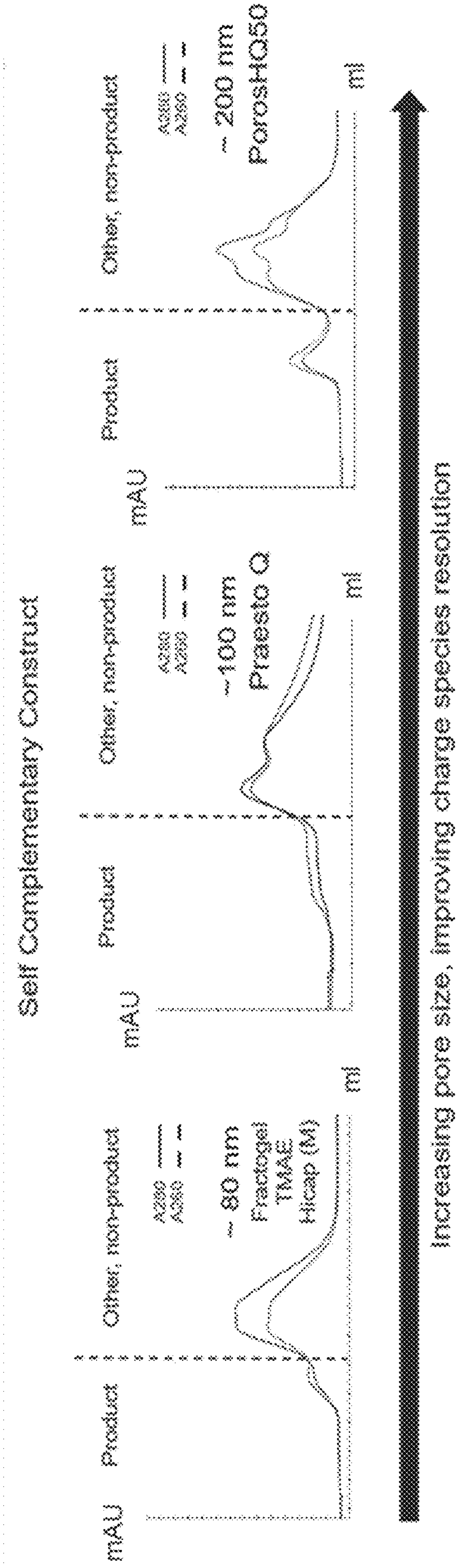
FIGS. 8A-8B are a series of elution profiles obtained from AEX process runs performed using AEX media having the indicated average pore sizes for representative AAV comprising a self-complementary vector genome (FIG. 8A) or single-stranded vector genome (FIG. 8B).
Figure 8B:
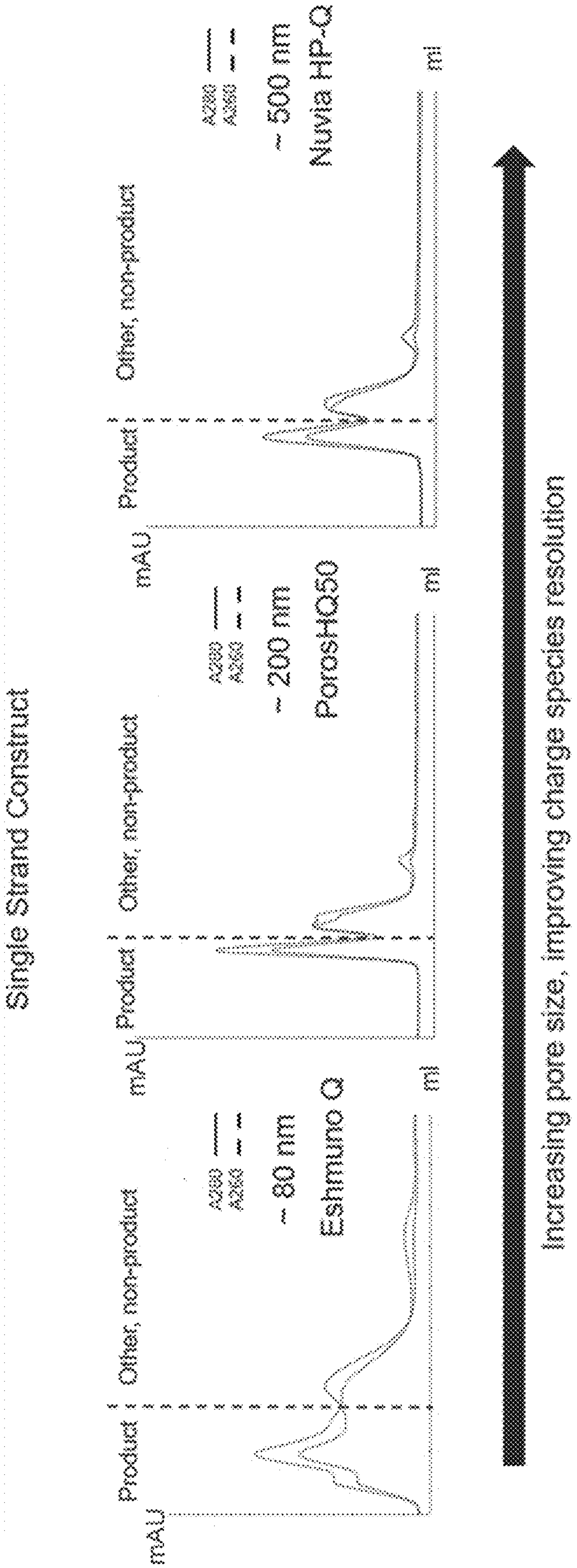

For AAV comprising self-complementary and single strand vector genome, affinity chromatography product was used as starting material. For each resin tried for self-complementary vector, the product was desorbed with an elution gradient of 10-400 mM Ammonium acetate over 60 column volumes at a 6 minute residence time. For each resin tried for single strand vector, the product was desorbed with an elution gradient of 10-1000 mM Ammonium acetate over 60 column volumes at a 3 minute residence time It was found that increasing AEX media pore size aids in the obtaining of higher quality product from the elution peak (FIGS. 8A and 8B). As shown in FIGS. 8A and 8B, improved separation performance was achieved when purifying AAV comprising single-stranded vector genomes (FIG. 8B) and AAV comprising self-complementary vector genomes (FIG. 8A).

Example 5: Optimization of AEX Process: Evaluation across AAV Capsid Serotypes In order to investigate the ability of the AEX process to separate empty capsids and full capsids for different AAV capsid serotypes, the AEX process was evaluated for AAV8, AAV9 and AAV2 capsid serotypes.

AAV8 Anion Exchange Chromatography with Linear Gradient Elution

The conditions listed in Table 8 were utilized to evaluate the anion exchange chromatography process with AAV8 vector packaged with a PAH transgene. Neutralized AAV8 affinity product was in 20.5 mM Ammonium Acetate, 2.14 mM Magnesium Chloride, 0.01% Poloxamer-188, pH 9.3 and loaded onto POROS HQ column equilibrated with a pH 9.3 and 3.0 mS/cm ammonium acetate buffer. Following the load, the column was washed with the 3.0 mS/cm equilibration buffer followed by a pH 9.3 and 1.0 mS/cm ammonium acetate buffer. Bound vector was eluted with a 10 to 400 mM ammonium acetate gradient at pH 9.3.

TABLE 8

Conditions for AAV8 Anion Exchange Chromatography with Linear Gradient Elution

| Step | Buffer Composition | CV | Residence Time (min) |
|---|---|---|---|
| Equilibration | 28 mM Ammonium Acetate, 2 mM Magnesium Chloride, 0.01% Poloxamer-188, pH 9.3 | 5 | 1 |

TABLE 8-continued

Conditions for AAV8 Anion Exchange Chromatography with Linear Gradient Elution

| Step | Buffer Composition | CV | Residence Time (min) |
|---|---|---|---|
| Sample Application | Neutralized AAV8 Affinity Product diluted in 20.5 mM Ammonium Acetate, 2.14 mM Magnesium Chloride, 0.01% Poloxamer-188, pH 9.3 | N/A | 2 |
| Wash 1 | 28 mM Ammonium Acetate, 2 mM Magnesium Chloride, 0.01% Poloxamer-188, pH 9.3 | 5 | 2 |
| Wash 2 | 10 mM Ammonium Acetate, 2 mM Magnesium Chloride, 0.01% Poloxamer-188, pH 9.3 | 5 | 2 |
| Linear Gradient Elution | 10-400 mM Ammonium Acetate, 0.01% Poloxamer-188, pH 9.3 | 60 | 3 |
| Elution Hold | 400 mM Ammonium Acetate, 0.01% Poloxamer-188, pH 9.3 | 20 | 3 |

Figure 9A:
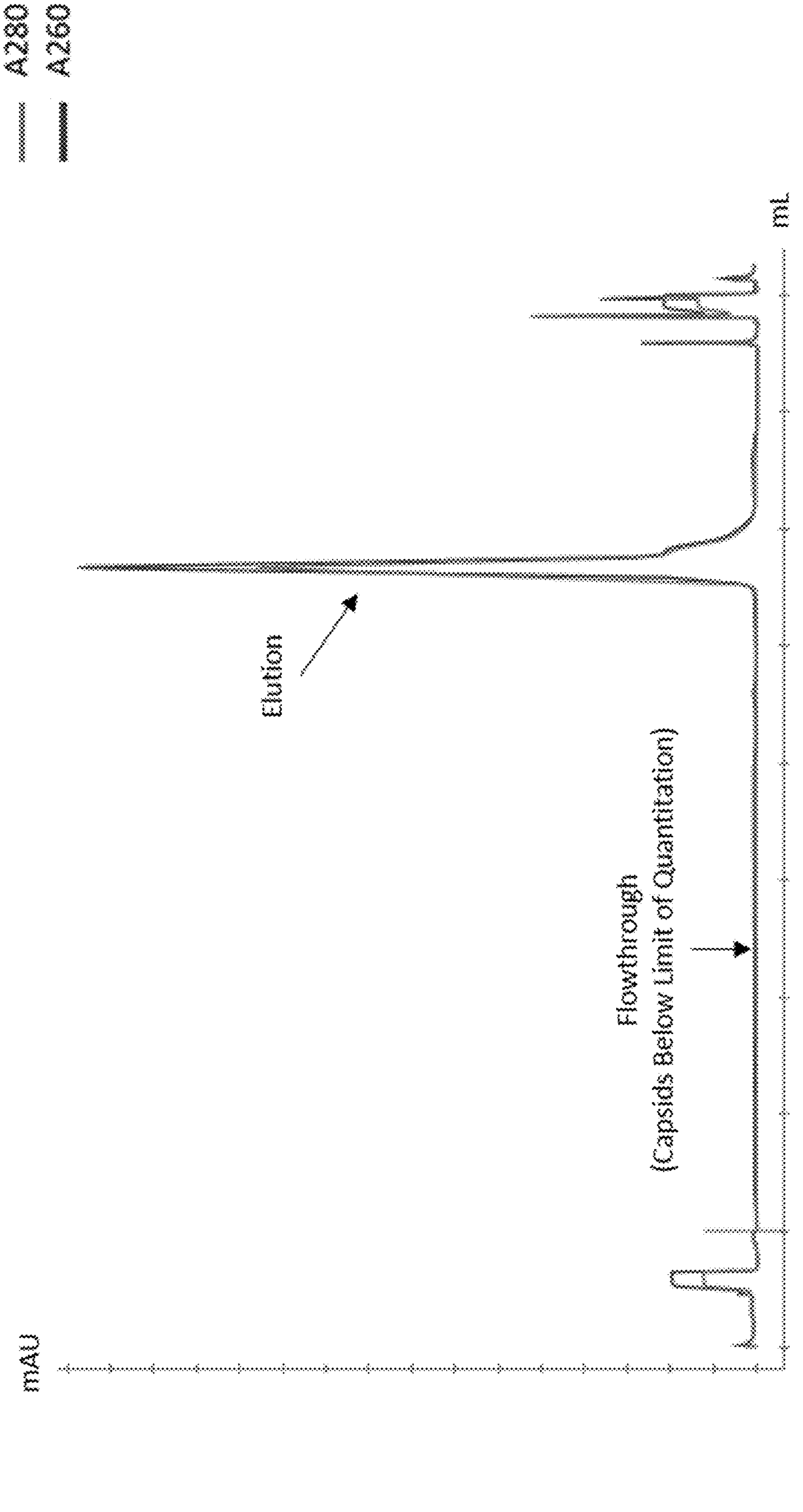
FIGS. 9A-9B are plots showing the full chromatogram (FIG. 9A) and elution profile (FIG. 9B) obtained from AEX with linear gradient elution for a representative AAV8 vector.
Figure 9B:
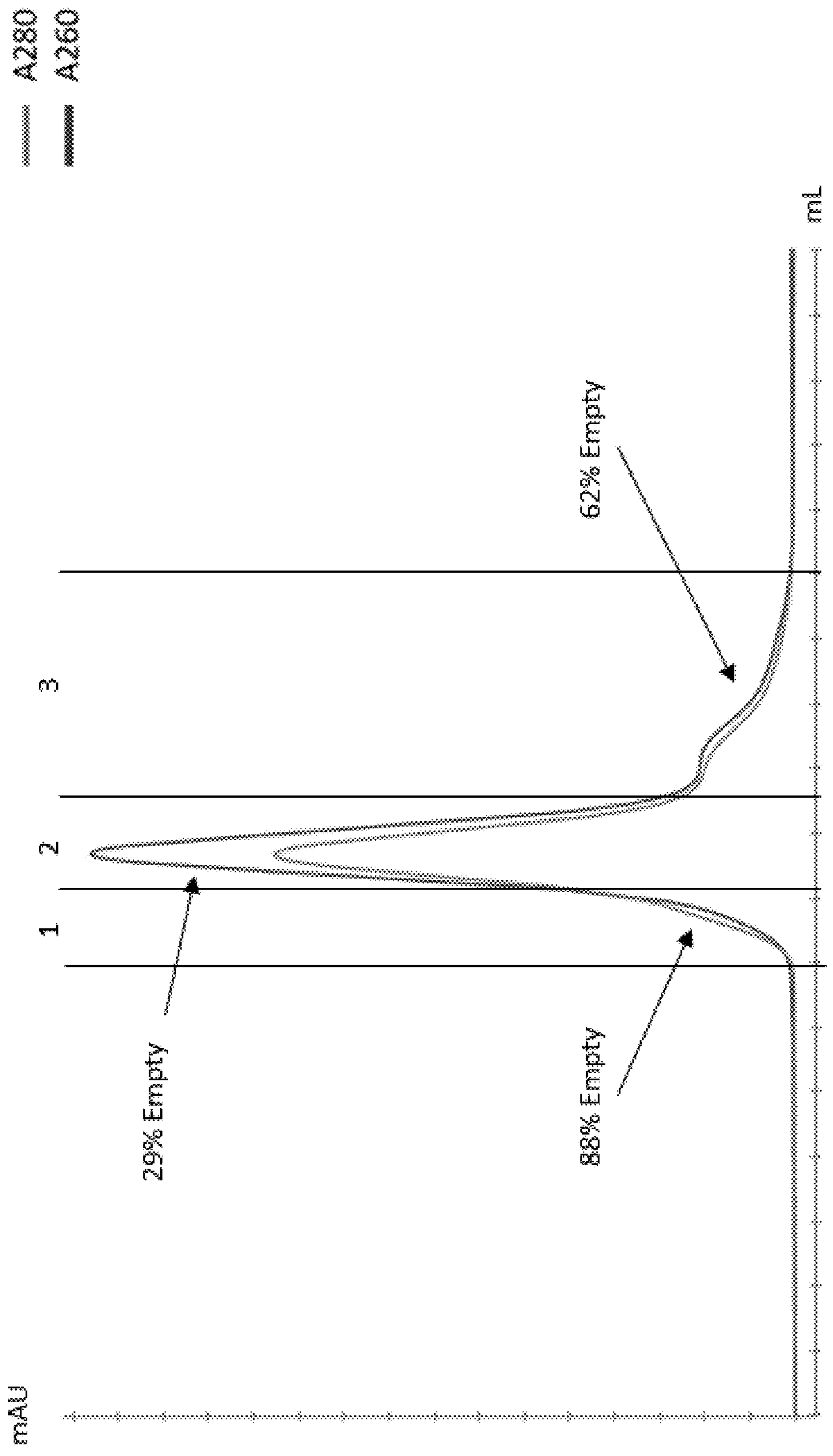

The AAV8 anion exchange purification with a linear gradient elution resulted in one elution peak that was split into three pools. The full chromatogram is shown in FIG. 9A and the elution peak profile is shown in FIG. 9B. Table 9 shows the percentage of empty capsids in the load and elution pools determined via analytical ultracentrifugation. The first pool at the front of the peak contained predominantly empty capsids. The middle of the peak, or the product pool, consisted of 29% empty capsids. The final pool at the tail of the peak contained mostly empty capsids.

TABLE 9

AAV8 Anion Exchange Chromatography with Linear Gradient Elution

| Fraction | % Empty Capsids |
|---|---|
| Load | 49% |
| Elution Pool 1 | 88% |
| Elution Pool 2 | 29% |
| Elution Pool 3 | 62% |

AAV8 Anion Exchange Chromatography with Isocratic Elution

The conditions listed in Table 10 were utilized to evaluate the anion exchange chromatography process with AAV8 vector packaged with a PAH transgene. The equilibration conditions were selected to promote weak partitioning of the empty capsids into the flowthrough and were identified from the linear gradient results in FIG. 9B. Neutralized AAV8 affinity product was diluted in a pH 9.3 and 13 mS/cm ammonium acetate buffer and loaded onto a POROS HQ column that was equilibrated with the 13 mS/cm buffer. Following the load, the column was washed with 13 mS/cm equilibration buffer followed by a pH 9.3 and 1.0 mS/cm ammonium acetate buffer. Bound vector was eluted over 5 CVs with a pH 9.3 and 19 mS/cm ammonium acetate buffer. The elution condition was identified from the linear gradient results in FIG. 9B.

TABLE 10

Conditions for AAV8 Anion Exchange Chromatography with Isocratic Elution

| Step | Buffer Composition | CV | Residence Time (min) |
|---|---|---|---|
| Equilibration | 153 mM Ammonium Acetate, 2 mM Magnesium Chloride, 0.01% Poloxamer-188, pH 9.3 | 5 | 1 |
| Sample Application | Neutralized AAV8 Affinity Product diluted in 153 mM Ammonium Acetate, 2 mM Magnesium Chloride, 0.01% Poloxamer-188, pH 9.3 | N/A | 2 |
| Wash 1 | 153 mM Ammonium Acetate, 2 mM Magnesium Chloride, 0.01% Poloxamer-188, pH 9.3 | 5 | 2 |
| Wash 2 | 10 mM Ammonium Acetate, 2 mM Magnesium Chloride, 0.01% Poloxamer-188, pH 9.3 | 5 | 2 |
| Elution | 305 mM Ammonium Acetate, 0.01% Poloxamer-188, pH 9.3 | 5 | 6 |

Figure 10A:
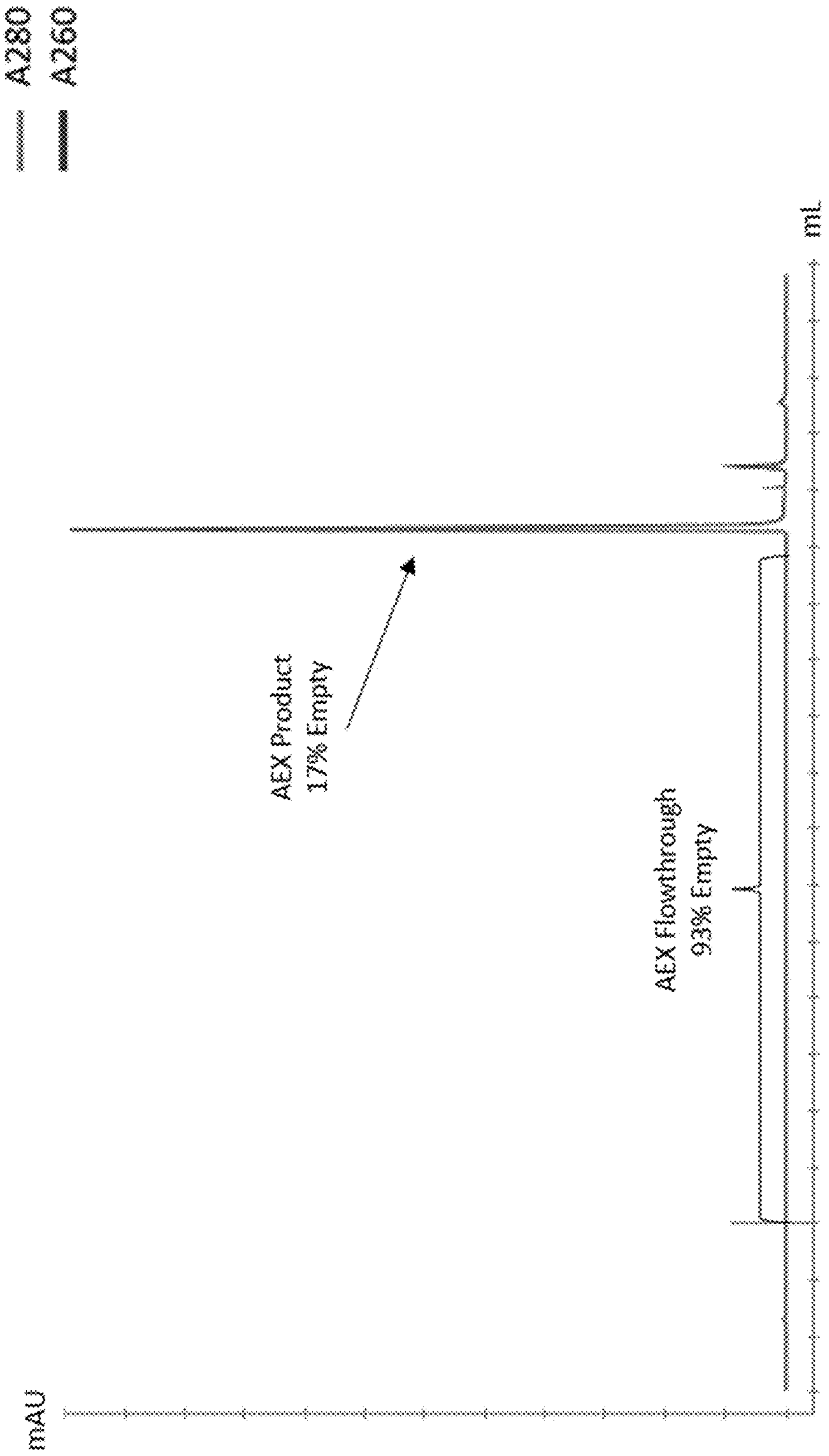
FIGS. 10A-10C are plots showing the full chromatogram (FIG. 10A) and elution profiles (FIGS. 10B-C) obtained from AEX with isocratic elution for a representative AAV8 vector. The elution profile is shown for the AEX process performed with the 13 mS/cm load condition relative to a 3 mS/cm load condition (FIG. 10C).
Figure 10B:
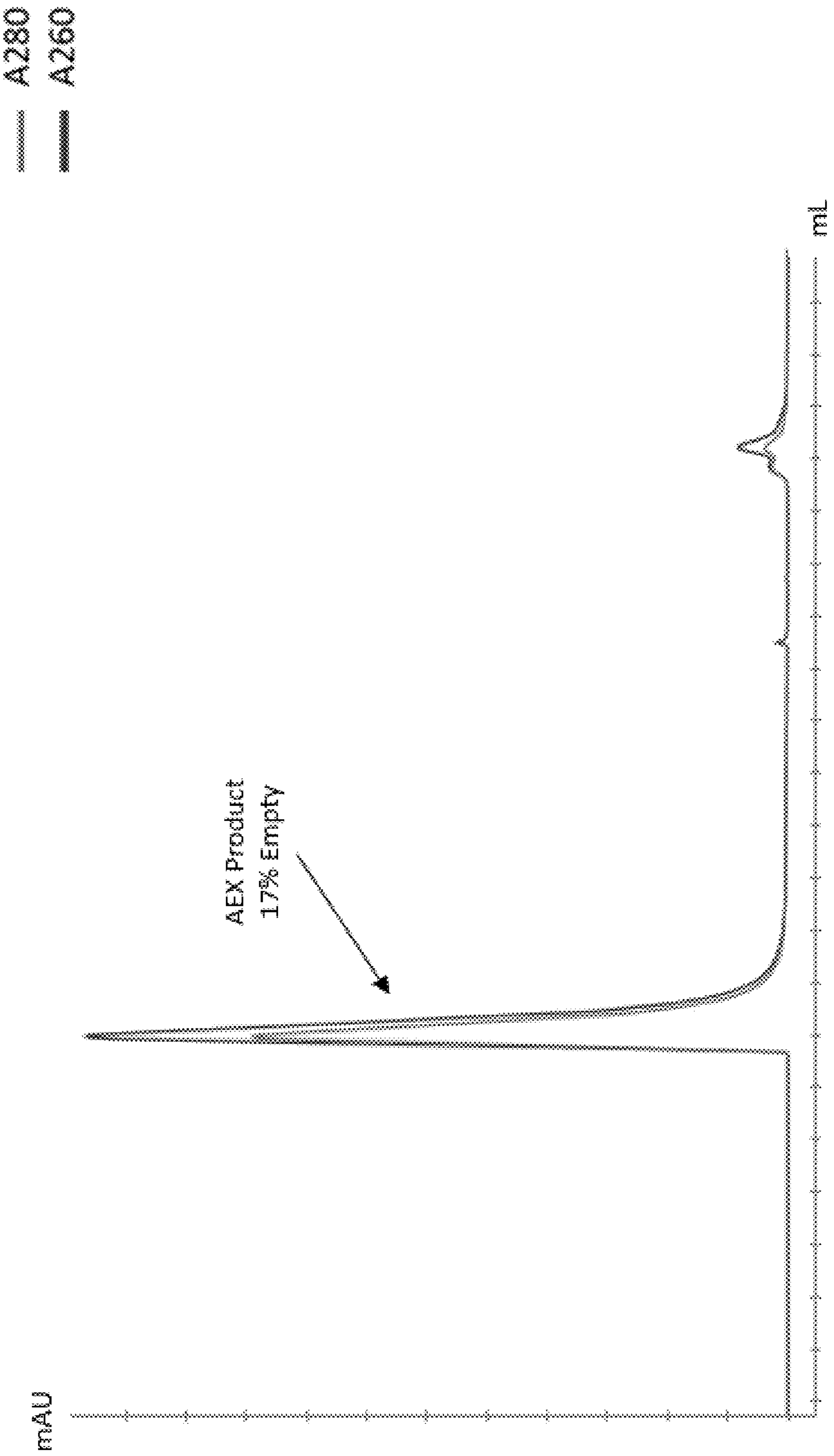
Figure 10C:
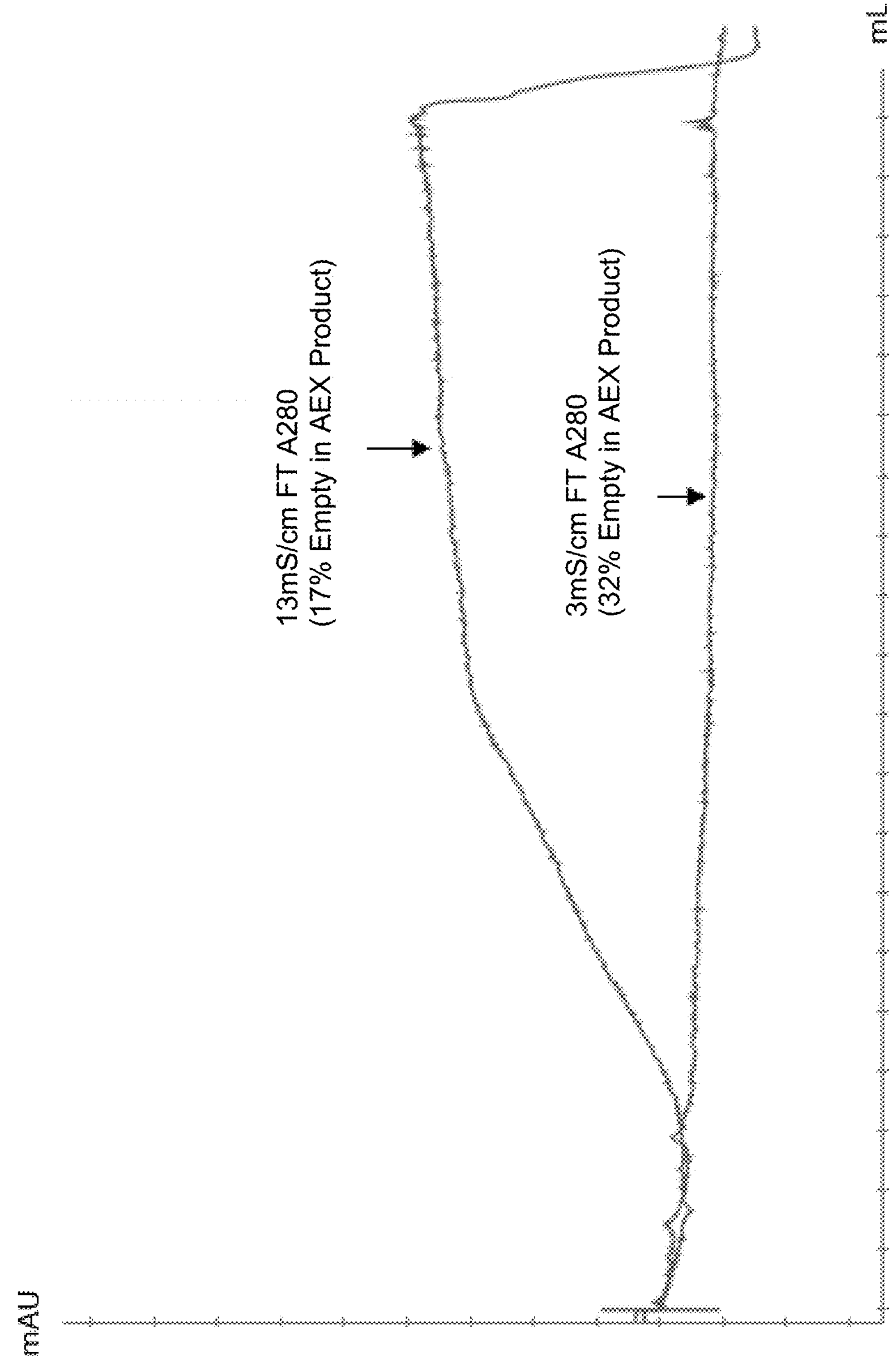

The AAV8 anion exchange purification with an isocratic elution resulted in a single elution peak consisting of low levels of empty capsids. The full chromatogram is shown in FIG. 10A and the elution peak is shown in FIG. 10B. The flowthrough A280 signal for the AAV8 anion exchange purification performed with the 13 mS/cm load condition relative to a 3 mS/cm load condition is shown in FIG. 10C. The increased A280 signal observed when loading at higher conductivity suggested the presence of empty capsids in the flowthrough. Analytical ultracentrifugation confirmed the presence of mainly empty capsids in the flowthrough and enrichment of full capsids through the anion exchange purification. The analytical ultracentrifugation capsid packaging data are shown in Table 11.

TABLE 11

AAV8 Anion Exchange Chromatography with Isocratic Elution

| Fraction | % Empty Capsids |
|---|---|
| Load | 35% |
| Flowthrough | 93% |
| Product | 17% |

AAV9 Anion Exchange Chromatography with Linear Gradient Elution

The conditions listed in Table 12 were utilized to evaluate the anion exchange chromatography process with AAV9 vector packaged with a PAH transgene. The AAV9 vector was loaded onto a POROS HQ50 column under the experimental parameters described in Table 12 below. Thawed affinity product was diluted with and adjusted to 28 mM Ammonium Acetate, 2 mM MgCl2, 0.01% (w/v %) Poloxamer 188 pH 9.3. The conductivity of the solution was adjusted to 3 mS/cm using 0.01% (w/v %) Poloxamer 188, 2 mM MgCl2. The final pH and conductivity of the solution was 9.30 and 3.0 mS/cm.

TABLE 12

Conditions for AAV9 Anion Exchange Chromatography with Linear Gradient Elution

| Step | Buffer Composition | CV | Residence Time (min) |
|---|---|---|---|
| Equilibration 1 | 28 mM Ammonium Acetate<br>0.01% Poloxamer-188<br>2 mM $MgCl_2$<br>pH 9.3 | 20 | 1 |
| Sample application | Load pH 9.3<br>Conductivity: 3 mS/cm | N/A | 1 |
| First wash step | 28 mM Ammonium Acetate<br>0.01% Poloxamer-188<br>2 mM $MgCl_2$<br>pH 9.3 | 10 | 1 |
| Second wash step | 10 mM Ammonium Acetate<br>0.01% Poloxamer-188<br>pH 9.3 | 20 | 1 |
| Linear gradient elution | 400 mM Ammonium Acetate<br>0.01% Poloxamer-188<br>pH 9.3<br>0-100% over 60 CV | 60 | 6 |

Figure 11A:
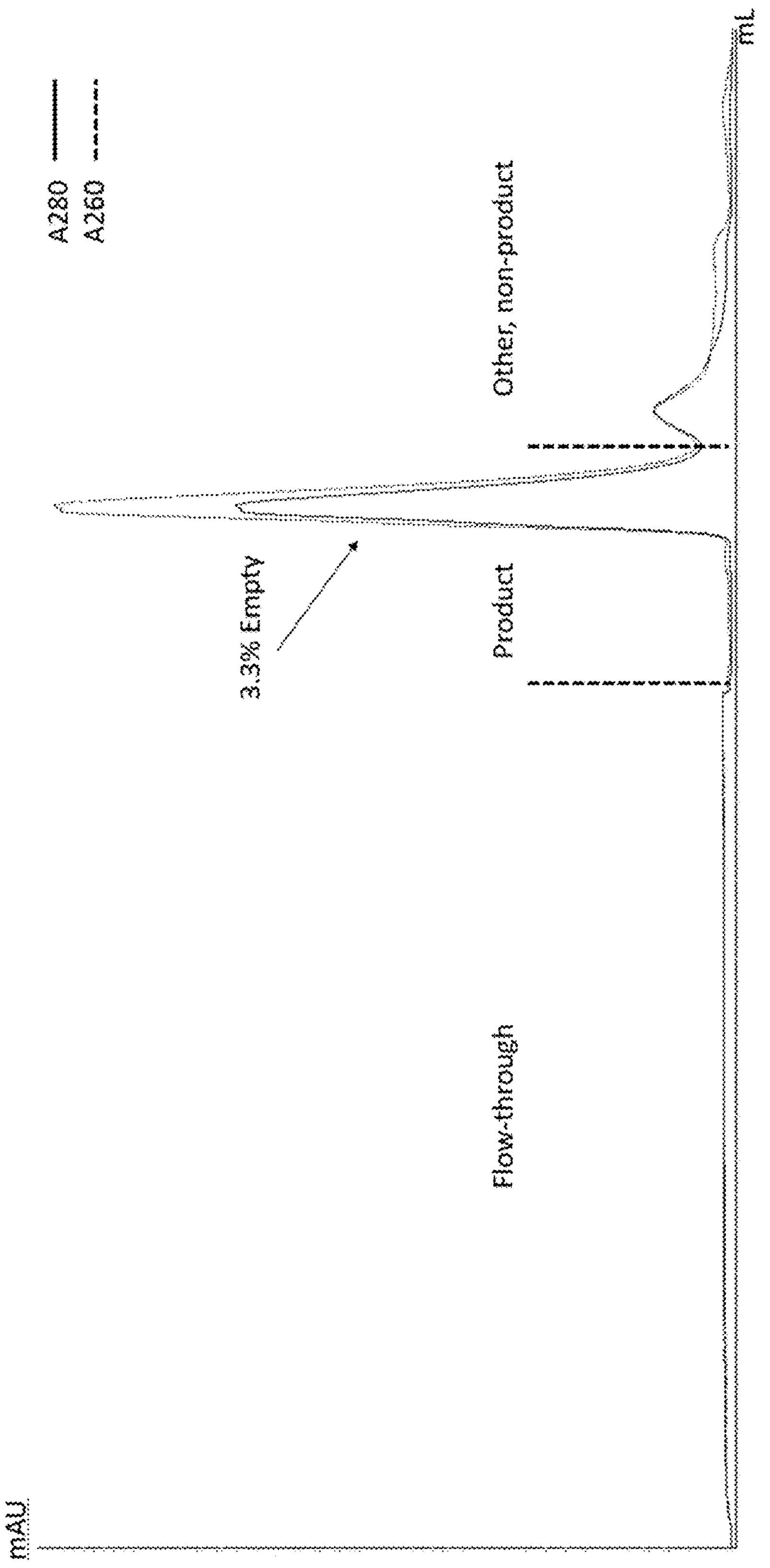
FIGS. 11A-11B are plots showing the full chromatogram (FIG. 11A) and elution profile (FIG. 11B) obtained from AEX with linear gradient elution for a representative AAV9 vector.
Figure 11B:
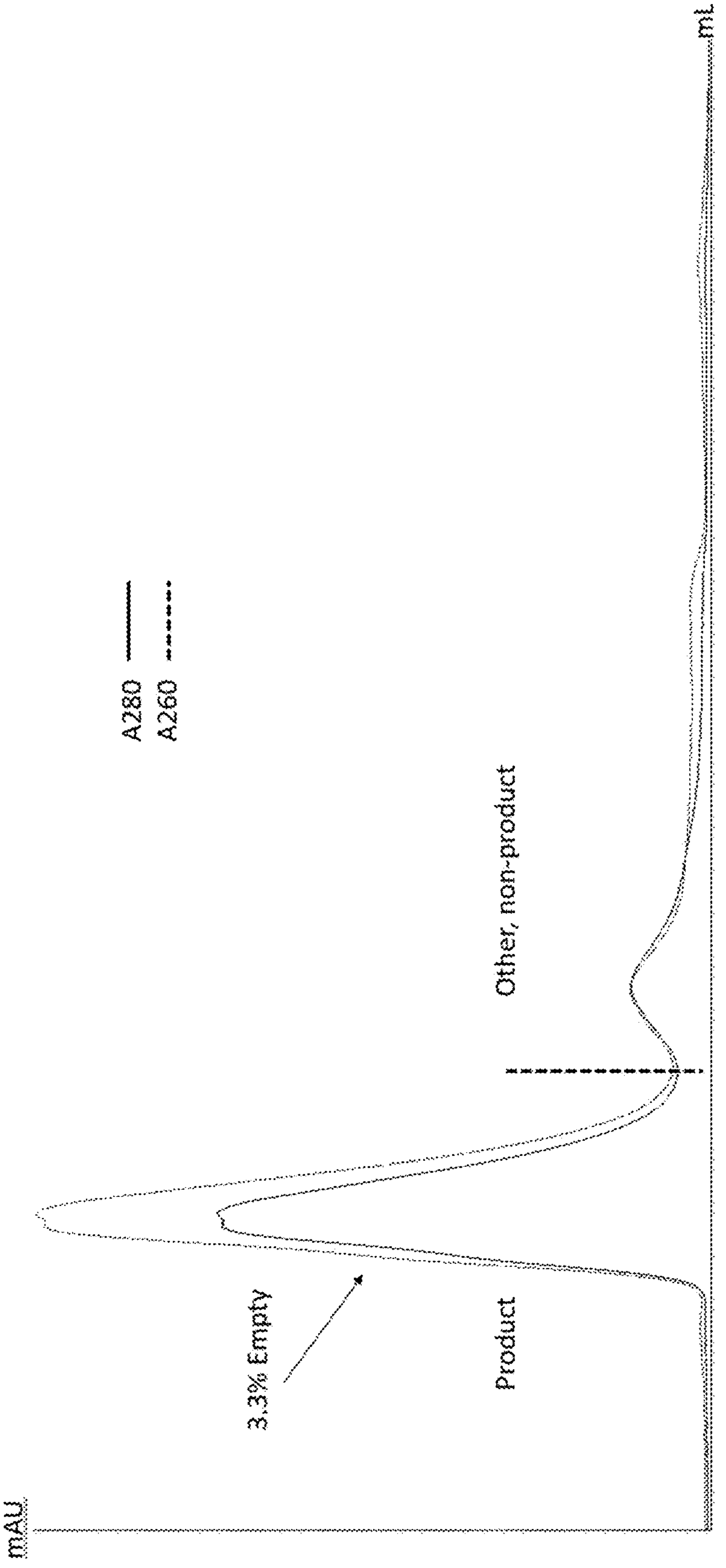

The AAV9 anion exchange purification with a linear gradient elution resulted in one elution peak that was split into three pools. The full chromatogram is shown in FIG. 11A and the elution peak profile is shown in FIG. 11B. Table 13 shows the percentage of empty capsids in the load and elution pools determined via analytical ultracentrifugation. The first pool at the front of the peak consisted of 45.5% empty capsids. The middle of the peak, or the product pool, consisted of 3.3% empty capsids. The final pool at the tail of the peak contained predominantly empty capsids.

TABLE 13

AAV9 Anion Exchange Chromatography with Linear Gradient Elution

| Fraction | % Empty Capsids |
|---|---|
| Load | 45.5% |
| Flowthrough | 94.7% |
| Product | 3.3% |

AAV9 Anion Exchange Chromatography with Step Gradient Elution

The conditions listed in Table 14 were utilized to evaluate the process with AAV9 vector packaged with a PAH transgene. The PAH-AAV9 vector was loaded onto a POROS HQ50 column under the experimental parameters described in Table 14 below. Thawed affinity product was diluted with and adjusted to 28 mM Ammonium Acetate, 2 mM MgCl2, 0.01% (w/v%) Poloxamer 188 pH 9.3. The conductivity of the solution was adjusted to 3 mS/cm using of 0.01% (w/v %) Poloxamer 188, 2 mM MgCl2. The final pH and conductivity of the solution was 9.28 and 3.06 mS/cm.

TABLE 14

Conditions for AAV9 Anion Exchange Chromatography with Step Gradient Elution

| Step | Buffer Composition | CV | Residence Time (min) |
|---|---|---|---|
| Equilibration 1 | 29 mM Ammonium Acetate<br>0.01% Poloxamer-188<br>2 mM $MgCl_2$<br>pH 9.3 | 20 | 1 |
| Sample application | Load pH 9.3<br>Conductivity: 3 mS/cm | N/A | 1 |
| First wash step | 29 mM Ammonium Acetate<br>0.01% Poloxamer-188<br>2 mM $MgCl_2$<br>pH 9.3 | 10 | 1 |
| Second wash step | 10 mM Ammonium Acetate<br>0.01% Poloxamer-188<br>pH 9.3 | 20 | 1 |
| Step gradient elution | 112 mM Ammonium Acetate<br>0.01% Poloxamer-188<br>pH 9.3 | 5 | 6 |

Figure 12A:
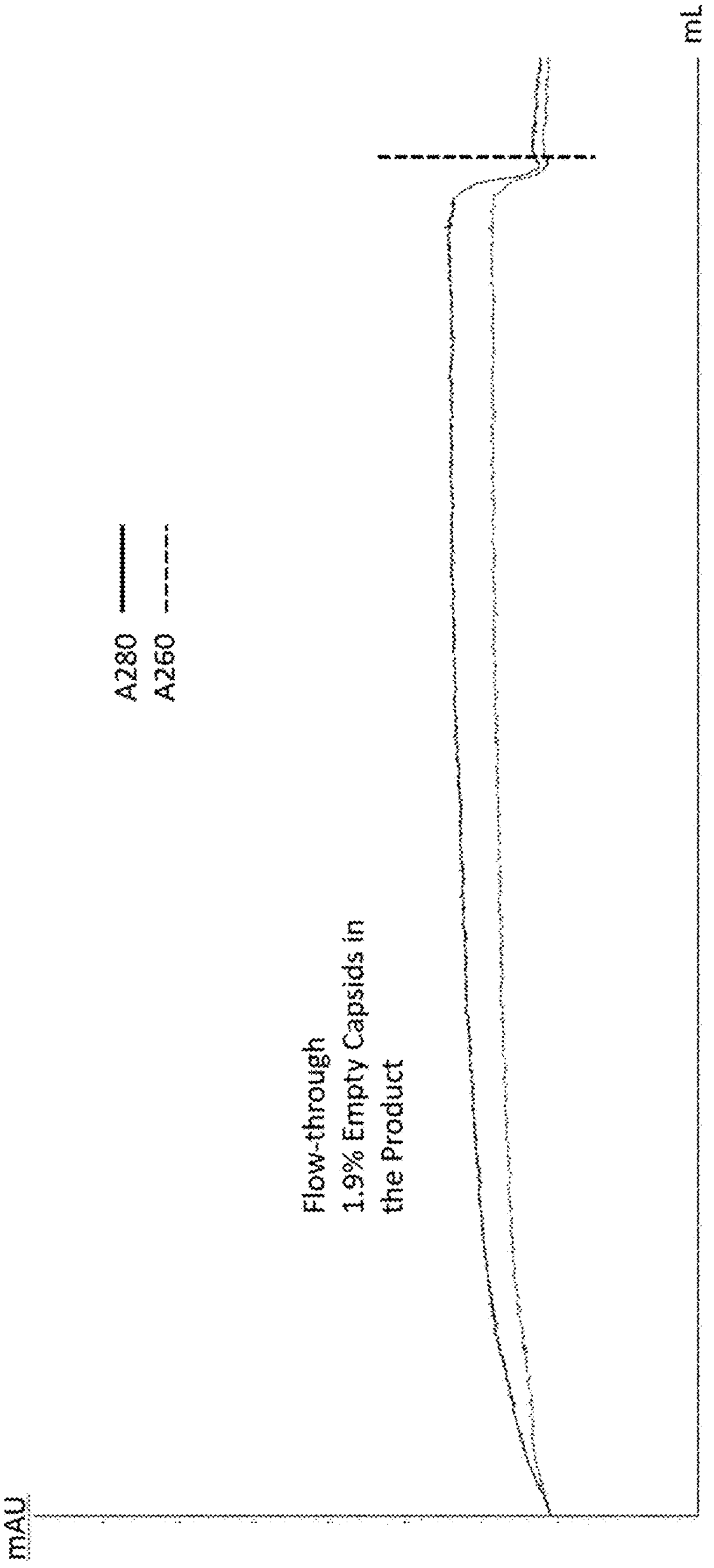
FIGS. 12A-12B are plots showing the full chromatogram (FIG. 12A) and elution profile (FIG. 12B) obtained from AEX with step gradient elution for a representative AAV9 vector.
Figure 12B:
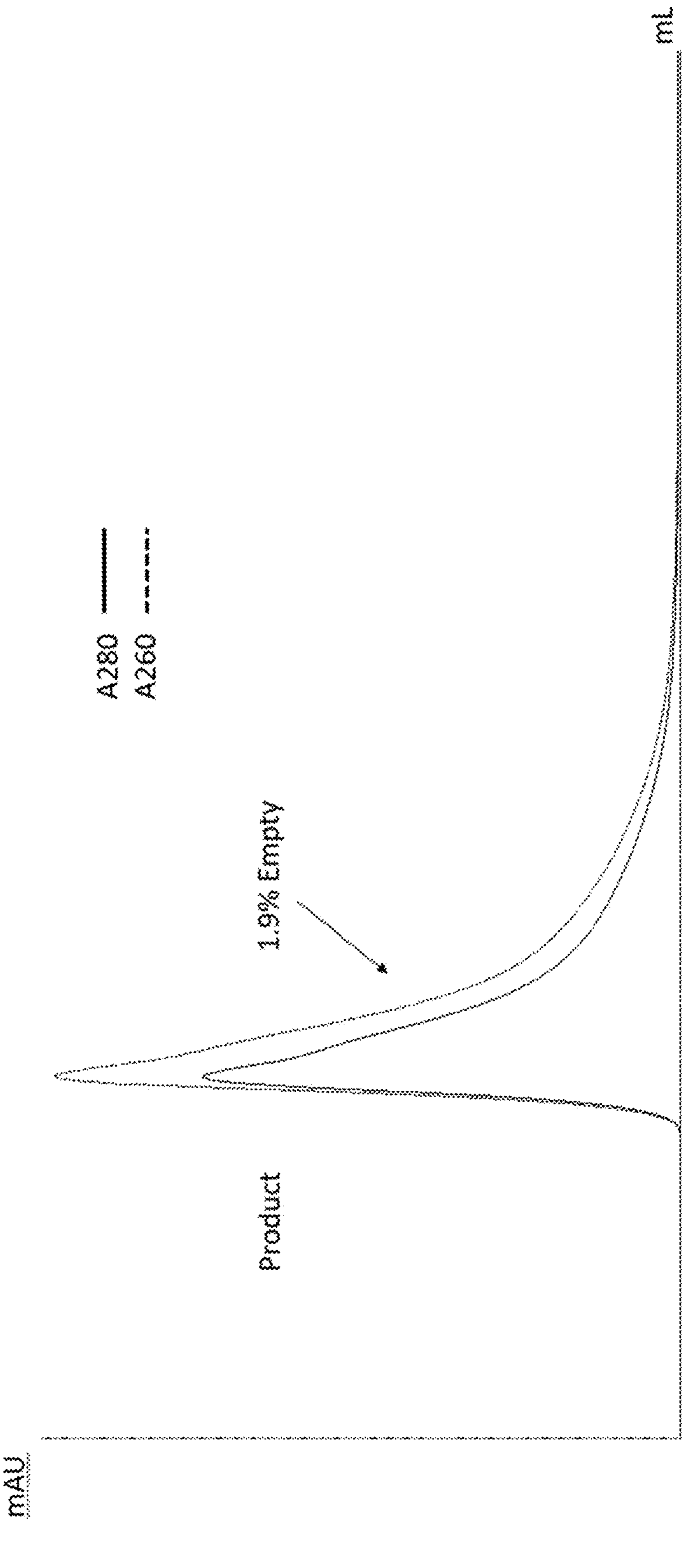

The AAV9 anion exchange purification with a step gradient elution resulted in a single elution peak consisting of low levels of empty capsids. The full chromatogram is shown in FIG. 12A and the elution peak is shown in FIG. 12B. These data show that the product pool consisted of 1.9% empty capsids, confirming the presence of mainly empty capsids in the flowthrough and enrichment of full capsids through the anion exchange purification.

AAV2 Anion Exchange Chromatography with Linear Gradient Elution

The conditions listed in Table 15 were utilized to evaluate the anion exchange chromatography process with AAV2 vector packaged with a PAH transgene. Neutralized AAV2 affinity product was in 20.5 mM Ammonium Acetate, 2.14 mM Magnesium Chloride, 0.01% Poloxamer-188, pH 9.3 and loaded onto POROS HQ column equilibrated with a pH 9.3 and 3.0 mS/cm ammonium acetate buffer. Following the load, the column was washed with the 3.0 mS/cm equilibration buffer followed by a pH 9.3 and 1.0 mS/cm ammonium acetate buffer. Bound vector was eluted with a 10 to 400 mM ammonium acetate gradient at pH 9.3.

TABLE 15

Conditions for AAV2 Anion Exchange Chromatography with Linear Gradient Elution

| Step | Buffer Composition | CV | Residence Time (min) |
|---|---|---|---|
| Equilibration | 28 mM Ammonium Acetate, 2 mM Magnesium Chloride, 0.01% Poloxamer-188, pH 9.3 | 5 | 1 |
| Sample Application | Neutralized AAV8 Affinity Product diluted in 20.5 mM Ammonium Acetate, 2.14 mM Magnesium Chloride, 0.01% Poloxamer-188, pH 9.3 | N/A | 2 |
| Wash 1 | 28 mM Ammonium Acetate, 2 mM Magnesium Chloride, 0.01% Poloxamer-188, pH 9.3 | 5 | 2 |

TABLE 15-continued

| Conditions for AAV2 Anion Exchange Chromatography with Linear Gradient Elution | | | |
|---|---|---|---|
| Step | Buffer Composition | CV | Residence Time (min) |
| Wash 2 | 10 mM Ammonium Acetate, 2 mM Magnesium Chloride, 0.01% Poloxamer-188, pH 9.3 | 5 | 2 |
| Linear Gradient Elution | 10-400 mM Ammonium Acetate, 0.01% Poloxamer-188, pH 9.3 | 60 | 3 |
| Elution Hold | 400 mM Ammonium Acetate, 0.01% Poloxamer-188, pH 9.3 | 20 | 3 |

Figure 13A:
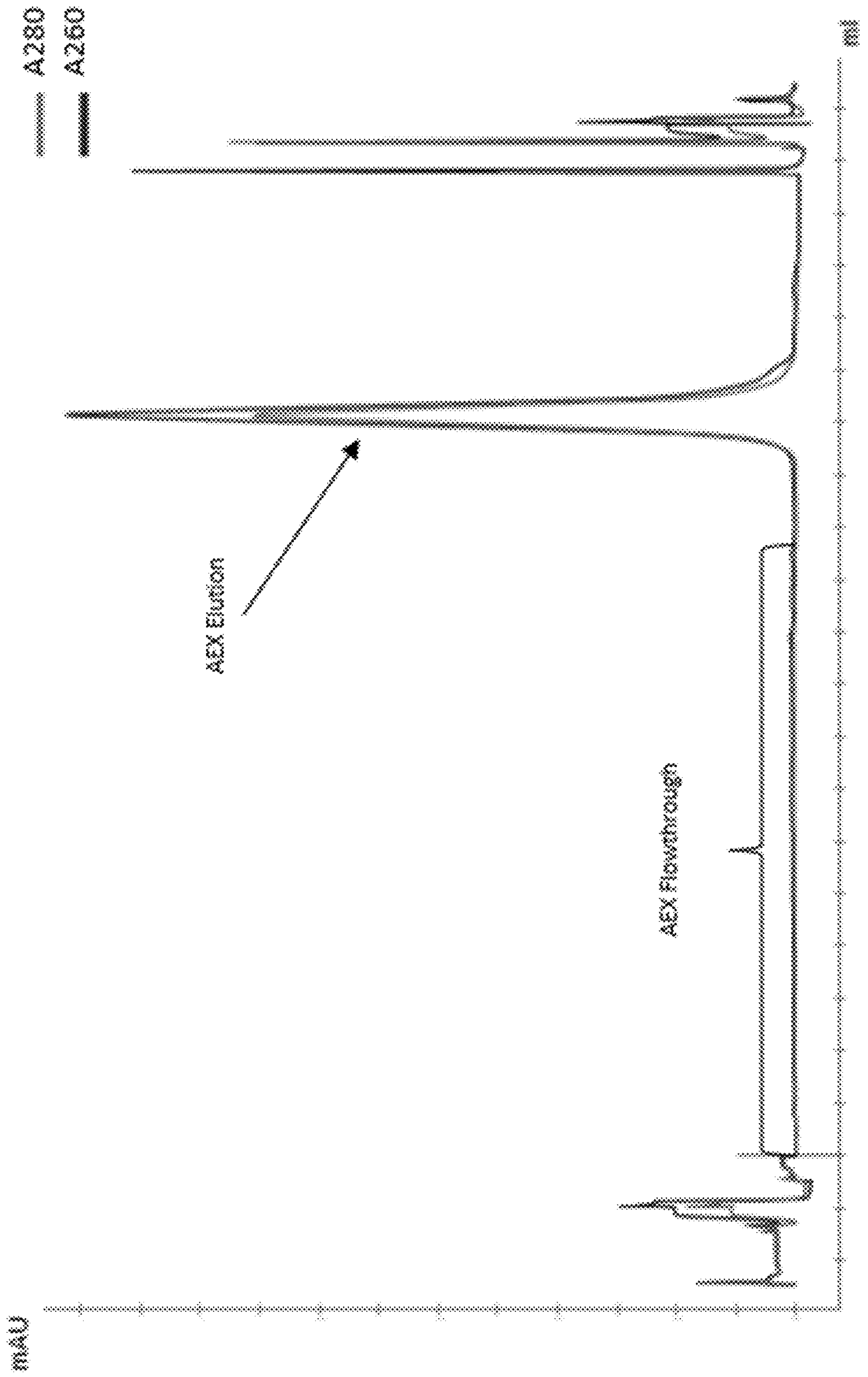
FIGS. 13A-13B are plots showing the full chromatogram (FIG. 13A) and elution profile (FIG. 13B) obtained from AEX with linear gradient elution for a representative AAV2 vector.
Figure 13B:
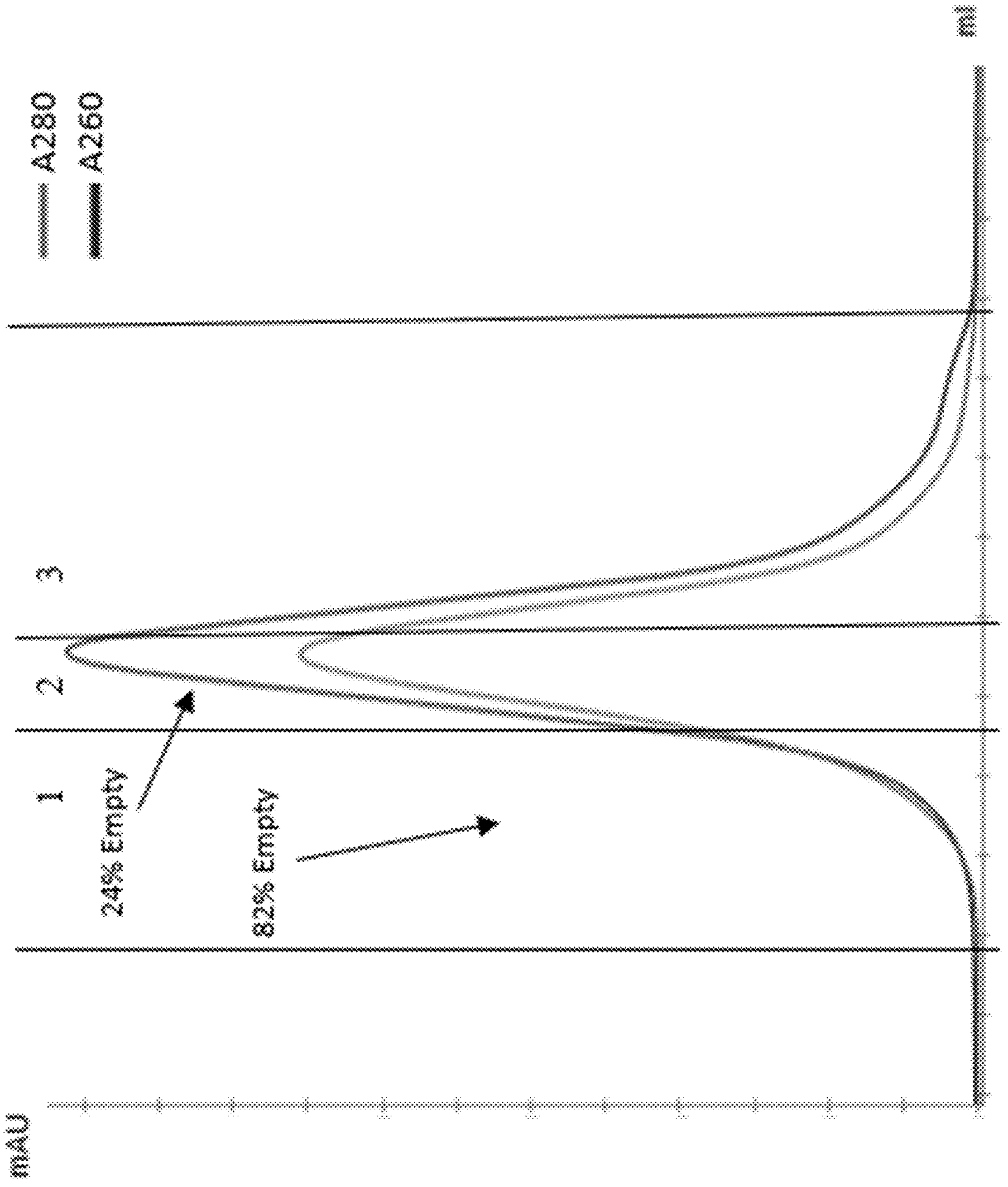

The AAV2 anion exchange purification with a linear gradient elution resulted in one elution peak that was split into three pools. The full chromatogram is shown in FIG. 13A and the elution peak profile is shown in FIG. 13B. Table 16 shows the percentage of empty capsids in the load and elution pools determined via analytical ultracentrifugation. The first pool at the front of the peak contained predominantly empty capsids. The middle of the peak, or the product pool, consisted of 24% empty capsids.

TABLE 16

| AAV2 Anion Exchange Chromatography with Linear Gradient Elution | |
|---|---|
| Fraction | % Empty Capsids |
| Load | 40% |
| Elution Pool 1 | 82% |
| Elution Pool 2 | 24% |
| Elution Pool 3 | NA |

AAV2 Anion Exchange Chromatography with Isocratic Elution

The conditions listed in Table 17 were utilized to evaluate the anion exchange chromatography process with AAV2 vector packaged with a PAH transgene. The equilibration conditions were selected to promote weak partitioning of the empty capsids into the flowthrough and were identified from the linear gradient results in FIG. 13B. Neutralized AAV2 affinity product was diluted in a pH 9.3 and 13 mS/cm ammonium acetate buffer and loaded onto a POROS HQ column that was equilibrated with the 13 mS/cm buffer. Following the load, the column was washed with 13 mS/cm equilibration buffer followed by a pH 9.3 and 1.0 mS/cm ammonium acetate buffer. Bound vector was eluted with a pH 9.3 and 18.5 mS/cm ammonium acetate buffer. The elution condition was identified from the linear gradient results in FIG. 13B.

TABLE 17

| Conditions for AAV2 Anion Exchange Chromatography with Isocratic Elution | | | |
|---|---|---|---|
| Step | Buffer Composition | CV | Residence Time (min) |
| Equilibration | 153 mM Ammonium Acetate, 2 mM Magnesium Chloride, 0.01% Poloxamer-188, pH 9.3 | 5 | 2 |
| Sample Application | Neutralized AAV8 Affinity Product diluted in 153 mM Ammonium Acetate, 2 mM Magnesium Chloride, 0.01% Poloxamer-188, pH 9.3 | N/A | 2 |
| Wash 1 | 153 mM Ammonium Acetate, 2 mM Magnesium Chloride, 0.01% Poloxamer-188, pH 9.3 | 5 | 2 |
| Wash 2 | 10 mM Ammonium Acetate, 2 mM Magnesium Chloride, 0.01% Poloxamer-188, pH 9.3 | 5 | 2 |
| Elution | 293 mM Ammonium Acetate, 0.01% Poloxamer-188, pH 9.3 | 5 | 6 |

Figure 14A:
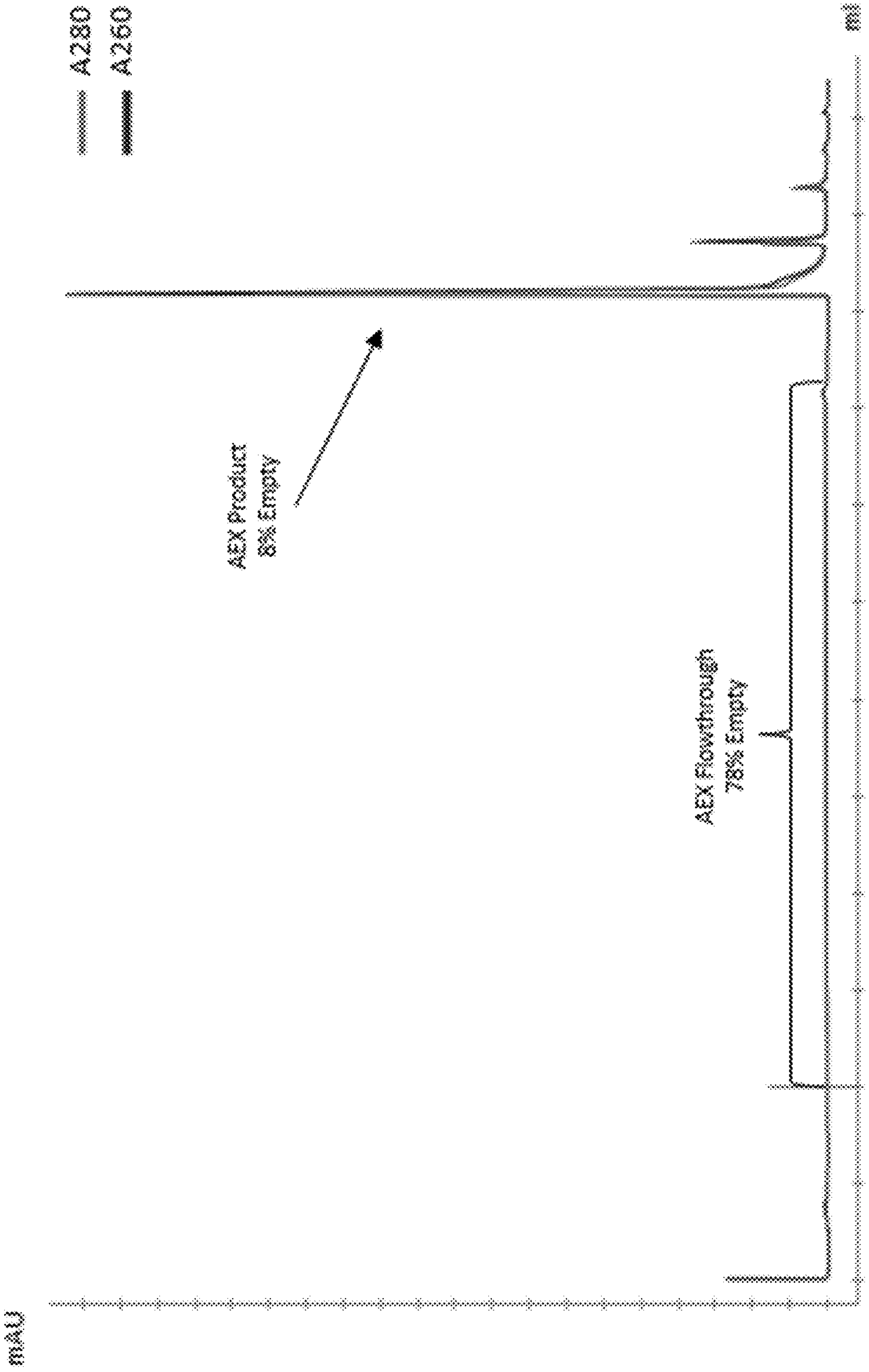
FIGS. 14A-14C are plots showing the full chromatogram (FIG. 14A) and elution profiles (FIGS. 14B-C) obtained from AEX with isocratic elution for a representative AAV2 vector. The elution profile shows the A260 (dashed lines) and A280 (solid lines) profiles for the AEX process performed with the 13 mS/cm load condition (FIG. 14C).
Figure 14B:
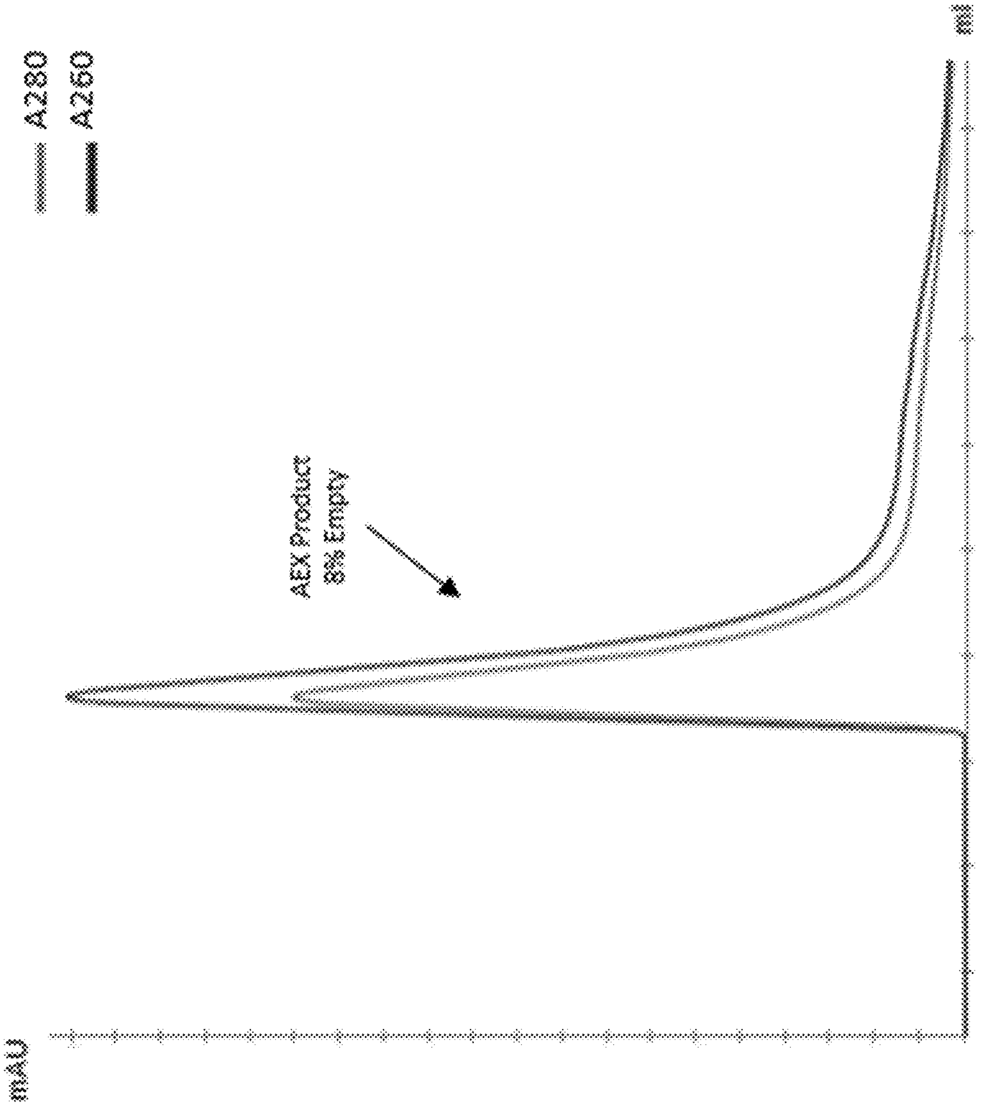
Figure 14C:
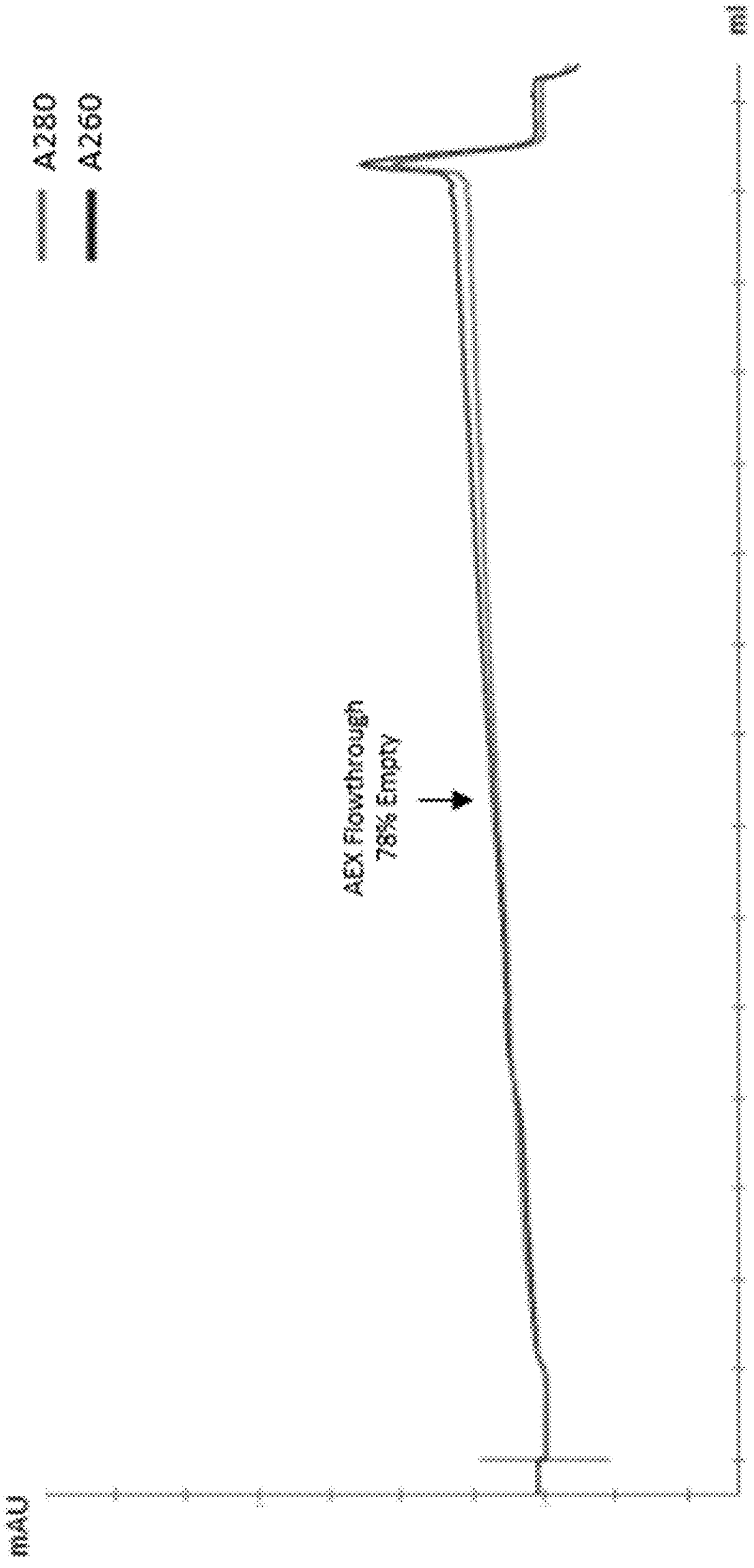

The AAV2 anion exchange purification with an isocratic elution resulted in a single elution peak consisting of low levels of empty capsids. The full chromatogram is shown in FIG. 14A and the elution peak is shown in FIG. 14B. The flowthrough A280 signal for the AAV8 anion exchange purification performed with the 13 mS/cm load condition is shown in FIG. 14C. Analytical ultracentrifugation confirmed the presence of mainly empty capsids in the flowthrough and enrichment of full capsids through the anion exchange purification. The analytical ultracentrifugation capsid packaging data are shown in Table 18.

TABLE 18

| AAV2 Anion Exchange Chromatography with Isocratic Elution | |
|---|---|
| Fraction | % Empty Capsids |
| Load | 31% |
| Flowthrough | 78% |
| Product | 8% |

The foregoing data demonstrate that the AEX process described herein can be applied across different AAV serotypes.

Further embodiments of the invention are set out in the following clauses:

Clause 1. A method for the separation of an adeno-associated virus (AAV) particle from a mixture of the AAV particle and at least one contaminant, the method comprising: contacting the mixture with an anion exchange chromatography (AEX) medium under conditions such that the AAV particle binds to the AEX medium, wherein the mixture comprises magnesium chloride and an acetate; and washing the AEX medium with a first wash solution under conditions such that the AAV particle remains bound to the AEX medium and the at least one contaminant does not bind the AEX medium, thereby separating the AAV particle from the at least one contaminant.

Clause 2. The method of Clause 1, wherein the first wash solution comprises an acetate.

Clause 3. The method of Clause 1 or 2, wherein the first wash solution comprises urea.

Clause 4. A method for the separation of an adeno-associated virus (AAV) particle from a mixture of the AAV particle and at least one contaminant, the method comprising: contacting the mixture with an anion exchange chromatography (AEX) medium under conditions such that the AAV particle binds to the AEX medium; and washing the AEX medium with a first wash solution comprising urea and an acetate under conditions such that the AAV particle remains bound to the AEX medium and the at least one contaminant does not bind to the AEX medium, thereby separating the AAV particle from the at least one contaminant.

Clause 5. The method of any one of Clauses 1-4, further comprising washing the anion exchange chromatography medium with a second wash solution.

Clause 6. A method for the separation of an adeno-associated virus (AAV) particle from a mixture of the AAV particle and at least one contaminant, the method comprising: providing an AEX medium that has been contacted with the mixture, wherein the mixture comprises magnesium chloride and an acetate, and wherein the AEX medium comprises the AAV particle bound thereto and has been washed with a first wash solution such that the AAV particle remained bound to the AEX medium and the at least one contaminant did not bind to the AEX medium; and washing the AEX medium with a second wash solution under conditions such that the AAV particle remains bound to the AEX medium and the at least one contaminant does not bind to the AEX medium, thereby separating the AAV particle from the at least one contaminant.

Clause 7. The method of Clause 6, wherein the first wash solution comprises an acetate.

Clause 8. The method of Clause 6 or 7, wherein the first wash solution comprises urea.

Clause 9. A method for the separation of an adeno-associated virus (AAV) particle from a mixture of the AAV particle and at least one contaminant, the method comprising: providing an AEX medium that has been contacted with the mixture, wherein the AEX medium comprises the AAV particle bound thereto and has been washed with a first wash solution comprising urea and an acetate such that the AAV particle remained bound to the AEX medium and the at least one contaminant did not bind to the AEX medium; and washing the AEX medium with a second wash solution under conditions such that the AAV particle remains bound to the AEX medium and the at least one contaminant does not bind to the AEX medium, thereby separating the AAV particle from the at least one contaminant.

Clause 10. The method of any preceding Clause, wherein the at least one contaminant is selected from the group consisting of an AAV particle lacking a complete genome, an AAV degradation product, a host cell protein, a host cell fragment, and any combination thereof.

Clause 11. The method of any preceding Clause, wherein the at least one contaminant is an AAV particle that lacks a complete genome.

Clause 12. The method of any preceding Clause, wherein the AEX medium has an average pore size of at least about 100 nm.

Clause 13. The method of any preceding Clause, wherein the AEX medium has an average pore size of at least about 500 nm.

Clause 14. The method of any preceding Clause, wherein the AEX medium comprises a quaternary amine.

Clause 15. The method of any preceding Clause, wherein the AEX medium comprises a quaternary polyethyleneimine group.

Clause 16. The method of any preceding Clause, wherein the mixture comprises an eluate of an affinity chromatography column.

Clause 17. The method of any preceding Clause, wherein the mixture comprises about 10 mM to about 40 mM of an acetate.

Clause 18. The method of any preceding Clause, wherein the mixture comprises about 10 mM to about 40 mM ammonium acetate.

Clause 19. The method of any preceding Clause, wherein the mixture comprises about 28 mM ammonium acetate.

Clause 20. The method of any preceding Clause, wherein the mixture comprises about 2 mM to about 6 mM magnesium chloride.

Clause 21. The method of any preceding Clause, wherein the mixture comprises about 2 mM magnesium chloride.

Clause 22. The method of any preceding Clause, wherein the mixture comprises about 0.001% (w/v) to about 0.05% (w/v) Poloxamer 188.

Clause 23. The method of any preceding Clause, wherein the mixture comprises about 0.01% (w/v) Poloxamer 188.

Clause 24. The method of any preceding Clause, wherein the pH of the mixture is about 9 to about 10.5.

Clause 25. The method of any preceding Clause, wherein the pH of the mixture is about 9.3.

Clause 26. The method of any preceding Clause, wherein the first wash solution comprises about 0.1 M to about 4 M urea.

Clause 27. The method of any preceding Clause, wherein the first wash solution comprises about 2 M urea.

Clause 28. The method of any preceding Clause, wherein the first wash solution comprises an acetate selected from the group consisting of ammonium acetate, potassium acetate, sodium acetate, and cesium acetate.

Clause 29. The method of any preceding Clause, wherein the first wash solution comprises ammonium acetate.

Clause 30. The method of any preceding Clause, wherein the first wash solution comprises about 10 mM to about 40 mM of the acetate.

Clause 31. The method of any preceding Clause, wherein the first wash solution comprises about 10 mM to about 40 mM ammonium acetate.

Clause 32. The method of any preceding Clause, wherein the first wash solution comprises about 28 mM ammonium acetate.

Clause 33. The method of any preceding Clause, wherein the first wash solution comprises about 2 mM to about 6 mM magnesium chloride.

Clause 34. The method of any preceding Clause, wherein the first wash solution comprises about 2 mM magnesium chloride.

Clause 35. The method of any preceding Clause, wherein the first wash solution comprises about 0.001% (w/v) to about 0.05% (w/v) Poloxamer 188.

Clause 36. The method of any preceding Clause, wherein the first wash solution comprises about 0.01% (w/v) Poloxamer 188.

Clause 37. The method of any preceding Clause, wherein the pH of the first wash solution is about 9 to about 10.5.

Clause 38. The method of any preceding Clause, wherein the pH of the first wash solution is about 9.3.

Clause 39. The method of any preceding Clause, wherein the first wash solution has a conductivity of about 1 mS/cm to about 3 mS/cm.

Clause 40. The method of any one of Clauses 5-39, wherein the second wash solution comprises about 0.1 mM to about 15 mM ammonium acetate.

Clause 41. The method of any one of Clauses 5-40, wherein the second wash solution comprises about 10 mM ammonium acetate.

Clause 42. The method of any one of Clauses 5-41, wherein the second wash solution comprises about 0.001% (w/v) to about 0.05% (w/v) Poloxamer 188.

Clause 43. The method of any one of Clauses 5-42, wherein the second wash solution comprises about 0.01% (w/v) Poloxamer 188.

Clause 44. The method of any one of Clauses 5-43, wherein the pH of the second wash solution is about 9 to about 10.5.

Clause 45. The method of any one of Clauses 5-44, wherein the pH of the second wash solution is about 9.3.

Clause 46. The method of any one of Clauses 5-45, wherein the second wash solution has a conductivity of less than about 3 mS/cm.

Clause 47. The method of any one of Clauses 5-46, wherein the second wash solution has a conductivity of about 1 mS/cm to about 3 mS/cm.

Clause 48. The method of any one of Clauses 5-47, wherein the second wash solution has a conductivity of about 1 mS/cm.

Clause 49. The method of any preceding Clause, further comprising eluting the AAV particle from the AEX medium.

Clause 50. The method of Clause 49, wherein the AAV particle is eluted from the AEX medium with an eluant using a step gradient.

Clause 51. The method of Clause 49, wherein the AAV particle is eluted from the AEX medium with an eluant using a linear gradient.

Clause 52. The method of Clause 50 or 51, wherein the eluant comprises a salt at a concentration of about 10 mM to about 1 M.

Clause 53. The method of Clause 52, wherein the salt is an acetate salt.

Clause 54. The method of Clause 53, wherein the acetate salt is selected from the group consisting of ammonium acetate, potassium acetate, sodium acetate, and cesium acetate.

Clause 55. The method of Clause 53 or 54, wherein the acetate salt is ammonium acetate.

Clause 56. The method of Clause 53 or 54, wherein the acetate salt is sodium acetate.

Clause 57. The method of any one of Clauses 50-56, wherein the eluant comprises about 10 mM to about 1 M ammonium acetate.

Clause 58. The method of any one of Clauses 50-57, wherein the eluant comprises about 10 mM to about 150 mM ammonium acetate.

Clause 59. The method of any one of Clauses 50-58, wherein the eluant comprises about 100 mM to about 300 mM ammonium acetate.

Clause 60. The method of any one of Clauses 50-59, wherein the eluant comprises about 0.001% (w/v) to about 0.05% (w/v) Poloxamer 188.

Clause 61. The method of any one of Clauses 50-60, wherein the eluant comprises about 0.01% (w/v) Poloxamer 188.

Clause 62. The method of any one of Clauses 50-61, wherein the pH of the eluant is about 9 to about 10.5.

Clause 63. The method of any one of Clauses 50-62, wherein the pH of the eluant is about 9.3.

Clause 64. The method of any one of Clauses 50-63, wherein the eluant further comprises about 50 mM ethanolamine.

Clause 65. The method of any one of Clauses 50-64, wherein the eluant has a conductivity of about 8.5 mS/cm to about 30 mS/cm.

Clause 66. The method of any one of Clauses 50-64, wherein the eluant has a conductivity of about 8.5 mS/cm to about 10.5 mS/cm.

Clause 67. The method of any one of Clauses 50-64, wherein the eluant has a conductivity of about 10 mS/cm to about 11.5 mS/cm.

Clause 68. The method of any one of Clauses 50-64, wherein the eluant has a conductivity of about 14 mS/cm to about 17.5 mS/cm.

Clause 69. The method of any one of Clauses 50-64, wherein the eluant has a conductivity of about 26 mS/cm.

Clause 70. The method of any preceding Clause, wherein the method results in an eluate comprising less than about 15% AAV particles that lack a complete genome.

Clause 71. The method of any preceding Clause, wherein the method results in an eluate comprising less than about 10% AAV particles that lack a complete genome.

Clause 72. The method of any one of Clauses 50-71, further comprising formulating the eluted AAV particle in a formulation buffer suitable for administration to a human subject.

Clause 73. The method of any preceding Clause, wherein the AAV is a recombinant AAV (rAAV) comprising an rAAV genome comprising a transgene.

Clause 74. The method of Clause 73, wherein the transgene encodes a polypeptide.

Clause 75. The method of Clause 73, wherein the transgene encodes an miRNA, shRNA, siRNA, antisense RNA, gRNA, antagomir, miRNA sponge, RNA aptazyme, RNA aptamer, lncRNA, ribozyme, or mRNA.

Clause 76. The method of Clause 73, wherein the transgene encodes a protein selected from the group consisting of iduronate-2-sulfatase (I2S), frataxin (FXN), glucose-6-phosphatase (G6Pase), phosphoenolpyruvate carboxykinase (PEPCK), cyclin-dependent kinase-like 5 (CDKL5/STK9), galactose-1 phosphate uridyltransferase, phenylalanine hydroxylase (PAH), branched-chain alpha-keto acid dehydrogenase, fumarylacetoacetate hydrolase, methylmalonyl-CoA mutase, medium-chain acyl-CoA dehydrogenase, ornithine transcarbamylase (OTC), argininosuccinic acid synthetase (ASS1), low density lipoprotein receptor (LDLR) protein, UDP-glucuronosyltransferase, adenosine deaminase, hypoxanthine guanine phosphoribosyltransferase, biotinidase, alpha-gal actosidase A, copper-transporting ATPase 24 (ATP7B), beta-glucocerebrosidase, 70 kDa peroxisomal membrane protein (PMP70), and arylsulfatase A (ARSA).

Clause 77. The method of Clause 73, wherein the transgene encodes an antibody or a fragment thereof selected from the group consisting of: muromonab-cd3, efalizumab, tositumomab, daclizumab, nebacumab, catumaxomab, edrecolomab, abciximab, rituximab, basiliximab, palivizumab, infliximab, trastuzumab, adalimumab, ibritumomab tiuxetan, omalizumab, cetuximab, bevacizumab, natalizumab, panitumumab, ranibizumab, eculizumab, certolizumab, ustekinumab, canakinumab, golimumab, ofatumumab, tocilizumab, denosumab, belimumab, ipilimumab, brentuximab vedotin, pertuzumab, raxibacumab, obinutuzumab, alemtuzumab, siltuximab, ramucirumab, vedolizumab, blinatumomab, nivolumab, pembrolizumab, idarucizumab, necitumumab, dinutuximab, secukinumab, mepolizumab, alirocumab, evolocumab, daratumumab, elotuzumab, ixekizumab, reslizumab, olaratumab, bezlotoxumab, atezolizumab, obiltoxaximab, inotuzumab ozogamicin, brodalumab, guselkumab, dupilumab, sarilumab, avelumab, ocrelizumab, emicizumab, benralizumab, gemtuzumab ozogamicin, durvalumab, burosumab, erenumab, galcanezumab, lanadelumab, mogamulizumab, tildrakizumab, cemiplimab, fremanezumab, ravulizumab, emapalumab, ibalizumab, moxetumomab, caplacizumab, romosozumab, risankizumab, polatuzumab, eptinezumab, leronlimab, sacituzumab, brolucizumab, isatuximab, and teprotumumab.

Clause 78. The method of any one of Clauses 73-77, wherein the rAAV genome further comprises a transcriptional regulatory element operably linked to the transgene.

Clause 79. The method of Clause 78, wherein the transcriptional regulatory element comprises a promoter element and/or an intron element.

Clause 80. The method of any one of Clauses 73-79, wherein the rAAV genome further comprises a polyadenylation sequence.

Clause 81. The method of Clause 80, wherein the polyadenylation sequence is 3' to the transgene.

Clause 82. The method of any one of Clauses 73-81, wherein the rAAV genome comprises a nucleotide sequence that is at least 85%, 86%, 87%, 88%, 89%, 90%, 91%, 92%, 93%, 94%, 95%, 96%, 97%, 98%, 99%, or 100% identical to the nucleotide sequence set forth in SEQ ID NO: 50, 51, 52, 53, or 54

Clause 83. The method of any one of Clauses 73-82, wherein the rAAV genome further comprises a 5' inverted terminal repeat (5' ITR) nucleotide sequence 5' of the transgene, and a 3' inverted terminal repeat (3' ITR) nucleotide sequence 3' of the transgene.

Clause 84. The method of Clause 83, wherein the 5' ITR nucleotide sequence is at least 85%, 86%, 87%, 88%, 89%, 90%, 91%, 92%, 93%, 94%, 95%, 96%, 97%, 98%, 99% or 100% identical to the nucleotide sequence set forth in SEQ ID NO: 39, 41, or 42, and/or the 3' ITR nucleotide sequence is at least 85%, 86%, 87%, 88%, 89%, 90%, 91%, 92%, 93%, 94%, 95%, 96%, 97%, 98%, 99% or 100% identical to the nucleotide sequence set forth in SEQ ID NO: 40, 43, or 44.

Clause 85. The method of any one of Clauses 73-84, wherein the rAAV genome comprises a nucleotide sequence that is at least 85%, 86%, 87%, 88%, 89%, 90%, 91%, 92%, 93%, 94%, 95%, 96%, 97%, 98%, 99%, or 100% identical to the nucleotide sequence set forth in SEQ ID NO: 55, 56, 57, 58, or 59.

Clause 86. The method of any one of Clauses 73-85, wherein the rAAV comprises an AAV capsid comprising an AAV capsid protein.

Clause 87. The method of Clause 86, wherein the AAV capsid protein is selected from the group consisting of AAV1, AAV2, AAV3, AAV4, AAVS, AAV6, AAV7, AAV8, AAV9, AAV-DJ, AAV-LK03, NP59, VOY101, VOY201, VOY701, VOY801, VOY1101, AAVPHP.N, AAVPHP.A, AAVPHP.B, PHP.B2, PHP.B3, G2A3, G2B4, G2B5, and PHP.S.

Clause 88. The method of Clause 86 or 87, wherein the AAV capsid protein comprises an amino acid sequence that is at least 85% identical to the amino acid sequence of amino acids 203-736 of SEQ ID NO: 1, 2, 3, 4, 5, 6, 7, 8, 9, 10, 11, 12, 13, 15, 16, or 17.

Clause 89. The method of Clause 88, wherein: the amino acid in the capsid protein corresponding to amino acid 206 of SEQ ID NO: 16 is C; the amino acid in the capsid protein corresponding to amino acid 296 of SEQ ID NO: 16 is H; the amino acid in the capsid protein corresponding to amino acid 312 of SEQ ID NO: 16 is Q; the amino acid in the capsid protein corresponding to amino acid 346 of SEQ ID NO: 16 is A; the amino acid in the capsid protein corresponding to amino acid 464 of SEQ ID NO: 16 is N; the amino acid in the capsid protein corresponding to amino acid 468 of SEQ ID NO: 16 is S; the amino acid in the capsid protein corresponding to amino acid 501 of SEQ ID NO: 16 is I; the amino acid in the capsid protein corresponding to amino acid 505 of SEQ ID NO: 16 is R; the amino acid in the capsid protein corresponding to amino acid 590 of SEQ ID NO: 16 is R; the amino acid in the capsid protein corresponding to amino acid 626 of SEQ ID NO: 16 is G or Y; the amino acid in the capsid protein corresponding to amino acid 681 of SEQ ID NO: 16 is M; the amino acid in the capsid protein corresponding to amino acid 687 of SEQ ID NO: 16 is R; the amino acid in the capsid protein corresponding to amino acid 690 of SEQ ID NO: 16 is K; the amino acid in the capsid protein corresponding to amino acid 706 of SEQ ID NO: 16 is C; or, the amino acid in the capsid protein corresponding to amino acid 718 of SEQ ID NO: 16 is G.

Clause 90. The method of Clause 89, wherein:

(a) the amino acid in the capsid protein corresponding to amino acid 626 of SEQ ID NO: 16 is G, and the amino acid in the capsid protein corresponding to amino acid 718 of SEQ ID NO: 16 is G;

(b) the amino acid in the capsid protein corresponding to amino acid 296 of SEQ ID NO: 16 is H, the amino acid in the capsid protein corresponding to amino acid 464 of SEQ ID NO: 16 is N, the amino acid in the capsid protein corresponding to amino acid 505 of SEQ ID NO: 16 is R, and the amino acid in the capsid protein corresponding to amino acid 681 of SEQ ID NO: 16 is M;

(c) the amino acid in the capsid protein corresponding to amino acid 505 of SEQ ID NO: 16 is R, and the amino acid in the capsid protein corresponding to amino acid 687 of SEQ ID NO: 16 is R;

(d) the amino acid in the capsid protein corresponding to amino acid 346 of SEQ ID NO: 16 is A, and the amino acid in the capsid protein corresponding to amino acid 505 of SEQ ID NO: 16 is R; or (e) the amino acid in the capsid protein corresponding to amino acid 501 of SEQ ID NO: 16 is I, the amino acid in the capsid protein corresponding to amino acid 505 of SEQ ID NO: 16 is R, and the amino acid in the capsid protein corresponding to amino acid 706 of SEQ ID NO: 16 is C.

Clause 91. The method of Clause 89, wherein the AAV capsid protein comprises the amino acid sequence of amino acids 203-736 of SEQ ID NO: 1, 2, 3, 4, 5, 6, 7, 8, 9, 10, 11, 12, 13, 15, 16, or 17.

Clause 92. The method of any one of Clauses 86-91, wherein the AAV capsid protein comprises an amino acid sequence that is at least 85% identical to the amino acid sequence of amino acids 138-736 of SEQ ID NO: 1, 2, 3, 4, 5, 6, 7, 8, 9, 10, 11, 12, 13, 15, 16, or 17.

Clause 93. The method of Clause 92, wherein: the amino acid in the capsid protein corresponding to amino acid 151 of SEQ ID NO: 16 is R; the amino acid in the capsid protein corresponding to amino acid 160 of SEQ ID NO: 16 is D; the amino acid in the capsid protein corresponding to amino acid 206 of SEQ ID NO: 16 is C; the amino acid in the capsid protein corresponding to amino acid 296 of SEQ ID NO: 16 is H; the amino acid in the capsid protein corresponding to amino acid 312 of SEQ ID NO: 16 is Q; the amino acid in the capsid protein corresponding to amino acid 346 of SEQ ID NO: 16 is A; the amino acid in the capsid protein corresponding to amino acid 464 of SEQ ID NO: 16 is N; the amino acid in the capsid protein corresponding to amino acid 468 of SEQ ID NO: 16 is S; the amino acid in the capsid protein corresponding to amino acid 501 of SEQ ID NO: 16 is I; the amino acid in the capsid protein corresponding to amino acid 505 of SEQ ID NO: 16 is R; the amino acid in the capsid protein corresponding to amino acid 590 of SEQ ID NO: 16 is R; the amino acid in the capsid protein corresponding to amino acid 626 of SEQ ID NO: 16 is G or Y; the amino acid in the capsid protein corresponding to amino acid 681 of SEQ ID NO: 16 is M; the amino acid in the capsid protein corresponding to amino acid 687 of SEQ ID NO: 16 is R; the amino acid in the capsid protein corresponding to amino acid 690 of SEQ ID NO: 16 is K; the amino acid in the capsid protein corresponding to amino acid 706 of SEQ ID NO: 16 is C; or, the amino acid in the capsid protein corresponding to amino acid 718 of SEQ ID NO: 16 is G.

Clause 94. The method of Clause 93, wherein:

(a) the amino acid in the capsid protein corresponding to amino acid 626 of SEQ ID NO: 16 is G, and the amino acid in the capsid protein corresponding to amino acid 718 of SEQ ID NO: 16 is G;

(b) the amino acid in the capsid protein corresponding to amino acid 296 of SEQ ID NO: 16 is H, the amino acid in the capsid protein corresponding to amino acid 464 of SEQ ID NO: 16 is N, the amino acid in the capsid protein corresponding to amino acid 505 of SEQ ID NO: 16 is R, and the amino acid in the capsid protein corresponding to amino acid 681 of SEQ ID NO: 16 is M;

(c) the amino acid in the capsid protein corresponding to amino acid 505 of SEQ ID NO: 16 is R, and the amino acid in the capsid protein corresponding to amino acid 687 of SEQ ID NO: 16 is R;

(d) the amino acid in the capsid protein corresponding to amino acid 346 of SEQ ID NO: 16 is A, and the amino acid in the capsid protein corresponding to amino acid 505 of SEQ ID NO: 16 is R; or (e) the amino acid in the capsid protein corresponding to amino acid 501 of SEQ ID NO: 16 is I, the amino acid in the capsid protein corresponding to amino acid 505 of SEQ ID NO: 16 is R, and the amino acid in the capsid protein corresponding to amino acid 706 of SEQ ID NO: 16 is C.

Clause 95. The method of Clause 93, wherein the AAV capsid protein comprises the amino acid sequence of amino acids 138-736 of SEQ ID NO: 1, 2, 3, 4, 5, 6, 7, 9, 10, 11, 12, 13, 15, 16, or 17.

Clause 96. The method of any one of Clauses 86-95, wherein the AAV capsid protein comprises an amino acid sequence that is at least 85% identical to the amino acid sequence of amino acids 1-736 of SEQ ID NO: 1, 2, 3, 4, 5, 6, 7, 8, 9, 10, 11, 12, 13, 15, 16, or 17.

Clause 97. The method of Clause 96, wherein: the amino acid in the capsid protein corresponding to amino acid 2 of SEQ ID NO: 16 is T; the amino acid in the capsid protein corresponding to amino acid 65 of SEQ ID NO: 16 is I; the amino acid in the capsid protein corresponding to amino acid 68 of SEQ ID NO: 16 is V; the amino acid in the capsid protein corresponding to amino acid 77 of SEQ ID NO: 16 is R; the amino acid in the capsid protein corresponding to amino acid 119 of SEQ ID NO: 16 is L; the amino acid in the capsid protein corresponding to amino acid 151 of SEQ ID NO: 16 is R; the amino acid in the capsid protein corresponding to amino acid 160 of SEQ ID NO: 16 is D; the amino acid in the capsid protein corresponding to amino acid 206 of SEQ ID NO: 16 is C; the amino acid in the capsid protein corresponding to amino acid 296 of SEQ ID NO: 16 is H; the amino acid in the capsid protein corresponding to amino acid 312 of SEQ ID NO: 16 is Q; the amino acid in the capsid protein corresponding to amino acid 346 of SEQ ID NO: 16 is A; the amino acid in the capsid protein corresponding to amino acid 464 of SEQ ID NO: 16 is N; the amino acid in the capsid protein corresponding to amino acid 468 of SEQ ID NO: 16 is S; the amino acid in the capsid protein corresponding to amino acid 501 of SEQ ID NO: 16 is I; the amino acid in the capsid protein corresponding to amino acid 505 of SEQ ID NO: 16 is R; the amino acid in the capsid protein corresponding to amino acid 590 of SEQ ID NO: 16 is R; the amino acid in the capsid protein corresponding to amino acid 626 of SEQ ID NO: 16 is G or Y; the amino acid in the capsid protein corresponding to amino acid 681 of SEQ ID NO: 16 is M; the amino acid in the capsid protein corresponding to amino acid 687 of SEQ ID NO: 16 is R; the amino acid in the capsid protein corresponding to amino acid 690 of SEQ ID NO: 16 is K; the amino acid in the capsid protein corresponding to amino acid 706 of SEQ ID NO: 16 is C; or, the amino acid in the capsid protein corresponding to amino acid 718 of SEQ ID NO: 16 is G.

Clause 98. The method of Clause 97, wherein:

(a) the amino acid in the capsid protein corresponding to amino acid 2 of SEQ ID NO: 16 is T, and the amino acid in the capsid protein corresponding to amino acid 312 of SEQ ID NO: 16 is Q;

(b) the amino acid in the capsid protein corresponding to amino acid 65 of SEQ ID NO: 16 is I, and the amino acid in the capsid protein corresponding to amino acid 626 of SEQ ID NO: 16 is Y;

(c) the amino acid in the capsid protein corresponding to amino acid 77 of SEQ ID NO: 16 is R, and the amino acid in the capsid protein corresponding to amino acid 690 of SEQ ID NO: 16 is K;

(d) the amino acid in the capsid protein corresponding to amino acid 119 of SEQ ID NO: 16 is L, and the amino acid in the capsid protein corresponding to amino acid 468 of SEQ ID NO: 16 is S;

(e) the amino acid in the capsid protein corresponding to amino acid 626 of SEQ ID NO: 16 is G, and the amino acid in the capsid protein corresponding to amino acid 718 of SEQ ID NO: 16 is G;

(f) the amino acid in the capsid protein corresponding to amino acid 296 of SEQ ID NO: 16 is H, the amino acid in the capsid protein corresponding to amino acid 464 of SEQ ID NO: 16 is N, the amino acid in the capsid protein corresponding to amino acid 505 of SEQ ID NO: 16 is R, and the amino acid in the capsid protein corresponding to amino acid 681 of SEQ ID NO: 16 is M;

(g) the amino acid in the capsid protein corresponding to amino acid 505 of SEQ ID NO: 16 is R, and the amino acid in the capsid protein corresponding to amino acid 687 of SEQ ID NO: 16 is R;

(h) the amino acid in the capsid protein corresponding to amino acid 346 of SEQ ID NO: 16 is A, and the amino acid in the capsid protein corresponding to amino acid 505 of SEQ ID NO: 16 is R; or (i) the amino acid in the capsid protein corresponding to amino acid 501 of SEQ ID NO: 16 is I, the amino acid in the capsid protein corresponding to amino acid 505 of SEQ ID NO: 16 is R, and the amino acid in the capsid protein corresponding to amino acid 706 of SEQ ID NO: 16 is C.

Clause 99. The method of Clause 97, wherein the AAV capsid protein comprises the amino acid sequence of amino acids 1-736 of SEQ ID NO: 1, 2, 3, 4, 5, 6, 7, 8, 9, 10, 11, 12, 13, 15, 16, or 17.

Clause 100. A composition comprising an AEX medium and a mixture comprising magnesium chloride ($MgCl_2$) and an acetate.

Clause 101. The composition of Clause 100, wherein the mixture comprises an eluate of an affinity chromatography column.

Clause 102. The composition of Clause 100 or 101, wherein the mixture comprises about 10 mM to about 40 mM of an acetate.

Clause 103. The composition of any one of Clauses 100-102, wherein the mixture comprises about 10 mM to about 40 mM ammonium acetate.

Clause 104. The composition of any one of Clauses 100-103, wherein the mixture comprises about 28 mM ammonium acetate.

Clause 105. The composition of any one of Clauses 100-104, wherein the mixture comprises about 2 mM to about 6 mM magnesium chloride.

Clause 106. The composition of any one of Clauses 100-105, wherein the mixture comprises about 2 mM magnesium chloride.

Clause 107. The composition of any one of Clauses 100-106, wherein the mixture comprises about 0.001% (w/v) to about 0.05% (w/v) Poloxamer 188.

Clause 108. The composition of any one of Clauses 100-107, wherein the mixture comprises about 0.01% (w/v) Poloxamer 188.

Clause 109. The composition of any one of Clauses 100-108, wherein the pH of the mixture is about 9 to about 10.5.

Clause 110. The composition of any one of Clauses 100-109, wherein the pH of the mixture is about 9.3.

Clause 111. A composition comprising an AEX medium and a first wash solution, wherein the first wash solution comprises urea and an acetate.

Clause 112. The composition of Clause 111, wherein the AEX medium has an average pore size of at least about 100 nm.

Clause 113. The composition of Clause 111 or 112, wherein the AEX medium has an average pore size of at least about 500 nm.

Clause 114. The composition of any one of Clauses 111-113, wherein the AEX medium comprises a quaternary amine.

Clause 115. The composition of any one of Clauses 111-114, wherein the AEX medium comprises a quaternary polyethyleneimine group.

Clause 116. The composition of any one of Clauses 111-115, wherein the first wash solution comprises about 0.1 M to about 4 M urea.

Clause 117. The composition of any one of Clauses 111-116, wherein the first wash solution comprises about 2 M urea.

Clause 118. The composition of any one of Clauses 111-117, wherein the first wash solution comprises about 10 mM to about 32 mM of the acetate.

Clause 119. The composition of any one of Clauses 111-118, wherein the first wash solution comprises about 10 mM to about 32 mM ammonium acetate.

Clause 120. The composition of any one of Clauses 111-119, wherein the first wash solution comprises about 28 mM ammonium acetate.

Clause 121. The composition of any one of Clauses 111-120, wherein the first wash solution comprises about 2 mM to about 5.7 mM magnesium chloride.

Clause 122. The composition of any one of Clauses 111-121, wherein the first wash solution comprises about 2 mM magnesium chloride.

Clause 123. The composition of any one of Clauses 111-122, wherein the first wash solution comprises about 0.001% (w/v) to about 0.05% (w/v) Poloxamer 188.

Clause 124. The composition of any one of Clauses 111-123, wherein the first wash solution comprises about 0.01% (w/v) Poloxamer 188.

Clause 125. The composition of any one of Clauses 111-124, wherein the pH of the first wash solution is about 9 to about 10.5.

Clause 126. The composition of any one of Clauses 111-125, wherein the pH of the first wash solution is about 9.3.

Clause 127. The composition of any one of Clauses 111-126, wherein the first wash solution has a conductivity of about 3 mS/cm.

The invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

All references (e.g., publications or patents or patent applications) cited herein are incorporated herein by reference in their entirety and for all purposes to the same extent as if each individual reference (e.g., publication or patent or patent application) was specifically and individually indicated to be incorporated by reference in its entirety for all purposes. Other embodiments are within the following claims.

We claim:

1. A method for separating intact adeno-associated virus (AAV) particles from empty AAV particles, the method comprising: contacting a load mixture comprising intact AAV particles, empty AAV particles, a divalent salt, and a first acetate with an anion exchange chromatography (AEX) medium; and, washing the AEX medium with a first wash solution under conditions that favor dissociation of empty AAV particles into the first wash solution as compared to intact AAV particles, wherein the first wash solution comprising empty AAV particles is eluted from the AEX medium, thereby separating at least a subset of empty AAV particles from intact AAV particles.

2. The method according to claim 1, wherein the divalent salt is chosen from magnesium chloride, manganese chloride, copper chloride, zinc chloride and combinations thereof.

3. The method according to claim 2, wherein the divalent salt is magnesium chloride.

4. The method according to claim 1, wherein the first wash solution comprises a second acetate.

5. The method according to claim 1, further comprising applying a re-equilibration buffer comprising the divalent salt to the AEX medium.

6. The method according to claim 5, wherein the first wash solution has a conductivity of about 1 mS/cm.

7. The method according to claim 6, further comprising washing the AEX medium with a second wash solution comprising urea.

8. The method according to claim 7, wherein the second wash solution is applied to the AEX medium before the first wash solution, and each of the first wash solution and second wash solution have a pH of about 9.3 when measured at about 20 degrees Celsius.

9. The method according to claim 1, wherein the AEX medium comprises a quaternary amine.

10. The method according to claim 1, wherein the AEX medium has an average pore size ranging from about 100 nm to about 500 nm.

11. The method according to claim 1, wherein the AEX medium has an average pore size of about 200 nm.

12. A chromatographic method for separating intact adeno-associated virus (AAV) particles from contaminant AAV particles lacking a complete genome, the method comprising:

a. contacting a load mixture with an anion exchange (AEX) chromatography medium, wherein the load mixture comprises (i) a first ratio of contaminant AAV particles to intact AAV particles, (ii) a first acetate, and (iii) a divalent salt; and, b. washing the AEX medium with a first wash solution, wherein the first wash solution is eluted from the AEX medium;

c. eluting a product mixture from the AEX medium;

wherein the product mixture comprises a majority of intact AAV particles and having second ratio of contaminant AAV particles to intact AVV particles that is lower than the first ratio, thereby separating intact AAV particles from contaminant AAV particles lacking a complete genome;

wherein the product mixture has a lower percentage of contaminant particles than a second product mixture which results from a similar process using a load composition that does not comprise the divalent salt.

13. The method according to claim 12, wherein the divalent salt is magnesium chloride.

14. The method according to claim 13, wherein the method further comprises applying a re-equilibration buffer comprising magnesium chloride to the AEX medium prior to step c.

15. The method according to claim 12, wherein the first wash solution comprises a second acetate and has a conductivity of about 1 mS/cm.

16. The method according to claim 12, further comprising washing the AEX medium with a second wash solution comprising urea and a third acetate prior to step c.

17. The method according to claim 16, wherein each of the first acetate, the second acetate and the third acetate are ammonium acetate.

18. The method according to claim 16, wherein the contaminant AAV particles comprise empty AAV particles, and wherein the product mixture comprises less than about 30% empty AAV particles, as measured by analytical ultracentrifugation.

19. The method according to claim 18, wherein the product mixture comprises less than about 20% empty AAV particles as measured by analytical ultracentrifugation.

* * * * *

SEQUENCE LISTING

```
Sequence total quantity: 64
SEQ ID NO: 1            moltype = AA  length = 736
FEATURE                 Location/Qualifiers
source                  1..736
                        mol_type = protein
                        organism = synthetic construct
SEQUENCE: 1
MAADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT INGSGQNQQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQSAQAQ AQTGWVQNQG  600
ILPGMVWQDR DVYLQGPIWA KIPHTDGNFH PSPLMGGFGM KHPPPQILIK NTPVPADPPT  660
AFNKDKLNSF ITQYSTGQVS VEIEWELQKE NSKRWNPEIQ YTSNYYKSNN VEFAVNTEGV  720
YSEPRPIGTR YLTRNL                                                 736

SEQ ID NO: 2            moltype = AA  length = 736
FEATURE                 Location/Qualifiers
source                  1..736
                        mol_type = protein
                        organism = synthetic construct
SEQUENCE: 2
MTADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KQLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT INGSGQNQQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQSAQAQ AQTGWVQNQG  600
ILPGMVWQDR DVYLQGPIWA KIPHTDGNFH PSPLMGGFGM KHPPPQILIK NTPVPADPPT  660
AFNKDKLNSF ITQYSTGQVS VEIEWELQKE NSKRWNPEIQ YTSNYYKSNN VEFAVNTEGV  720
YSEPRPIGTR YLTRNL                                                 736

SEQ ID NO: 3            moltype = AA  length = 736
FEATURE                 Location/Qualifiers
source                  1..736
                        mol_type = protein
                        organism = synthetic construct
SEQUENCE: 3
MAADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT INGSGQNQQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQSAQAQ AQTGWVQNQG  600
ILPGMVWQDR DVYLQGPIWA KIPHTGGNFH PSPLMGGFGM KHPPPQILIK NTPVPADPPT  660
AFNKDKLNSF ITQYSTGQVS VEIEWELQKE NSKRWNPEIQ YTSNYYKSNN VEFAVNTGGV  720
YSEPRPIGTR YLTRNL                                                 736

SEQ ID NO: 4            moltype = AA  length = 736
FEATURE                 Location/Qualifiers
source                  1..736
                        mol_type = protein
                        organism = synthetic construct
SEQUENCE: 4
MAADGYLPDW LEDNLSEGIR EWWALKPGAP QPKANQQHQD NARGLVLPGY KYLGPGNGLD  60
KGEPINAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT INGSGQNQQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQSAQAQ AQTGWVQNQG  600
ILPGMVWQDR DVYLQGPIWA KIPHTYGNFH PSPLMGGFGM KHPPPQILIK NTPVPADPPT  660
```

```
AFNKDKLNSF ITQYSTGQVS VEIEWELQKE NSKRWNPEIQ YTSNYYKSNN VEFAVNTEGV  720
YSEPRPIGTR YLTRNL                                                 736

SEQ ID NO: 5            moltype = AA  length = 736
FEATURE                 Location/Qualifiers
source                  1..736
                        mol_type = protein
                        organism = synthetic construct
SEQUENCE: 5
MAADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGID KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT INGSGQNQQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQSAQAQ AQTGWVQNQG  600
ILPGMVWQDR DVYLQGPIWA KIPHTDGNFH PSPLMGGFGM KHPPPQILIK NTPVPADPPT  660
AFNKDKLNSF ITQYSTGQVS VEIEWELQKE NSKRWNPEIQ YTSNYYKSNN VEFAVNTEGV  720
YSEPRPIGTR YLTRNL                                                 736

SEQ ID NO: 6            moltype = AA  length = 736
FEATURE                 Location/Qualifiers
source                  1..736
                        mol_type = protein
                        organism = synthetic construct
SEQUENCE: 6
MAADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QERLKEDTSF GGNLGRAVLQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT INGSGQNQQT LKFSVAGSSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQSAQAQ AQTGWVQNQG  600
ILPGMVWQDR DVYLQGPIWA KIPHTDGNFH PSPLMGGFGM KHPPPQILIK NTPVPADPPT  660
AFNKDKLNSF ITQYSTGQVS VEIEWELQKE NSKRWNPEIQ YTSNYYKSNN VEFAVNTEGV  720
YSEPRPIGTR YLTRNL                                                 736

SEQ ID NO: 7            moltype = AA  length = 736
FEATURE                 Location/Qualifiers
source                  1..736
                        mol_type = protein
                        organism = synthetic construct
SEQUENCE: 7
MAADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT INGSGQNQQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQSAQAR AQTGWVQNQG  600
ILPGMVWQDR DVYLQGPIWA KIPHTDGNFH PSPLMGGFGM KHPPPQILIK NTPVPADPPT  660
AFNKDKLNSF ITQYSTGQVS VEIEWELQKE NSKRWNPEIQ YTSNYYKSNN VEFAVNTEGV  720
YSEPRPIGTR YLTRNL                                                 736

SEQ ID NO: 8            moltype = AA  length = 736
FEATURE                 Location/Qualifiers
source                  1..736
                        mol_type = protein
                        organism = synthetic construct
SEQUENCE: 8
MAADGYLPDW LEDNLSEGIR EWWALKPGAP QPKANQQHQD NARGLVLPGY KYLGPGNGLD  60
KGEPVNAVDA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT INGSGQNQQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQSAQAQ AQTGWVQNQG  600
```

```
ILPGMVWQDR DVYLQGPIWA KIPHTDGNFH PSPLMGGFGM KHPPPQILIK NTPVPADPPT  660
AFNKDKLNSF ITQYSTGQVS VEIEWELQKE NSKRWNPEIQ YTSNYYKSNN VEFAVNTEGV  720
YSEPRPIGTR YLTRNL                                                 736

SEQ ID NO: 9           moltype = AA  length = 736
FEATURE                Location/Qualifiers
source                 1..736
                       mol_type = protein
                       organism = synthetic construct
SEQUENCE: 9
MAADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP REPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT INGSGQNQQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQSAQAQ AQTGWVQNQG  600
ILPGMVWQDR DVYLQGPIWA KIPHTDGNFH PSPLMGGFGM KHPPPQILIK NTPVPADPPT  660
AFNKDKLNSF ITQYSTGQVS VEIEWELQKE NSKRWNPEIQ YTSNYYKSNN VEFAVNTEGV  720
YSEPRPIGTR YLTRNL                                                 736

SEQ ID NO: 10          moltype = AA  length = 736
FEATURE                Location/Qualifiers
source                 1..736
                       mol_type = protein
                       organism = synthetic construct
SEQUENCE: 10
MAADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASCGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT INGSGQNQQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQSAQAQ AQTGWVQNQG  600
ILPGMVWQDR DVYLQGPIWA KIPHTDGNFH PSPLMGGFGM KHPPPQILIK NTPVPADPPT  660
AFNKDKLNSF ITQYSTGQVS VEIEWELQKE NSKRWNPEIQ YTSNYYKSNN VEFAVNTEGV  720
YSEPRPIGTR YLTRNL                                                 736

SEQ ID NO: 11          moltype = AA  length = 736
FEATURE                Location/Qualifiers
source                 1..736
                       mol_type = protein
                       organism = synthetic construct
SEQUENCE: 11
MAADGYLPDW LEDNLSEGIR EWWALKPGAP QPKANQQHQD NARGLVLPGY KYLGPGNGLD  60
KGEPVNAADA AALEHDRAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT INGSGQNQQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQSAQAQ AQTGWVQNQG  600
ILPGMVWQDR DVYLQGPIWA KIPHTDGNFH PSPLMGGFGM KHPPPQILIK NTPVPADPPT  660
AFNKDKLNSF ITQYSTGQVS VEIEWELQKK NSKRWNPEIQ YTSNYYKSNN VEFAVNTEGV  720
YSEPRPIGTR YLTRNL                                                 736

SEQ ID NO: 12          moltype = AA  length = 736
FEATURE                Location/Qualifiers
source                 1..736
                       mol_type = protein
                       organism = synthetic construct
SEQUENCE: 12
MAADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPHDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT INGSGQNQQT LKFNVAGPSN MAVQGRNYIP  480
GPSYRQQRVS TTVTQNNNSE FAWPRASSWA LNGRNSLMNP GPAMASHKEG EDRFFPLSGS  540
```

-continued

```
LIFGKQGTGR DNVDADKVMI TNEEEIKTTN PVATESYGQV ATNHQSAQAQ AQTGWVQNQG  600
ILPGMVWQDR DVYLQGPIWA KIPHTDGNFH PSPLMGGFGM KHPPPQILIK NTPVPADPPT  660
AFNKDKLNSF ITQYSTGQVS MEIEWELQKE NSKRWNPEIQ YTSNYYKSNN VEFAVNTEGV  720
YSEPRPIGTR YLTRNL                                                 736

SEQ ID NO: 13          moltype = AA  length = 736
FEATURE                Location/Qualifiers
source                 1..736
                       mol_type = protein
                       organism = synthetic construct
SEQUENCE: 13
MAADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT INGSGQNQQT LKFSVAGPSN MAVQGRNYIP  480
GPSYRQQRVS TTVTQNNNSE FAWPRASSWA LNGRNSLMNP GPAMASHKEG EDRFFPLSGS  540
LIFGKQGTGR DNVDADKVMI TNEEEIKTTN PVATESYGQV ATNHQSAQAQ AQTGWVQNQG  600
ILPGMVWQDR DVYLQGPIWA KIPHTDGNFH PSPLMGGFGM KHPPPQILIK NTPVPADPPT  660
AFNKDKLNSF ITQYSTGQVS VEIEWELQKE NSKRWNPEIQ YTSNYYKSNN VEFAVNTEGV  720
YSEPRPIGTR YLTRNL                                                 736

SEQ ID NO: 14          moltype = DNA  length = 198
FEATURE                Location/Qualifiers
source                 1..198
                       mol_type = other DNA
                       organism = synthetic construct
SEQUENCE: 14
gatccagaca tgataagata cattgatgag tttggacaaa ccacaactag aatgcagtga  60
aaaaaatgct ttatttgtga aatttgtgat gctattgctt tatttgtaac cattataagc  120
tgcaataaac aagttaacaa caacaattgc attcatttta tgtttcaggt tcagggggag  180
gtgtgggagg ttttttaa                                               198

SEQ ID NO: 15          moltype = AA  length = 736
FEATURE                Location/Qualifiers
source                 1..736
                       mol_type = protein
                       organism = synthetic construct
SEQUENCE: 15
MAADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT INGSGQNQQT LKFSVAGPSN MAVQGRNYIP  480
GPSYRQQRVS TTVTQNNNSE FAWPRASSWA LNGRNSLMNP GPAMASHKEG EDRFFPLSGS  540
LIFGKQGTGR DNVDADKVMI TNEEEIKTTN PVATESYGQV ATNHQSAQAQ AQTGWVQNQG  600
ILPGMVWQDR DVYLQGPIWA KIPHTDGNFH PSPLMGGFGM KHPPPQILIK NTPVPADPPT  660
AFNKDKLNSF ITQYSTGQVS VEIEWERQKE NSKRWNPEIQ YTSNYYKSNN VEFAVNTEGV  720
YSEPRPIGTR YLTRNL                                                 736

SEQ ID NO: 16          moltype = AA  length = 736
FEATURE                Location/Qualifiers
source                 1..736
                       mol_type = protein
                       organism = synthetic construct
SEQUENCE: 16
MAADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFADSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT INGSGQNQQT LKFSVAGPSN MAVQGRNYIP  480
GPSYRQQRVS TTVTQNNNSE FAWPRASSWA LNGRNSLMNP GPAMASHKEG EDRFFPLSGS  540
LIFGKQGTGR DNVDADKVMI TNEEEIKTTN PVATESYGQV ATNHQSAQAQ AQTGWVQNQG  600
ILPGMVWQDR DVYLQGPIWA KIPHTDGNFH PSPLMGGFGM KHPPPQILIK NTPVPADPPT  660
AFNKDKLNSF ITQYSTGQVS VEIEWELQKE NSKRWNPEIQ YTSNYYKSNN VEFAVNTEGV  720
YSEPRPIGTR YLTRNL                                                 736

SEQ ID NO: 17          moltype = AA  length = 736
FEATURE                Location/Qualifiers
source                 1..736
```

```
                         mol_type = protein
                         organism = synthetic construct
SEQUENCE: 17
MAADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT INGSGQNQQT LKFSVAGPSN MAVQGRNYIP  480
GPSYRQQRVS TTVTQNNNSE IAWPRASSWA LNGRNSLMNP GPAMASHKEG EDRFFPLSGS  540
LIFGKQGTGR DNVDADKVMI TNEEEIKTTN PVATESYGQV ATNHQSAQAQ AQTGWVQNQG  600
ILPGMVWQDR DVYLQGPIWA KIPHTDGNFH PSPLMGGFGM KHPPPQILIK NTPVPADPPT  660
AFNKDKLNSF ITQYSTGQVS VEIEWELQKE NSKRWNPEIQ YTSNYCKSNN VEFAVNTEGV  720
YSEPRPIGTR YLTRNL                                                 736

SEQ ID NO: 18            moltype = DNA  length = 365
FEATURE                  Location/Qualifiers
source                   1..365
                         mol_type = other DNA
                         organism = synthetic construct
SEQUENCE: 18
ctagttatta atagtaatca attacggggt cattagttca tagcccatat atggagttcc  60
gcgttacata acttacggta aatggcccgc ctggctgacc gcccaacgac ccccgcccat  120
tgacgtcaat aatgacgtat gttcccatag taacgccaat agggactttc cattgacgtc  180
aatgggtgga gtatttacgg taaactgccc acttggcagt acatcaagtg tatcatatgc  240
caagtccgcc ccctattgac gtcaatgacg gtaaatggcc cgcctggcat tatgcccagt  300
acatgacctt acgggacttt cctacttggc agtacatcta cgtattagtc atcgctatta  360
ccatg                                                             365

SEQ ID NO: 19            moltype = DNA  length = 380
FEATURE                  Location/Qualifiers
source                   1..380
                         mol_type = other DNA
                         organism = synthetic construct
SEQUENCE: 19
ggcattgatt attgactagt tattaatagt aatcaattac ggggtcatta gttcatagcc  60
catatatgga gttccgcgtt acataactta cggtaaatgg cccgcctggc tgaccgccca  120
acgacccccg cccattgacg tcaataatga cgtatgttcc catagtaacg ccaataggga  180
ctttccattg acgtcaatgg gtggagtatt tacggtaaac tgcccacttg gcagtacatc  240
aagtgtatca tatgccaagt ccgcccccta ttgacgtcaa tgacggtaaa tggcccgcct  300
ggcattatgc ccagtacatg accttacggg actttcctac ttggcagtac atctacgtat  360
tagtcatcgc tattaccatg                                             380

SEQ ID NO: 20            moltype = DNA  length = 479
FEATURE                  Location/Qualifiers
source                   1..479
                         mol_type = other DNA
                         organism = synthetic construct
SEQUENCE: 20
tcgaggtgag ccccacgttc tgcttcactc tccccatctc ccccccctcc ccacccccaa  60
ttttgtattt atttattttt taattatttt gtgcagcgat gggggcgggg gggggggggg  120
ggcgcgcgcc aggcggggcg gggcggggcg aggggcgggg cggggcgagg cggagaggtg  180
cggcggcagc caatcagagc ggcgcgctcc gaaagtttcc ttttatggcg aggcggcggc  240
ggcggcggcc ctataaaaag cgaagcgcgc ggcgggcggg agtcgctgcg cgctgccttc  300
gccccgtgcc ccgctccgcc gccgcctcgc gccgcccgcc ccggctctga ctgaccgcgt  360
tactcccaca ggtgagcggg cgggacggcc cttctcctcc gggctgtaat tagcgcttgg  420
tttaatgacg gcttgtttct tttctgtggc tgcgtgaaag ccttgagggg ctccgggag   479

SEQ ID NO: 21            moltype = DNA  length = 1246
FEATURE                  Location/Qualifiers
source                   1..1246
                         mol_type = other DNA
                         organism = synthetic construct
SEQUENCE: 21
tcgaggtgag ccccacgttc tgcttcactc tccccatctc ccccccctcc ccacccccaa  60
ttttgtattt atttattttt taattatttt gtgcagcgat gggggcgggg gggggggggg  120
ggcgcgcgcc aggcggggcg gggcggggcg aggggcgggg cggggcgagg cggagaggtg  180
cggcggcagc caatcagagc ggcgcgctcc gaaagtttcc ttttatggcg aggcggcggc  240
ggcggcggcc ctataaaaag cgaagcgcgc ggcgggcggg agtcgctgcg cgctgccttc  300
gccccgtgcc ccgctccgcc gccgcctcgc gccgcccgcc ccggctctga ctgaccgcgt  360
tactcccaca ggtgagcggg cgggacggcc cttctcctcc gggctgtaat tagcgcttgg  420
tttaatgacg gcttgtttct tttctgtggc tgcgtgaaag ccttgagggg ctccgggagg  480
gccctttgtg cggggggagc ggctcggggg gtgcgtgcgt gtgtgtgtgc gtggggagcg  540
ccgcgtgcgg ctccgcgctg cccggcggct gtgagcgctg cgggcgcggc gcggggcttt  600
gtgcgctccg cagtgtgcgc gaggggagcg cggccggggg cggtgccccg cggtgcgggg  660
ggggctgcga ggggaacaaa ggctgcgtgc ggggtgtgtg cgtggggggg tgagcagggg  720
gtgtgggcgc gtcggtcggg ctgcaacccc ccctgcaccc ccctccccga gttgctgagc  780
```

```
acggcccggc ttcgggtgcg gggctccgta cggggcgtgg cgcggggctc gccgtgccgg  840
gcggggggtg gcggcaggtg ggggtgccgg gcggggcggg gccgcctcgg gccggggagg  900
gctcggggga ggggcgcggc ggcccccgga gcgccggcgg ctgtcgaggc gcggcgagcc  960
gcagccattg ccttttatgg taatcgtgcg agagggcgca gggacttcct ttgtcccaaa  1020
tctgtgcgga gccgaaatct gggaggcgcc gccgcacccc ctctagcggg cgcggggcga  1080
agcggtgcgg cgccggcagg aaggaaatgg gcggggaggg ccttcgtgcg tcgccgcgcc  1140
gccgtcccct tctccctctc cagcctcggg gctgtccgcg gggggacggc tgccttcggg  1200
ggggacgggg cagggcgggg ttcggcttct ggcgtgtgac cggcgg                1246

SEQ ID NO: 22          moltype = DNA  length = 953
FEATURE                Location/Qualifiers
source                 1..953
                       mol_type = other DNA
                       organism = synthetic construct
SEQUENCE: 22
aattcggtac cctagttatt aatagtaatc aattacgggg tcattagttc atagcccata  60
tatggagttc cgcgttacat aacttacggt aaatggcccg cctggctgac cgcccaacga  120
cccccgccca ttgacgtcaa taatgacgta tgttcccata gtaacgccaa tagggacttt  180
ccattgacgt caatgggtgg actatttacg gtaaactgcc cacttggcag tacatcaagt  240
gtatcatatg ccaagtacgc cccctattga cgtcaatgac ggtaaatggc ccgcctggca  300
ttatgcccag tacatgacct tatgggactt tcctacttgg cagtacatct acgtattagt  360
catcgctatt accatggtcg aggtgagccc cacgttctgc ttcactctcc ccatctcccc  420
cccctcccca cccccaattt tgtatttatt tatttttaa ttattttgtg cagcgatggg  480
ggcggggggg gggggggggc gcgcgccagg cggggcgggg cggggcgagg ggcggggcgg  540
ggcgaggcgg agaggtgcgg cggcagccaa tcagagcggc gcgctccgaa agtttccttt  600
tatggcgagg cggcggcggc ggcggcccta taaaaagcga agcgcgcggc gggcgggagt  660
cgctgcgacg ctgccttcgc cccgtgcccc gctccgccgc cgcctcgcgc cgcccgcccc  720
ggctctgact gaccgcgtta ctcccacagg tgagcgggcg ggacggccct tctcctccgg  780
gctgtaatta gcgcttggtt taatgacggc ttgtttcttt tctgtggctg cgtgaaagcc  840
ttgaggggct ccgggagcta gagcctctgc taaccatgtt catgccttct tctttttcct  900
acagctcctg ggcaacgtgc tggttattgt gctgtctcat cattttggca aag        953

SEQ ID NO: 23          moltype = DNA  length = 1168
FEATURE                Location/Qualifiers
source                 1..1168
                       mol_type = other DNA
                       organism = synthetic construct
SEQUENCE: 23
cgtgaggctc cggtgcccgt cagtgggcag agcgcacatc gcccacagtc cccgagaagt  60
tggggggagg ggtcggcaat tgaaccggtg cctagagaag gtggcgcggg gtaaactggg  120
aaagtgatgt cgtgtactgg ctccgccttt ttcccgaggg tgggggagaa ccgtatataa  180
gtgcagtagt cgccgtgaac gttctttttc gcaacgggtt tgccgccaga acacaggtaa  240
gtgccgtgtg tggttcccgc gggcctggcc tctttacggg ttatggccct tgcgtgcctt  300
gaattacttc cacctggctc cagtacgtga ttcttgatcc cgagctggag ccaggggcgg  360
gccttgcgct ttaggagccc cttcgcctcg tgcttgagtt gaggcctggc ctgggcgctg  420
gggccgccgc gtgcgaatct ggtggcacct tcgcgcctgt ctcgctgctt tcgataagtc  480
tctagccatt taaaattttt gatgacctgc tgcgacgctt tttttctggc aagatagtct  540
tgtaaatgcg ggccaggatc tgcacactgg tatttcggtt tttggggccg cgggcggcga  600
cggggcccgt gcgtcccagc gcacatgttc ggcgaggcgg ggcctgcgag cgcggccacc  660
gagaatcgga cgggggtagt ctcaagctgg ccggcctgct ctggtgcctg gcctcgcgcc  720
gccgtgtatc gccccgccct gggcggcaag gctggcccgg tcggcaccag ttgcgtgagc  780
ggaaagatgg ccgcttcccg gccctgctcc agggggctca aaatggagga cgcggcgctc  840
gggagagcgg gcgggtgagt cacccacaca aaggaaaggg gcctttccgt cctcagccgt  900
cgcttcatgt gactccacgg agtaccgggc gccgtccagg cacctcgatt agttctggag  960
cttttggagt acgtcgtctt taggttgggg ggaggggttt tatgcgatgg agtttcccca  1020
cactgagtgg gtggagactg aagttaggcc agcttggcac ttgatgtaat tctccttgga  1080
atttgccctt tttgagtttg gatcttggtt cattctcaag cctcagacag tggttcaaag  1140
ttttttttctt ccatttcagg tgtcgtga                                  1168

SEQ ID NO: 24          moltype = DNA  length = 92
FEATURE                Location/Qualifiers
source                 1..92
                       mol_type = other DNA
                       organism = synthetic construct
SEQUENCE: 24
aagaggtaag ggtttaaggg atggttggtt ggtggggtat taatgtttaa ttacctggag  60
cacctgcctg aaatcacttt ttttcaggtt gg                              92

SEQ ID NO: 25          moltype = DNA  length = 79
FEATURE                Location/Qualifiers
source                 1..79
                       mol_type = other DNA
                       organism = synthetic construct
SEQUENCE: 25
aagaggtaag ggtttaaggg atggttggtt ggtggggtat taatgtttaa ttacctggag  60
cacctgcctg aaatcactt                                             79

SEQ ID NO: 26          moltype = DNA  length = 95
FEATURE                Location/Qualifiers
```

```
source                  1..95
                        mol_type = other DNA
                        organism = synthetic construct
SEQUENCE: 26
cctctgctaa ccatgttcat gccttcttct ttttcctaca gctcctgggc aacgtgctgg  60
ttattgtgct gtctcatcat tttggcaaag aattc                              95

SEQ ID NO: 27           moltype = DNA  length = 90
FEATURE                 Location/Qualifiers
source                  1..90
                        mol_type = other DNA
                        organism = synthetic construct
SEQUENCE: 27
cctctgctaa ccatgttcat gccttcttct ttttcctaca gctcctgggc aacgtgctgg  60
ttattgtgct gtctcatcat tttggcaaag                                    90

SEQ ID NO: 28           moltype = DNA  length = 918
FEATURE                 Location/Qualifiers
source                  1..918
                        mol_type = other DNA
                        organism = synthetic construct
SEQUENCE: 28
ggcatcctaa aaaatattca gtggaaacgt aaaaacatta aagactgatt aaacatcgca  60
gcatgacaca gatttagcaa ctgagcataa ataatttgac tcggatactg ctccaaaatc  120
cgaagaggac caatttcttc caggaggaca actacctcgt cctctgcaga cccctctcct  180
cggcagctga aggagtgtgg ccaatctgcc tccacctccc cgcggacccc ctactctcag  240
gacctcctgc agcaccccaa actggaagtg gccgctgcag acccaaggac gaggggcacg  300
cgggagccgg cagccctagt ggagcggttg gagatgttga ggtgggaggg tcacccaggt  360
ggggtgaggc tggggtaggt agcggagtga acggcttccg aagctctggg ccgcccccag  420
gttggactaa gcaggcgctc tgtcttcgcc cccgcccagg gtgggcgtct cctgaggact  480
ccccgccaca cctgacccga gaccgcgcgc ccagcctaga acgcttcccc gacccagcgt  540
agggccgccg cgactggcgg gcgagggtcg gcgggaggcc tggcgaaccc gggggcggga  600
ccaggcgggc aaggcccggc tgccgcagcg ccgctctgcg cgaggcggct ccgccgcggc  660
ggagggatac ggcgcaccat atatatatcg cggggcgcag actcgcgctc cggcagtggt  720
gctgggagtg tcgtggacgc cgtgccgtta ctcgtagtca ggcggcggcg caggcggcgg  780
cggcggcata gcgcacagcg cgccttagca gcagcagcag cagcagcggc atcggaggta  840
cccccgccgt cgcagccccc gcgctggtgc agccaccctc gctccctctg ctcttcctcc  900
cttcgctcgc accaagag                                                 918

SEQ ID NO: 29           moltype = DNA  length = 192
FEATURE                 Location/Qualifiers
source                  1..192
                        mol_type = other DNA
                        organism = synthetic construct
SEQUENCE: 29
ccctaaaatg ggcaaacatt gcaagcagca aacagcaaac acacagccct ccctgcctgc  60
tgaccttgga gctggggcag aggtcagaga cctctctggg cccatgccac ctccaacatc  120
cactcgaccc cttggaattt cggtggagag gagcagaggt tgtcctggcg tggtttaggt  180
agtgtgagag gg                                                       192

SEQ ID NO: 30           moltype = DNA  length = 205
FEATURE                 Location/Qualifiers
source                  1..205
                        mol_type = other DNA
                        organism = synthetic construct
SEQUENCE: 30
aatgactcct ttcggtaagt gcagtggaag ctgtacactg cccaggcaaa gcgtccgggc  60
agcgtaggcg ggcgactcag atcccagcca gtggacttag cccctgtttg ctcctccgat  120
aactggggtg accttggtta atattcacca gcagcctccc ccgttgcccc tctggatcca  180
ctgcttaaat acggacgagg acagg                                         205

SEQ ID NO: 31           moltype = DNA  length = 913
FEATURE                 Location/Qualifiers
source                  1..913
                        mol_type = other DNA
                        organism = synthetic construct
SEQUENCE: 31
tagggaggtc ctgcacagaa ggggaggagg gggcagcagc tgtctgacca ctgttggtct  60
tgcaacttgt gtccccaggt taatttttaa aaagcagtca aaagtccaag tggcccttgg  120
cagcatttac tctctctgtt tgctctggtt aataatctca ggagcacaaa cattcctgga  180
ggcaggagaa gaaatcaaca tcctggactt atcctctggg cctctcccca cccccaggat  240
tgtaactgaa atgcttcact ggtgctcctt ttgttttaag gcattggatc ttcatagcta  300
ctgatcgtgc ccaagcacac agtatctgca gcaaccactt aggcctccag gaatgtggtg  360
accattgacc ctaattcatt ccccttcatg gatcctatgt aaccatcctc caaaaagagc  420
tttcgcaaac tcaaataaac acaggaaagg aagaccttct tatctttgag agtatatgtt  480
tagccctata gctctaaccc actctgatct cccagggcgg cagtaagtct tcagcatcag  540
gcattttggg gtgactcagt aaatggtaga tcttgctacc agtggaacag ccactaagga  600
ttctgcagtg agagcagagg gccagctaag tggtactctc ccagagactg tctgactcac  660
gccaccccct ccaccttgga cacaggacgc tgtggtttct gagccaggta caatgactcc  720
```

```
tttcggtaag tgcagtggaa gctgtacact gcccaggcaa agcgtccggg cagcgtaggc  780
gggcgactca gatcccagcc agtggactta gcccctgttt gctcctccga taactggggt  840
gaccttggtt aatattcacc agcagcctcc cccgttgccc ctctggatcc actgcttaaa  900
tacggacgag gac                                                      913

SEQ ID NO: 32          moltype = DNA  length = 423
FEATURE                Location/Qualifiers
source                 1..423
                       mol_type = other DNA
                       organism = synthetic construct
SEQUENCE: 32
gctctaaccc actctgatct cccagggcgg cagtaagtct tcagcatcag gcattttggg  60
gtgactcagt aaatggtaga tcttgctacc agtggaacag ccactaagga ttctgcagtg  120
agagcagagg gccagctaag tggtactctc ccagagactg tctgactcac gccacccct  180
ccaccttgga cacaggacgc tgtggtttct gagccaggta caatgactcc tttcggtaag  240
tgcagtggaa gctgtacact gcccaggcaa agcgtccggg cagcgtaggc gggcgactca  300
gatcccagcc agtggactta gcccctgttt gctcctccga taactggggt gaccttggtt  360
aatattcacc agcagcctcc cccgttgccc ctctggatcc actgcttaaa tacggacgag  420
gac                                                                 423

SEQ ID NO: 33          moltype = DNA  length = 592
FEATURE                Location/Qualifiers
source                 1..592
                       mol_type = other DNA
                       organism = synthetic construct
SEQUENCE: 33
gtaaatttta tggaatgtga atcataattc aatttttcaa catgcgttag gagggacatt  60
tcaaactctt ttttacccta gactttccta ccatcaccca gagtatccag ccaggagggg  120
aggggctaga gacaccagaa gtttagcagg gaggagggcg tagggattcg gggaatgaag  180
ggatgggatt cagactaggg ccaggaccca gggatggaga gaaagagatg agagtggttt  240
gggggcttgg tgacttagag aacagagctg caggctcaga ggcacacagg agtttctggg  300
ctcaccctgc cccccttccaa cccctcagtt cccatcctcc agcagctgtt tgtgtgctgc  360
ctctgaagtc cacactgaac aaacttcagc ctactcatgt ccctaaaatg ggcaaacatt  420
gcaagcagca aacagcaaac acacagccct ccctgcctgc tgaccttgga gctggggcag  480
aggtcagaga cctctctggg cccatgccac ctccaacatc cactcgaccc cttggaattt  540
cggtggagag gagcagaggt tgtcctggcg tggtttaggt agtgtgagag gg          592

SEQ ID NO: 34          moltype = DNA  length = 72
FEATURE                Location/Qualifiers
source                 1..72
                       mol_type = other DNA
                       organism = synthetic construct
SEQUENCE: 34
gggggaggct gctggtgaat attaaccaag gtcaccccag ttatcggagg agcaaacagg  60
ggctaagtcc ac                                                       72

SEQ ID NO: 35          moltype = DNA  length = 170
FEATURE                Location/Qualifiers
source                 1..170
                       mol_type = other DNA
                       organism = synthetic construct
SEQUENCE: 35
cgatgctcta atctctctag acaaggttca tatttgtatg ggttacttat tctctctttg  60
ttgactaagt caataatcag aatcagcagg tttgcagtca gattggcagg gataagcagc  120
ctagctcagg agaagtgagt ataaaagccc caggctggga gcagccatca             170

SEQ ID NO: 36          moltype = DNA  length = 1873
FEATURE                Location/Qualifiers
source                 1..1873
                       mol_type = other DNA
                       organism = synthetic construct
SEQUENCE: 36
gatcttcaat attggccatt agccatatta ttcattggtt atatagcata aatcaatatt  60
ggctattggc cattgcatac gttgtatcta tatcataata tgtacattta tattggctca  120
tgtccaatat gaccgccatg ttggcattga ttattgacta gttattaata gtaatcaatt  180
acggggtcat tagttcatag cccatatatg gagttccgcg ttacataact tacggtaaat  240
ggcccgcctg gctgaccgcc caacgacccc cgcccattga cgtcaataat gacgtatgtt  300
cccatagtaa cgccaatagg gactttccat tgacgtcaat gggtggagta tttacggtaa  360
actgcccact tggcagtaca tcaagtgtat catatgccaa gtccgccccc tattgacgtc  420
aatgacggta aatggcccgc ctggcattat gcccagtaca tgaccttacg ggactttcct  480
acttggcagt acatctacgt attagtcatc gctattacca tggtcgaggt gagccccacg  540
ttctgcttca ctctccccat ctcccccccc tccccacccc caattttgta tttatttatt  600
ttttaattat tttgtgcagc gatgggggcg gggggggggg gggggcgcgc gccaggcggg  660
gcggggcggg gcgaggggcg gggcggggcg aggcggagag gtgcggcggc agccaatcag  720
agcggcgcgc tccgaaagtt tccttttatg gcgaggcggc ggcggcggcg gccctataaa  780
aagcgaagcg cgcggcgggc gggagtcgct gcgacgctgc cttcgccccg tgccccgctc  840
cgccgccgcc tcgcgccgcc cgccccggct ctgactgacc gcgttactcc cacaggtgag  900
cgggcgggac ggcccttctc ctccgggctg taattagcgc ttggtttaat gacggcttgt  960
ttcttttctg tggctgcgtg aaagccttga ggggctccgg gagggccctt tgtgcggggg  1020
```

```
ggagcggctc ggggggtgcg tgcgtgtgtg tgtgcgtggg gagcgccgcg tgcggcccgc  1080
gctgcccggc ggctgtgagc gctgcgggcg cggcgcgggg ctttgtgcgc tccgcagtgt  1140
gcgcgagggg agcgcggccg ggggcggtgc cccgcggtgc ggggggggct gcgaggggaa  1200
caaaggctgc gtgcggggtg tgtgcgtggg ggggtgagca gggggtgtgg gcgcggcggt  1260
cgggctgtaa cccccccctg cacccccctc cccgagttgc tgagcacggc ccggcttcgg  1320
gtgcggggct ccgtacgggg cgtggcgcgg ggctcgccgt gccgggcggg gggtggcggc  1380
aggtgggggt gccgggcggg gcggggccgc ctcgggccgg ggagggctcg ggggaggggc  1440
gcggcggccc ccggagcgcc ggcggctgtc gaggcgcggc gagccgcagc cattgccttt  1500
tatggtaatc gtgcgagagg gcgcagggac ttcctttgtc ccaaatctgt gcggagccga  1560
aatctgggag gcgccgccgc acccccctcta gcgggcgcgg ggcgaagcgg tgcggcgccg  1620
gcaggaagga aatgggcggg gagggccttc gtgcgtcgcc gcgccgccgt ccccttctcc  1680
ctctccagcc tcggggctgt ccgcgggggg acggctgcct tcggggggga cggggcaggg  1740
cggggttcgg cttctggcgt gtgaccggcg gctctagagc ctctgctaac catgttcatg  1800
ccttcttctt tttcctacag ctcctgggca acgtgctggt tattgtgctg tctcatcatt  1860
ttggcaaaga att                                                     1873

SEQ ID NO: 37          moltype = DNA  length = 1061
FEATURE                Location/Qualifiers
source                 1..1061
                       mol_type = other DNA
                       organism = synthetic construct
SEQUENCE: 37
tagggaggtc ctgcacgtta cataacttac ggtaaatggc ccgcctggct gaccgcccaa  60
cgacccccgc ccattgacgt caataatgac gtatgttccc atagtaacgc caatagggac  120
tttccattga cgtcaatggg tggagtattt acggtaaact gcccacttgg cagtacatca  180
agtgtatcat atgccaagta cgccccctat tgacgtcaat gacggtaaat ggcccgcctg  240
gcattatgcc cagtacatga ccttatggga ctttcctact tggcagtaca tctacgtatt  300
agtcatcgct attaccatgg tcgaggtgag ccccacgttc tgcttcactc tccccatctc  360
ccccccctcc ccacccccaa ttttgtattt atttattttt taattatttt gtgcagcgat  420
gggggcgggg gggggggggg gcgcgcgcca ggcggggcgg ggcggggcga ggggcggggc  480
ggggcgaggc ggagaggtgc ggcggcagcc aatcagagcg gcgcgctccg aaagtttcct  540
tttatggcga ggcggcggcg gcggcggccc tataaaaagc gaagcgcgcg gcgggcggga  600
gtcgctgcgc gctgccttcg ccccgtgccc cgctccgccg ccgcctcgcg ccgcccgccc  660
cggctctgac tgaccgcgtt actaaaacag gtaagtccgg cctccgcgcc gggttttggc  720
gcctcccgcg ggcgcccccc tcctcacggc gagcgctgcc acgtcagacg aagggcgcag  780
cgagcgtcct gatccttccg cccggacgct caggacagcg gcccgctgct cataagactc  840
ggccttagaa ccccagtatc agcagaagga cattttagga cgggacttgg gtgactctag  900
ggcactggtt ttctttccag agagcggaac aggcgaggaa aagtagtccc ttctcggcga  960
ttctgcggag ggatctccgt ggggcggtga acgccgatga tgcctctact aaccatgttc  1020
atgttttctt ttttttttcta caggtcctgg gtgacgaaca g                          1061

SEQ ID NO: 38          moltype = DNA  length = 398
FEATURE                Location/Qualifiers
source                 1..398
                       mol_type = other DNA
                       organism = synthetic construct
SEQUENCE: 38
ccctaaaatg ggcaaacatt gcaagcagca aacagcaaac acacagccct ccctgcctgc  60
tgaccttgga gctggggcag aggtcagaga cctctctggg cccatgccac ctccaacatc  120
cactcgaccc cttggaattt cggtggagag gagcagaggt tgtcctggcg tggtttaggt  180
agtgtgagag gggaatgact cctttcggta agtgcagtgg aagctgtaca ctgcccaggc  240
aaagcgtccg ggcagcgtag gcgggcgact cagatcccag ccagtggact tagcccctgt  300
ttgctcctcc gataactggg gtgaccttgg ttaatattca ccagcagcct cccccgttgc  360
ccctctggat ccactgctta aatacggacg aggacagg                          398

SEQ ID NO: 39          moltype = DNA  length = 145
FEATURE                Location/Qualifiers
source                 1..145
                       mol_type = other DNA
                       organism = synthetic construct
SEQUENCE: 39
ttggccactc cctctctgcg cgctcgctcg ctcactgagg ccgggcgacc aaaggtcgcc  60
cgacgcccgg gctttgcccg ggcggcctca gtgagcgagc gagcgcgcag agagggagtg  120
gccaactcca tcactagggg ttcct                                        145

SEQ ID NO: 40          moltype = DNA  length = 145
FEATURE                Location/Qualifiers
source                 1..145
                       mol_type = other DNA
                       organism = synthetic construct
SEQUENCE: 40
aggaacccct agtgatggag ttggccactc cctctctgcg cgctcgctcg ctcactgagg  60
ccgggcgacc aaaggtcgcc cgacgcccgg gctttgcccg ggcggcctca gtgagcgagc  120
gagcgcgcag agagggagtg gccaa                                        145

SEQ ID NO: 41          moltype = DNA  length = 106
FEATURE                Location/Qualifiers
source                 1..106
                       mol_type = other DNA
```

```
                          organism = synthetic construct
SEQUENCE: 41
ctgcgcgctc gctcgctcac tgaggccgcc cgggcaaagc ccgggcgtcg ggcgaccttt  60
ggtcgcccgg cctcagtgag cgagcgagcg cgcagagagg gagtgg                 106

SEQ ID NO: 42             moltype = DNA  length = 167
FEATURE                   Location/Qualifiers
source                    1..167
                          mol_type = other DNA
                          organism = synthetic construct
SEQUENCE: 42
ctctccccccc tgtcgcgttc gctcgctcgc tggctcgttt gggggggtgg cagctcaaag  60
agctgccaga cgacggccct ctggccgtcg cccccccaaa cgagccagcg agcgagcgaa  120
cgcgacaggg gggagagtgc cacactctca agcaaggggg ttttgta                167

SEQ ID NO: 43             moltype = DNA  length = 167
FEATURE                   Location/Qualifiers
source                    1..167
                          mol_type = other DNA
                          organism = synthetic construct
SEQUENCE: 43
tacaaaacct ccttgcttga gagtgtggca ctctcccccc tgtcgcgttc gctcgctcgc  60
tggctcgttt gggggggtgg cagctcaaag agctgccaga cgacggccct ctggccgtcg  120
cccccccaaa cgagccagcg agcgagcgaa cgcgacaggg gggagag                167

SEQ ID NO: 44             moltype = DNA  length = 143
FEATURE                   Location/Qualifiers
source                    1..143
                          mol_type = other DNA
                          organism = synthetic construct
SEQUENCE: 44
aggaacccct agtgatggag ttggccactc cctctctgcg cgctcgctcg ctcactgagg  60
ccgggcgacc aaaggtcgcc cgacgcccgg gctttgcccg ggcggcctca gtgagcgagc  120
gagcgcgcag agagggagtg gcc                                          143

SEQ ID NO: 45             moltype = DNA  length = 46
FEATURE                   Location/Qualifiers
source                    1..46
                          mol_type = other DNA
                          organism = synthetic construct
SEQUENCE: 45
ggaggggtgg agtcgtgacg tgaattacgt catagggtta gggagg                 46

SEQ ID NO: 46             moltype = DNA  length = 37
FEATURE                   Location/Qualifiers
source                    1..37
                          mol_type = other DNA
                          organism = synthetic construct
SEQUENCE: 46
gtagataagt agcatggcgg gttaatcatt aactaca                           37

SEQ ID NO: 47             moltype = DNA  length = 122
FEATURE                   Location/Qualifiers
source                    1..122
                          mol_type = other DNA
                          organism = synthetic construct
SEQUENCE: 47
aacttgttta ttgcagctta taatggttac aaataaagca atagcatcac aaatttcaca  60
aataaagcat ttttttcact gcattctagt tgtggtttgt ccaaactcat caatgtatct  120
ta                                                                 122

SEQ ID NO: 48             moltype = DNA  length = 133
FEATURE                   Location/Qualifiers
source                    1..133
                          mol_type = other DNA
                          organism = synthetic construct
SEQUENCE: 48
tgctttattt gtgaaatttg tgatgctatt gctttatttg taaccattat aagctgcaat  60
aaacaagtta acaacaacaa ttgcattcat tttatgtttc aggttcaggg ggaggtgtgg  120
gaggtttttt aaa                                                     133

SEQ ID NO: 49             moltype = DNA  length = 171
FEATURE                   Location/Qualifiers
source                    1..171
                          mol_type = other DNA
                          organism = synthetic construct
SEQUENCE: 49
ctgtgccttc tagttgccag ccatctgttg tttgcccctc ccccgtgcct tccttgaccc  60
tggaaggtgc cactcccact gtcctttcct aataaaatga ggaaattgca tcgcattgtc  120
```

```
tgagtaggtg tcattctatt ctggggggtg gggtggggca ggacagcaag g          171

SEQ ID NO: 50          moltype = DNA  length = 4075
FEATURE                Location/Qualifiers
source                 1..4075
                       mol_type = other DNA
                       organism = synthetic construct
SEQUENCE: 50
ccttgctgtc ctgccccacc ccacccccca gaatagaatg acacctactc agacaatgcg  60
atgcaatttc ctcattttat taggaaagga cagtgggagt ggcaccttcc agggtcaagg  120
aaggcacggg ggaggggcaa acaacagatg gctggcaact agaaggcaca gcctcgagga  180
acgttttatt ttcccagaga caggctcagg gacttctggg tgtagtggct gtgcagggct  240
tcgtggagca cgctgcagct aaacacgttg ccctcttgcc atcggctctt gtccacggtc  300
agccgtgaat acaggaagaa gctgccatcg ctgtccagca ctggaggggt cgtcttgtag  360
ttgttttcag gctgtccgtt gctctcccat tcgacggcga tgtcgctggg gtagaagccc  420
ttcaccaggc aggtcagaga cacttggttc tttgtcattt cttcttgaga aggaggcagt  480
gtatagactt ggggctctct gggctggccc ttggcctttg agatggtctt ctcgatgctg  540
ctaggcaggc ccttgttaga caccttgcac ttgtactctt tgccgttcag ccagtcctgg  600
tgcagcactg tcagcacgga caccacccgg taggtgctgt taaactgttc ctcgcggggt  660
ttggtcttgg cattatgaac ttccactccg tcaacgtacc aattaaactg cacctcagga  720
tcctcctggg acacatccac caccacacat gtcacttcag gggtccggct gatcatcagg  780
gtgtctttgg gctttggtgg gaacaggaaa acagaagggc cggcgactgg tggagctgga  840
catggtgggc attccacgca gcactttctc tcaacggtct tatccacttt ggtgttgcta  900
ggcttgtggt ccacattaca ggtgtaggtc tgtgtgccga agttggagct aggaacggtg  960
accacgctac tcagagaata caggccagag ctctgcagca cggctgggaa ggtgtgcacg  1020
ccgcttgtca gggcgccgct gttccagctc actgtcacgg gttcggggaa gtagtctttg  1080
accagacaac ccagggcggc tgtgctttca gatgtgcttc tgctgcatgg ggccagtggg  1140
aacacgctgg gtcccttagt actggcgctg ctgacggtga caagggtgcc ttggccccac  1200
acgtcgaagt accagttagg ggatgagcca aaaaagtatc tggcgcagta gtacacagct  1260
gtgtcctcgc ttctcaggct gctcagttcc atgtacacgg tgcttgtgga ggtatctctg  1320
gtcatggtca ctctatcctt gaagttctct gtgtactcgg tgtggccaga tcctggcagg  1380
atctcgccca tccattccag gccttggcca ggggcctgcc gcacccactg gatccagtag  1440
ttgctgaaga tgtggccgct ggccttgcag gacaccttca cgctagctcc gggctttttc  1500
acttcggctc cgctttgaac cagctgcact tggctgtgca cgcctgtggc ggtggccacc  1560
aggaacagga tgatgcagga ccagcccatg gtggcactag ttcagttcca aaggttggaa  1620
tctaaaagag agaaacaatt agaatcagta gtttaacaca ttatacactt aaaaatttta  1680
tatttacctt agaggattca ctgtcccagg tcagtggtgg tgcctgaagc tgaggagaca  1740
gggccctgtc ctcgtccgta tttaagcagt ggatccagag gggcaacggg ggaggctgct  1800
ggtgaatatt aaccaaggtc accccagtta tcggaggagc aaacaggggc taagtccact  1860
ggctgggatc tgagtcgccc gcctacgctg cccggacgct ttgcctgggc agtgtacagc  1920
ttccactgca cttaccgaaa ggagtcattc ccctctcaca ctacctaaac cacgccagga  1980
caacctctgc tcctctccac cgaaattcca aggggtcgag tggatgttgg aggtggcatg  2040
ggcccagaga ggtctctgac ctctgcccca gctccaaggt cagcaggcag ggagggctgt  2100
gtgtttgctg tttgctgctt gcaatgtttg cccattttag ggccgcggca cgtgcttaag  2160
gccccctttt gcatccagtt tattcctaca tttgtcacac tgttaacagc ccacccctc  2220
caatgagacc agtggtatca gtgagttgtg gagatcagga aaagggctca agagaaaggc  2280
agtcaaagcc ctttttctgt ccctgtccca gctgctttaa taagatctcc ataagagaag  2340
agggacagct atgactggga gtagtcagga gaggaggaaa aatctggcta gtaaaacatg  2400
taaggaaaat tttagggatg ttaaagaaaa aaataacaca aaacaaaata taaaaaaaat  2460
ctaacctcaa gtcaaggctt ttctatggaa taaggaatgg acagcagggg gctgtttcat  2520
atactgatga cctctttata gccaaccttt gttcatggca gccagcatat gggcatatgt  2580
tgccaaactc taaaccaaat actcattctg atgttttaaa tgatttgccc tcccatatgt  2640
ccttccgagt gagagacaca aaaaattcca acacactatt gcaatgaaaa taaatttcct  2700
ttattagcca gaagtcagat gctcaagggg cttcatgatg tccccataat ttttggcaga  2760
gggaaaaaga tctccggagg gggaggctgc tggtgaatat taaccaaggt caccccagtt  2820
atcggaggag caaacagggg ctaagtccac ctcgagccat ggcgatgctc taatctctct  2880
agacaaggtt catatttgta tgggttactt attctctctt tgttgactaa gtcaataatc  2940
agaatcagca ggtttgcagt cagattggca gggataagca gcctagctca ggagaagtga  3000
gtataaaagc cccaggctgg gagcagccat cagctagcgc cggcaagagg taagggttta  3060
agggatggtt ggttggtggg gtattaatgt ttaattacct ggagcacctg cctgaaatca  3120
ctttttttca ggttggaccg gtgccaccat ggacatgagg gtccctgctc agctgctggg  3180
gctcctgctg ctctggctca gcggtgccag atgtgatatc cagatgaccc agtctccatc  3240
tagcctgtcc gccagcgtgg gcgacagagt gaccatcacc tgcggcgcca gcgagaacat  3300
ctatggcgct ctgaactggt accagcagaa acctggcaag gcccctaagc tgctgatcta  3360
cggcgccacc aacctggccg atggcgtgcc tagtagattc agcggatctg gcagcggcac  3420
agacttcacc ctgaccatca gcagcctgca acctgaggac tttgccacat actactgcca  3480
gaacgtgctg aatacacctc tgacattcgg ccaaggaacc aaagtggaaa tcaagcggac  3540
cgtggccgct cctagcgtgt tcatcttccc tccttccgat gaacaactga agagcggaac  3600
cgcctctgtg gtgtgcctgc tgaacaactt ctaccctaga gaggccaagg tgcagtggaa  3660
ggtcgacaac gccctgcaga gcggcaacag ccaggagagc gtgacggaac aggacagcaa  3720
ggacagcacc tacagcctga gctccaccct tacactgtct aaagccgact acgagaagca  3780
caaggtgtac gcctgtgaag tgacacacca gggcctgagc agccctgtga ccaagtcttt  3840
taaccggggc gagtgctgaa ttcgaatcgt acctagggat ccagacatga taagatacat  3900
tgatgagttt ggacaaacca caactagaat gcagtgaaaa aaatgcttta tttgtgaaat  3960
ttgtgatgct attgctttat ttgtaaccat tataagctgc aataaacaag ttaacaacaa  4020
caattgcatt cattttatgt ttcaggttca gggggaggtg tgggaggttt tttaa       4075

SEQ ID NO: 51          moltype = DNA  length = 3533
FEATURE                Location/Qualifiers
```

```
source                1..3533
                      mol_type = other DNA
                      organism = synthetic construct
SEQUENCE: 51
gcttcaggag cagttgtgcg aatagctgga gaacaccagg ctggatttaa acccagatcg  60
ctcttacatt tgctctttac ctgctgtgct cagcgttcac gtgccctcta gctgtagttt  120
tctgaagtca gcgcacagca aggcagtgtg cttagaggtt aacagaaggg aaaacaacaa  180
caacaaaaat ctaaatgaga atcctgactg tttcagctgg gggtaagggg ggcggattat  240
tcatataatt gttataccag acggtcgcag gcttagtcca attgcagaga actcgcttcc  300
caggcttctg agagtcccgg aagtgcctaa acctgtctaa tcgacggggc ttgggtggcc  360
cgtcgctccc tggcttcttc cctttaccca gggcgggcag cgaagtggtg cctcctgcgt  420
cccccacacc ctccctcagc ccctcccctc cggcccgtcc tgggcaggtg acctggagca  480
tccggcaggc tgccctggcc tcctgcgtca ggacaacgcc cacgaggggc gttactgtgc  540
ggagatgcac cacgcaagag acacccttg taactctctt ctcctcccta gtgcgaggtt  600
aaaaccttca gccccacgtg ctgtttgcaa acctgcctgt acctgaggcc ctaaaaagcc  660
agagacctca ctcccgggga gccagcatgt ccactgcggt cctggaaaac ccaggcttgg  720
gcaggaaact ctctgacttt ggacaggtga gccacggcag cctgagctgc tcagttaggg  780
gaatttgggc ctccagagaa agagatctga agactgctgg tgcttcctgg tttcataagc  840
tcagtaagaa gtctgaattc gttggaagct gatgagaata tccaggaagt caacagacaa  900
atgtcctcaa caattgtttc taagtaggag aacatctgtc ctcggtggct ttcacaggaa  960
aagcttctga cctcttctct tcctcccaca gggcggtacc agatctggca gcggagaggg  1020
cagaggaagt cttctaacat gcggtgacgt ggaggagaat cccggccctt ccaccgctgt  1080
gctggagaac cctgggctgg ggaggaaact gtcagacttc gggcaggaga cttcatacat  1140
tgaggataac tgtaaccaga atggcgccat ctctctgatc ttcagcctga aggaggaagt  1200
gggcgccctg gcaaaggtgc tgcgcctgtt tgaggagaac gacgtgaatc tgacccacat  1260
cgagtcccgg ccttctagac tgaagaagga cgagtacgag ttctttaccc acctggataa  1320
gcggtccctg ccagccctga caaacatcat caagatcctg aggcacgaca tcggagcaac  1380
cgtgcacgag ctgtctcggg acaagaagaa ggataccgtg ccctggttcc ctcggacaat  1440
ccaggagctg gatagatttg ccaaccagat cctgtcttac ggagcagagc tggacgcaga  1500
tcaccctggc ttcaaggacc cagtgtatcg ggcccggaga aagcagtttg ccgatatcgc  1560
ctacaattat aggcacggac agccaatccc tcgcgtggag tatatggagg aggagaagaa  1620
gacctggggc acagtgttca agaccctgaa gagcctgtac aagacacacg cctgctacga  1680
gtataaccac atcttccccc tgctggagaa gtattgtggc tttcacgagg acaatatccc  1740
tcagctggag gacgtgagcc agttcctgca gacctgcaca ggctttaggc tgaggccagt  1800
ggcaggactg ctgagctccc gggacttcct gggaggactg gccttcagag tgtttcactg  1860
cacccagtac atcaggcacg gctccaagcc aatgtataca ccagagcccg acatctgtca  1920
cgagctgctg ggccacgtgc ccctgtttag cgatagatcc ttcgcccagt tttcccagga  1980
gatcggactg gcatctctgg gagcacctga cgagtacatc gagaagctgg ccaccatcta  2040
ttggttcaca gtggagtttg gcctgtgcaa gcagggcgat agcatcaagg cctacggagc  2100
aggactgctg tctagcttcg gcgagctgca gtattgtctg tccgagaagc caaagctgct  2160
gcccctggag ctggagaaga ccgccatcca gaactacacc gtgacagagt tccagcccct  2220
gtactatgtg gccgagtctt ttaacgatgc caaggagaag gtgagaaatt tcgccgccac  2280
aatccctagg cccttcagcg tgcggtacga cccttatacc cagaggatcg aggtgctgga  2340
taatacacag cagctgaaga tcctggctga ctcaatcaat agcgaaatcg gaatcctgtg  2400
ctccgccctg cagaaaatca aatgagatcc agacatgata agatacattg atgagtttgg  2460
acaaaccaca actagaatgc agtgaaaaaa atgctttatt tgtgaaattt gtgatgctat  2520
tgctttattt gtaaccatta taagctgcaa taaacaagtt aacaacaaca attgcattca  2580
ttttatgttt caggttcagg gggaggtgtg ggaggttttt taactgggat gggatgtgga  2640
atccttctag atttcttttg taatatttat aaagtgctct cagcaaggta tcaaaatggc  2700
aaaattgtga gtaactatcc tcctttcatt ttgggaagaa gatgaggcat gaagagaatt  2760
cagacagaaa cttactcaga ccaggggagg cagaaactaa gcagagagga aaatgaccaa  2820
gagttagccc tgggcatgga atgtgaaaga accctaaacg tgacttggaa ataatgccca  2880
aggtatattc cattctccgg gatttgttgg catttttcttg aggtgaagaa ttgcagaata  2940
cattctttaa tgtgacctac atatttaccc atgggaggaa gtctgctcct ggactcttga  3000
gattcagtca taaagcccag gccagggaaa taatgtaagt ctgcaggccc ctgtcatcag  3060
taggattagg gagaagagtt ctcagtagaa aacagggagg ctggagagaa aagaatggtt  3120
aatgttaacg ttaatataac tagaaagact gcagaactta ggactgattt ttatttgaat  3180
ccttaaaaaa aaaatttctt atgaaaatag tacatggctc ttaggagaca gaacttattg  3240
tacagaggaa cagcgtgaga gtcagagtga tcccagaaca ggtcctggct ccatcctgca  3300
catagttttg gtgctgctgg caatacggtc cccacaactg tgggaagggg ttaggggcag  3360
ggatctcatc aggaaagcat aggggtttaa agttctttat agagcactta gaagattgag  3420
aatccacaaa ttatattaat aacaaacaaa gtagtgtcgt gttatatagt aaatgtgaat  3480
ttgcagacac atttagggaa aagttataat taaaaaaata ggctgtatat ata         3533

SEQ ID NO: 52         moltype = DNA  length = 4061
FEATURE               Location/Qualifiers
source                1..4061
                      mol_type = other DNA
                      organism = synthetic construct
SEQUENCE: 52
tgcggccgct tcaggagcag ttgtgcgaat agctggagaa caccaggctg gatttaaacc  60
cagatcgctc ttacatttgc tctttacctg ctgtgctcag cgttcacgtg ccctctagct  120
gtagttttct gaagtcagcg cacagcaagg cagtgtgctt agaggttaac agaagggaaa  180
acaacaacaa caaaaatcta aatgagaatc ctgactgttt cagctggggg taagggggggc  240
ggattattca tataattgtt ataccagacg gtcgcaggct tagtccaatt gcagagaact  300
cgcttcccag gcttctgaga gtcccggaag tgcctaaacc tgtctaatcg acggggcttg  360
ggtggcccgt cgctccctgg cttcttccct ttacccaggg cgggcagcga agtggtgcct  420
cctgcgtccc ccacaccctc cctcagcccc tcccctccgg cccgtcctgg gcaggtgacc  480
tggagcatcc ggcaggctgc cctggcctcc tgcgtcagga caacgcccac gaggggcgtt  540
```

-continued

```
actgtgcgga gatgcaccac gcaagagaca ccctttgtaa ctctcttctc ctccctagtg  600
cgaggttaaa accttcagcc ccacgtgctg tttgcaaacc tgcctgtacc tgaggcccta  660
aaaagccaga gacctcactc ccggggagcc agcatgtcca ctgcggtcct ggaaaaccca  720
ggcttgggca ggaaactctc tgactttgga caggtgagcc acggcagcct gagctgctca  780
gttaggggaa tttgggcctc cagagaaaga gatctgaaga ctgctggtgc ttcctggttt  840
cataagctca gtaagaagtc tgaattcgtt ggaagctgat gagaatatcc aggaagtcaa  900
cagacaaatg tcctcaacaa ttgtttctaa gtaggagaac atctgtcctc ggtggctttc  960
acaggaaccc taaaatgggc aaacattgca agcagcaaac agcaaacaca cagccctccc  1020
tgcctgctga ccttggagct ggggcagagg tcagagacct ctctgggccc atgccacctc  1080
caacatccac tcgacccctt ggaatttcgg tggagaggag cagaggttgt cctggcgtgg  1140
tttaggtagt gtgagagggg aatgactcct ttcggtaagt gcagtggaag ctgtacactg  1200
cccaggcaaa gcgtccgggc agcgtaggcg ggcgactcag atcccagcca gtggacttag  1260
cccctgtttg ctcctccgat aactggggtg accttggtta atattcacca gcagcctccc  1320
ccgttgcccc tctggatcca ctgcttaaat acggacgagg acagggccct gtctcctcag  1380
cttcaggcac caccactgac ctgggacagt gaatcctcta aggtaaatat aaaattttta  1440
agtgtataat gtgttaaact actgattcta attgtttctc tcttttagat tccaaccttt  1500
ggaactgacc gccaccatgt ccaccgctgt gctggagaac cctgggctgg ggaggaaact  1560
gtcagacttc gggcaggaga cttcatacat tgaggataac tgtaaccaga atggcgccat  1620
ctctctgatc ttcagcctga aggaggaagt gggcgccctg gcaaaggtgc tgcgcctgtt  1680
tgaggagaac gacgtgaatc tgacccacat cgagtcccgg ccttctagac tgaagaagga  1740
cgagtacgag ttctttaccc acctggataa gcggtccctg ccagccctga caaacatcat  1800
caagatcctg aggcacgaca tcggagcaac cgtgcacgag ctgtctcggg acaagaagaa  1860
ggataccgtg ccctggttcc ctcggacaat ccaggagctg gatagatttg ccaaccagat  1920
cctgtcttac ggagcagagc tggacgcaga tcaccctggc ttcaaggacc cagtgtatcg  1980
ggcccggaga aagcagtttg ccgatatcgc ctacaattat aggcacggac agccaatccc  2040
tcgcgtggag tatatggagg aggagaagaa gacctggggc acagtgttca agaccctgaa  2100
gagcctgtac aagacacacg cctgctacga gtataaccac atcttccccc tgctggagaa  2160
gtattgtggc tttcacgagg acaatatccc tcagctggag gacgtgagcc agttcctgca  2220
gacctgcaca ggctttaggc tgaggccagt ggcaggactg ctgagctccc gggacttcct  2280
gggaggactg gccttcagag tgtttcactg cacccagtac atcaggcacg gctccaagcc  2340
aatgtataca ccagagcccg acatctgtca cgagctgctg ggccacgtgc ccctgtttag  2400
cgatagatcc ttcgcccagt tttcccagga gatcggactg gcatctctgg gagcacctga  2460
cgagtacatc gagaagctgg ccaccatcta ttggttcaca gtggagtttg gcctgtgcaa  2520
gcagggcgat agcatcaagg cctacggagc aggactgctg tctagcttcg gcgagctgca  2580
gtattgtctg tccgagaagc caaagctgct gcccctggag ctggagaaga ccgccatcca  2640
gaactacacc gtgacagagt tccagcccct gtactatgtg gccgagtctt ttaacgatgc  2700
caaggagaag gtgagaaatt tcgccgccac aatccctagg cccttcagtg tgcgttacga  2760
cccttatacc cagaggatcg aggtgctgga taatacacag cagctgaaga tcctggctga  2820
ctcaatcaat agcgaaatcg gaatcctgtg ctccgccctg cagaaaatca aatgagaatt  2880
caaggcctct cgagcctcta gaactatagt gagtcgtatt acgtagatcc agacatgata  2940
agatacattg atgagtttgg acaaaccaca actagaatgc agtgaaaaaa atgctttatt  3000
tgtgaaattt gtgatgctat tgctttattt gtaaccatta taagctgcaa taaacaagtt  3060
aacaacaaca attgcattca ttttatgttt caggttcagg gggaggtgtg ggaggttttt  3120
taagctttac gtacgatcgt cgactgggat gggatgtgga atccttctag atttcttttg  3180
taatatttat aaagtgctct cagcaaggta tcaaaatggc aaaattgtga gtaactatcc  3240
tcctttcatt ttgggaagaa gatgaggcat gaagagaatt cagacagaaa cttactcaga  3300
ccaggggagg cagaaactaa gcagagagga aaatgaccaa gagttagccc tgggcatgga  3360
atgtgaaaga accctaaacg tgacttggaa ataatgccca aggtatattc cattctccgg  3420
gatttgttgg cattttcttg aggtgaagaa ttgcagaata cattctttaa tgtgacctac  3480
atatttaccc atgggaggaa gtctgctcct ggactcttga gattcagtca taaagcccag  3540
gccagggaaa taatgtaagt ctgcaggccc ctgtcatcag taggattagg gagaagagtt  3600
ctcagtagaa aacagggagg ctggagagaa aagaatggtt aatgttaacg ttaatataac  3660
tagaaagact gcagaactta ggactgattt ttatttgaat ccttaaaaaa aaaatttctt  3720
atgaaaatag tacatggctc ttaggagaca gaacttattg tacagaggaa cagcgtgaga  3780
gtcagagtga tcccagaaca ggtcctggct ccatcctgca catagttttg gtgctgctgg  3840
caatacggtc cccacaactg tgggaagggg ttaggggcag ggatctcatc aggaaagcat  3900
aggggtttaa agttctttat agagcactta gaagattgag aatccacaaa ttatattaat  3960
aacaaacaaa gtagtgtcgt gttatatagt aaatgtgaat ttgcagacac atttagggaa  4020
aagttataat taaaaaaata ggctgtatat atacctgcag g                     4061

SEQ ID NO: 53           moltype = DNA  length = 2141
FEATURE                 Location/Qualifiers
source                  1..2141
                        mol_type = other DNA
                        organism = synthetic construct
SEQUENCE: 53
gcggccgcaa ctcacgggga tttccaagtc tccaccccat tgacgtcaat gggagtttgt  60
tttggcacca aaatcaacgg gactttccaa aatgtcgtaa taaccccgcc ccgttgacgc  120
aaatgggcgg taggcgtgta cggtgggagg tctatataag cagagctcgt ttagtgaacc  180
gtgccaccat gcccccaccc aggaccggaa gaggcctgct gtggctgggc ctggtgctct  240
cttccgtgtg cgtggccctg ggaagcgaaa cccaggccaa cagcacaacc gacgccctga  300
atgtgctgct gatcattgtg gacgatctga gaccctccct gggctgttac ggcgacaaac  360
tggtgcggtc cccaaacatc gaccagctgg cctcccactc cctgctgttc cagaacgcct  420
tcgcccagca ggccgtgtgt gcccccagca gggtgagctt cctgaccggc agaagacctg  480
acaccaccag gctgtacgac tttaacagct actggcgggt gcacgccggc aatttcagca  540
ccattcctca gtacttcaag gagaatggct acgtgacaat gtccgtgggc aaggtgtttc  600
atcccggcat tagctccaac cacaccgacg atagcccata ctcctggtcc ttccccccct  660
accatccctc cagcgagaag tacgagaaca ccaaaacctg cagaggccct gacggagagc  720
tgcacgccaa cctgctgtgc cctgtggatg tcctggatgt gcccgaaggt aagggtttaa  780
```

```
gggatggttg gttggtgggg tattaatgtt taattacctg gagcacctgc ctgaaatcac  840
ttttttttcag gcaccctgcc agacaagcag tccacagagc aggccatcca gctgctggag  900
aagatgaaga caagcgccag cccctttcttt ctggccgtgg gataccacaa gcctcacatt  960
ccattccggt acccaaaaga gttccagaag ctgtaccctc tggaaaacat caccctggcc  1020
cctgaccccg aggtgccaga cggctgcct cctgtggcct acaatccctg gatggacatc  1080
agacagcggg aggatgtgca ggccctgaat atttccgtgc cctatgggcc catccctgtg  1140
gactttcagc ggaaaatcag acagtcttac tttgccagcg tgtcctacct ggacacccag  1200
gtgggccgcc tgctctcagc cctggacgac ctgcagctgg ccaattccac catcatcgcc  1260
ttcaccagcg atcacggctg ggccctgggc gagcacgggg agtgggccaa atacagcaac  1320
ttcgatgtgg ccacccacgt gcctctgatt ttttatgtgc ccggccggac agccagcctg  1380
cccgaggccg gggagaagct ctttccttac ctggaccctt tcgactctgc cagccagctg  1440
atggaacctg gcagacagag catggacctg gtggagctgg tgagcctctt ccccactctg  1500
gccggcctgg ctggcctgca ggtgccacca agatgcccag tgccttcttt ccacgtggag  1560
ctgtgtagag agggaaagaa cctgctgaag cacttcagat ttagagatct ggaggaggat  1620
ccctacctgc caggcaaccc aagggagctg atcgcctaca gccagtatcc cagaccctct  1680
gatatccccc agtggaacag cgataagccc tccctgaaag acatcaagat tatgggctac  1740
tccatcagga ccattgacta ccggtacaca gtgtgggtgg gcttcaaccc cgatgagttt  1800
ctggccaact tcagcgacat ccacgccggc gagctgtatt ttgtggactc cgaccccctg  1860
caggaccaca acatgtacaa cgactcccag ggcggcgacc tgttccagct gctgatgccc  1920
tgagatccag acatgataag atacattgat gagtttggac aaaccacaac tagaatgcag  1980
tgaaaaaaat gctttatttg tgaaatttgt gatgctattg ctttatttgt aaccattata  2040
agctgcaata aacaagttaa caacaacaat tgcattcatt ttatgtttca ggttcagggg  2100
gaggtgtggg aggtttttta acctgcaggt ctagatacgt a                        2141

SEQ ID NO: 54           moltype = DNA  length = 2042
FEATURE                 Location/Qualifiers
source                  1..2042
                        mol_type = other DNA
                        organism = synthetic construct
SEQUENCE: 54
ccctaaaatg ggcaaacatt gcaagcagca aacagcaaac acacagccct ccctgcctgc  60
tgaccttgga gctggggcag aggtcagaga cctctctggg cccatgccac ctccaacatc  120
cactcgaccc cttggaattt cggtggagag gagcagaggt tgtcctggcg tggtttaggt  180
agtgtgagag gggaatgact cctttcggta agtgcagtgg aagctgtaca ctgcccaggc  240
aaagcgtccg ggcagcgtag gcgggcgact cagatcccag ccagtggact tagcccctgt  300
ttgctcctcc gataactggg gtgaccttgg ttaatattca ccagcagcct cccccgttgc  360
ccctctggat ccactgctta aatacggacg aggacagggc cctgtctcct cagcttcagg  420
caccaccact gacctgggac agtgaatcct ctaaggtaaa tataaaattt ttaagtgtat  480
aatgtgttaa actactgatt ctaattgttt ctctctttta gattccaacc tttggaactg  540
accgccacca tgtccaccgc tgtgctggag aaccctgggc tggggaggaa actgtcagac  600
ttcgggcagg agacttcata cattgaggat aactgtaacc agaatggcgc catctctctg  660
atcttcagcc tgaaggagga agtgggcgcc ctggcaaagg tgctgcgcct gtttgaggag  720
aacgacgtga atctgaccca catcgagtcc cggccttcta gactgaagaa ggacgagtac  780
gagttcttta cccacctgga taagcggtcc ctgccagccc tgacaaacat catcaagatc  840
ctgaggcacg acatcggagc aaccgtgcac gagctgtctc gggacaagaa gaaggatacc  900
gtgccctggt tccctcggac aatccaggag ctggatagat ttgccaacca gatcctgtct  960
tacggagcag agctggacgc agatcaccct ggcttcaagg acccagtgta tcgggcccgg  1020
agaaagcagt ttgccgatat cgcctacaat tataggcacg gacagccaat ccctcgcgtg  1080
gagtatatgg aggaggagaa gaagacctgg ggcacagtgt tcaagaccct gaagagcctg  1140
tacaagacac acgcctgcta cgagtataac cacatcttcc ccctgctgga gaagtattgt  1200
ggctttcacg aggacaatat ccctcagctg gaggacgtga gccagttcct gcagacctgc  1260
acaggcttta ggctgaggcc agtggcagga ctgctgagct cccgggactt cctgggagga  1320
ctggccttca gagtgtttca ctgcacccag tacatcaggc acggctccaa gccaatgtat  1380
acaccagagc ccgacatctg tcacgagctg ctgggccacg tgcccctgtt tagcgataga  1440
tccttcgccc agttttccca ggagatcgga ctggcatctc tgggagcacc tgacgagtac  1500
atcgagaagc tggccaccat ctattggttc acagtggagt ttggcctgtg caagcagggc  1560
gatagcatca aggcctacgg agcaggactg ctgtctagct tcggcgagct gcagtattgt  1620
ctgtccgaga agccaaagct gctgcccctg gagctggaga agaccgccat ccagaactac  1680
accgtgacag agttccagcc cctgtactat gtggccgagt cttttaacga tgccaaggag  1740
aaggtgagaa atttcgccgc cacaatccct aggcccttca gcgtgcggta cgacccttat  1800
acccagagga tcgaggtgct ggataataca cagcagctga agatcctggc tgactcaatc  1860
aatagcgaaa tcggaatcct gtgctccgcc ctgcagaaaa tcaaatgaat gctttatttg  1920
tgaaatttgt gatgctattg ctttatttgt aaccattata agctgcaata aacaagttaa  1980
caacaacaat tgcattcatt ttatgtttca ggttcagggg gaggtgtggg aggtttttta  2040
aa                                                                2042

SEQ ID NO: 55           moltype = DNA  length = 3939
FEATURE                 Location/Qualifiers
source                  1..3939
                        mol_type = other DNA
                        organism = synthetic construct
SEQUENCE: 55
ttggccactc cctctctgcg cgctcgctcg ctcactgagg ccgggcgacc aaaggtcgcc  60
cgacgcccgg gctttgcccg ggcggcctca gtgagcgagc gagcgcgcag agagggagtg  120
gccaactcca tcactagggg ttcctggagg ggtggagtcg tgacgtgaat tacgtcatag  180
ggttagggag gtcctgcata tgcggccgct tcaggagcag ttgtgcgaat agctggagaa  240
caccaggctg gatttaaacc cagatcgctc ttacatttgc tctttacctg ctgtgctcag  300
cgttcacgtg ccctctagct gtagttttct gaagtcagcg cacagcaagg cagtgtgctt  360
agaggttaac agaagggaaa acaacaacaa caaaaatcta aatgagaatc ctgactgttt  420
```

```
cagctggggg taagggggc ggattattca tataattgtt ataccagacg gtcgcaggct  480
tagtccaatt gcagagaact cgcttcccag gcttctgaga gtcccggaag tgcctaaacc  540
tgtctaatcg acggggcttg ggtggcccgt cgctccctgg cttcttccct ttacccaggg  600
cgggcagcga agtggtgcct cctgcgtccc ccacaccctc cctcagcccc tcccctccgg  660
cccgtcctgg gcaggtgacc tggagcatcc ggcaggctgc cctggcctcc tgcgtcagga  720
caacgcccac gaggggcgtt actgtgcgga gatgcaccac gcaagagaca ccctttgtaa  780
ctctcttctc ctccctagtg cgaggttaaa accttcagcc ccacgtgctg tttgcaaacc  840
tgcctgtacc tgaggcccta aaaagccaga gacctcactc ccggggagcc agcatgtcca  900
ctgcggtcct ggaaaaccca ggcttgggca ggaaactctc tgactttgga caggtgagcc  960
acggcagcct gagctgctca gttaggggaa tttgggcctc cagagaaaga gatctgaaga  1020
ctgctggtgc ttcctggttt cataagctca gtaagaagtc tgaattcgtt ggaagctgat  1080
gagaatatcc aggaagtcaa cagacaaatg tcctcaacaa ttgtttctaa gtaggagaac  1140
atctgtcctc ggtggctttc acaggaaaag cttctgacct cttctcttcc tcccacaggg  1200
cggtaccaga tctggcagcg gagagggcag aggaagtctt ctaacatgcg gtgacgtgga  1260
ggagaatccc ggcccttcca ccgctgtgct ggagaaccct gggctgggga ggaaactgtc  1320
agacttcggg caggagactt catacattga ggataactgt aaccagaatg gcgccatctc  1380
tctgatcttc agcctgaagg aggaagtggg cgccctggca aaggtgctgc gcctgtttga  1440
ggagaacgac gtgaatctga cccacatcga gtcccggcct tctagactga agaaggacga  1500
gtacgagttc tttacccacc tggataagcg gtccctgcca gccctgacaa acatcatcaa  1560
gatcctgagg cacgacatcg gagcaaccgt gcacgagctg tctcgggaca agaagaagga  1620
taccgtgccc tggttccctc ggacaatcca ggagctggat agatttgcca accagatcct  1680
gtcttacgga gcagagctgg acgcagatca ccctggcttc aaggacccag tgtatcgggc  1740
ccggagaaag cagtttgccg atatcgccta caattatagg cacggacagc caatccctcg  1800
cgtggagtat atggaggagg agaagaagac ctggggcaca gtgttcaaga ccctgaagag  1860
cctgtacaag acacacgcct gctacgagta taaccacatc ttcccccctgc tggagaagta  1920
ttgtggcttt cacgaggaca atatccctca gctggaggac gtgagccagt tcctgcagac  1980
ctgcacaggc tttaggctga ggccagtggc aggactgctg agctcccggg acttcctggg  2040
aggactggcc ttcagagtgt ttcactgcac ccagtacatc aggcacggct ccaagccaat  2100
gtatacacca gagcccgaca tctgtcacga gctgctgggc cacgtgcccc tgtttagcga  2160
tagatccttc gcccagtttt cccaggagat cggactggca tctctgggag cacctgacga  2220
gtacatcgag aagctggcca ccatctattg gttcacagtg gagtttggcc tgtgcaagca  2280
gggcgatagc atcaaggcct acggagcagg actgctgtct agcttcggcg agctgcagta  2340
ttgtctgtcc gagaagccaa agctgctgcc cctggagctg gagaagaccg ccatccagaa  2400
ctacaccgtg acagagttcc agcccctgta ctatgtggcc gagtctttta acgatgccaa  2460
ggagaaggtg agaaatttcg ccgccacaat ccctaggccc ttcagcgtgc ggtacgaccc  2520
ttatacccag aggatcgagg tgctggataa tacacagcag ctgaagatcc tggctgactc  2580
aatcaatagc gaaatcggaa tcctgtgctc cgccctgcag aaaatcaaat gagatccaga  2640
catgataaga tacattgatg agtttggaca aaccacaact agaatgcagt gaaaaaaatg  2700
ctttatttgt gaaatttgtg atgctattgc tttatttgta accattataa gctgcaataa  2760
acaagttaac aacaacaatt gcattcattt tatgtttcag gttcaggggg aggtgtggga  2820
ggttttttaa ctgggatggg atgtggaatc cttctagatt tcttttgtaa tatttataaa  2880
gtgctctcag caaggtatca aaatggcaaa attgtgagta actatcctcc tttcattttg  2940
ggaagaagat gaggcatgaa gagaattcag acagaaactt actcagacca ggggaggcag  3000
aaactaagca gagaggaaaa tgaccaagag ttagccctgg gcatggaatg tgaaagaacc  3060
ctaaacgtga cttggaaata atgcccaagg tatattccat tctccgggat ttgttggcat  3120
tttcttgagg tgaagaattg cagaatacat tctttaatgt gacctacata tttacccatg  3180
ggaggaagtc tgctcctgga ctcttgagat tcagtcataa agcccaggcc agggaaataa  3240
tgtaagtctg caggcccctg tcatcagtag gattagggag aagagttctc agtagaaaac  3300
agggaggctg gagagaaaag aatggttaat gttaacgtta atataactag aaagactgca  3360
gaacttagga ctgattttta tttgaatcct taaaaaaaaa atttcttatg aaaatagtac  3420
atggctctta ggagacagaa cttattgtac agaggaacag cgtgagagtc agagtgatcc  3480
cagaacaggt cctggctcca tcctgcacat agttttggtg ctgctggcaa tacggtcccc  3540
acaactgtgg gaaggggtta ggggcaggga tctcatcagg aaagcatagg ggtttaaagt  3600
tctttataga gcacttagaa gattgagaat ccacaaatta tattaataac aaacaaagta  3660
gtgtcgtgtt atatagtaaa tgtgaatttg cagacacatt tagggaaaag ttataattaa  3720
aaaaataggc tgtatatata cctgcaggtc tagatacgta gataagtagc atggcgggtt  3780
aatcattaac tacaaggaac ccctagtgat ggagttggcc actccctctc tgcgcgctcg  3840
ctcgctcact gaggccgggc gaccaaaggt cgcccgacgc ccgggctttg cccgggcggc  3900
ctcagtgagc gagcgagcgc gcagagaggg agtggccaa                         3939

SEQ ID NO: 56          moltype = DNA  length = 2356
FEATURE                Location/Qualifiers
source                 1..2356
                       mol_type = other DNA
                       organism = synthetic construct
SEQUENCE: 56
ctgcgcgctc gctcgctcac tgaggccgcc cgggcaaagc ccgggcgtcg ggcgaccttt  60
ggtcgcccgg cctcagtgag cgagcgagcg cgcagagagg gagtggaatt cacgcgtgga  120
tctgaattca attcacgcgt ggtacctccc taaaatgggc aaacattgca agcagcaaac  180
agcaaacaca cagccctccc tgcctgctga ccttggagct ggggcagagg tcagagacct  240
ctctgggccc atgccacctc caacatccac tcgacccctt ggaatttcgg tggagaggag  300
cagaggttgt cctggcgtgg tttaggtagt gtgagagggg aatgactcct ttcggtaagt  360
gcagtggaag ctgtacactg cccaggcaaa gcgtccgggc agcgtaggcg ggcgactcag  420
atcccagcca gtggacttag cccctgtttg ctcctccgat aactggggtg accttggtta  480
atattcacca gcagcctccc ccgttgcccc tctggatcca ctgcttaaat acggacgagg  540
acagggccct gtctcctcag cttcaggcac caccactgac ctgggacagt gaatcctcta  600
aggtaaatat aaaattttta agtgtataat gtgttaaact actgattcta attgtttctc  660
tcttttagat tccaaccttt ggaactgacc gccaccatgt ccaccgctgt gctggagaac  720
cctgggctgg ggaggaaact gtcagacttc gggcaggaga cttcatacat tgaggataac  780
```

```
tgtaaccaga atggcgccat ctctctgatc ttcagcctga aggaggaagt gggcgccctg  840
gcaaaggtgc tgcgcctgtt tgaggagaac gacgtgaatc tgacccacat cgagtcccgg  900
ccttctagac tgaagaagga cgagtacgag ttctttaccc acctggataa gcggtccctg  960
ccagccctga caaacatcat caagatcctg aggcacgaca tcggagcaac cgtgcacgag  1020
ctgtctcggg acaagaagaa ggataccgtg ccctggttcc ctcggacaat ccaggagctg  1080
gatagatttg ccaaccagat cctgtcttac ggagcagagc tggacgcaga tcaccctggc  1140
ttcaaggacc cagtgtatcg ggcccggaga aagcagtttg ccgatatcgc ctacaattat  1200
aggcacggac agccaatccc tcgcgtggag tatatggagg aggagaagaa gacctggggc  1260
acagtgttca agaccctgaa gagcctgtac aagacacacg cctgctacga gtataaccac  1320
atcttccccc tgctggagaa gtattgtggc tttcacgagg acaatatccc tcagctggag  1380
gacgtgagcc agttcctgca gacctgcaca ggctttaggc tgaggccagt ggcaggactg  1440
ctgagctccc gggacttcct gggaggactg gccttcagag tgtttcactg cacccagtac  1500
atcaggcacg gctccaagcc aatgtataca ccagagcccg acatctgtca cgagctgctg  1560
ggccacgtgc ccctgtttag cgatagatcc ttcgcccagt tttcccagga gatcggactg  1620
gcatctctgg gagcacctga cgagtacatc gagaagctgg ccaccatcta ttggttcaca  1680
gtggagtttg gcctgtgcaa gcagggcgat agcatcaagg cctacggagc aggactgctg  1740
tctagcttcg gcgagctgca gtattgtctg tccgagaagc caaagctgct gcccctggag  1800
ctggagaaga ccgccatcca gaactacacc gtgacagagt tccagcccct gtactatgtg  1860
gccgagtctt ttaacgatgc caaggagaag gtgagaaatt tcgccgccac aatccctagg  1920
cccttcagcg tgcggtacga ccccttatacc cagaggatcg aggtgctgga taatacacag  1980
cagctgaaga tcctggctga ctcaatcaat agcgaaatcg gaatcctgtg ctccgccctg  2040
cagaaaatca aatgaatgct ttatttgtga aatttgtgat gctattgctt tatttgtaac  2100
cattataagc tgcaataaac aagttaacaa caacaattgc attcatttta tgtttcaggt  2160
tcagggggag gtgtgggagg ttttttaaag catgctgggg agagatcgat ctgaggaacc  2220
cctagtgatg gagttggcca ctccctctct gcgcgctcgc tcgctcactg aggccgggcg  2280
accaaaggtc gcccgacgcc cgggctttgc ccgggcggcc tcagtgagcg agcgagcgcg  2340
cagagaggga gtggcc                                                  2356

SEQ ID NO: 57          moltype = DNA  length = 4452
FEATURE                Location/Qualifiers
source                 1..4452
                       mol_type = other DNA
                       organism = synthetic construct
SEQUENCE: 57
ttggccactc cctctctgcg cgctcgctcg ctcactgagg ccgggcgacc aaaggtcgcc  60
cgacgcccgg gctttgcccg ggcggcctca gtgagcgagc gagcgcgcag agagggagtg  120
gccaactcca tcactagggg ttcctggagg ggtggagtcg tgacgtgaat tacgtcatag  180
ggttagggag gtcctgcata tgcggccgct tcaggagcag ttgtgcgaat agctggagaa  240
caccaggctg gatttaaacc cagatcgctc ttacatttgc tctttacctg ctgtgctcag  300
cgttcacgtg ccctctagct gtagttttct gaagtcagcg cacagcaagg cagtgtgctt  360
agaggttaac agaagggaaa acaacaacaa caaaaatcta aatgagaatc ctgactgttt  420
cagctggggg taagggggc ggattattca tataattgtt ataccagacg gtcgcaggct  480
tagtccaatt gcagagaact cgcttcccag gcttctgaga gtcccggaag tgcctaaacc  540
tgtctaatcg acggggcttg ggtggcccgt cgctccctgg cttcttccct ttacccaggg  600
cgggcagcga agtggtgcct cctgcgtccc ccacaccctc cctcagcccc tcccctccgg  660
cccgtcctgg gcaggtgacc tggagcatcc ggcaggctgc cctggcctcc tgcgtcagga  720
caacgcccac gaggggcgtt actgtgcgga gatgcaccac gcaagagaca ccctttgtaa  780
ctctcttctc ctccctagtg cgaggttaaa accttcagcc ccacgtgctg tttgcaaacc  840
tgcctgtacc tgaggcccta aaaagccaga gacctcactc ccggggagcc agcatgtcca  900
ctgcggtcct ggaaaaccca ggcttgggca ggaaactctc tgactttgga caggtgagcc  960
acggcagcct gagctgctca gttaggggaa tttgggcctc cagagaaaga gatctgaaga  1020
ctgctggtgc ttcctggttt cataagctca gtaagaagtc tgaattcgtt ggaagctgat  1080
gagaatatcc aggaagtcaa cagacaaatg tcctcaacaa ttgtttctaa gtaggagaac  1140
atctgtcctc ggtggctttc acaggaaccc taaaatgggc aaacattgca agcagcaaac  1200
agcaaacaca cagccctccc tgcctgctga ccttggagct ggggcagagg tcagagacct  1260
ctctgggccc atgccacctc caacatccac tcgacccctt ggaatttcgg tggagaggag  1320
cagaggttgt cctggcgtgg tttaggtagt gtgagagggg aatgactcct ttcggtaagt  1380
gcagtggaag ctgtacactg cccaggcaaa gcgtccgggc agcgtaggcg ggcgactcag  1440
atcccagcca gtggacttag cccctgtttg ctcctccgat aactggggtg accttggtta  1500
atattcacca gcagcctccc ccgttgcccc tctggatcca ctgcttaaat acggacgagg  1560
acagggccct gtctcctcag cttcaggcac caccactgac ctgggacagt gaatcctcta  1620
aggtaaatat aaaattttta agtgtataat gtgttaaact actgattcta attgtttctc  1680
tcttttagat tccaaccttt ggaactgacc gccaccatgt ccaccgctgt gctggagaac  1740
cctgggctgg ggaggaaact gtcagacttc gggcaggaga cttcatacat tgaggataac  1800
tgtaaccaga atggcgccat ctctctgatc ttcagcctga aggaggaagt gggcgccctg  1860
gcaaaggtgc tgcgcctgtt tgaggagaac gacgtgaatc tgacccacat cgagtcccgg  1920
ccttctagac tgaagaagga cgagtacgag ttctttaccc acctggataa gcggtccctg  1980
ccagccctga caaacatcat caagatcctg aggcacgaca tcggagcaac cgtgcacgag  2040
ctgtctcggg acaagaagaa ggataccgtg ccctggttcc ctcggacaat ccaggagctg  2100
gatagatttg ccaaccagat cctgtcttac ggagcagagc tggacgcaga tcaccctggc  2160
ttcaaggacc cagtgtatcg ggcccggaga aagcagtttg ccgatatcgc ctacaattat  2220
aggcacggac agccaatccc tcgcgtggag tatatggagg aggagaagaa gacctggggc  2280
acagtgttca agaccctgaa gagcctgtac aagacacacg cctgctacga gtataaccac  2340
atcttccccc tgctggagaa gtattgtggc tttcacgagg acaatatccc tcagctggag  2400
gacgtgagcc agttcctgca gacctgcaca ggctttaggc tgaggccagt ggcaggactg  2460
ctgagctccc gggacttcct gggaggactg gccttcagag tgtttcactg cacccagtac  2520
atcaggcacg gctccaagcc aatgtataca ccagagcccg acatctgtca cgagctgctg  2580
ggccacgtgc ccctgtttag cgatagatcc ttcgcccagt tttcccagga gatcggactg  2640
gcatctctgg gagcacctga cgagtacatc gagaagctgg ccaccatcta ttggttcaca  2700
```

```
gtggagtttg gcctgtgcaa gcagggcgat agcatcaagg cctacggagc aggactgctg  2760
tctagcttcg gcgagctgca gtattgtctg tccgagaagc caaagctgct gcccctggag  2820
ctggagaaga ccgccatcca gaactacacc gtgacagagt tccagcccct gtactatgtg  2880
gccgagtctt ttaacgatgc caaggagaag gtgagaaatt tcgccgccac aatccctagg  2940
cccttcagtg tgcgttacga ccccttatacc cagaggatcg aggtgctgga taatacacag  3000
cagctgaaga tcctggctga ctcaatcaat agcgaaatcg gaatcctgtg ctccgccctg  3060
cagaaaatca aatgagaatt caaggcctct cgagcctcta gaactatagt gagtcgtatt  3120
acgtagatcc agacatgata agatacattg atgagtttgg acaaaccaca actagaatgc  3180
agtgaaaaaa atgctttatt tgtgaaattt gtgatgctat tgctttattt gtaaccatta  3240
taagctgcaa taaacaagtt aacaacaaca attgcattca ttttatgttt caggttcagg  3300
gggaggtgtg ggaggttttt taagctttac gtacgatcgt cgactgggat gggatgtgga  3360
atccttctag atttcttttg taatatttat aaagtgctct cagcaaggta tcaaaatggc  3420
aaaattgtga gtaactatcc tcctttcatt ttgggaagaa gatgaggcat gaagagaatt  3480
cagacagaaa cttactcaga ccaggggagg cagaaactaa gcagagagga aaatgaccaa  3540
gagttagccc tgggcatgga atgtgaaaga accctaaacg tgacttggaa ataatgccca  3600
aggtatattc cattctccgg gatttgttgg cattttcttg aggtgaagaa ttgcagaata  3660
cattctttaa tgtgacctac atatttaccc atgggaggaa gtctgctcct ggactcttga  3720
gattcagtca taaagcccag gccagggaaa taatgtaagt ctgcaggccc ctgtcatcag  3780
taggattagg gagaagagtt ctcagtagaa aacagggagg ctggagagaa aagaatggtt  3840
aatgttaacg ttaatataac tagaaagact gcagaactta ggactgattt ttatttgaat  3900
ccttaaaaaa aaaatttctt atgaaaatag tacatggctc ttaggagaca gaacttattg  3960
tacagaggaa cagcgtgaga gtcagagtga tcccagaaca ggtcctggct ccatcctgca  4020
catagttttg gtgctgctgg caatacggtc cccacaactg tgggaagggg ttaggggcag  4080
ggatctcatc aggaaagcat aggggtttaa agttctttat agagcactta gaagattgag  4140
aatccacaaa ttatattaat aacaaacaaa gtagtgtcgt gttatatagt aaatgtgaat  4200
ttgcagacac atttagggaa aagttataat taaaaaaata ggctgtatat atacctgcag  4260
gtctagatac gtagataagt agcatggcgg gttaatcatt aactacaagg aacccctagt  4320
gatggagttg gccactccct ctctgcgcgc tcgctcgctc actgaggccg ggcgaccaaa  4380
ggtcgcccga cgcccgggct ttgcccgggc ggcctcagtg agcgagcgag cgcgcagaga  4440
gggagtggcc aa                                                       4452
```

```
SEQ ID NO: 58          moltype = DNA  length = 2521
FEATURE                Location/Qualifiers
source                 1..2521
                       mol_type = other DNA
                       organism = synthetic construct
SEQUENCE: 58
ttggccactc cctctctgcg cgctcgctcg ctcactgagg ccgggcgacc aaaggtcgcc  60
cgacgcccgg gctttgcccg ggcggcctca gtgagcgagc gagcgcgcag agagggagtg  120
gccaactcca tcactagggg ttcctggagg ggtggagtcg tgacgtgaat tacgtcatag  180
ggttagggag gtcctgcata tgcggccgca actcacgggg atttccaagt ctccacccca  240
ttgacgtcaa tgggagtttg ttttggcacc aaaatcaacg ggactttcca aaatgtcgta  300
ataaccccgc cccgttgacg caaatgggcg gtaggcgtgt acggtgggag gtctatataa  360
gcagagctcg tttagtgaac cgtgccacca tgccccccacc caggaccgga agaggcctgc  420
tgtggctggg cctggtgctc tcttccgtgt gcgtggccct gggaagcgaa acccaggcca  480
acagcacaac cgacgccctg aatgtgctgc tgatcattgt ggacgatctg agaccctccc  540
tgggctgtta cggcgacaaa ctggtgcggt ccccaaacat cgaccagctg gcctcccact  600
ccctgctgtt ccagaacgcc ttcgcccagc aggccgtgtg tgcccccagc agggtgagct  660
tcctgaccgg cagaagacct gacaccacca ggctgtacga ctttaacagc tactggcggg  720
tgcacgccgg caatttcagc accattcctc agtacttcaa ggagaatggc tacgtgacaa  780
tgtccgtggg caaggtgttt catcccggca ttagctccaa ccacaccgac gatagcccat  840
actcctggtc cttccccccc taccatccct ccagcgagaa gtacgagaac accaaaacct  900
gcagaggccc tgacggagag ctgcacgcca acctgctgtg ccctgtggat gtcctggatg  960
tgcccgaagg taagggttta agggatggtt ggttggtggg gtattaatgt ttaattacct  1020
ggagcacctg cctgaaatca cttttttca ggcaccctgc cagacaagca gtccacagag  1080
caggccatcc agctgctgga gaagatgaag acaagcgcca gccccttctt tctggccgtg  1140
ggataccaca agcctcacat tccattccgg tacccaaaag agttccagaa gctgtaccct  1200
ctggaaaaca tcaccctggc ccctgacccc gaggtgccag acgggctgcc tcctgtggcc  1260
tacaatccct ggatggacat cagacagcgg gaggatgtgc aggccctgaa tatttccgtg  1320
ccctatgggc ccatccctgt ggactttcag cggaaaatca gacagtctta ctttgccagc  1380
gtgtcctacc tggacaccca ggtgggccgc ctgctctcag ccctggacga cctgcagctg  1440
gccaattcca ccatcatcgc cttcaccagc gatcacggct gggccctggg cgagcacggg  1500
gagtgggcca aatacagcaa cttcgatgtg gccacccacg tgcctctgat tttttatgtg  1560
cccggccgga cagccagcct gcccgaggcc ggggagaagc tctttcctta cctggaccct  1620
ttcgactctg ccagccagct gatggaacct ggcagacaga gcatggacct ggtggagctg  1680
gtgagcctct tccccactct ggccggcctg gctggcctgc aggtgccacc aagatgccca  1740
gtgccttctt tccacgtgga gctgtgtaga gagggaaaga acctgctgaa gcacttcaga  1800
tttagagatc tggaggagga tccctacctg ccaggcaacc caagggagct gatcgcctac  1860
agccagtatc ccagaccctc tgatatcccc cagtggaaca gcgataagcc ctccctgaaa  1920
gacatcaaga ttatgggcta ctccatcagg accattgact accggtacac agtgtgggtg  1980
ggcttcaacc ccgatgagtt tctggccaac ttcagcgaca tccacgccgg cgagctgtat  2040
tttgtggact ccgacccccct gcaggaccac aacatgtaca acgactccca gggcggcgac  2100
ctgttccagc tgctgatgcc ctgagatcca gacatgataa gatacattga tgagtttgga  2160
caaaccacaa ctagaatgca gtgaaaaaaa tgctttattt gtgaaatttg tgatgctatt  2220
gctttatttg taaccattat aagctgcaat aaacaagtta acaacaacaa ttgcattcat  2280
tttatgtttc aggttcaggg ggaggtgtgg gaggtttttt aacctgcagg tctagatacg  2340
tagataagta gcatggcggg ttaatcatta actacaagga acccctagtg atggagttgg  2400
ccactccctc tctgcgcgct cgctcgctca ctgaggccgc ccgggcaaag cccgggcgtc  2460
gggcgacctt tggtcgcccg gcctcagtga gcgagcgagc gcgcagagag ggagtggcca  2520
```

```
a                                                                 2521

SEQ ID NO: 59           moltype = DNA  length = 4483
FEATURE                 Location/Qualifiers
source                  1..4483
                        mol_type = other DNA
                        organism = synthetic construct
SEQUENCE: 59
ttggccactc cctctctgcg cgctcgctcg ctcactgagg ccgggcgacc aaaggtcgcc  60
cgacgcccgg gctttgcccg ggcggcctca gtgagcgagc gagcgcgcag agagggagtg  120
gccaactcca tcactagggg ttcctggagg ggtggagtcg tgacgtgaat tacgtcatag  180
ggttagggag gtcctgcaca cgtgacgcgt ccttgctgtc ctgccccacc ccacccccca  240
gaatagaatg acacctactc agacaatgcg atgcaatttc ctcattttat taggaaagga  300
cagtgggagt ggcaccttcc agggtcaagg aaggcacggg ggaggggcaa acaacagatg  360
gctggcaact agaaggcaca gcctcgagga acgttttatt ttcccagaga caggctcagg  420
gacttctggg tgtagtggct gtgcagggct tcgtggagca cgctgcagct aaacacgttg  480
ccctcttgcc atcggctctt gtccacggtc agccgtgaat acaggaagaa gctgccatcg  540
ctgtccagca ctggaggggt cgtcttgtag ttgttttcag gctgtccgtt gctctcccat  600
tcgacggcga tgtcgctggg gtagaagccc ttcaccaggc aggtcagaga cacttggttc  660
tttgtcattt cttcttgaga aggaggcagt gtatagactt ggggctctct gggctggccc  720
ttggcctttg agatggtctt ctcgatgctg ctaggcaggc ccttgttaga caccttgcac  780
ttgtactctt tgccgttcag ccagtcctgg tgcagcactg tcagcacgga caccacccgg  840
taggtgctgt taaactgttc ctcgcggggt ttggtcttgg cattatgaac ttccactccg  900
tcaacgtacc aattaaactg cacctcagga tcctcctggg acacatccac caccacacat  960
gtcacttcag ggtccggct gatcatcagg gtgtctttgg gctttggtgg gaacaggaaa  1020
acagaagggc cggcgactgg tggagctgga catggtgggc attccacgca gcactttctc  1080
tcaacggtct tatccacttt ggtgttgcta ggcttgtggt ccacattaca ggtgtaggtc  1140
tgtgtgccga agttggagct aggaacggtg accacgctac tcagagaata caggccagag  1200
ctctgcagca cggctgggaa ggtgtgcacg ccgcttgtca gggcgccgct gttccagctc  1260
actgtcacgg gttcggggaa gtagtctttg accagacaac ccagggcggc tgtgctttca  1320
gatgtgcttc tgctgcatgg ggccagtggg aacacgctgg gtcccttagt actggcgctg  1380
ctgacggtga caagggtgcc ttggccccac acgtcgaagt accagttagg ggatgagcca  1440
aaaaagtatc tggcgcagta gtacacagct gtgtcctcgc ttctcaggct gctcagttcc  1500
atgtacacgg tgcttgtgga ggtatctctg gtcatggtca ctctatcctt gaagttctct  1560
gtgtactcgg tgtggccaga tcctggcagg atctcgccca tccattccag gccttggcca  1620
ggggcctgcc gcacccactg gatccagtag ttgctgaaga tgtggccgct ggccttgcag  1680
gacaccttca cgctagctcc gggctttttc acttcggctc cgctttgaac cagctgcact  1740
tggctgtgca cgcctgtggc ggtggccacc aggaacagga tgatgcagga ccagcccatg  1800
gtggcactag ttcagttcca aaggttggaa tctaaaagag agaaacaatt agaatcagta  1860
gtttaacaca ttatacactt aaaaatttta tatttacctt agaggattca ctgtcccagg  1920
tcagtggtgg tgcctgaagc tgaggagaca gggccctgtc ctcgtccgta tttaagcagt  1980
ggatccagag gggcaacggg ggaggctgct ggtgaatatt aaccaaggtc accccagtta  2040
tcggaggagc aaacaggggc taagtccact ggctgggatc tgagtcgccc gcctacgctg  2100
cccggacgct tgcctgggc agtgtacagc ttccactgca cttaccgaaa ggagtcattc  2160
ccctctcaca ctacctaaac cacgccagga caacctctgc tcctctccac cgaaattcca  2220
aggggtcgag tggatgttgg aggtggcatg ggcccagaga ggtctctgac ctctgcccca  2280
gctccaaggt cagcaggcag ggagggctgt gtgtttgctg tttgctgctt gcaatgtttg  2340
cccattttag ggccgcggca cgtgcttaag gcccccttt gcatccagtt tattcctaca  2400
tttgtcacac tgttaacagc ccacccttc caatgagacc agtggtatca gtgagttgtg  2460
gagatcagga aaagggctca agagaaaggc agtcaaagcc ctttttctgt ccctgtccca  2520
gctgctttaa taagatctcc ataagagaag agggacagct atgactggga gtagtcagga  2580
gaggaggaaa aatctggcta gtaaaacatg taaggaaaat tttagggatg ttaaagaaaa  2640
aaataacaca aaacaaaata taaaaaaaat ctaacctcaa gtcaaggctt ttctatggaa  2700
taaggaatgg acagcagggg gctgtttcat atactgatga cctctttata gccaaccttt  2760
gttcatggca gccagcatat gggcatatgt tgccaaactc taaaccaaat actcattctg  2820
atgttttaaa tgatttgccc tcccatatgt ccttccgagt gagagacaca aaaaattcca  2880
acacactatt gcaatgaaaa taaatttcct ttattagcca gaagtcagat gctcaagggg  2940
cttcatgatg tccccataat ttttggcaga gggaaaaaga tctccggagg gggaggctgc  3000
tggtgaatat taaccaaggt caccccagtt atcggaggag caaacagggg ctaagtccac  3060
ctcgagccat ggcgatgctc taatctctct agacaaggtt catatttgta tgggttactt  3120
attctctctt tgttgactaa gtcaataatc agaatcagca ggtttgcagt cagattggca  3180
gggataagca gcctagctca ggagaagtga gtataaaagc cccaggctgg gagcagccat  3240
cagctagcgc cggcaagagg taagggttta agggatggtt ggttggtggg gtattaatgt  3300
ttaattacct ggagcacctg cctgaaatca cttttttca ggttggaccg gtgccaccat  3360
ggacatgagg gtccctgctc agctgctggg gctcctgctg ctctggctca gcggtgccag  3420
atgtgatatc cagatgaccc agtctccatc tagcctgtcc gccagcgtgg gcgacagagt  3480
gaccatcacc tgcggcgcca gcgagaacat ctatggcgct ctgaactggt accagcagaa  3540
acctggcaag gcccctaagc tgctgatcta cggcgccacc aacctggccg atggcgtgcc  3600
tagtagattc agcggatctg gcagcggcac agacttcacc ctgaccatca gcagcctgca  3660
acctgaggac tttgccacat actactgcca gaacgtgctg aatacacctc tgacattcgg  3720
ccaaggaacc aaagtggaaa tcaagcggac cgtggccgct cctagcgtgt tcatcttccc  3780
tccttccgat gaacaactga agagcggaac cgcctctgtg gtgtgcctgc tgaacaactt  3840
ctaccctaga gaggccaagg tgcagtggaa ggtcgacaac gccctgcaga gcggcaacag  3900
ccaggagagc gtgacggaac aggacagcaa ggacagcacc tacagcctga gctccaccct  3960
tacactgtct aaagccgact acgagaagca caaggtgtac gcctgtgaag tgacacacca  4020
gggcctgagc agccctgtga ccaagtcttt taaccggggc gagtgctgaa ttcgaatcgt  4080
acctagggat ccagacatga taagatacat tgatgagttt ggacaaacca caactagaat  4140
gcagtgaaaa aaatgcttta tttgtgaaat ttgtgatgct attgctttat ttgtaaccat  4200
tataagctgc aataaacaag ttaacaacaa caattgcatt cattttatgt ttcaggttca  4260
```

```
gggggaggtg tgggaggttt tttaagcttg tttaaacgta cgtagataag tagcatggcg  4320
ggttaatcat taactacaag gaacccctag tgatggagtt ggccactccc tctctgcgcg  4380
ctcgctcgct cactgaggcc gggcgaccaa aggtcgcccg acgcccgggc tttgcccggg  4440
cggcctcagt gagcgagcga gcgcgcagag agggagtggc caa                    4483

SEQ ID NO: 60          moltype = DNA  length = 2208
FEATURE                Location/Qualifiers
source                 1..2208
                       mol_type = other DNA
                       organism = synthetic construct
SEQUENCE: 60
ttacagatta cgagtcaggt atctggtgcc aatggggcga ggctctgaat acacgccatt  60
agtgtccaca gtaaagtcca cattaacaga cttgttgtag ttggaagtgt actgaatttc  120
gggattccag cgtttgctgt ttccttctg cagctcccac tcgatctcca cgctgacctg   180
tcccgtggag tactgtgtga tgaaggaagc aaactttgcc gcactgaagg tggtcgaagg  240
attcgcaggt accggggtgt tcttgatgag aatctgtgga ggagggtgtt taagtccgaa  300
tccacccatg aggggagagg ggtgaaaatg tccgtccgtg tgtggaatct ttgcccagat  360
gggcccctga aggtacacat ctctgtcctg ccagaccatg cctggaagaa cgccttgtgt  420
gttgacatct gcggtagctg cttgtctgtt gcctctctgg aggttggtag atacagaacc  480
atactgctcc gtagccacgg gattggttgt cctgatttcc tcttcgtctg taatcatgac  540
cttttcaatg tccacatttg ttttctctga gccttgcttc ccaaagatga gaaccccgct  600
ctgaggaaaa aacttttctt catcgtcctt gtggcttgcc atggccgggc ccggattcac  660
cagagagtct ctgccattga ggtggtactt ggtagctcca gtccacgagt attcactgtt  720
gttgttatcc gcagatgtct ttgatactcg ctgctggcgg taacagggtc caggaagcca  780
gttcctagac tggtcccgaa tgtcactcgc tccggcctga gaaaactgaa gccttgactg  840
cgtggtggtt ccacttggag tgtttgttct gctcaagtaa tacaggtact ggtcgatgag  900
aggattcatg agacggtcca gactctggct gtgagcgtag ctgctgtgga aaggaacgtc  960
ctcaaaagtg tagctgaagg taaagttgtt tccggtacgc agcatctgag aaggaaagta  1020
ctccaggcag taaaatgaag agcgtcctac tgcctgactc ccgttgttca gggtgaggta  1080
tccatactgt ggcaccatga agacgtctgc tgggaacggc gggaggcatc cttgatgcgc  1140
cgagccgagg acgtacggga gctggtactc cgagtcagta aacacctgaa ccgtgctggt  1200
aaggttattg gcaatcgtcg tcgtaccgtc attctgcgtg acctctttga cttgaatgtt  1260
aaagagcttg aagttgagtc tcttgggtcg gaatccccag ttgttgttga tgagtctttg  1320
ccagtcacgt ggtgaaaagt ggcagtggaa tctgttgaag tcaaaatacc cccaaggggt  1380
gctgtagcca aagtagtgat tgtcgttcga ggctcctgat tggctggaaa tttgtttgta  1440
gaggtggttg ttgtaggtgg gcagggccca ggttcgggtg ctggtggtga tgactctgtc  1500
gcccatccat gtggaatcgc aatgccaatt tcccgaggaa ttacccactc cgtcggcgcc  1560
ctcgttattg tctgccattg gtgcgccact gcctgtagcc atcgtattag ttcccagacc  1620
agagggggct gctggtggct gtccgagagg ctgggggtca ggtactgagt ctgcgtctcc  1680
agtctgacca aaattcaatc ttttcttgc aggctgctgg cccgcctttc cggttcccga   1740
ggaggagtct ggctccacag gagagtgctc taccggcctc ttttttcccg gagccgtctt  1800
aacaggttcc tcaaccaggc ccagaggttc aagaaccctc tttttcgcct ggaagactgc  1860
tcgtccgagg ttgcccccaa aagacgtatc ttctttaagg cgctcctgaa actccgcgtc  1920
ggcgtggttg tacttgaggt acgggttgtc tccgctgtcg agctgccggt cgtaggcttt  1980
gtcgtgctcg agggcgcggg cgtctgcctc gttgaccggc tctcccttgt cgagtccgtt  2040
gaagggtccg aggtacttgt acccaggaag cacaagaccc ctgctgtcgt ccttatgccg  2100
ctctgcgggc tttggtggtg gtgggccagg tttgagcttc caccactgtc ttattccttc  2160
agagagagtg tcctcgagcc aatctggaag ataaccatcg gcagccat               2208

SEQ ID NO: 61          moltype = DNA  length = 2217
FEATURE                Location/Qualifiers
source                 1..2217
                       mol_type = other DNA
                       organism = synthetic construct
SEQUENCE: 61
atggctgccg atggttatct tccagattgg ctcgaggaca acctctctga gggcattcgc  60
gagtggtggg cgctgaaacc tggagccccg aagcccaaag ccaaccagca aaagcaggac  120
gacggccggg gtctggtgct tcctggctac aagtacctcg gacccttcaa cggactcgac  180
aagggggagc ccgtcaacgc ggcggacgca gcggccctcg agcacgacaa ggcctacgac  240
cagcagctgc aggcgggtga caatccgtac ctgcggtata accacgccga cgccgagttt  300
caggagcgtc tgcaagaaga tacgtctttt gggggcaacc tcgggcgagc agtcttccag  360
gccaagaagc gggttctcga acctctcggt ctggttgagg aaggcgctaa gacggctcct  420
ggaaagaaga gaccggtaga gccatcaccc cagcgttctc cagactcctc tacgggcatc  480
ggcaagaaag gccaacagcc cgccagaaaa agactcaatt ttggtcagac tggcgactca  540
gagtcagttc cagaccctca acctctcgga gaacctccag cagcgccctc tggtgtggga  600
cctaatacaa tggctgcagg cggtggcgca ccaatggcag acaataacga aggcgccgac  660
ggagtgggta gttcctcggg aaattggcat tgcgattcca catggctggg cgacagagtc  720
atcaccacca gcacccgaac ctgggccctg cccacctaca acaaccacct ctacaagcaa  780
atctccaacg ggacatcggg aggagccacc aacgacaaca cctacttcgg ctacagcacc  840
ccctgggggt attttgactt taacagattc cactgccact tttcaccacg tgactggcag  900
cgactcatca acaacaactg gggattccgg cccaagagac tcagcttcaa gctcttcaac  960
atccaggtca aggaggtcac gcagaatgaa ggcaccaaga ccatcgccaa taacctcacc  1020
agcaccatcc aggtgtttac ggactcggag taccagctgc cgtacgttct cggctctgcc  1080
caccagggct gcctgcctcc gttcccggcg gacgtgttca tgattcccca gtacggctac  1140
ctaacactca acaacggtag tcaggccgtg ggacgctcct ccttctactg cctggaatac  1200
tttccttcgc agatgctgag aaccggcaac aacttccagt ttacttacac cttcgaggac  1260
gtgcctttcc acagcagcta cgcccacagc cagagcttgg accggctgat gaatcctctg  1320
attgaccagt acctgtacta cttgtctcgg actcaaacaa caggaggcac ggcaaatacg  1380
cagactctgg gcttcagcca aggtgggcct aatacaatgg ccaatcaggc aaagaactgg  1440
```

```
ctgccaggac cctgttaccg ccaacaacgc gtctcaacga caaccgggca aaacaacaat  1500
agcaactttg cctggactgc tgggaccaaa taccatctga atggaagaaa ttcattggct  1560
aatcctggca tcgctatggc aacacacaaa gacgacgagg agcgtttttt tcccagtaac  1620
gggatcctga tttttggcaa acaaaatgct gccagagaca atgcggatta cagcgatgtc  1680
atgctcacca gcgaggaaga aatcaaaacc actaaccctg tggctacaga ggaatacggt  1740
atcgtggcag ataacttgca gcagcaaaac acggctcctc aaattggaac tgtcaacagc  1800
cagggggcct tacccggtat ggtctggcag aaccgggacg tgtacctgca gggtcccatc  1860
tgggccaaga ttcctcacac ggacggcaac ttccaccccgt ctccgctgat gggcggcttt  1920
ggcctgaaac atcctccgcc tcagatcctg atcaagaaca cgcctgtacc tgcggatcct  1980
ccgaccacct tcaaccagtc aaagctgaac tctttcatca cgcaatacag caccggacag  2040
gtcagcgtgg aaattgaatg ggagctgcag aaggaaaaca gcaagcgctg gaaccccgag  2100
atccagtaca cctccaacta ctacaaatct acaagtgtgg actttgctgt taatacagaa  2160
ggcgtgtact ctgaaccccg ccccattggc acccgttacc tcacccgtaa tctgtaa     2217

SEQ ID NO: 62          moltype = DNA  length = 2211
FEATURE                Location/Qualifiers
source                 1..2211
                       mol_type = other DNA
                       organism = synthetic construct
SEQUENCE: 62
atggctgccg atggttatct tccagattgg ctcgaggaca accttagtga aggaattcgc  60
gagtggtggg ctttgaaacc tggagcccct caacccaagg caaatcaaca acatcaagac  120
aacgctcgag gtcttgtgct tccgggttac aaataccttg gacccggcaa cggactcgac  180
aagggggagc cggtcaacgc agcagacgcg gcggccctcg agcacgacaa ggcctacgac  240
cagcagctca aggccggaga caacccgtac ctcaagtaca accacgccga cgccgagttc  300
caggagcggc tcaaagaaga tacgtctttt gggggcaacc tcgggcgagc agtcttccag  360
gccaaaaaga ggcttcttga acctcttggt ctggttgagg aagcggctaa gacggctcct  420
ggaaagaaga ggcctgtaga gcagtctcct caggaaccgg actcctccgc gggtattggc  480
aaatcgggtg cacagcccgc taaaaagaga ctcaatttcg gtcagactgg cgacacagag  540
tcagtcccag accctcaacc aatcggagaa cctcccgcag ccccctcagg tgtgggatct  600
cttacaatgg cttcaggtgg tggcgcacca gtggcagaca ataacgaagg tgccgatgga  660
gtgggtagtt cctcgggaaa ttggcattgc gattcccaat ggctgggga cagagtcatc  720
accaccagca cccgaacctg ggccctgccc acctacaaca atcacctcta caagcaaatc  780
tccaacagca catctggagg atcttcaaat gacaacgcct acttcggcta cagcaccccc  840
tgggggtatt ttgacttcaa cagattccac tgccacttct caccacgtga ctggcagcga  900
ctcatcaaca acaactgggg attccggcct aagcgactca acttcaagct cttcaacatt  960
caggtcaaag aggttacgga caacaatgga gtcaagacca tcgccaataa ccttaccagc  1020
acggtccagg tcttcacgga ctcagactat cagctcccgt acgtgctcgg gtcggctcac  1080
gagggctgcc tcccgccgtt cccagcggac gttttcatga ttcctcagta cgggtatctg  1140
acgcttaatg atggaagcca ggccgtgggt cgttcgtcct ttactgcct ggaatatttc  1200
ccgtcgcaaa tgctaagaac gggtaacaac ttccagttca gctacgagtt tgagaacgta  1260
cctttccata gcagctacgc tcacagccaa agcctggacc gactaatgaa tccactcatc  1320
gaccaatact tgtactatct ctcaaagact attaacggtt ctggacagaa tcaacaaacg  1380
ctaaaattca gtgtggccgg acccagcaac atggctgtcc agggaagaaa ctacatacct  1440
ggacccagct accgacaaca acgtgtctca accactgtga ctcaaaacaa caacagcgaa  1500
tttgcttggc ctggagcttc ttcttgggct ctcaatggac gtaatagctt gatgaatcct  1560
ggacctgcta tggccagcca caaagaagga gaggaccgtt tctttccttt gtctggatct  1620
ttaatttttg gcaaacaagg aactggaaga gacaacgtgg atgcggacaa agtcatgata  1680
accaacgaag aagaaattaa aactactaac ccggtagcaa cggagtccta tggacaagtg  1740
gccacaaacc accagagtgc ccaagcacag gcgcagaccg gctgggttca aaaccaagga  1800
atacttccgg gtatggtttg gcaggacaga gatgtgtacc tgcaaggacc catttgggcc  1860
aaaattcctc acacggacgg caactttcac ccttctccgc tgatgggagg gtttggaatg  1920
aagcacccgc ctcctcagat cctcatcaaa aacacacctg tacctgcgga tcctccaacg  1980
gccttcaaca aggacaagct gaactctttc atcacccagt attctactgg ccaagtcagc  2040
gtggagatcg agtgggagct gcagaaggaa aacagcaagc gctggaaccc ggagatccag  2100
tacacttcca actattacaa gtctaataat gttgaatttg ctgttaatac tgaaggtgta  2160
tatagtgaac cccgccccat tggcaccaga tacctgactc gtaatctgta a           2211

SEQ ID NO: 63          moltype = DNA  length = 2323
FEATURE                Location/Qualifiers
source                 1..2323
                       mol_type = other DNA
                       organism = synthetic construct
SEQUENCE: 63
ttggccactc cctctctgcg cgctcgctcg ctcactgagg ccgggcgacc aaaggtcgcc  60
cgacgcccgg gctttgcccg ggcggcctca gtgagcgagc gagcgcgcag agagggagtg  120
gccaactcca tcactagggg ttcctggagg ggtggagtcg tgacgtgaat tacgtcatag  180
ggttagggag gtcctgcagg gggaggctgc tggtgaatat taaccaaggt caccccagtt  240
atcggaggag caaacagggg ctaagtccac ctcgagccat ggcgatgctc taatctctct  300
agacaaggtt catatttgta tgggttactt attctctctt tgttgactaa gtcaataatc  360
agaatcagca ggtttgcagt cagattggca gggataagca gcctagctca ggagaagtga  420
gtataaaagc cccaggctgg gagcagccat cagctagcgc cggcaagagg taagggttta  480
agggatggtt ggttggtggg gtattaatgt ttaattacct ggagcacctg cctgaaatca  540
ctttttttca ggttgggcca ccatgtccac cgctgtgctg gagaaccctg ggctggggag  600
gaaactgtca gacttcgggc aggagacttc atacattgag gataactgta accagaatgg  660
cgccatctct ctgatcttca gcctgaagga ggaagtgggc gccctggcaa aggtgctgcg  720
cctgtttgag gagaacgacg tgaatctgac ccacatcgag tcccggcctt ctagactgaa  780
gaaggacgag tacgagttct ttacccacct ggataagcgg tccctgccag ccctgacaaa  840
catcatcaag atcctgaggc acgacatcgg agcaaccgtg cacgagctgt ctcgggacaa  900
```

-continued

```
gaagaaggat accgtgccct ggttccctcg gacaatccag gagctggata gatttgccaa  960
ccagatcctg tcttacggag cagagctgga cgcagatcac cctggcttca aggacccagt  1020
gtatcgggcc cggagaaagc agtttgccga tatcgcctac aattataggc acggacagcc  1080
aatccctcgc gtggagtata tggaggagga gaagaagacc tggggcacag tgttcaagac  1140
cctgaagagc ctgtacaaga cacacgcctg ctacgagtat aaccacatct tcccccctgct  1200
ggagaagtat tgtggctttc acgaggacaa tatccctcag ctggaggacg tgagccagtt  1260
cctgcagacc tgcacaggct ttaggctgag gccagtggca ggactgctga gctcccggga  1320
cttcctggga ggactggcct tcagagtgtt tcactgcacc cagtacatca ggcacggctc  1380
caagccaatg tatacaccag agcccgacat ctgtcacgag ctgctgggcc acgtgcccct  1440
gtttagcgat agatccttcg cccagttttc ccaggagatc ggactggcat ctctgggagc  1500
acctgacgag tacatcgaga agctggccac catctattgg ttcacagtgg agtttggcct  1560
gtgcaagcag ggcgatagca tcaaggccta cggagcagga ctgctgtcta gcttcggcga  1620
gctgcagtat tgtctgtccg agaagccaaa gctgctgccc ctggagctgg agaagaccgc  1680
catccagaac tacaccgtga cagagttcca gcccctgtac tatgtggccg agtcttttaa  1740
cgatgccaag gagaaggtga gaaatttcgc cgccacaatc cctaggccct tcagcgtgcg  1800
gtacgaccct tatacccaga ggatcgaggt gctggataat acacagcagc tgaagatcct  1860
ggctgactca atcaatagcg aaatcggaat cctgtgctcc gccctgcaga aaatcaaatg  1920
aatcgtagat ccagacatga taagatacat tgatgagttt ggacaaacca caactagaat  1980
gcagtgaaaa aaatgcttta tttgtgaaat ttgtgatgct attgctttat ttgtaaccat  2040
tataagctgc aataaacaag ttaacaacaa caattgcatt cattttatgt ttcaggttca  2100
gggggaggtg tgggaggttt tttaagcttg tttaaacgta cgtagataag tagcatggcg  2160
ggttaatcat taactacaag gaacccctag tgatggagtt ggccactccc tctctgcgcg  2220
ctcgctcgct cactgaggcc gggcgaccaa aggtcgcccg acgcccgggc tttgcccggg  2280
cggcctcagt gagcgagcga gcgcgcagag agggagtggc caa                   2323

SEQ ID NO: 64          moltype = DNA  length = 1927
FEATURE                Location/Qualifiers
source                 1..1927
                       mol_type = other DNA
                       organism = synthetic construct
SEQUENCE: 64
gggggaggct gctggtgaat attaaccaag gtcaccccag ttatcggagg agcaaacagg  60
ggctaagtcc acctcgagcc atggcgatgc tctaatctct ctagacaagg ttcatatttg  120
tatgggttac ttattctctc tttgttgact aagtcaataa tcagaatcag caggtttgca  180
gtcagattgg cagggataag cagcctagct caggagaagt gagtataaaa gccccaggct  240
gggagcagcc atcagctagc gccggcaaga ggtaagggtt taagggatgg ttggttggtg  300
gggtattaat gtttaattac ctggagcacc tgcctgaaat cacttttttt caggttgggc  360
caccatgtcc accgctgtgc tggagaaccc tgggctgggg aggaaactgt cagacttcgg  420
gcaggagact tcatacattg aggataactg taaccagaat ggcgccatct ctctgatctt  480
cagcctgaag gaggaagtgg gcgccctggc aaaggtgctg cgcctgtttg aggagaacga  540
cgtgaatctg acccacatcg agtcccggcc ttctagactg aagaaggacg agtacgagtt  600
ctttacccac ctggataagc ggtccctgcc agccctgaca aacatcatca agatcctgag  660
gcacgacatc ggagcaaccg tgcacgagct gtctcgggac aagaagaagg ataccgtgcc  720
ctggttccct cggacaatcc aggagctgga tagatttgcc aaccagatcc tgtcttacgg  780
agcagagctg gacgcagatc accctggctt caaggaccca gtgtatcggg cccggagaaa  840
gcagtttgcc gatatcgcct acaattatag gcacggacag ccaatccctc gcgtggagta  900
tatggaggag gagaagaaga cctggggcac agtgttcaag accctgaaga gcctgtacaa  960
gacacacgcc tgctacgagt ataaccacat cttcccccctg ctggagaagt attgtggctt  1020
tcacgaggac aatatccctc agctggagga cgtgagccag ttcctgcaga cctgcacagg  1080
ctttaggctg aggccagtgg caggactgct gagctcccgg gacttcctgg gaggactggc  1140
cttcagagtg tttcactgca cccagtacat caggcacggc tccaagccaa tgtatacacc  1200
agagcccgac atctgtcacg agctgctggg ccacgtgccc ctgtttagcg atagatcctt  1260
cgcccagttt tcccaggaga tcggactggc atctctggga gcacctgacg agtacatcga  1320
gaagctggcc accatctatt ggttcacagt ggagtttggc ctgtgcaagc agggcgatag  1380
catcaaggcc tacggagcag gactgctgtc tagcttcggc gagctgcagt attgtctgtc  1440
cgagaagcca aagctgctgc ccctggagct ggagaagacc gccatccaga actacaccgt  1500
gacagagttc cagcccctgt actatgtggc cgagtctttt aacgatgcca aggagaaggt  1560
gagaaatttc gccgccacaa tccctaggcc cttcagcgtg cggtacgacc cttataccca  1620
gaggatcgag gtgctggata atacacagca gctgaagatc ctggctgact caatcaatag  1680
cgaaatcgga atcctgtgct ccgccctgca gaaaatcaaa tgaatcgtag atccagacat  1740
gataagatac attgatgagt ttggacaaac cacaactaga atgcagtgaa aaaaatgctt  1800
tatttgtgaa atttgtgatg ctattgcttt atttgtaacc attataagct gcaataaaca  1860
agttaacaac aacaattgca ttcattttat gtttcaggtt cagggggagg tgtgggaggt  1920
tttttaa                                                           1927
```